(12) United States Patent
Matheu et al.

(10) Patent No.: US 11,085,018 B2
(45) Date of Patent: *Aug. 10, 2021

(54) THREE-DIMENSIONAL PRINTED ORGANS, DEVICES, AND MATRICES

(71) Applicant: Prellis Biologics, Inc., Hayward, CA (US)

(72) Inventors: Melanie P. Matheu, San Francisco, CA (US); Kathryn J. Parkinson, Palo Alto, CA (US); Emma R. Moulton, Hayward, CA (US)

(73) Assignee: PRELLIS BIOLOGICS, INC., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/669,439

(22) Filed: Oct. 30, 2019

(65) Prior Publication Data

US 2020/0063093 A1 Feb. 27, 2020

Related U.S. Application Data

(63) Continuation-in-part of application No. 16/044,413, filed on Jul. 24, 2018, now Pat. No. 10,513,691, which is a continuation of application No. PCT/US2018/034489, filed on May 24, 2018, which is a continuation-in-part of application No. 15/925,582, filed on Mar. 19, 2018, now Pat. No. 10,933,579, which is a continuation of application No. PCT/US2018/021850, filed on Mar. 9, 2018.

(60) Provisional application No. 62/556,242, filed on Sep. 8, 2017, provisional application No. 62/511,275, filed on May 25, 2017, provisional application No. 62/511,205, filed on May 25, 2017, provisional application No. 62/469,948, filed on Mar. 10, 2017.

(51) Int. Cl.

| | |
|---|---|
| *C12N 5/00* | (2006.01) |
| *B33Y 70/00* | (2020.01) |
| *B33Y 80/00* | (2015.01) |
| *C12N 5/071* | (2010.01) |
| *B29C 64/135* | (2017.01) |
| *B29L 31/00* | (2006.01) |
| *B33Y 30/00* | (2015.01) |
| *B33Y 10/00* | (2015.01) |

(52) U.S. Cl.
CPC ............ *C12N 5/0062* (2013.01); *B33Y 70/00* (2014.12); *B33Y 80/00* (2014.12); *C12N 5/0697* (2013.01); *B29C 64/135* (2017.08); *B29L 2031/7532* (2013.01); *B33Y 10/00* (2014.12); *B33Y 30/00* (2014.12); *C12N 2513/00* (2013.01)

(58) Field of Classification Search
None
See application file for complete search history.

(56) References Cited

U.S. PATENT DOCUMENTS

| | | | |
|---|---|---|---|
| 4,669,812 | A | 6/1987 | Hoebing |
| 5,024,508 | A | 6/1991 | Horner et al. |
| 5,194,971 | A | 3/1993 | Haines et al. |
| 5,561,537 | A | 10/1996 | Aritake et al. |
| 6,139,574 | A | 10/2000 | Vacanti et al. |
| 6,259,450 | B1 | 7/2001 | Chiabrera et al. |
| 6,304,263 | B1 | 10/2001 | Chiabrera et al. |
| 6,608,228 | B1 | 8/2003 | Cumpston et al. |
| 6,819,469 | B1 | 11/2004 | Koba |
| 7,535,607 | B2 | 5/2009 | Schwerdtner et al. |
| 8,184,276 | B2 | 5/2012 | Embry |
| 8,339,695 | B2 | 12/2012 | Haussler et al. |
| 8,435,438 | B1 | 5/2013 | Gross et al. |
| 8,663,539 | B1 | 3/2014 | Kolodziejska et al. |
| 9,114,032 | B1 | 8/2015 | Pulugurtha et al. |
| 9,631,171 | B2 | 4/2017 | Soman et al. |
| 10,239,237 | B1 | 3/2019 | Ensberg et al. |
| 10,500,796 | B1 | 12/2019 | Lazarovits |
| 2003/0090752 | A1 | 5/2003 | Rosenberger et al. |
| 2004/0067433 | A1 | 4/2004 | Nirmal et al. |
| 2004/0089804 | A1 | 5/2004 | Dantus et al. |
| 2004/0126694 | A1 | 7/2004 | Devoe et al. |
| 2004/0196524 | A1 | 10/2004 | Hughes et al. |
| 2004/0263930 | A1 | 12/2004 | Payne et al. |
| 2005/0208431 | A1 | 9/2005 | Devoe et al. |
| 2005/0226856 | A1 | 10/2005 | Ahlfors et al. |
| 2005/0286101 | A1 | 12/2005 | Garner et al. |

(Continued)

FOREIGN PATENT DOCUMENTS

| | | |
|---|---|---|
| CN | 203344507 U | 12/2013 |
| CN | 105176816 A | 12/2015 |

(Continued)

OTHER PUBLICATIONS

Allen et al. Imaging of Germinal Center Selection Events During Affinity Maturation. Science 315:528-531 (2007).
Bajaj et al. 3D Biofabrication Strategies for Tissue Engineering and Regenerative Medicine. Annu rev Biomed Eng 16:247-276 (2014).
Billiet et al. A review of trends and limitations in hydrogel-rapid prototyping for tissue engineering. Biomaterials 33:6020-6041 (2012).
Collins. Bioprinting Is Changing Regenerative Medicine Forever. Stem Cells Dev 23 Suppl 1:79-82 (2014).
Cuchiara et al. Integration of Self-Assembled Microvascular Networks with Microfabricated PEG-Based Hydrogels. Adv Funct Mater 22(21):4511-4518 (2012 ).

(Continued)

*Primary Examiner* — Michelle F. Paguio Frising
(74) *Attorney, Agent, or Firm* — Wilson Sonsini Goodrich & Rosati

(57) ABSTRACT

Provided herein are methods and systems for forming a three-dimensional object corresponding to an organ or organoid. A method for forming a three-dimensional object corresponding to an organ or organoid may comprise generating a plurality of discrete focal points patterned as a 3D projection corresponding to the organ or organoid in a medium comprising one or more precursors of a polymer, to form at least a portion of the 3D object corresponding to the organ or organoid.

21 Claims, 43 Drawing Sheets

(56) References Cited

U.S. PATENT DOCUMENTS

| | | | |
|---|---|---|---|
| 2006/0050340 | A1 | 3/2006 | Schwerdtner et al. |
| 2008/0194721 | A1 | 8/2008 | Arney et al. |
| 2008/0286482 | A1 | 11/2008 | Cheung et al. |
| 2009/0323508 | A1 | 12/2009 | Tomura et al. |
| 2010/0296148 | A1 | 11/2010 | Reichelt et al. |
| 2011/0033887 | A1 | 2/2011 | Fang et al. |
| 2011/0128555 | A1 | 6/2011 | Rotschild et al. |
| 2011/0149359 | A1 | 6/2011 | Leister et al. |
| 2011/0171689 | A1 | 7/2011 | Warren et al. |
| 2011/0254916 | A1 | 10/2011 | Fan et al. |
| 2011/0318528 | A1 | 12/2011 | Cho et al. |
| 2013/0012612 | A1 | 1/2013 | Houbertz-Krauss et al. |
| 2013/0203146 | A1 | 8/2013 | Ying et al. |
| 2013/0234372 | A1 | 9/2013 | Almutairi et al. |
| 2013/0304233 | A1 | 11/2013 | Dean et al. |
| 2014/0017651 | A1 | 1/2014 | Sugimoto et al. |
| 2014/0028663 | A1 | 1/2014 | Smithwick et al. |
| 2014/0113373 | A1 | 4/2014 | Chien et al. |
| 2014/0126029 | A1 | 5/2014 | Fuetterer et al. |
| 2015/0037445 | A1 | 2/2015 | Murphy et al. |
| 2015/0097315 | A1 | 4/2015 | Desimone et al. |
| 2015/0165020 | A1 | 6/2015 | Jaklenec et al. |
| 2015/0355379 | A1 | 12/2015 | Wolter et al. |
| 2015/0375453 | A1 | 12/2015 | Yost et al. |
| 2015/0375455 | A1 | 12/2015 | Williams et al. |
| 2016/0033874 | A1 | 2/2016 | Tang et al. |
| 2016/0107380 | A1 | 4/2016 | Smoot et al. |
| 2016/0282813 | A1 | 9/2016 | Urbach |
| 2016/0297131 | A1 | 10/2016 | Kameoka et al. |
| 2016/0298087 | A1 | 10/2016 | Qu et al. |
| 2016/0303797 | A1 | 10/2016 | Moran |
| 2016/0322560 | A1 | 11/2016 | Sirbuly et al. |
| 2017/0057162 | A1 | 3/2017 | Spadaccini et al. |
| 2017/0087766 | A1 | 3/2017 | Chung et al. |
| 2017/0120337 | A1 | 5/2017 | Kanko et al. |
| 2017/0136692 | A1 | 5/2017 | Zheng et al. |
| 2017/0281828 | A1 | 10/2017 | Zhang et al. |
| 2017/0283766 | A1 | 10/2017 | Hribar et al. |
| 2017/0348907 | A1 | 12/2017 | Melde et al. |
| 2017/0371248 | A1 | 12/2017 | Tang et al. |
| 2018/0002658 | A1 | 1/2018 | Miller et al. |
| 2018/0015672 | A1* | 1/2018 | Shusteff ............... G03H 1/0005 |
| 2018/0117219 | A1 | 5/2018 | Yang et al. |
| 2018/0126630 | A1 | 5/2018 | Panzer et al. |
| 2018/0147776 | A1 | 5/2018 | Kotani et al. |
| 2018/0188684 | A1 | 7/2018 | Mullins |
| 2018/0257297 | A1 | 9/2018 | Matheu |
| 2018/0290384 | A1 | 10/2018 | Hyde et al. |
| 2018/0370144 | A1 | 12/2018 | Revanur et al. |
| 2018/0371389 | A1 | 12/2018 | Delrot et al. |
| 2019/0010463 | A1 | 1/2019 | Matheu et al. |
| 2019/0016052 | A1 | 1/2019 | Clark |
| 2019/0031911 | A1 | 1/2019 | Rolland et al. |
| 2019/0111622 | A1 | 4/2019 | Khalip |
| 2020/0041957 | A1* | 2/2020 | Mullins ............... G03H 1/2294 |
| 2020/0080060 | A1 | 3/2020 | Matheu et al. |

FOREIGN PATENT DOCUMENTS

| | | |
|---|---|---|
| CN | 105574927 A | 5/2016 |
| CN | 105582571 A | 5/2016 |
| CN | 105877875 A | 8/2016 |
| CN | 106139244 A | 11/2016 |
| CN | 106163581 A | 11/2016 |
| CN | 105818383 B | 12/2017 |
| EP | 3096171 A1 | 11/2016 |
| JP | H04267132 A | 9/1992 |
| WO | WO-2016083784 A1 | 6/2016 |
| WO | WO-2017181773 A1 | 10/2017 |
| WO | WO-2018165613 A1 | 9/2018 |
| WO | WO-2018218085 A2 | 11/2018 |
| WO | WO-2020028431 A1 | 2/2020 |
| WO | WO-2020028436 A1 | 2/2020 |
| WO | WO-2020102260 A1 | 5/2020 |

OTHER PUBLICATIONS

Culver et al. Three-dimensional biomimetic patterning in hydrogels to guide cellular organization. Adv Mater 24(17):2344-2348 (2012).
Farsari et al. Two-photon polymerization of an Eosin Y-sensitized acrylate composite. Journal of Photochemistry and Photobiology A: Chemistry 181(1):132-135 (2006).
Hernandez et al. Three-dimensional spatiotemporal focusing of holographic patterns. Nat Commun 7:11928 (2016).
Huh et al. Reconstituting Organ-Level Lung Functions on a Chip. Science 328(5986):1662-1668 (2010).
Itoh et al. Scaffold-Free Tubular Tissues Created by a Bio-3D Printer Undergo Remodeling and Endothelialization when Implanted in Rat Aortae. PLoS One 10(9):e0136681 (2015).
Jang et al. Human kidney proximal tubule-on-a-chip for drug transport and nephrotoxicity assessment. Integrative Biology 5(9):1089-1198 (2013).
King et al. 3D Proximal Tubule Tissues Recapitulate Key Aspects of Renal Physiology to Enable Nephrotoxicity Testing. Front Physiol 8:123 (2017).
Koo et al. Laser-assisted biofabrication in tissue engineering and regenerative medicine. J Mat Res 32(1):128-142 (2017).
Linnenberger. Live cell lithography and non-invasive mapping of neural networks. Univ of Colorado. Thesis (127 pgs) (2014).
Murphy et al. 3D bioprinting of tissues and organs. Nat Biotech 32:773-785 (2014).
Ovsianikov et al. Laser photofabrication of cell-containing hydrogel constructs. Langmuir 30:3787-3794 (2013).
PCT/US2018/021850 International Search Report and Written Opinion dated Jul. 24, 2018.
PCT/US2018034489 International Search Report and Written Opinion dated Jan. 17, 2019.
Pereira et al. 3D Photo-Fabrication for Tissue Engineering and Drug Delivery. Engineering 1(1):90-112 (2015).
Shusteff et al. Additive fabrication of 3D structures by holographic lithography/ in: Solid Freeform Fabrication 2016: Proceedings of the 27th Annual International Solid Freeform Fabrication Symposium— An additive Manufacturing Conference, Edited by Bourell, David L. et al., University of Texas, 2016, pp. 1183-1192.
Sistare et al. The Promise of New Technologies to Reduce, Refine, or Replace Animal Use while Reducing Risks of Drug Induced Liver Injury in Pharmaceutical Development. Ilar J 57(2):186-211 (2016).
Stankevicius et al. Holographic lithography for biomedical applications. Proc. of SPIE 8433:843312-1 to 843312-7 (May 11, 2012).
Suematsu et al. Generation of a synthetic lymphoid tissue-like organoid in mice. Nat Biotech 22(12):1539-1545 (2004).
Tas et al. Visualizing antibody affinity maturation in germinal centers. Science 10.1126/science.aad3439 (2016).
U.S. Appl. No. 15/925,582 Office Action dated Jan. 11, 2019.
U.S. Appl. No. 15/925,582 Office Action dated Jun. 29, 2018.
U.S. Appl. No. 15/925,582 Office Action dated Sep. 5, 2019.
U.S. Appl. No. 16/044,413 Office Action dated Apr. 4, 2019.
Yanagawa et al. Hydrogel microfabrication technology toward three dimensional tissue engineering. Regenerative Therapy 3:45-57 (2016).
Yuan et al. Laser Scanning Holographic Lithography for Flexible 3D Fabrication of Multi-Scale Integrated Nano-structures and Optical Biosensors. Sci Rep 6:22294 (2016).
Zhang et al. Optimized holographic femtosecond laser patterning method towards rapid integration of high-quality functional devices in microchannels. Sci Rep 6:33281 (2016).
Zheren et al. 3D Micro-concrete Hybrid Structures Fabricated by Femtosecond Laser Two-Photon Polymerization for Biomedical and Photonic Applications. 2016 IEEE International Conference on Industrial Technology (ICIT), Taipei, Taiwan (pp. 1108-1114) (2016).
Zhu et al. Direct 3D bioprinting of prevascularized tissue constructs with complex microarchitecture. Biomaterials 124:106-115 (2017).
PCT/US2019/044238 International Search Report and Written Opinion dated Nov. 15, 2019.
PCT/US2019/044243 International Search Report and Written Opinion dated Nov. 19, 2019.
PCT/US2019/061035 International Search Report and Written Opinion dated Apr. 9, 2020.

(56) References Cited

OTHER PUBLICATIONS

U.S. Appl. No. 15/925,582 Office Action dated Apr. 2, 2020.
PCT/US2020/052897 International Search Report and Written Opinion dated Jan. 13, 2021.

* cited by examiner

SINGLE FIBER CABLE

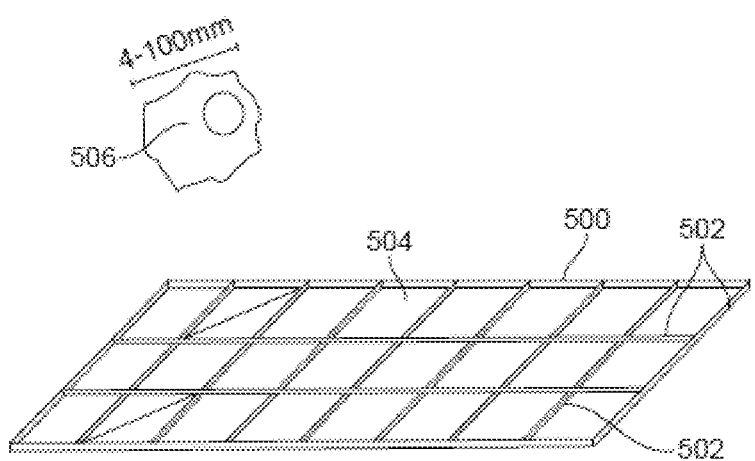
FIG. 11
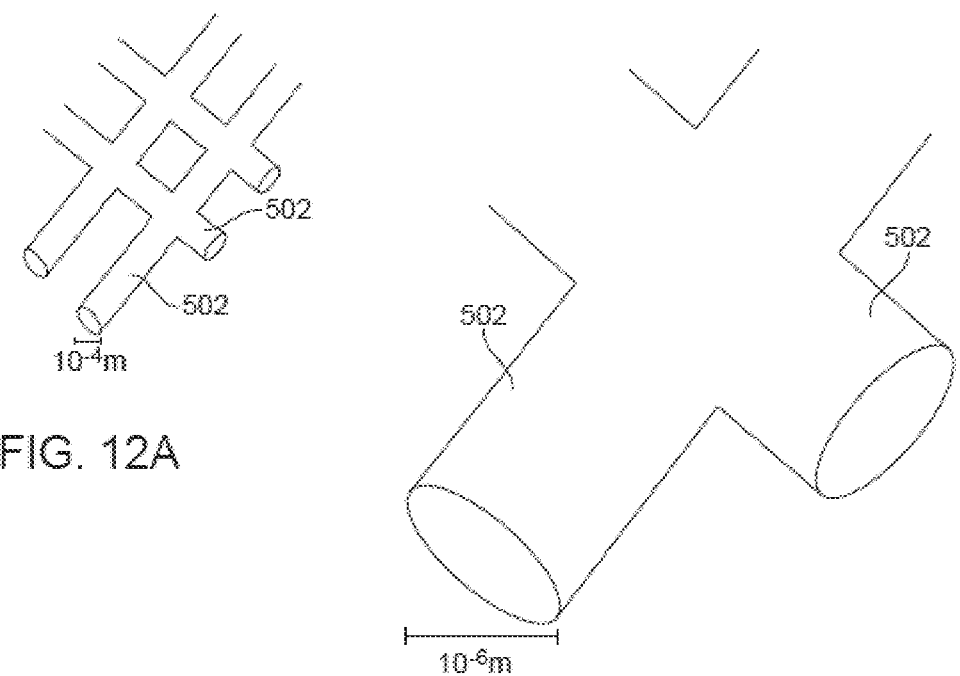
FIG. 12A
FIG. 12B

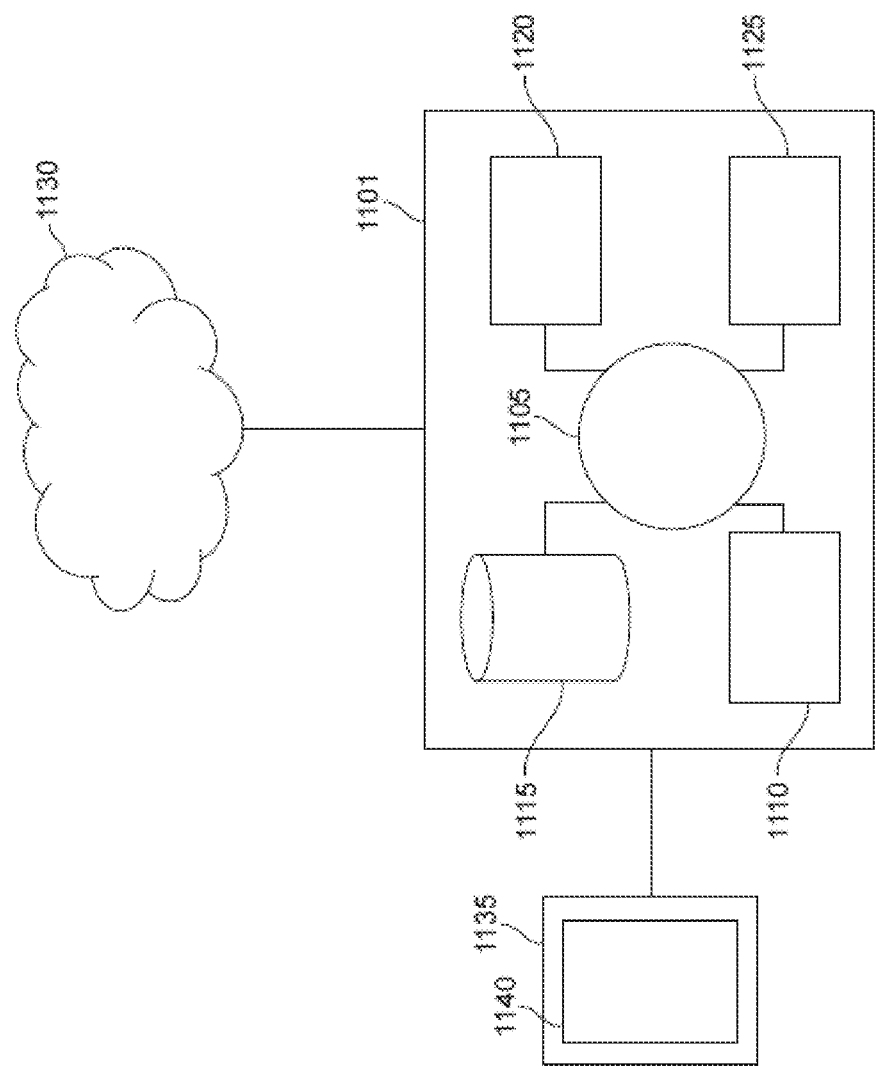

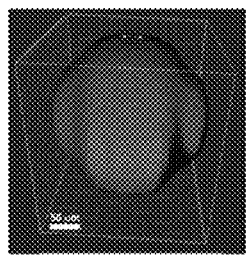 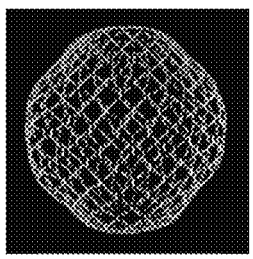 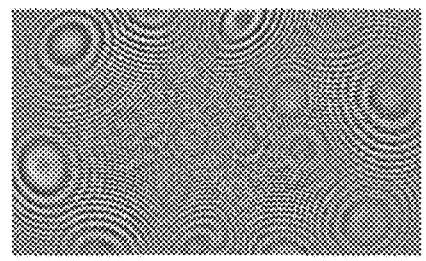 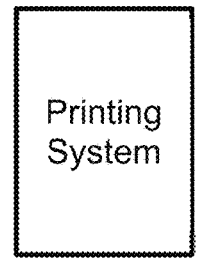
FIG. 49A     FIG. 49B     FIG. 49C     FIG. 49D
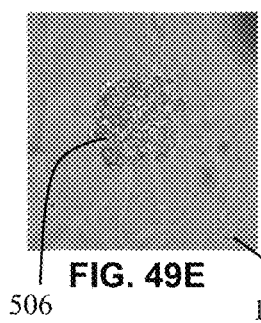 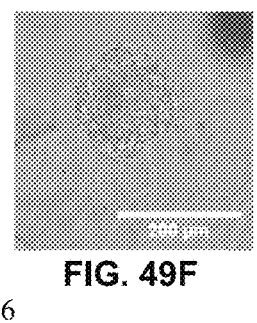 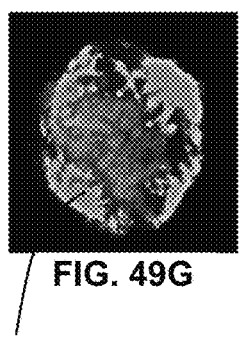 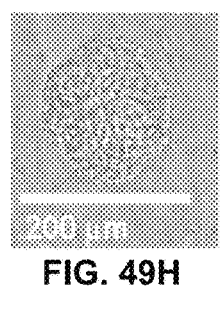
FIG. 49E     FIG. 49F     FIG. 49G     FIG. 49H
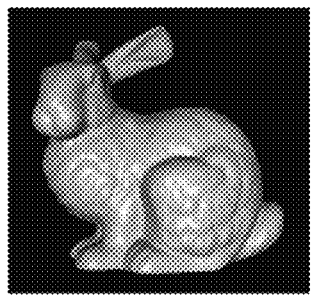 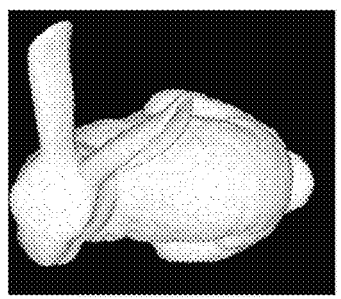 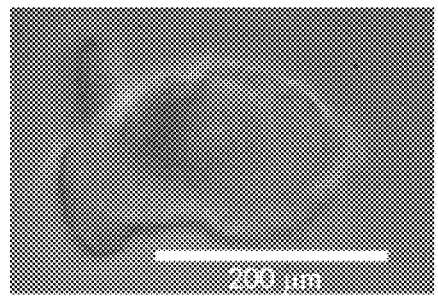
FIG. 50A     FIG. 50B     FIG. 50C

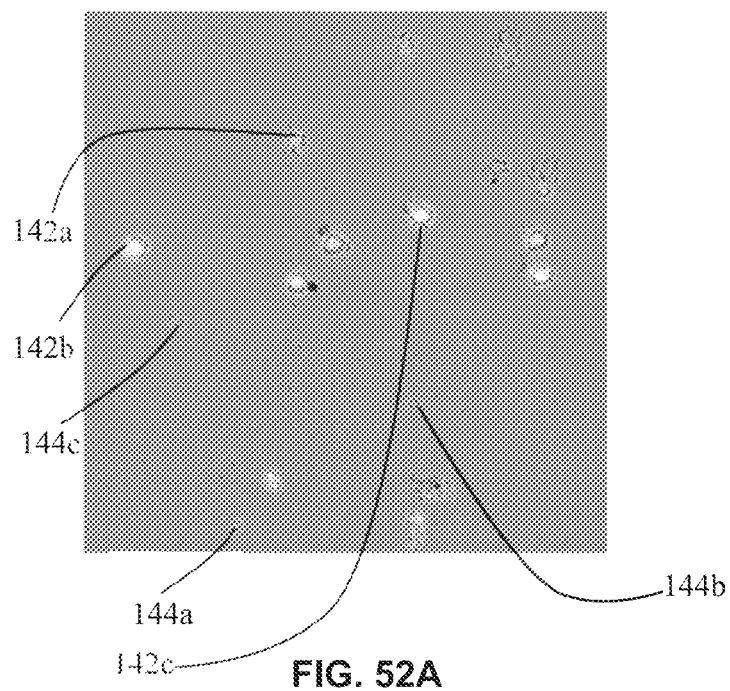
FIG. 52A
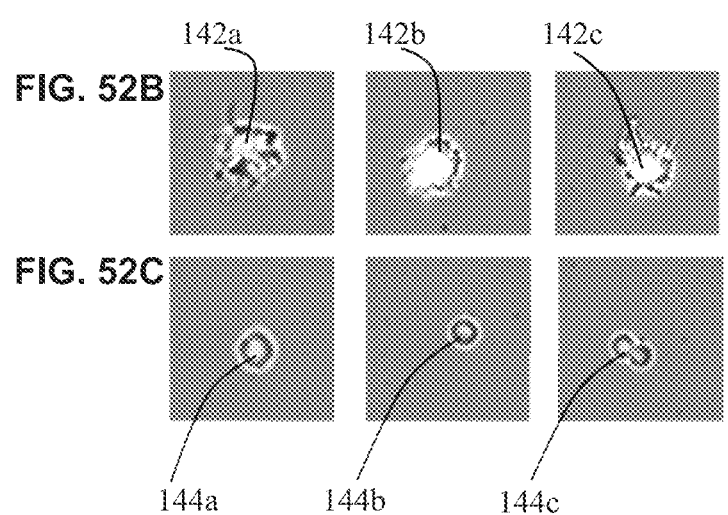
FIG. 52B
FIG. 52C

THREE-DIMENSIONAL PRINTED ORGANS, DEVICES, AND MATRICES

CROSS-REFERENCE

This application is a continuation-in-part of U.S. patent application Ser. No. 16/044,413, filed Jul. 24, 2018, now issued as U.S. Pat. No. 10,513,691 on Dec. 24, 2019, which is a continuation of International Application No. PCT/US2018/034489, filed on May 24, 2018, which claims the benefit of U.S. Provisional Patent Application No. 62/511,205, filed May 25, 2017, U.S. Provisional Patent Application No. 62/511,275, filed May 25, 2017, and U.S. Provisional Patent Application No. 62/556,242, filed Sep. 8, 2017; this application is a continuation in part of U.S. application Ser. No. 15/925,582, filed Mar. 19, 2018, which is a Continuation of International Application No. PCT/US2018/021850, filed on Mar. 9, 2018, which claims the benefit of U.S. Provisional Patent Application No. 62/469,948, filed on Mar. 10, 2017, each of which is entirely incorporated herein by reference.

BACKGROUND

Despite significant advances in the fields of cell biology, microfluidics, engineering, and three-dimensional printing, to date, conventional approaches have failed to re-create functional capillaries that feed and support the thick tissue necessary to construct a human organ. To date, these approaches in tissue engineering have relied on the in-growth of blood vessels into tissue-engineered devices to achieve permanent vascularization. This strategy has worked for some tissues that are either very thin such as a bladder wall replacement or tissues such as bone replacements that do not require vasculature to function. However, current tissue engineering techniques fall short in the creation of complex tissues such as large vital organs, including liver, kidney, thick skin, and heart. Larger tissues can also be thought of as an organization of smaller tissue sub-units; for example, the kidney is comprised of hundreds of thousands of nephron units, the functional unit of the lungs, i.e., the alveolar spaces, have a combined surface area of 70 to 80 meters squared ($m^2$), but are only 1 cell wall, 5 to 10 micrometers ($\mu m$), thick. Current tissue printing methodology not only fails to re-create the fine microvasculature necessary to support tissues thicker than 300 micrometers ($\mu m$), but cannot organize cells into the structural orientations and niches that are necessary for organ function.

Multi-photon laser based excitation is used in chemistry and physics for the generation of microstructures at sub-nanometer resolutions using photo-polymerization reactions, where photopolymerization is the light-based polymerization of a material. The use of two-photon microscopy to induce polymerization was first described in 1981. It was subsequently used to construct micrometer-to-nanometer-scale parts and tools by raster-scanning the pin-point focused laser in the x-y dimensions, tracing out the structure line by line. The high-resolution pin-point of the two-photon excitation allowed for sub-nanometer print resolution and additive manufacturing with plastics that may be photo-polymerized. As two-photon technology evolved and two-photon excitation was combined with laser-scanning microscopy, imaging of living tissues became possible. Long-wavelengths, typically greater than 700 nanometers (nm) used in multi-photon excitation allowed for greater tissue penetration due to reduced Rayleigh scattering, minimal photo-bleaching of fluorescent probes, and minimal to no detectable tissue toxicity. Thus, multi-photon laser excitation became useful in biology for non-invasive imaging of tissues at depths greater than those achievable with single-photon laser based confocal imaging.

Extended time periods of live-cell imaging, typically greater than a few hours, through the use of endogenous probes that are excited by two- and three-photon absorption were described shortly thereafter. One of the first applications of two-photon imaging was in the field of botany, which first described the inherently low toxicity of two-photon excitation to living cells. With its use in the study of neuronal signaling, two-photon microscopy was demonstrated to be an important low-toxicity photo-imaging tool in mammalian cells, wherein two-photon excitation was mild enough to not trigger the firing of a single neuron until external stimulus was applied. In 2002, video-rate two-photon imaging was demonstrated to be non-toxic to mammalian living cells in whole tissues, such as lymph nodes. Later, living cells in skin, lung, spleen, liver, and various other tissues were examined using two-photon microscopy. Extended imaging time courses are now up to 24 hours without observable negative effects on the biological activity or viability of cells, and have been conducted in a number of mammalian cells and tissues.

Together, high viability of individual cells combined with the ability to polymerize biomaterials have made multi-photon excitation an ideal tool for polymerization of materials in both cell-free medium and medium that contain cells to be embedded. Thus, multi-photon laser based excitation has been used for tissue engineering of some three-dimensional tissue structures, however significant limitations in the speed associated with printing complex structures with 2-dimensional raster scanning as described with current technology make the creation of complex, multicellular three-dimensional tissue structures including functional organs to date, infeasible. This is due to the inherent trade off in manufacturing speed and resolution for a single-unit (scan line) process. For example, it is estimated that raster-scanning of a laser at a resolution fine enough to create a centimeter cubed of tissue may take over three decades to perform. However, in the field of tissue engineering, the prospect of three-dimensional tissue structures offers a hope of promising treatment options to patients in need of organ transplantation and improved drug discovery and investigation based on whole, human-derived tissues rather than animal models, which are subject to error.

Multi-photon excitation methods of tissue engineering have been shown to be superior to extrusion or spray-based printing techniques which rely upon deposition of materials forced through a nozzle into a predefined pattern or form generating structure. Spray or droplet based cell printing lacks resolution, biocompatibility, is relatively slow, and is not scalable such that whole tissues cannot be built. Microvasculature or capillaries that are present in all organs and tissues are a maximum of e.g. 5 to 10 micrometers in diameter. This finely structured vasculature is necessary for tissue to be viable. Current droplet or spray printing methods do not have the capability of producing vascular structures smaller than 50 micrometers. Therefore, to date, no tissue structure thicker than roughly e.g. 250 to 300 micrometers, which is the limit of oxygen diffusion and waste exchange, has been reported to be viable. Without proper perfusion from microvasculature, tissues thicker than e.g. 250 to 300 micrometers become hypoxic and starve for nutrients, eventually becoming necrotic and dying from the inside out. Furthermore, single-cell layers and fine branching necessary to print the microvasculature necessary for support of tissue integrity and function cannot be achieved using current extrusion or droplet-based printing methods.

Lack of resolution at the cellular level further limits the development of complex or small scale three dimensional structures and cell niches that are dependent on direct interactions of multiple cell types or layers of cells. Pre-printing of fine structures or using pre-printed acellular scaffolds can achieve the resolution necessary to create microvasculature, however these structures require cell seeding, limiting the ability to place cells in specific orientations or niches, increasing development time of tissues, and leading to reduced cell viability as many cell seeding techniques require force to embed cells into small porous structures. Furthermore, the rigidity of printed scaffold structures impedes development of fully compatible biologically functional tissues by limiting cell-guided architectural and structural changes and by limiting the development of new blood vessels. Additionally, the rigidity of printed scaffold structures limits functional niche-adapting architectural changes, which prevents vascularized tissue development since cells are fixed and only a few types of cells can be deposited in such rigid structures.

In extrusion printing, cell viability is also compromised and print time is too slow to maintain cell viability over an extended period of time necessary to print a tissue structure. The scalability of extrusion printing is also inherently limited such that it does not solve issues of resolution and thus, extrusion printing does not have the capability to print tissues at a large scale. The size and functionality of printed tissues is limited by a series of factors. These limiting factors include the inability to scale to a larger organ sized structure (time to print), cell viability during the printing process, ability to create multicellular three dimensional niches, inflexibility of the final structure such that natural cell-induced development can occur, and the lack of microvasculature that only allows the maximum tissue thickness to be e.g. 250 to 300 micrometers. Thus, the utility of current extrusion printing techniques in tissue engineering is limited by the extensive time to production and the lack of fine enough resolution to accurately produce complex, vascularized three dimensional structures. Additionally, extrusion techniques often do not allow for cells to be placed directly in the print medium, are not biocompatible, and do not allow for changes in structure through the developmental process.

Two-photon excitation has been employed in the field of tissue microfabrication to speed time to production and improve printing resolution. Pulsed, two-photon lasers are wavelength-tunable and produce pinpoint, ultrafast, sub-nanometer-resolution polymerization of materials. Two-photon photo-polymerization has been applied to isolation of single cell types within defined structures. However, the technology for two-photon encapsulation of cell technology is significantly limited for multiple reasons, primarily the time associated with step-wise additive creation of a three-dimensional structure and therefore cannot yield the necessary complex capillary networks or multicellular structures necessary to produce vascularized tissues.

Primary limitations include the issue that these techniques are not always biocompatible, in large part due to reliance on biologically incompatible photo-initiators. Further limitations include, but are not limited to the speed of printing such that only small structures containing only a few cells are capable of being produced within the window of cell viability. Therefore, current two-photon cell encapsulation methods cannot generate large enough tissue structures to be useful for organ transplant and for most tissue-based applications. In addition, there are no provisions that allow for the necessary flow of cell supra-structures during tissue growth and development, and for the promotion of cell-cell contact, both of which are necessary for the growth and development of functional tissues. There are no provisions for additive cell layers to be introduced. And, finally, there are no provisions for specific structuring of networks that allow for certain forces of tension to be applied to a bed of developing cells, a necessary step in vascular development.

Current printing or deposition technologies do not allow for specific cell movement, cell-cell interactions, and the resultant development of tissue structures. These cell-intrinsic behaviors that occur naturally during development are essential for the formation of viable tissues. Tissues are three-dimensional structures comprised of cells in various states of differentiation, each with a specific function. Development of a biologically-active and self-maintaining tissue that can effectively perform as a replacement tissue requires proper localization of cells relative both to other cells and to such structural elements as vasculature, tendon, bone matrices, and other structural components of tissue. Differentiation is often driven by genetic changes, which may directly result in structural changes, such as involution, significant shifts in structure and/or may facilitate tissue development through changes in expression of tissue-specific structural, functional, or signaling proteins. During morphogenesis, wound repair, and cancer invasion, for example, cells move collectively as large sheets, strands, or clusters allowing for rapid contact-based force generation or collective polarization. These cell movements en masse are necessary for proper tissue formation and function. These cell movements and exposure to different environmental forces, such as blood flow, are causative of critical developmental cues for differentiation of functional tissues. For example, as arterial and venous capillaries are formed from uniform precursor cells that undergo significant shifts in gene expression that drives phenotype differentiation and results in functional vascular structures arising from the same cell type. Furthermore, support for and allowance of structural tolerance of stretch and pressure changes is necessary for vascular function and maintenance of vascular endothelial cell identity. Indeed, vascular walls have elastic fiber deposition as one of their primary components. Despite the numerous methods to develop blood vessels with bioprinting techniques, no current process reported or hypothesized allows for the combined deposition of strand-based structures for creation of cell niches for vascular development or cell movement in sheet or strand components. In short, currently developed and described structures for tissue based cell printing are not designed to tolerate or support these forces, and proper vascularization or microvascular (capillary) development has yet to be demonstrated. Without vascularization with capillaries, printed cells can only survive in extremely thin sheets that are limited to, e.g., 200-300 micrometers by oxygen and nutrient diffusion to provide for waste and nutrient exchange. Therefore, it may not be possible to develop a functional transplantable tissue without microvasculature.

SUMMARY

Recognized herein are various issues with previously described methods for printing of cells into tissue-forming structures. Such methods may be limited by (i) the sheer variety of cells necessary to create a complex vascularized tissue; (ii) rigid structures that do not allow for the supra-structural movement that occurs as a necessary element of, or facilitates developmental changes necessary for further differentiation; (iii) elements of varied structural rigidity or moment that can facilitate or adapt to cell-cell interactions between like or unlike cell layers during development, (iv) lack of cell-type specific channels or nets; and (v) lack of pre-printed (first step) or reprinted (intermediate or final step) vascular cells, (vi) structures designed to allow for cell-cell interactions while withstanding mechanical forces including pressure, tension, twisting, stretch, or motion necessary for vascular development, differentiation, and function, within tissues.

Additionally, single photon raster-scan printing and two dimensional projection of a sheet of light may be both significantly slower as manufacturing processes than the methods and systems provided herein. In some instances, it may be estimated that a structure that would take decades to create with single-photon raster scanning, and weeks in the case of 2D projection, may be created in a matter of 24 hours or fewer with the three-dimensional (3D) holographic printing methods and systems provided herein. Furthermore, the 3D holographic printing methods and systems provided herein may be fill-factor independent when the entire structure is projected at once because the printing occurs simultaneously at all points within a cubic volume. Therefore, a printing speed may be decoupled from a resolution when using a holographic printing projection such as the one used by the 3D holographic printing methods and systems provided herein. A printing speed may be volume dependent, and the print volume may be dictated by static optical components, when using the 3D holographic printing methods and systems provided herein.

Thus far, the field of tissue engineering may have failed to produce responsive, biologically-active vascularized tissues that behave as native tissue in large enough structures be useful for transplantation, systems-integrative drug testing, and/or development of biologic therapeutics, such as human antibodies.

Two-photon lasers may provide a low cellular toxicity profile based on: 1) pinpoint sites of two-photon excitation that fall off as a function of the square of the distance from the focal point in the x, y, and z dimensions such that peak laser power may not be spread throughout the sample; 2) rapid x, y scanning of the excitation point minimizing the time a cell may be exposed to the peak laser power at the point of excitation; and 3) ultra-short, sub-picosecond pulse widths that may allow for gaps in time where few to no photons are engaging the material or cells.

In an aspect, the present disclosure provides a method for printing a three-dimensional (3D) biological material, comprising: (a) providing a media chamber comprising a medium comprising (i) a plurality of cells and (ii) one or more polymer precursors; and (b) directing at least one energy beam to the medium in the media chamber along at least one energy beam path that is patterned into a 3D projection in accordance with computer instructions for printing the 3D biological material in computer memory, to form at least a portion of the 3D biological material comprising (i) at least a subset of the plurality of cells, and (ii) a polymer formed from the one or more polymer precursors.

In some embodiments, the biological material develops into a biologically functional tissue. In some embodiments, the method further comprises prior to (b), generating a point-cloud representation or lines-based representation of the 3D biological material in computer memory, and using the point-cloud representation or lines-based representation to generate the computer instructions. In some embodiments, the method further comprises converting the point-cloud representation or lines-based representation into an image.

In some embodiments, the image is projected in a holographic manner. In some embodiments, the image is deconstructed and reconstructed prior to projection in a holographic manner. In some embodiments, the point-cloud representation or the lines-based representation comprises multi-dimensional structural elements corresponding to the 3D biological material. In some embodiments, the point-cloud representation or the lines-based representation comprises structural elements in two dimensions, wherein the structural elements are associated with tissue function and/or cellular segregation. In some embodiments, point-cloud representation or the lines-based representation comprises structural elements in three dimensions, wherein the structural elements are associated with tissue function and/or cellular segregation.

In some embodiments, the at least one energy beam comprises coherent light. In some embodiments, the at least one energy beam is generated by a laser. In some embodiments, the at least one energy beam is phase modulated. In some embodiments, the one or more polymer precursors comprise at least two different polymeric precursors.

In some embodiments, the method further comprises repeating (b) along one or more additional energy beam paths to form at least another portion of the 3D biological material. In some embodiments, the at least another portion of the 3D biological material is linked to the 3D biological material formed in (b). In some embodiments, the at least another portion of the 3D biological material is not linked to the 3D biological material formed in (b). In some embodiments, (b) further comprises directing at least two energy beams to the medium in the media chamber along at least two energy beam paths in accordance with the computer instructions, to permit multiple portions of the medium in the media chamber to simultaneously form at least a portion of the 3D biological material.

In some embodiments, the at least two energy beams are of identical wavelengths. In some embodiments, the at least two energy beams are of different wavelengths. In some embodiments, the at least the portion of the 3D biological material comprises microvasculature for providing one or more nutrients to the plurality of cells. In some embodiments, the microvasculature is a blood microvasculature, a lymphatic microvasculature, or any combination thereof. In some embodiments, the microvasculature has a cross-section from about 1 µm to about 20 µm. In some embodiments, the 3D biological material has a thickness or diameter from about 100 µm to about 5 cm.

In some embodiments, the medium further comprises a plurality of beads, and wherein in (b) the at least the portion of the 3D biological material, as formed, includes the plurality of beads. In some embodiments, the beads further comprise signaling molecules or proteins. In some embodiments, the signaling molecules or proteins promote formation of the 3D biological material to permit organ function. In some embodiments, the at least the portion of the 3D biological material comprises a cell-containing scaffold, which cell-containing scaffold comprises at least a subset of the plurality of cells. In some embodiments, the 3D biological material comprises cell-containing scaffolds.

In some embodiments, the cell-containing scaffolds are coupled together. In some embodiments, the cell-containing scaffolds are cohesively or mechanically coupled together. In some embodiments, the cell-containing scaffolds are mechanically coupled together through one or more members selected from the group consisting of joints, hinges, locking joints and hinges, Velcro-like elements, springs, coils, points of stretch, interlocking loops, sockets, gears, ratchets, screw, and chain links. In some embodiments, the cell-containing scaffolds comprise a network, wherein the network comprises a plurality of strands. In some embodiments, the plurality of strands forms a mesh structure, a grid structure, a sheet structure, or a tube structure. In some embodiments, the individual strands of the plurality of strands have a thickness from about 0.1 nm to about 5 cm.

In some embodiments, subsequent to (b), the at least another portion of the 3D biological material is formed within the at least the portion of the 3D biological material. In some embodiments, the computer instructions comprise a set of images corresponding to the 3D biological material. In some embodiments, the computer instructions direct adjustment of at least (i) one or more parameters of the at least one energy beam as a function of time during formation of the 3D biological material, and/or (ii) location of a stage upon which the 3D biological material is formed.

In some embodiments, the method further comprises subjecting at least a portion of the at least the subset of the plurality of cells to differentiation to form the cells of the at least two different types. In some embodiments, the at least the subset of the plurality of cells comprises cells of at least two different types. In some embodiments, in (b), the plurality of cells comprises the cells of the at least two different types. In some embodiments, the at least one energy beam is a multi-photon energy beam. In some embodiments, the multi-photon energy beam is a two-photon energy beam.

In another aspect, the present disclosure provides a method of printing a three-dimensional (3D) biological material, comprising: (a) providing a media chamber comprising a first medium, wherein the first medium comprises a first plurality of cells and a first polymeric precursor; (b) directing at least one energy beam to the first medium in the media chamber along at least one energy beam path in accordance with computer instructions for printing the 3D biological material in computer memory, to subject at least a portion of the first medium in the media chamber to form a first portion of the 3D biological material; (c) providing a second medium in the media chamber, wherein the second medium comprises a second plurality of cells and a second polymeric precursor, wherein the second plurality of cells is of a different type than the first plurality of cells; and (d) directing at least one energy beam to the second medium in the media chamber along at least one energy beam path in accordance with the computer instructions, to subject at least a portion of the second medium in the media chamber to form at least a second portion of the 3D biological material.

In some embodiments, the biological material is a biologically functional tissue. In some embodiments, the method further comprises, subsequent to (d), removing a remainder of the first medium from the media chamber to leave the first portion of the 3D biological material in the media chamber. In some embodiments, the first portion of the 3D biological material left in the medium chamber is removably fixed to the media chamber. In some embodiments, the method further comprises prior to (b), generating a point-cloud representation or lines-based representation of the 3D biological material in computer memory, and using the point-cloud representation or lines-based representation to generate the computer instructions.

In some embodiments, the method further comprises converting the point-cloud representation or lines-based representation into an image or image set that is used to spatially modulate an incoming coherent light source such that biological structures are projected in one dimension. In some embodiments, the method further comprises converting the point-cloud representation or lines-based representation into an image or image set that is used to spatially modulate an incoming coherent light source such that biological structures are projected in two dimensions. In some embodiments, the method further comprises converting the point-cloud representation or lines-based representation into an image or image set that is used to spatially modulate an incoming coherent light source such that biological structures are projected in three dimensions.

In some embodiments, the method further comprises converting the point-cloud representation or lines-based representation into an image or image set that is used to spatially modulate at least one incoming coherent light source such that biological structures are projected in a mixture of one-dimensional, two-dimensional and/or three-dimensional structures. In some embodiments, the image or image set is projected in a holographic manner. In some embodiments, the image or image set is deconstructed and reconstructed into partial elements or representative structures prior to projection in a holographic manner.

In some embodiments, the point-cloud representation or the lines-based representation comprises multi-dimensional structural elements corresponding to the 3D biological material. In some embodiments, the point-cloud representation or the lines-based representation comprises structural elements in two dimensions, wherein the structural elements are associated with tissue function and/or cellular segregation. In some embodiments, the point-cloud representation or the lines-based representation comprises structural elements in three dimensions, wherein the structural elements are associated with tissue function and/or cellular segregation.

In some embodiments, the at least one energy beam comprises coherent light. In some embodiments, the at least one energy beam is generated by a laser. In some embodiments, the at least one energy beam is phase modulated. In some embodiments, the at least one energy beam is phase modulated and raster-scanned throughout the sample medium. In some embodiments, the at least a portion of the 3D biological material comprises microvasculature for providing one or more nutrients to the plurality of cells. In some embodiments, the microvasculature is a blood microvasculature, a lymphatic microvasculature, or any combination thereof. In some embodiments, the microvasculature has a cross-section from about 1 µm to about 20 µm. In some embodiments, the 3D biological material has a thickness or diameter from about 100 µm to about 5 cm.

In some embodiments, the first medium and/or the second medium further comprise a plurality of beads, and wherein in (b) the at least the portion of the 3D biological material, as formed, includes the plurality of beads. In some embodiments, the beads further comprise signaling molecules or proteins. In some embodiments, the signaling molecules or the proteins promote formation of the 3D biological material to permit organ function. In some embodiments, the 3D biological material is printed in a time period of at most about 350 hours. In some embodiments, the 3D biological material is printed in a time period of at most about 72 hours. In some embodiments, the 3D biological material is printed in a time period of at most about 12 hours.

In some embodiments, the at least the portion of the 3D biological material comprises a cell-containing scaffold, which cell-containing scaffold comprises at least a subset of the plurality of cells. In some embodiments, the 3D biological material, as formed, includes a plurality of cell-containing scaffolds. In some embodiments, the plurality of cell-containing scaffolds is coupled together. In some embodiments, the plurality of cell-containing scaffolds are coupled together to form a cohesive structure. In some embodiments, the plurality of the cell-containing scaffolds is mechanically coupled together. In some embodiments, the plurality of cell-containing scaffolds are mechanically coupled together through one or more members selected from the group consisting of joints, hinges, locking joints and hinges, Velcro-like elements, springs, coils, points of stretch, interlocking loops, sockets, gears, ratchets, screw, and chain links.

In some embodiments, the cell-containing scaffolds comprise a network, wherein the network comprises a plurality of strands. In some embodiments, the plurality of strands forms a mesh structure, a grid structure, a sheet structure, or a tube structure. In some embodiments, the plurality of strands has a thickness from about 0.1 nm to about 5 cm. In some embodiments, subsequent to (d), the at least another portion of the 3D biological material is formed within the first portion of the 3D biological material and/or the second portion of the 3D biological material. In some embodiments, the first medium and/or the second medium further comprise glutathione or a functional variant thereof.

In another aspect, the present disclosure provides a system for printing a three-dimensional (3D) biological material, comprising: (a) a media chamber configured to contain a medium comprising a plurality of cells comprising cells of at least two different types and one or more polymer precursors; (b) at least one energy source configured to direct at least one energy beam to the media chamber; and (c) one or more computer processors operatively coupled to the at least one energy source, wherein the one or more computer processors are individually or collectively programmed to (i) receive computer instructions for printing the 3D biological material from computer memory; and (ii) direct the at least one energy source to direct the at least one energy beam to the medium in the media chamber along at least one energy beam path in accordance with the computer instructions, to subject at least a portion of the polymer precursors to form at least a portion of the 3D biological material.

In some embodiments, the one or more computer processors are individually or collectively programmed to generate a point-cloud representation or lines-based representation of the 3D biological material in computer memory, and use the point-cloud representation or lines-based representation to generate the computer instructions for printing the 3D biological material in computer memory. In some embodiments, the one or more computer processors are individually or collectively programmed to convert the point-cloud representation or lines-based representation into an image. In some embodiments, the one or more computer processors are individually or collectively programmed to project the image in a holographic manner.

In some embodiments, the at least one energy source is a plurality of energy sources. In some embodiments, the plurality of energy sources directs a plurality of the at least one energy beam. In some embodiments, the at least one energy source is a laser. In some embodiments, the at least one energy source is derived from a coherent light source. In some embodiments, the coherent light source comprises a wavelength from about 300 nm to about 5 mm. In some embodiments, the one or more computer processors are individually or collectively programmed to direct the at least one energy source to direct the at least one energy beam along one or more additional energy beam paths to form at least another portion of the 3D biological material. In some embodiments, the one or more additional energy beam paths are along an x axis, an x and y plane, or the x, y, and z planes.

In some embodiments, the method further comprises at least one objective lens for directing the at least one energy beam to the medium in the media chamber. In some embodiments, the at least one objective lens comprises a water dipping objective lens. In some embodiments, the one or more computer processors are individually or collectively programmed to receive images of the edges of the 3D biological material. In some embodiments, the one or more computer processors are individually or collectively programmed to direct linking of the 3D biological material with other tissue, which linking is in accordance with the computer instructions. In some embodiments, the plurality of cells comprises cells of at least two different types. In some embodiments, the medium further comprises glutathione or a functional variant thereof.

In another aspect, the present disclosure provides a system for printing a three-dimensional (3D) biological material, comprising: (a) a media chamber configured to contain a medium comprising a plurality of cells and a plurality of polymer precursors; (b) at least one energy source configured to direct at least one energy beam to the media chamber; and (c) one or more computer processors operatively coupled to the at least one energy source, wherein the one or more computer processors are individually or collectively programmed to (i) receive computer instructions for printing the 3D biological material from computer memory; (ii) direct the at least one energy source to direct the at least one energy beam to the medium in the media chamber along at least one energy beam path in accordance with the computer instructions, to subject at least a portion of the polymer precursors to form at least a portion of the 3D biological material; and (iii) direct the at least one energy source to direct the at least one energy beam to a second medium in the media chamber along at least one energy beam path in accordance with the computer instructions, to subject at least a portion of the second medium in the media chamber to form at least a second portion of the 3D biological material, wherein the second medium comprises a second plurality of cells and a second polymeric precursor, wherein the second plurality of cells is of a different type than the first plurality of cells.

In some embodiments, the one or more computer processors are individually or collectively programmed to generate a point-cloud representation or lines-based representation of the 3D biological material, and use the point-cloud representation or lines-based representation to generate the computer instructions for printing the 3D biological material in computer memory. In some embodiments, the one or more computer processors are individually or collectively programmed to convert the point-cloud representation or lines-based representation into an image. In some embodiments, the one or more computer processors are individually or collectively programmed to project the image in a holographic manner. In some embodiments, the at least one energy source is a plurality of energy sources. In some embodiments, the plurality of energy sources directs a plurality of the at least one energy beam. In some embodiments, the at least one energy source is a laser. In some embodiments, the at least one energy source is derived from a coherent light source.

In some embodiments, the coherent light source comprises a wavelength from about 300 nm to about 5 mm. In some embodiments, the one or more computer processors are individually or collectively programmed to direct the least one energy source to direct the at least one energy beam along one or more additional energy beam paths to form at least another portion of the 3D biological material. In some embodiments, the one or more additional energy beam paths are along an x axis, an x and y plane, or the x, y, and z planes. In some embodiments, the system further comprises at least one objective lens for directing the at least one energy beam to the medium in the media chamber. In some embodiments, the at least one objective lens comprises a water dipping objective lens. In some embodiments, the one or more computer processors are individually or collectively programmed to receive images of the edges of the 3D biological material. In some embodiments, the one or more computer processors are individually or collectively programmed to direct linking of the 3D biological material with other tissue, which linking is in accordance with the computer instructions. In some embodiments, the medium further comprises glutathione or a functional variant thereof.

In another aspect, the present disclosure provides a method for printing a three-dimensional (3D) object, comprising: directing at least one energy beam into a medium comprising one or more precursors, to generate the 3D object comprising a material formed from the one or more precursors, wherein the at least one energy beam is directed into the medium as a 3D projection corresponding to the 3D object.

In some embodiments, the material is a polymeric material. In some embodiments, the medium comprises cells or cellular constituents. In some embodiments, the one or more precursors are polymeric precursors. In some embodiments, the one or more precursors include one or more metals. In some embodiments, the 3D projection is a hologram. In some embodiments, the medium further comprises glutathione or a functional variant thereof.

In another aspect, the present disclosure provides a method for printing a three-dimensional (3D) biological material, comprising: (a) directing at least a first energy beam into a media chamber comprising a first medium comprising (i) a first plurality of cells and (ii) a first polymeric precursor, to generate a first portion of the 3D biological material, and; (b) directing at least a second energy beam into the media chamber comprising a second medium comprising (i) a second plurality of cells and (ii) a second polymeric precursor, to generate a second portion of the 3D biological material adjacent to the first portion of the 3D biological material.

In some embodiments, the at least first energy beam and the at least second energy beam are from the same energy source. In some embodiments, the at least first energy beam and the at least second energy beam are laser beams. In some embodiments, the cells of the first plurality of cells and the cells of the second plurality of cells are of different types. In some embodiments, the cells of the first plurality of cells and the cells of the second plurality of cells are of the same type. In some embodiments, the first polymeric precursor and the second polymeric precursor are different. In some embodiments, the first polymeric precursor and the second polymeric precursor are the same. In some embodiments, the first medium and/or second medium further comprise glutathione or a functional variant thereof.

The present disclosure provides methods and systems for rapid generation of multilayered vascularized tissues using spatial light modulation of multi-photon excitation sources. Using this approach, a method for rapid creation of cell-containing structures is provided by layering cell-size specific nets with embedded mechanical and, or biological elements such as microvasculature. The deposition of cells contained in nets of collagen or another biologically compatible, or inert material, is a rapid, iterative, process based on a three dimensional (holographic) projection, a two-dimensional projection, and/or in any planar axis such as x, y, x, z, or y, z, which may be combined with scanning of the multi-photon laser excitation. Three dimensional scanning, two-dimensional scanning, and raster scanning may be used simultaneously in various combinations to achieve rapid creation of a complete structure. The dynamic shifts between modes of laser projection allows for rapid generation of complex structures in a large field of view, while maintaining fine micrometer to nanometer resolution. This method allows for rapid production of large (e.g., up to about 5 centimeters (cm)) multi-layered and small vasculature (e.g. 1-10 micrometers (µm)) single-cell layered vasculature.

The present disclosure permits layering of multiple cell types in two dimensions and/or three dimensions such that tissue may be constructed in a manner that is not limited by multiple cell types, sizes, or complexities. In some cases, this is achieved using multiphoton (e.g., two-photon) excitation light, as may be provided, for example, by a laser.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

In an aspect, the present disclosure provides a method for forming a 3D object corresponding to an organ or organoid, comprising generating a three-dimensional (3D) projection corresponding to the organ or organoid in a medium comprising one or more precursors of a polymer, to form at least a portion of the 3D object corresponding to the organ or organoid.

In some embodiments the medium comprises at least one photoinitiator, at least one cross-linker, collagen, hyaluronic acid, other glycosaminoglycans, poly-dl-lactic-co-glycolic acid, poly-1-lactic acid, polyglycolic acid, alginate, gelatin, agar, or any combination thereof. In some embodiments the organ or organoid is selected from the group consisting of a lymph node, an islet of Langerhans, a hair follicle, a tumor or a tumor spheroid, a neural bundle and support cell(s), a nephron, a liver organoid, an intestinal crypt, a primary lymphoid organ, a secondary lymphoid organ, a spleen, a liver, a pancreas, a gallbladder, an appendix, a small intestine, a large intestine, a heart, a lung, a bladder, a kidney, a bone, a cochlea, an ovary, a thymus, a trachea, a cornea, a heart valve, skin, a ligament, a tendon, a muscle, a thyroid gland, a nerve, and a blood vessel.

In some embodiments the method further comprises receiving computer instructions for printing the organ or organoid, and forming at least the portion of the organ or organoid based at least in part on the computer instructions. In some embodiments the computer instructions comprise a computer model of the organ or organoid. In some embodiments the method further comprises obtaining a native architecture of the organ or organoid from imaging data of a native organ or organoid.

In some embodiments the native structure is rendered into at least one two-dimensional or three-dimensional image. In some embodiments the image is a model for the printing. In some embodiments the organ or organoid contains at least one cell. In some embodiments the at least one cell is of a subject. In some embodiments the at least one cell comprises one or more cell types. In some embodiments the 3D object is configured to facilitate a growth of at least one cell to yield the organ or organoid. In some embodiments the 3D projection comprises a 3D projection corresponding to the organ or organoid of one or more energy beams from one or more energy sources.

In some embodiments the energy source is selected from the group consisting of a laser, a diode laser, a multiple diode laser, a fiber laser, a short-pulsed laser, a femtosecond pulsed laser, a light emitting diode, an electromagnetic radiation source, and a light source. In some embodiments the energy beam is selected from the group consisting of white light, gamma waves, x-rays, ultraviolet light, visible light, infrared light, microwaves, radio waves, coherent light beams, near infrared light, and a particle beam. In some embodiments the 3D projection is a holographic projection. In some embodiments the method further comprises using the 3D object to form the organ or organoid for use in a subject. In some embodiments the method further comprises using the 3D object to form the organ or organoid, and combining the organ or organoid with an additional organ or organoid. In some embodiments the 3D projection is generated in the medium with aid of a spatial light modulator or a digital micromirror device, but not both.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2A illustrates the media chamber containing media comprising a first cell group.

FIG. 2B illustrates the media chamber containing media comprising a second cell group. FIG. 2C illustrates delivery of pulses of the multi-photon laser beam to the media. FIG. 2D illustrates an embodiment wherein the cell-containing scaffolding is printed along the bottom of the media chamber containing media.

FIG. 3A illustrates an embodiment of a laser system having a single multi-photon laser source. FIG. 3B illustrates an embodiment of a laser system having multiple laser lines. FIG. 3C illustrates an embodiment of a laser system comprising multiple laser lines, photomultipliers (PMTs), and an objective lens.

FIG. 4A illustrates an embodiment of the printing system comprising a beam expander, an optical focusing lens, an additional laser focusing lens, and no axicon or TAG lens. FIG. 4B illustrates an embodiment of the printing system comprising a beam expander, an optical focusing lens, an additional laser focusing lens, and an axicon or TAG lens. FIG. 4C illustrates a Z-step projection printing setup comprising a single SLM or DMD for 2D, x, y sheet or hologram projection for printing around cells and resultant structures printed with given Z-steps.

FIG. 5A illustrates an embodiment of the multi-photon tissue print head comprising a single, upright objective lens. FIG. 5B illustrates an embodiment of the multi-photon tissue print head having inverted optics for imaging structures.

FIG. 6A illustrates the fiber optic cable accessory and fiber optic cable. FIG. 6B illustrates the fiber optic cable accessory being used to print the desired complex tissue structure.

FIG. 11 illustrates an example net structure formed from polymerizable material.

FIGS. 12A-12B illustrate various embodiments of net structures. FIG. 12A illustrates a net comprised of strands having a thickness of about 0.1 micrometers. FIG. 12B illustrates a net comprised of strands having a thickness of approximately 5 micrometers.

FIG. 15A illustrates the generation of a net structure. FIG. 15B illustrates a second projection of a multi-photon laser beam from the laser beam targeting specific coordinates within the net structure. FIG. 15C illustrates the final net structure having the various points of reinforcement at the pre-determined intersections of the net strands.

FIG. 16A shows the generation of a net structure by projecting the multi-photon laser beam from the optics of the multi-photon tissue printing print-head into the media. FIG. 16B illustrates a second projection of a multi-photon laser beam targeting specific coordinates within the net structure. FIG. 16C illustrates the final net structure having the reinforced zig-zag shaped structural feature. FIG. 16D illustrates thicker net regions directing structural deformation.

FIG. 17A illustrates a net structure formed within the media wherein the net structure includes structural reinforcements. FIG. 17B illustrates first net strand and the second net strand drawn towards each other.

FIG. 18A illustrates the downward motion of the cells (indicated by arrows) as the cells move and communicate, to form the folds. FIG. 18B illustrates the cells having formed the folds between the first net strand, the second net strand, and the third net strand drawing the first net strand and the second net strand toward each other.

FIG. 19A illustrates a net structure formed within media wherein the net structure includes a first structural reinforcement, a second structural reinforcement, and a third structural reinforcement.

FIG. 19B illustrates the first net strand and the second net strand drawn toward each other. FIG. 19C provides a side view of the tissue showing the first unreinforced portion, the second unreinforced portion, and the third unreinforced portion drawn together, forming folds or wrinkles.

FIG. 23A illustrates a first example of a textured element. FIG. 23B illustrates a second example of a textured element. FIG. 23C illustrates a third example of a textured element. FIG. 23D illustrates a fourth example of a textured element. FIG. 23E illustrates a fifth example of a textured element.

FIG. 24A illustrates a sixth example of a textured element. FIG. 24B illustrates a seventh example of a textured element.

FIG. 27A illustrates a pivot joint comprising a first protrusion and a second protrusion. FIG. 27B illustrates the first protrusion being attached to a first net structure and the second protrusion being attached to a second net structure.

FIG. 28A illustrates a ball-and-socket joint comprising a first protrusion having a rounded ball head and a second protrusion having a concave socket head. FIG. 28B illustrates a ball-and-socket joint that is printed so that the first protrusion is attached to a first net structure and the second protrusion is attached to a second net structure.

FIG. 29A illustrates a saddle joint comprising a first protrusion and a second protrusion having a having a saddle-shaped indentation. FIG. 28B illustrates a saddle joint that is printed so that the first protrusion and second protrusions are attached to the net structures.

FIG. 34A illustrates an embodiment of a spring. FIG. 34B illustrates an embodiment of spring that is printed so that its ends are attached to the net structures.

FIG. 35A illustrates an embodiment of a chain comprising two ends and four links. FIG. 35B illustrates an embodiment of a chain that is printed so that its ends are attached to net structures.

FIG. 36A illustrates an embodiment of a hooking joint having a curved shape. FIG. 36B illustrates an embodiment of hooking joint that is printed so that the hooks are attached to the net structures.

FIG. 37A illustrates an embodiment of a hook-and-loop joint comprising a hook surface that is mateable with a loop surface. FIG. 37B illustrates an embodiment of the hook-and-loop joint being disengaged. FIG. 37C illustrates an embodiment of a hook-and-loop joint that is printed so that the hook surface is attached to the net structures.

FIG. 38A illustrates an embodiment of a hinge comprising brackets. FIG. 38B illustrates a rod extending through and joining two brackets. FIG. 38C illustrates an embodiment of a hinge that is printed so that the brackets are attached to net structures.

FIG. 41A illustrates two nets having an edge. FIG. 41B illustrates the cells being held along the edges, favoring the occurrence of cell-cell interactions with each other.

FIG. 42A illustrates net structure comprising a longitudinal region wherein the first apertures are sized to trap particular cells and the surrounding second apertures are sized to exclude cells. FIG. 42B illustrates the creation of a cell strand using variable density nets.

FIG. 43 shows a computer control system that is programmed or otherwise configured to implement methods provided herein.

FIG. 48A shows a top-down view of the 3D microvasculature. FIG. 48B shows a top-down view of the outer tube of the 3D microvasculature. FIG. 48C shows a completed 3D microvasculature structure. FIG. 48D shows a fluorescent image of three microvasculature structures encapsulating cells. FIG. 48E shows a bright field image of three microvasculature structures encapsulating cells after five days of holographic printing.

FIGS. 49A-49H show an exemplary process of the generation of a cell-containing structure using holographic printing. FIG. 49A shows a computer generated three-dimensional (3D) image of a cell-containing structure. FIG. 49B shows a point-cloud representation of the 3D image of the cell-containing structure. FIG. 49C shows a hologram corresponding to the point-cloud representation of the 3D image of the cell-containing structure. FIG. 49D illustrates the computer printing system. FIG. 49E shows an image of a cluster of cells suspended in liquid print media. FIG. 49F shows an image of the same cluster of living cells after three dimensional printing of the point-cloud representation. FIG. 49G shows a cut-away image showing cells within the printed, 3D cell-containing structure. FIG. 49H shows a representative image of the completed 3D cell-containing structure after printing.

FIGS. 50A-50C show images of the holographic printing of the "Stanford Bunny." FIG. 50A shows a computer generated three-dimensional (3D) image of the "Stanford Bunny." FIG. 50B shows a top-down view of the computer generated 3D image of the "Stanford Bunny." FIG. 50C shows a representative 3D print of the "Stanford Bunny" as imaged using in bright-field microscopy.

FIG. 51A shows the threshold for printing in Formulation A. FIG. 51B shows the threshold for printing in Formulation B.

FIGS. 52A-52C show targeted single cell encapsulation using holographic printing. FIG. 52A shows a plurality of encapsulated cells and non-encapsulated cells suspended in print media. FIG. 52B shows zoomed-in images of a plurality of encapsulated cells. FIG. 52C shows zoomed-in images of a plurality of non-encapsulated cells.

FIG. 54A illustrates a single photon laser beam projection into a media chamber containing a photosensitive print medium. FIG. 54B illustrates a multi-photon absorption process. FIG. 54C illustrates a representative graphic of wavefront shaping to produce a hologram. FIG. 54D illustrates a complete image projection (i.e., a 3D hologram) in multiple planes allowing for the holographic printing of a complex structure.

FIG. 55A illustrates a printed microvasculature structure. FIG. 55B shows an image of a printed microvasculature structure. FIG. 55C illustrates the use of a multi-photon laser beam to project a hologram of a sphere into the lumen of the 3D microvasculature structure.

FIG. 55D shows an image of the 3D microvasculature structure exactly when a multi-photon laser beam was used to project a hologram of a sphere into the lumen of the 3D microvasculature structure. FIG. 55E illustrates a sphere inside the lumen of the microvasculature structure. FIG. 55F shows the sphere (outlined by the dashed circle) was deposited within the lumen of the microvasculature structure without disrupting it.

FIG. 56A shows an image of the vasculature bed during the holographic printing process. FIG. 56B shows an image of the vasculature bed after the holographic printing process is completed.

DETAILED DESCRIPTION

Figure 1:
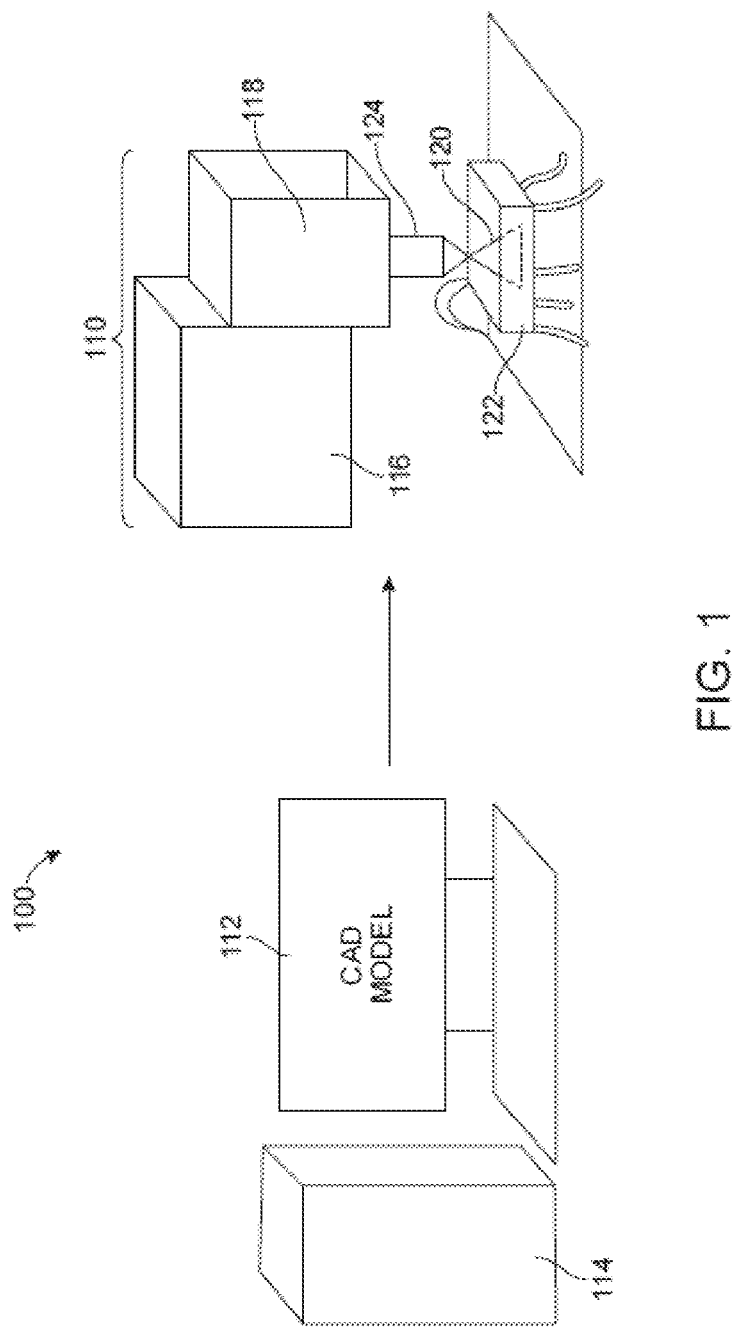
FIG. 1 illustrates an embodiment of a system for rapid multi-photon printing of a desired tissue is illustrated.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" refers to an amount that is near the stated amount by about 10%, 5%, or 1%, including increments therein. For example, "about" or "approximately" can mean a range including the particular value and ranging from 10% below that particular value and spanning to 10% above that particular value.

The term "biological material," as used herein, generally refers to any material that may serve a chemical or biological function. Biological material may be biologically functional tissue or functional tissue, which may be a biological structure that is capable of serving, or serving, a biomechanical or biological function. Biologically functional tissue may comprise cells that are within diffusion distance from each other, comprises at least one cell type wherein each cell is within diffusion distance of a capillary or vascular network component, facilitates and/or inhibits the fulfillment of protein function, or any combination thereof. Biologically functional tissue may be at least a portion of tissue or an organ, such as a vital organ. In some examples, the biological material may be used for drug development, such as, for example, screening multiple cells or tissue with different therapeutic agents.

Biological material may include a matrix, such as a polymeric matrix, including one or more other types of material, such as cells. Biological material may be in various shapes, sizes or configurations. In some instances, biological material may be consumable by a subject (e.g., an animal), such as meat or meat-like material.

The term "three-dimensional printing" (also "3D printing"), as used herein, generally refers to a process or method for generating a 3D part (or object). Such process may be used to form a 3D part (or object), such as a 3D biological material.

The term "energy beam," as used herein, generally refers to a beam of energy. The energy beam may be a beam of electromagnetic energy or electromagnetic radiation. The energy beam may be a particle beam. An energy beam may be a light beam (e.g., gamma waves, x-ray, ultraviolet, visible light, infrared light, microwaves, or radio waves). The light beam may be a coherent light beam, as may be provided by light amplification by stimulated emission of radiation ("laser"). In some examples, the light beam is generated by a laser diode or a multiple diode laser.

The term "energy source," as used herein, refers to a laser, such as a fiber laser, a short-pulsed laser, or a femto-second pulsed laser; a heat source, such as a thermal plate, a lamp, an oven, a heated water bath, a cell culture incubator, a heat chamber, a furnace, or a drying oven; a light source, such as white light, infrared light, ultraviolet (UV) light, near infrared (NIR) light, visible light, or a light emitting diode (LED); a sound energy source, such as an ultrasound probe, a sonicator, or an ultrasound bath; an electromagnetic radiation source, such as a microwave source; or any combination thereof.

The present disclosure provides methods and systems for printing a three-dimensional (3D) biological material. In an aspect, a method for printing the 3D biological material comprises providing a media chamber comprising a medium comprising (i) a plurality of cells and (ii) one or more polymer precursors. Next, at least one energy beam may be directed to the medium in the media chamber along at least one energy beam path that is patterned into a 3D projection in accordance with computer instructions for printing the 3D biological material in computer memory. This may form at least a portion of the 3D biological material comprising (i) at least a subset of the plurality of cells, which at least the subset of the plurality of cells comprises cells of at least two different types, and (ii) a polymer formed from the one or more polymer precursors.

Methods and systems of the present disclosure may be used to print multiple layers of a 3D object, such as a 3D biological material, at the same time. Such 3D object may be formed of a polymeric material, a metal, metal alloy, composite material, or any combination thereof. In some examples, the 3D object is formed of a polymeric material, in some cases including biological material (e.g., one or more cells or cellular components). In some cases, the 3D object may be formed by directing an energy beam (e.g., a laser) as a 3D projection (e.g., hologram) to one or more precursors of the polymeric material, to induce polymerization and/or cross-linking to form at least a portion of the 3D object. This may be used to form multiple layers of the 3D object at the same time.

As an alternative, the 3D object may be formed of a metal or metal alloy, such as, e.g., gold, silver, platinum, tungsten, titanium, or any combination thereof. In such a case, the 3D object may be formed by sintering or melting metal particles, as may be achieved, for example, by directing an energy beam (e.g., a laser beam) at a powder bed comprising particles of a metal or metal alloy. In some cases, the 3D object may be formed by directing such energy beam as a 3D projection (e.g., hologram) into the powder bed to facilitate sintering or melting of particles. This may be used to form multiple layers of the 3D object at the same time. The 3D object may be formed of an organic material such as graphene. The 3D object may be formed of an inorganic material such as silicone. In such cases, the 3D object may be formed by sintering or melting organic and/or inorganic particles, as may be achieved, for example, by directing an energy beam (e.g., a laser beam) at a powder bed comprising particles of an organic and/or inorganic material. In some cases, the 3D object may be formed by directing such energy beam as a 3D projection (e.g., hologram) into the powder bed to facilitate sintering or melting of organic and/or inorganic particles.

The depth of the energy beam penetration may be dictated by the interaction of the beam wavelength and the electron field of a given metal, metal alloy, inorganic material, and/or organic material. The organic material may be graphene. The inorganic material may be silicone. These particles may be functionalized or combined in to allow for greater interaction or less interaction with a given energy beam.

In some examples, the at least one energy beam is at least 1, 2, 3, 4, 5, 6, 7, 8, 9, 10, 20, 30, 40, 50, 100, or more energy beams. The at least one energy beam may be or include coherent light. In some cases, the at least one energy beam is a laser beam.

The at least one energy beam may be directed as an image or image set. The image may be fixed with time or changed with time. The at least one energy beam may be directed as a video.

The computer instructions may correspond to a computer model or representation of the 3D biological material. The computer instructions may be part of the computer model. The computer instructions may comprise a set of images corresponding to the 3D biological material.

The at least one energy beam may be directed as a holographic image or video. This may enable different points in the medium to be exposed to the at least one energy beam at the same time, to, for example, induce formation of a polymer matrix (e.g., by polymerization) at multiple layers at the same time. In some cases, a 3D image or video may be projected into the medium at different focal points using, e.g., a spatial light modulator (SLM).

The computer instructions may include and/or direct adjustment of one or more parameters of the at least one energy beam as a function of time during formation of the 3D biological material, such as, for example, application of power to a source of the at least one energy beam (e.g., laser on/off). Such adjustment may be made in accordance with an image or video (e.g., holographic image or video) corresponding to the 3D biological material. Alternatively or in addition to, the computer instructions may include and/or direct adjustment of a location of a stage upon which the 3D biological material is formed.

In some cases, during or subsequent to formation of the 3D biological material, at least a portion of the at least the subset of the plurality of cells may be subjected to differentiation to form the cells of the at least two different types. This may be employed, for example, by exposing the cells to an agent or subjecting the cells to a condition that induces differentiation. Alternatively or in addition to, the cells may be subjected to de-differentiation.

Another aspect of the present disclosure provides a method for printing a 3D biological material, providing a media chamber comprising a first medium. The first medium may comprise a first plurality of cells and a first polymeric precursor. At least one energy beam may be directed to the first medium in the media chamber along at least one energy beam path in accordance with computer instructions for printing the 3D biological material, to subject at least a portion of the first medium in the media chamber to form a first portion of the 3D biological material. Next, a second medium may be provided in the media chamber. The second medium may comprise a second plurality of cells and a second polymeric precursor. The second plurality of cells may be of a different type than the first plurality of cells. Next, at least one energy beam may be directed to the second medium in the media chamber along at least one energy beam path in accordance with the computer instructions, to subject at least a portion of the second medium in the media chamber to form at least a second portion of the 3D biological material.

In another aspect of the present disclosure, a system for printing a 3D biological material comprises a media chamber configured to contain a medium comprising a plurality of cells comprising cells of at least two different types and one or more polymer precursors; at least one energy source configured to direct at least one energy beam to the media chamber; and one or more computer processors operatively coupled to the at least one energy source, wherein the one or more computer processors are individually or collectively programmed to (i) receive computer instructions for printing the 3D biological material from computer memory; and (ii) direct the at least one energy source to direct the at least one energy beam to the medium in the media chamber along at least one energy beam path in accordance with the computer instructions, to subject at least a portion of the polymer precursors to form at least a portion of the 3D biological material.

In another aspect, a system for printing a 3D biological material, comprising: a media chamber configured to contain a medium comprising a plurality of cells and a plurality of polymer precursors; at least one energy source configured to direct at least one energy beam to the media chamber; and one or more computer processors operatively coupled to the at least one energy source, wherein the one or more computer processors are individually or collectively programmed to (i) receive computer instructions for printing the 3D biological material from computer memory; (ii) direct the at least one energy source to direct the at least one energy beam to the medium in the media chamber along at least one energy beam path in accordance with the computer instructions, to subject at least a portion of the polymer precursors to form at least a portion of the 3D biological material; and (iii) direct the at least one energy source to direct the at least one energy beam to a second medium in the media chamber along at least one energy beam path in accordance with the computer instructions, to subject at least a portion of the second medium in the media chamber to form at least a second portion of the 3D biological material, wherein the second medium comprises a second plurality of cells and a second polymeric precursor, wherein the second plurality of cells is of a different type than the first plurality of cells.

In another aspect of the present disclosure, methods for printing a three-dimensional (3D) object, may comprise directing at least one energy beam into a medium comprising one or more precursors, to generate the 3D object comprising a material formed from the one or more precursors, wherein the at least one energy beam is directed into the medium as a 3D projection corresponding to the 3D object.

In another aspect, methods for printing a three-dimensional (3D) biological material, may comprise directing at least one energy beam to: 1) a first medium comprising a first plurality of cells and a first polymeric precursor, and 2) a second medium comprising a second plurality of cells and a second polymeric precursor, to generate a first portion of the 3D biological material and a second portion of the 3D biological material.

Referring to FIG. 1, an embodiment of a system 100 for rapid multi-photon printing of a desired tissue is illustrated. Here, the system 100 comprises a laser printing system 110 driven by a solid-model computer-aided design (CAD) modeling system 112. In this embodiment, the CAD modeling system 112 comprises a computer 114 which controls the laser printing system 110 based on a CAD model of the desired tissue and additional parameters. The laser printing system 110 comprises a laser system 116 in communication with a multi-photon tissue printing print-head 118 which projects waveforms of a multi-photon laser beam 120 into a media chamber 122 to match the desired structure in complete or in specific parts. The multi-photon tissue print-head 118 includes at least one objective lens 124 that delivers the multi-photon laser beam 120 in the lateral and axial planes of the media chamber 122 to provide a two-dimensional and/or three dimensional and thus holographic projection of the CAD modeled tissue within the media chamber 122. The objective lens 124 may be a water-immersion objective lens, an air objective lens, or an oil-immersion objective lens. Two dimensional and three dimensional holographic projections may be generated simultaneously and projected into different regions by lens control. The media chamber 122 contains media comprised of cells, polymerizable material, and culture medium. The polymerizable material may comprise polymerizable monomeric units that are biologically compatible, dissolvable, and, in some cases, biologically inert. The monomeric units (or subunits) may polymerize, cross-link, or react in response to the multi-photon laser beam 120 to create cell containing structures, such as cell matrices and basement membrane structures, specific to the tissue to be generated. The monomeric units may polymerize and/or cross-link to form a matrix. In some cases, the polymerizable monomeric units may comprise mixtures of collagen with other extracellular matrix components including but not limited to elastin and hyaluronic acid to varying percentages depending on the desired tissue matrix.

Non-limiting examples of extracellular matrix components used to create cell containing structures may include proteoglycans such as heparan sulfate, chondroitin sulfate, and keratan sulfate, non-proteoglycan polysaccharide such as hyaluronic acid, collagen, and elastin, fibronectin, laminin, nidogen, or any combination thereof. These extracellular matrix components may be functionalized with acrylate, diacrylate, methacrylate, cinnamoyl, coumarin, thymine, or other side-group or chemically reactive moiety to facilitate cross-linking induced directly by multi-photon excitation or by multi-photon excitation of one or more chemical doping agents. In some cases, photopolymerizable macromers and/ or photopolymerizable monomers may be used in conjunction with the extracellular matrix components to create cell-containing structures. Non-limiting examples of photopolymerizable macromers may include polyethylene glycol (PEG) acrylate derivatives, PEG methacrylate derivatives, and polyvinyl alcohol (PVA) derivatives. In some instances, collagen used to create cell containing structure may be fibrillar collagen such as type I, II, III, V, and XI collagen, facit collagen such as type IX, XII, and XIV collagen, short chain collagen such as type VIII and X collagen, basement membrane collagen such as type IV collagen, type VI collagen, type VII collagen, type XIII collagen, or any combination thereof.

Specific mixtures of monomeric units can be created to alter the final properties of the polymerized biogel. This base print mixture may contain other polymerizable monomers that are synthesized and not native to mammalian tissues, comprising a hybrid of biologic and synthetic materials. An example mixture may comprise about 0.4% w/v collagen methacrylate plus the addition of about 50% w/v polyethylene glycol diacrylate (PEGDA). Photoinitiators to induce polymerization may be reactive in the ultraviolet (UV), infrared (IR), or visible light range. Examples of two such photo initiators are Eosin Y (EY) and triethanolamine (TEA), that when combined may polymerize in response to exposure to visible light (e.g., wavelengths of about 390 to 700 nanometers). Non-limiting examples of photoinitiators may include azobisisobutyronitrile (AIBN), benzoin derivatives, benziketals, hydroxyalkylphenones, acetophenone derivatives, trimethylolpropane triacrylate (TPT), acryloyl chloride, benzoyl peroxide, camphorquinone, benzophenone, thioxanthones, and 2-hydroxy-1-[4-(hydroxyethoxy) phenyl]-2-methyl-1-propanone. Hydroxyalkylphenones may include 4-(2-hydroxyethylethoxy)-phenyl-(2-hydroxy-2-methyl propyl) ketone (Irgacure® 295), 1-hydroxycyclohexyl-1-phenyl ketone (Irgacure® 184) and 2,2-dimethoxy-2-phenylacetophenone (Irgacure® 651). Acetophenone derivatives may include 2,2-dimethoxy-2-phenylacetophenone (DMPA). Thioxanthones may include isopropyl thioxanthone.

Specific mixtures of monomeric units of biological materials can be created to alter the final properties of the polymerized biogel, an example mixture may include about 1 mg/mL type I collagen-methacrylate, about 0.5 mg/mL type III collagen, about 0.2 mg/mL methacrylated hyaluronic acid, about 0.1% Eosin Y, and about 0.1% triethanolamine.

In some cases, the polymerized biogel may comprise at least about 0.01% of a photoinitiator. In some cases, the polymerized biogel may comprise about 10% of a photoinitiator or more. In some cases, the polymerized biogel comprises about 0.1% of a photoinitiator. In some cases, the polymerized biogel may comprise about 0.01% to about 0.05%, about 0.01% to about 0.1%, about 0.01% to about 0.2%, about 0.01% to about 0.3%, about 0.01% to about 0.4%, about 0.01% to about 0.5%, about 0.01% to about 0.6%, about 0.7% to about 0.8%, about 0.9% to about 1%, about 0.01% to about 2%, about 0.01% to about 3%, about 0.01%% to about 4%, about 0.01% to about 5%, about 0.01% to about 6%, about 0.01% to about 7%, about 0.01% to about 8%, about 0.01% to about 9%, or about 0.01% to about 10% of a photoinitiator.

The polymerized biogel may comprise about 0.05% of a photoinitiator. The polymerized biogel may comprise 0.1% of a photoinitiator. The polymerized biogel may comprise about 0.2% of a photoinitiator. The polymerized biogel may comprise about 0.3% of a photoinitiator. The polymerized biogel may comprise about 0.4% of a photoinitiator. The polymerized biogel may comprise about 0.5% of a photoinitiator. The polymerized biogel may comprise about 0.6% of a photoinitiator. The polymerized biogel may comprise about 0.7% of a photoinitiator. The polymerized biogel may comprise about 0.8% of a photoinitiator. The polymerized biogel may comprise about 0.9% of a photoinitiator. The polymerized biogel may comprise about 1% of a photoinitiator. The polymerized biogel may comprise about 1.1% of a photoinitiator. The polymerized biogel may comprise about 1.2% of a photoinitiator. The polymerized biogel may comprise about 1.3% of a photoinitiator. The polymerized biogel may comprise about 1.4% of a photoinitiator. The polymerized biogel may comprise about 1.5% of a photoinitiator. The polymerized biogel may comprise about 1.6% of a photoinitiator. The polymerized biogel may comprise about 1.7% of a photoinitiator. The polymerized biogel may comprise about 1.8% of a photoinitiator. The polymerized biogel may comprise about 1.9% of a photoinitiator. The polymerized biogel may comprise about 2% of a photoinitiator. The polymerized biogel may comprise about 2.5% of a photoinitiator. The polymerized biogel may comprise about 3% of a photoinitiator. The polymerized biogel may comprise about 3.5% of a photoinitiator. The polymerized biogel may comprise about 4% of a photoinitiator. The polymerized biogel may comprise about 4.5% of a photoinitiator. The polymerized biogel may comprise about 5% of a photoinitiator. The polymerized biogel may comprise about 5.5% of a photoinitiator. The polymerized biogel may comprise about 6% of a photoinitiator. The polymerized biogel may comprise about 6.5% of a photoinitiator. The polymerized biogel may comprise about 7% of a photoinitiator. The polymerized biogel may comprise about 7.5% of a photoinitiator. The polymerized biogel may comprise about 8% of a photoinitiator. The polymerized biogel may comprise about 8.5% of a photoinitiator. The polymerized biogel may comprise about 9% of a photoinitiator. The polymerized biogel may comprise about 9.5% of a photoinitiator. The polymerized biogel may comprise about 10% of a photoinitiator.

In some cases, the polymerized biogel may comprise at least about 10% of a photopolymerizable macromer and/or photopolymerizable monomer. In some cases, the polymerized biogel may comprise about 99% or more of a photopolymerizable macromer and/or photopolymerizable monomer. In some cases, the polymerized biogel may comprise about 50% of a photopolymerizable macromer and/or photopolymerizable monomer. In some cases, the polymerized biogel may comprise about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 10% to about 75%, about 10% to about 80%, about 10% to about 85%, about 10% to about 90%, about 10% to about 95%, or about 10% to about 99% of a photopolymerizable macromer and/or photopolymerizable monomer.

The polymerized biogel may comprise about 10% of a photopolymerizable macromer and/or photopolymerizable monomer. The polymerized biogel may comprise about 15% of a photopolymerizable macromer and/or photopolymerizable monomer. The polymerized biogel may comprise about 20% of a photopolymerizable macromer and/or photopolymerizable monomer. The polymerized biogel may comprise about 25% of a photopolymerizable macromer and/or photopolymerizable monomer. The polymerized biogel may comprise about 30% of a photopolymerizable macromer and/or photopolymerizable monomer. The polymerized biogel may comprise about 35% of a photopolymerizable macromer and/or photopolymerizable monomer. The polymerized biogel may comprise about 40% photopolymerizable macromer and/or photopolymerizable monomer. The polymerized biogel may comprise about 45% of a photopolymerizable macromer and/or photopolymerizable monomer. The polymerized biogel may comprise about 50% of a photopolymerizable macromer and/or photopolymerizable monomer. The polymerized biogel may comprise about 55% of a photopolymerizable macromer and/or photopolymerizable monomer. The polymerized biogel may comprise about 60% of a photopolymerizable macromer and/or photopolymerizable monomer. The polymerized biogel may comprise about 65% of a photopolymerizable macromer and/or photopolymerizable monomer. The polymerized biogel may comprise about 70% of a photopolymerizable macromer and/or photopolymerizable monomer. The polymerized biogel may comprise about 75% of a photopolymerizable macromer and/or photopolymerizable monomer. The polymerized biogel may comprise about 80% of a photopolymerizable macromer and/or photopolymerizable monomer. The polymerized biogel may comprise about 85% of a photopolymerizable macromer and/or photopolymerizable monomer. The polymerized biogel may comprise about 90% of a photopolymerizable macromer and/or photopolymerizable monomer. The polymerized biogel may comprise about 95% of a photopolymerizable macromer and/or photopolymerizable monomer. The polymerized biogel may comprise about 96% of a photopolymerizable macromer and/or photopolymerizable monomer. The polymerized biogel may comprise about 97% of a photopolymerizable macromer and/or photopolymerizable monomer. The polymerized biogel may comprise about 98% of a photopolymerizable macromer and/or photopolymerizable monomer. The polymerized biogel may comprise about 99% of a photopolymerizable macromer and/or photopolymerizable monomer.

Two-photon absorption is non-linear and cannot be accurately predicted or calculated based on single photon absorption properties of a chemical. A photo-reactive chemical may have a peak, two-photon absorption at or around double the single photon absorption or be slightly-redshifted in absorption spectra. Therefore, wavelengths at or about 900 nanometers through about 1400 nanometers may be used for polymerization of monomeric materials by exciting mixtures of catalysts of the polymerization reaction, for example EY or TEA. Single wavelength polymerization may be sufficient for creating all structural elements, however to further speed up the printing process, multiple wavelengths may be employed simultaneously through the same printing apparatus and into the same printing chamber.

Premixing or pre-reacting of polymerizable monomeric units with catalysts comprising differing absorption bands may allow for printing at different wavelengths to form different substrate-based structural elements simultaneously within the media chamber 122. Thus, certain structural elements may be generated by tuning the excitation wavelength of the laser to a particular wavelength, and then other structural elements may be generated around the existing elements by tuning another or the same laser to a different excitation wavelength that may interact with a distinct photoinitiator that initiates polymerization of one material base with greater efficiency. Likewise, different wavelengths may be used for different structural elements, wherein increased rigidity is desired in some locations and soft or elastic structures are desired in other locations. Because of the different physical properties of polymerizable materials this may allow for potentially more rigid, soft, or elastic structures to be created in the same print step with the same cells by simply tuning the excitation wavelength of the laser electronically, by switching between different lasers, or by simultaneously projecting two different wavelengths.

Figure 2A:
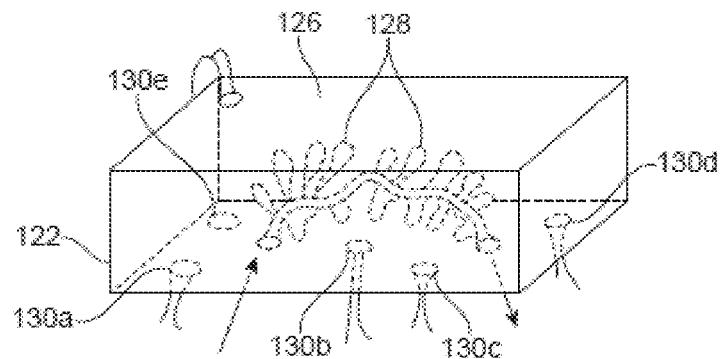
FIGS. 2A-2D illustrate example stages of the generation of a desired tissue within the media chamber.
Figure 2B:
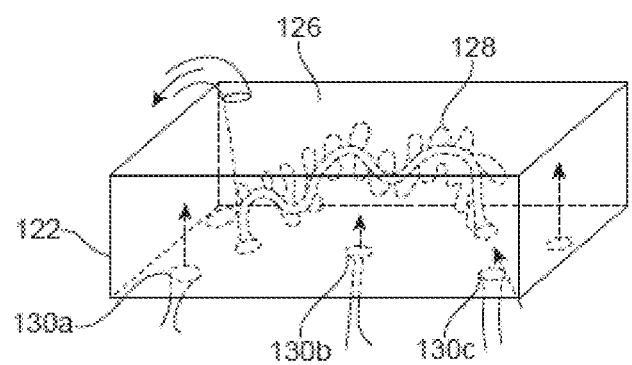
Figure 2C:
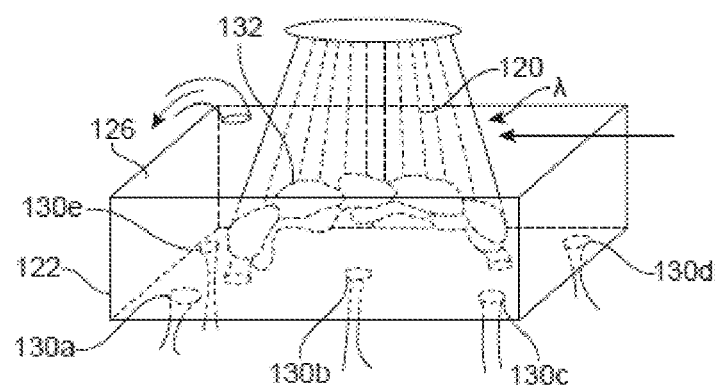

FIGS. 2A-2C illustrate example stages of the generation of a desired tissue within the media chamber 122. FIG. 2A illustrates the media chamber 122 containing media 126 comprised of a first cell group, polymerizable material and culture medium. In this embodiment, pulses of the multi-photon laser beam 120 may be delivered to the media 126 according to the CAD model corresponding to the vascular structure and microvasculature of the desired tissue. In some instances, the first cell group may comprise vascular and/or microvascular cells including but not limited to endothelial cells, microvascular endothelial cells, pericytes, smooth muscle cells, fibroblasts, endothelial progenitor cells, stem cells, or any combination thereof. Thus, portions of the media 126 may polymerize, cross-link or react to form cell-containing scaffolding 128 representing the vasculature and microvasculature of the desired tissue. In this embodiment, the media 126 may then be drained through a first port 130a, a second port 130b, a third port 130c, a fourth port 130d, and a fifth port 130e to remove the first cell group and associated media. In some instances, the media chamber 122 may comprise at least one port. In some instances, the media chamber 122 may comprise a plurality of ports ranging from at least one port to 100 ports at most. The media chamber 122 may comprise at least two ports. The media chamber 122 may comprise at least three ports. The media chamber 122 may comprise at least four ports. The media chamber 122 may comprise at least five ports.

Referring to FIG. 2B, the media chamber 122 may be filled with media 126 containing a second cell group, polymerizable material and culture medium through ports 130. This second cell group may be used to generate tissue structures around the existing cell-containing scaffolding 128. In some instances, the cell-containing scaffolding 128 may be a vascular scaffold. The printed vascular scaffolding may comprise endothelial cells, vascular endothelial cells, pericytes, smooth muscle cells, fibroblasts, endothelial progenitor cells, stem cells, or any combination thereof.

The first cell group and/or second cell group may comprise endothelial cells, microvascular endothelial cells, pericytes, smooth muscle cells, fibroblasts, endothelial progenitor cells, lymph cells, T cells such as helper T cells and cytotoxic T cells, B cells, natural killer (NK) cells, reticular cells, hepatocytes, or any combination thereof. The first cell group and/or second cell group may comprise exocrine secretory epithelial cells, hormone-secreting cells, epithelial cells, nerve cells, adipocytes, kidney cells, pancreatic cells, pulmonary cells, extracellular matrix cells, muscle cells, blood cells, immune cells, germ cells, interstitial cells, or any combination thereof.

The first cell group and/or second cell group may comprise exocrine secretory epithelial cells including but not limited to salivary gland mucous cells, mammary gland cells, sweat gland cells such as eccrine sweat gland cell and apocrine sweat gland cell, sebaceous gland cells, type II pneumocytes, or any combination thereof.

The first cell group and/or second cell group may comprise hormone-secreting cells including but not limited to anterior pituitary cells, intermediate pituitary cells, magnocellular neurosecretory cells, gut tract cells, respiratory tract cells, thyroid gland cells, parathyroid gland cells, adrenal gland cells, Leydig cells, theca interna cells, corpus luteum cells, juxtaglomerular cells, macula densa cells, peripolar cells, mesangial cells, pancreatic islet cells such as alpha cells, beta cells, delta cells, PP cells, and epsilon cells, or any combination thereof.

The first cell group and/or second cell group may comprise epithelial cells including but not limited to keratinizing epithelial cells such as keratinocytes, basal cells, and hair shaft cells, stratified barrier epithelial cells such as surface epithelial cells of stratified squamous epithelium, basal cells of epithelia, and urinary epithelium cells, or any combination thereof.

The first cell group and/or second cell group may comprise nerve cells or neurons including but not limited to sensory transducer cells, autonomic neuron cells, peripheral neuron supporting cells, central nervous system neurons such as interneurons, spindle neurons, pyramidal cells, stellate cells, astrocytes, oligodendrocytes, ependymal cells, glial cells, or any combination thereof.

The first cell group and/or second cell group may comprise kidney cells including but not limited to, parietal cells, podocytes, mesangial cells, distal tubule cells, proximal tubule cells, Loop of Henle thin segment cells, collecting duct cells, interstitial kidney cells, or any combination thereof.

The first cell group and/or second cell group may comprise pulmonary cells including, but not limited to type I pneumocyte, alveolar cells, capillary endothelial cells, alveolar macrophages, bronchial epithelial cells, bronchial smooth muscle cells, tracheal epithelial cells, small airway epithelial cells, or any combination thereof.

The first cell group and/or second cell group may comprise extracellular matrix cells including, but not limited to epithelial cells, fibroblasts, pericytes, chondrocytes, osteoblasts, osteocytes, osteoprogenitor cells, stellate cells, hepatic stellate cells, or any combination thereof.

The first cell group and/or second cell group may comprise muscle cells including, but not limited to skeletal muscle cells, cardiomyocytes, Purkinje fiber cells, smooth muscle cells, myoepithelial cells, or any combination thereof.

The first cell group and/or second cell group may comprise blood cells and/or immune cells including, but not limited to erythrocytes, megakaryocytes, monocytes, macrophages, osteoclasts, dendritic cells, microglial cells, neutrophils, eosinophils, basophils, mast cells, helper T cells, suppressor T cells, cytotoxic T cells, natural killer T cells, B cells, natural killer (NK) cells, reticulocytes, or any combination thereof.

FIG. 2C illustrates delivery of pulses of the multi-photon laser beam 120 to the media 126 according to the CAD model of the remaining tissue. Thus, additional portions of the media 126 may polymerize, cross-link or react to form cell-containing structures 132 around the existing cell-containing scaffolding 128 (no longer visible) without damaging or impacting the existing vascular scaffolding 128. The steps of draining the media 126, refilling with new media 126 and delivering laser energy may be repeated any number of times to create the desired complex tissue.

Figure 2D:
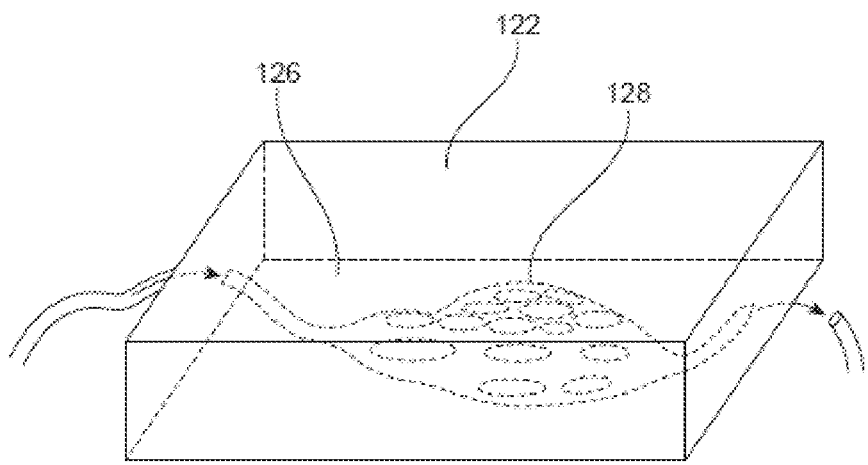

FIG. 2D illustrates an embodiment wherein the cell-containing scaffolding 128 may be printed along the bottom of the media chamber 122 containing media 126. Thus, the scaffolding 128 may not be free standing or free floating. The multi-channel input may reduce shear forces associated with bulk flow from one direction, uneven washing of fine structures as bulk flow may not wash unwanted cells from small features, and uneven distribution of new cell containing media as it is cycled into the tissue printing chamber. The multiple inputs may come from the top, bottom, sides or all three simultaneously. Multiple inputs are particularly desired for tissue printing because cell-containing structures are relatively fragile and potentially disrupted by the application of fluid forces associated with media exchange through the chamber. FIG. 2D shows that the tissues may be printed above the bottom plate of the media chamber. In some embodiments, the cells and tissue may be printed flush against the bottom of the media chamber. Additionally, this design may allow for easy transport of printed tissues and positioning under a laser print head (focusing objective) and is a closed system that may allow for media exchange and printing to occur without exposure to room air. This may be desired as exposure to room air can introduce infectious agents into the cell culture media which may disrupt or completely destroy the development of useful tissues.

Laser Printing Systems

In an aspect, the present disclosure provides systems for printing a three-dimensional (3D) biological material. The x, y, and z dimensions may be simultaneously accessed by the systems provided herein. A system for printing a 3D biological material may comprise a media chamber configured to contain a medium comprising a plurality of cells comprising cells and one or more polymer precursors. The plurality of cells may comprise cells of at least one type. The plurality of cells may comprise cells of at least two different types. The system may comprise at least one energy source configured to direct at least one energy beam to the media chamber. The system may comprise at least one energy source configured to direct at least one energy beam to the media chamber and/or to the cell-containing chamber. The system may comprise one or more computer processors operatively coupled to the at least one energy source, wherein the one or more computer processors may be individually or collectively programmed to: receive computer instructions for printing the 3D biological material from computer memory; and direct the at least one energy source to direct the at least one energy beam to the medium in the media chamber along at least one energy beam path in accordance with the computer instructions, to subject at least a portion of the polymer precursors to form at least a portion of the 3D biological material.

In another aspect, the present disclosure provides an additional system for printing a 3D biological material, comprising a media chamber configured to contain a medium comprising a plurality of cells and a plurality of polymer precursors. The system may comprise at least one energy source configured to direct at least one energy beam to the media chamber. In addition, the system may comprise one or more computer processors that may be operatively coupled to the at least one energy source. The one or more computer processors may be individually or collectively programmed to: (i) receive computer instructions for printing the 3D biological material from computer memory; (ii) direct the at least one energy source to direct the at least one energy beam to the medium in the media chamber along at least one energy beam path in accordance with the computer instructions, to subject at least a portion of the polymer precursors to form at least a portion of the 3D biological material; and (iii) direct the at least one energy source to direct the at least one energy beam to a second medium in the media chamber along at least one energy beam path in accordance with the computer instructions, to subject at least a portion of the second medium in the media chamber to form at least a second portion of the 3D biological material, wherein the second medium comprises a second plurality of cells and a second polymeric precursor, wherein the second plurality of cells is of a different type than the first plurality of cells.

The one or more computer processors are individually or collectively programmed to generate a point-cloud representation or lines-based representation of the 3D biological material in computer memory, and use the point-cloud representation or lines-based representation to generate the computer instructions for printing the 3D biological material in computer memory. The one or more computer processors may be individually or collectively programmed to direct the at least one energy source to direct the at least one energy beam along one or more additional energy beam paths to form at least another portion of the 3D biological material.

The system may comprise one or more computer processors operatively coupled to at least one energy source and/or to at least one light patterning element. The point-cloud representation or the lines-based representation of the computer model may be a holographic point-cloud representation or a holographic lines-based representation. The one or more computer processors may be individually or collectively programmed to use the light patterning element to re-project the holographic image as illuminated by the at least one energy source.

In some cases, one or more computer processors may be individually or collectively programmed to convert the point-cloud representation or lines-based representation into an image. The one or more computer processors may be individually or collectively programmed to project the image in a holographic manner. The one or more computer processors may be individually or collectively programmed to project the image as a hologram. The one or more computer processors may be individually or collectively programmed to project the image as partial hologram. In some cases, one or more computer processors may be individually or collectively programmed to convert the point-cloud representation or lines-based representation of a complete image set into a series of holographic images via an algorithmic transformation. This transformed image set may then be projected in sequence by a light patterning element, such as a spatial light modulator (SLM) or digital mirror device (DMD), through the system, recreating the projected image within the printing chamber with the projected light that is distributed in 2D and or 3D simultaneously. An expanded or widened laser beam may be projected onto the SLMs and/or DMDs, which serve as projection systems for the holographic image. In some cases, one or more computer processors may be individually or collectively programmed to project the image in a holographic manner. In some cases, one or more computer processors may be individually or collectively programmed to project the images all at once or played in series as a video to form a larger 3D structure in a holographic manner.

Holography is a technique that projects a multi-dimensional (e.g. 2D and/or 3D) holographic image or a hologram. When a laser that can photo-polymerize a medium is projected as a hologram, the laser may photopolymerize, solidify, cross-link, bond, harden, and/or change a physical property of the medium along the projected laser light path; thus, the laser may allow for the printing of 3D structures. Holography may require a light source, such as a laser light or coherent light source, to create the holographic image. The holographic image may be constant over time or varied with time (e.g., a holographic video). Furthermore, holography may require a shutter to open or move the laser light path, a beam splitter to split the laser light into separate paths, mirrors to direct the laser light paths, a diverging lens to expand the beam, and additional patterning or light directing elements.

A holographic image of an object may be created by expanding the laser beam with a diverging lens and directing the expanded laser beam onto the hologram and/or onto at least one pattern forming element, such as, for example a spatial light modulator or SLM. The pattern forming element may encode a pattern comprising the holographic image into a laser beam path. The pattern forming element may encode a pattern comprising a partial hologram into a laser beam path. Next, the pattern may be directed towards and focused in the medium chamber containing the printing materials (i.e., the medium comprising the plurality of cells and polymeric precursors), where it may excite a light-reactive photoinitiator found in the printing materials (i.e., in the medium). Next, the excitation of the light-reactive photoinitiator may lead to the photopolymerization of the polymeric-based printing materials and forms a structure in the desired pattern (i.e., holographic image). In some cases, one or more computer processors may be individually or collectively programmed to project the holographic image by directing an energy source along distinct energy beam paths.

In some cases, at least one energy source may be a plurality of energy sources. The plurality of energy sources may direct a plurality of the at least one energy beam. The energy source may be a laser. In some examples, the laser may be a fiber laser. For example, a fiber laser may be a laser with an active gain medium that includes an optical fiber doped with rare-earth elements, such as, for example, erbium, ytterbium, neodymium, dysprosium, praseodymium, thulium and/or holmium. The energy source may be a short-pulsed laser. The energy source may be a femtosecond pulsed laser. The femtosecond pulsed laser may have a pulse width less than or equal to about 500 femtoseconds (fs), 250, 240, 230, 220, 210, 200, 150, 100, 50 fs, 40 fs, 30 fs, 20 fs, 10 fs, 9 fs, 8 fs, 7 fs, 6 fs, 5 fs, 4 fs, 3 fs, 2 fs, 1 fs, or less. The femtosecond pulsed laser may be, for example, a titanium:sapphire (Ti:Sa) laser. The at least one energy source may be derived from a coherent light source.

The coherent light source may provide light with a wavelength from about 300 nanometers (nm) to about 5 millimeters (mm). The coherent light source may comprise a wavelength from about 350 nm to about 1800 nm, or about 1800 nm to about 5 mm. The coherent light source may provide light with a wavelength of at least about 300 nm, 400 nm, 500 nm, 600 nm, 700 nm, 800 nm, 900 nm, 1 mm, 1.1 mm, 1.2, mm, 1.3 mm, 1.4 mm, 1.5 mm, 1.6 mm, 1.7 mm, 1.8 mm, 1.9 mm, 2 mm, 3 mm, 4 mm, 5 mm, or greater.

The computer processors may be individually or collectively programmed to direct the at least one energy source to direct the at least one energy beam along one or more additional energy beam paths to form at least another portion of the 3D biological material. The one or more additional energy beam paths may be along an x axis, an x and y plane, or the x, y, and z planes. The one or more additional energy beam paths may be along an x axis. The one or more additional energy beam paths may be along a y axis. The one or more additional energy beam paths may be along a z axis. The energy beam path may converge with one or more other beams on the same axis. The one or more additional energy beam paths may be in the x and y plane. The one or more additional energy beam paths may be in the x and z plane. The one or more additional energy beam paths may be in the y and z plane. The one or more additional energy beam paths may be in the x, y, and z planes.

The system may further comprise at least one objective lens for directing the at least one energy beam to the medium in the media chamber. In some instances, at least one objective lens may comprise a water-immersion objective lens. In some instances, at least one objective lens may comprise a water-immersion objective lens. In some instances, at least one objective lens may comprise a water dipping objective lens. In some instances, at least one objective lens may comprise an oil immersion objective lens. In some instances, at least one objective lens may comprise an achromatic objective lens, a semi-apochromatic objective lens, a plans objective lens, an immersion objective lens, a Huygens objective lens, a Ramsden objective lens, a periplan objective lens, a compensation objective lens, a wide-field objective lens, a super-field objective lens, a condenser objective lens, or any combination thereof. Non-limiting examples of a condenser objective lens may include an Abbe condenser, an achromatic condenser, and a universal condenser.

The one or more computer processors may be individually or collectively programmed to receive images of the edges of the 3D biological material. The one or more computer processors may be individually or collectively programmed to receive images of the exterior surfaces of the 3D biological material. The one or more computer processors may be individually or collectively programmed to receive images of the interior surfaces of the 3D biological material. The one or more computer processors may be individually or collectively programmed to receive images of the interior of the 3D biological material.

The one or more computer processors may be individually or collectively programmed to direct linking of the 3D biological material with other tissue, which linking may be in accordance with the computer instructions. The one or more computer processors may be individually or collectively programmed to directly link, merge, bond, or weld 3D printed material with already printed structures, where linking is in accordance with the computer model. In some cases, linking of the 3D biological material with other tissue may involve chemical cross-linking, mechanical linking, and/or cohesively coupling.

In another aspect, the system may comprise a media chamber configured to contain a medium comprising a plurality of cells and a plurality of polymer precursors. The system may comprise at least one energy source configured to direct at least one energy beam to the media chamber. The system may comprise one or more computer processors operatively coupled to at least one energy source, wherein the one or more computer processors are individually or collectively programmed to: receive a computer model of the 3D biological material in computer memory; generate a point-cloud representation or lines-based representation of the computer model of the 3D biological material in computer memory; direct the at least one energy source to direct the at least one energy beam to the medium in the media chamber along at least one energy beam path in accordance with the computer model of the 3D biological material, to subject at least a portion of the polymer precursors to form at least a portion of the 3D biological material; and direct the at least one energy source to direct the at least one energy beam to a second medium in the media chamber along at least one energy beam path in accordance with the computer model of the 3D biological material, to subject at least a portion of the second medium in the media chamber to form at least a second portion of the 3D biological material, wherein the second medium comprises a second plurality of cells and a second polymeric precursor, wherein the second plurality of cells is of a different type than the first plurality of cells.

In laser printing of cellular structures, rapid three-dimensional structure generation using minimally toxic laser excitation is critical for maintaining cell viability and in the case of functional tissue printing, necessary for large-format, high resolution, multicellular tissue generation. Other methods of two-photon printing may rely upon raster-scanning of two-photon excitation in a two-dimensional plane (x, y) (e.g., selective laser sintering), while moving the microscope or stage in the z direction to create a three-dimensional structure. This technique may be prohibitively slow for large format multicellular tissue printing such that cell viability may be unlikely to be maintained during printing of complex structures. Certain hydrogels with high rates of polymerization may also be utilized for two-dimensional projection of tissue sheets that are timed such that one slice of a structure is projected with each step in in an x, y, or z plane. Additionally, mixed plane angles representing a sheet or comprising an orthogonal slice may also be utilized. In the case of rapidly polymerizing hydrogels, these projections may work in time-scales that are compatible with tissue printing whereas laser sintering or raster scanning (e.g. layer-by-layer deposition) may be prohibitively slow for building a complex structure.

The laser printing system 110 of the present disclosure may be equipped with an objective lens 124 that may allow for focusing of the three-dimensional or two-dimensional holographic projection in the lateral and axial planes for rapid creation of cell containing structures. The objective lens 124 may be a water-immersion objective lens, an air objective lens, or an oil-immersion objective lens. In some cases, the laser printing system 110 may include a laser system 116 having multiple laser lines and may be capable of three-dimensional holographic projection of images for photolithography via holographic projection into cell containing media.

Figure 3A:
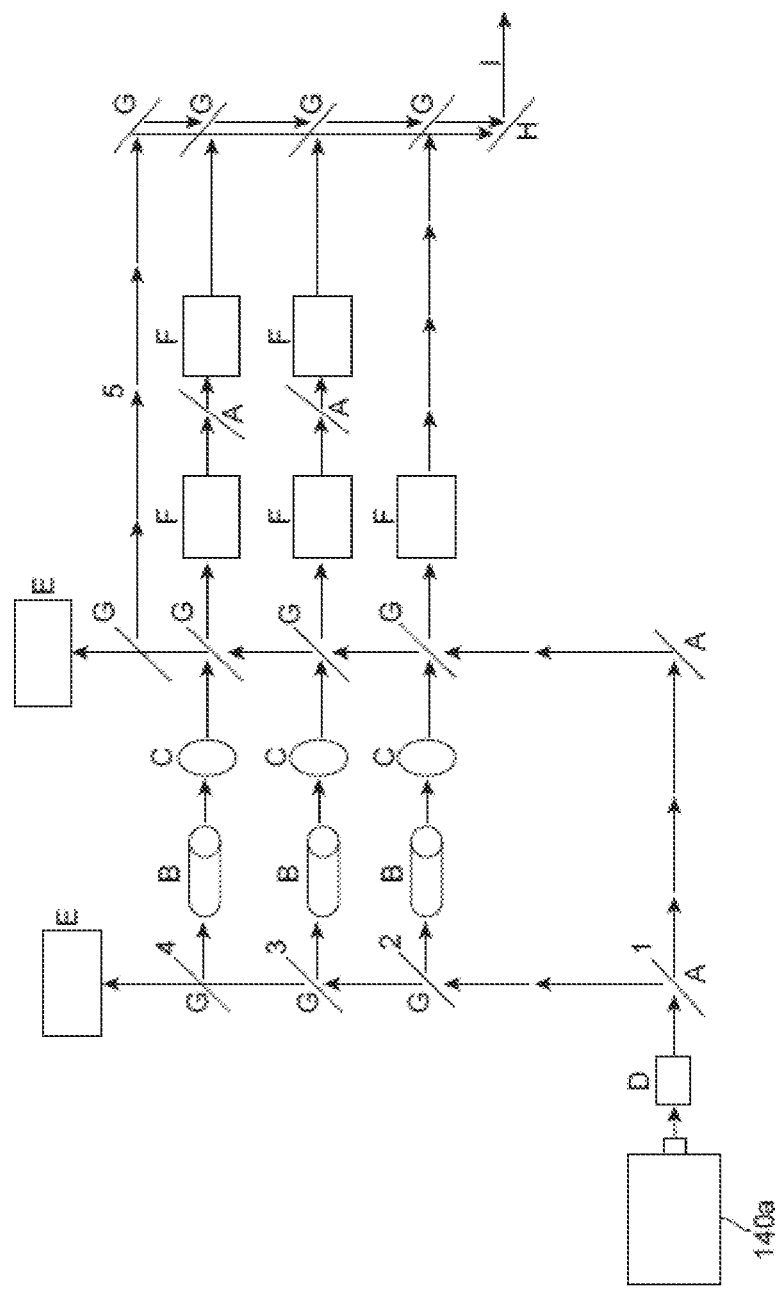
FIGS. 3A-3C illustrate various embodiments of a laser system.

FIG. 3A illustrates an embodiment of a laser system 116 having a first multi-photon laser source 140a. Here, the laser line one, multi-photon laser beam may be reflected by a spatial light modulator (SLM) with a video rate or faster re-fresh rate for image projection, to allow for rapid changes in the three-dimensional structure being projected.

In some cases, spatial light modulators (SLMs) may be used to print a 3D biological material. In some cases, the method presented herein may comprise receiving a computer model of the 3D biological material in computer memory and further processing the computer model such that the computer model is "sliced" into layers, creating a two-dimensional (2D) image of each layer. The computer model may be a computer-aided design (CAD) model. The system disclosed herein may comprise at least one computer processor which may be individually or collectively programmed to calculate a laser scan path based on the "sliced" computer model, which determines the boundary contours and/or fill sequences of the 3D biological material to be printed. Holographic 3D printing may be used with one or more polymer precursors described herein. SLM may be used with two or more polymer precursors described herein.

A spatial light modulator (SLM) is an electrically programmable device that can modulate amplitude, phase, polarization, propagation direction, intensity or any combination thereof of light waves in space and time according to a fixed spatial (i.e., pixel) pattern. The SLM may be based on translucent, e.g. liquid crystal display (LCD) microdisplays. The SLM may be based on reflective, e.g. liquid crystal on silicon (LCOS) microdisplays. The SLM may be a microchannel spatial light modulator (MSLM), a parallel-aligned nematic liquid crystal spatial light modulator (PAL-SLM), a programmable phase modulator (PPM), a phase spatial light modulator (LCOS-SLM), or any combination thereof. An LCOS-SLM may comprise a chip that includes a liquid crystal layer arranged on top of a silicon substrate. A circuit may be built on the chip's silicon substrate by using semiconductor technology. A top layer of the LCOS-SLM chip may contain aluminum electrodes that are able to control their voltage potential independently. A glass substrate may be placed on the silicon substrate while keeping a constant gap, which is filled by the liquid crystal material. The liquid crystal molecules may be aligned in parallel by the alignment control technology provided in the silicon and glass substrates. The electric field across this liquid crystal layer can be controlled pixel by pixel. The phase of light can be modulated by controlling the electric field; a change in the electric field may cause the liquid crystal molecules to tilt accordingly. When the liquid crystal molecules tilt, the liquid crystal refractive indexes may change further changing the optical path length and thus, causing a phase difference.

An SLM may be used to print the 3D biological material. A liquid crystal on silicon (LCOS)-SLM may be used to print the 3D biological material. A liquid crystal SLM may be used to print the 3D biological material. The SLM may be used to project a point-cloud representation or a lines-based representation of a computer model of the 3D biological material. The methods disclosed herein may comprise converting the point-cloud representation or lines-based representation into a holographic image. The SLM may be used to project the holographic image of the computer model of the 3D biological material. The SLM may be used to modulate the phase of light of a point-cloud representation or a lines-based representation of a computer model of the 3D biological material. The SLM may be used to modulate the phase of light of the holographic image of the computer model of the 3D biological material.

Projection of multi-photon excitation in three dimensions can also be achieved with the use of a dual digital micromirror device (DMD) system alone or in combination with a spatial light modulator (SLM). A pair of DMDs may be used with a pair of SLMs to print a 3D material using the methods described herein. At least one SLM and at least one DMD may be used to print a 3D material using the methods described herein. A pair of SLMs may be used to print a 3D material using the methods described herein. A pair of DMDs may be used to print a 3D material using the methods described herein. At least one SLM may be used to print a 3D material using the methods described herein. At least one DMD may be used to print a 3D material using the methods described herein. A DMD is an electrical input, optical output micro-electrical-mechanical system (MEMS) that allows for high speed, efficient, and reliable spatial light modulation. A DMD may comprise a plurality of microscopic mirrors (usually in the order of hundreds of thousands or millions) arranged in a rectangular array. Each microscopic mirror in a DMD may correspond to a pixel of the image to be displayed and can be rotated about e.g. 10-12° to an "on" or "off" state. In the "on" state, light from a projector bulb can be reflected into the microscopic mirror making its corresponding pixel appear bright on a screen. In the "off" state, the light can be directed elsewhere (usually onto a heatsink), making the microscopic mirror's corresponding pixel appear dark. The microscopic mirrors in a DMD may be composed of highly reflective aluminum and their length across is approximately 16 micrometers (μm). Each microscopic mirror may be built on top of an associated semiconductor memory cell and mounted onto a yoke which in turn is connected to a pair of support posts via torsion hinges. The degree of motion of each microscopic mirror may be controlled by loading each underlying semiconductor memory cell with a "1" or a "0." Next, a voltage is applied, which may cause each microscopic mirror to be electrostatically deflected about the torsion hinge to the associated+/−degree state via electrostatic attraction.

Figure 3B:
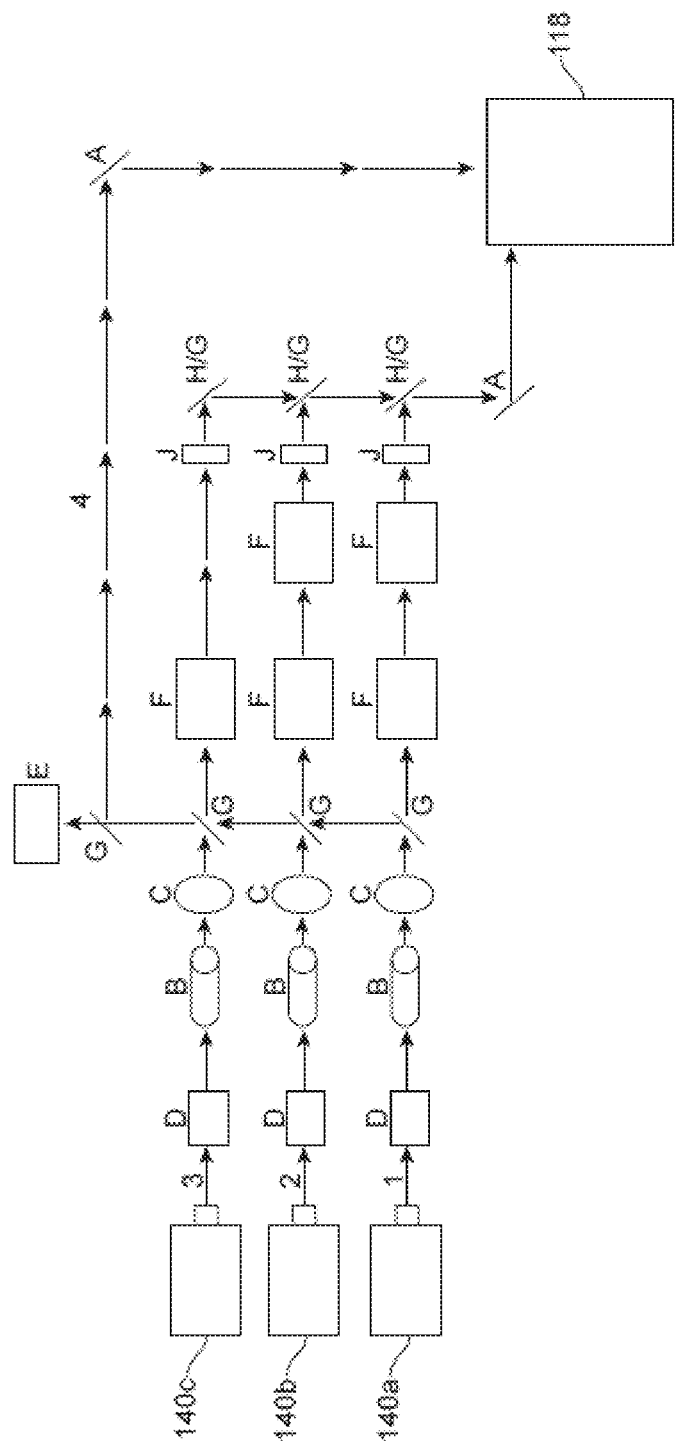
Figure 3C:
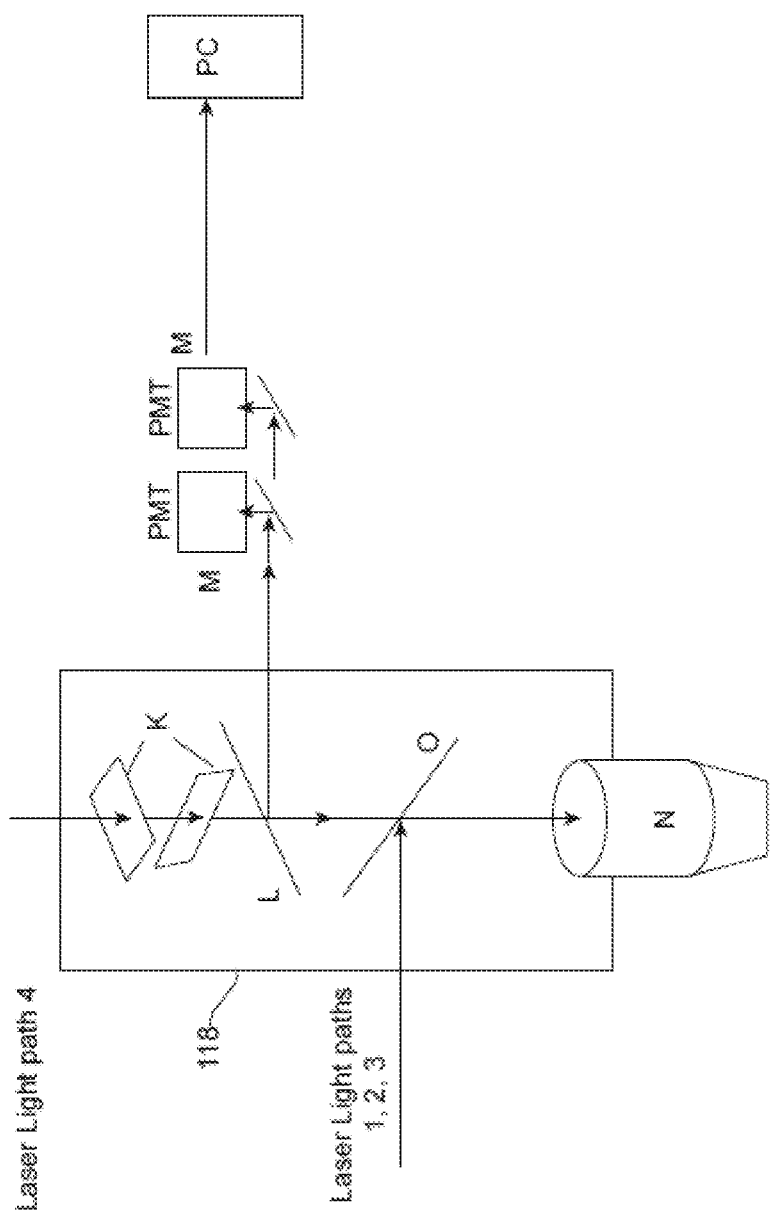

With reference to FIGS. 3A-3C, the addition of an optional beam expander followed by a Bessel beam generating lens that is either a fixed axicon or a tunable acoustic gradient (TAG) lens may be added to alter the properties of the laser to achieve higher resolution and greater tissue printing depth, particularly in turbid solutions. The laser line, which may include the optional beam expander and/or Bessel beam generating lens, is directed with fast switch mirrors to distinct projection systems that have material advantages in the formation of specific structures associated with tissue printing. In some cases, a high resolution DMD mirror in conjunction with an SLM system may achieve higher axial resolution than is capable with two SLM systems. Finally, a laser line may be used with a single DMD or SLM system in conjunction with a mirror to allow for scan-less projection of a two-dimensional image in any of the axial planes. A 3D projection pattern may also be raster-scanned across a larger field of view by scan mirrors where in laser emission patterns, wavelength, and or power is controlled to match the raster scan speed such that a cohesive and complex structure may be deposited. Within the system containing more than one laser line the configurations may be any combination of dual SLM, dual DMD, single SLM, single DMD or simple planar scanning.

In some cases, one or more light paths, such as the ones shown in FIGS. 3A-3C, may be used independently or in concert. The lenses, gratings, and mirrors that focus and distribute the light or energy beam within the optical path may be placed between the primary, wave-front shaping elements necessary to distribute the light through key elements or modulate incoming light in the case of a grating, as described in FIG. 3A. At least one grating or mirror may be placed between wave-front shaping elements "F" (i.e., between an SLM, a DMD, and/or a TAG lens) for the purpose of focusing, distributing, or clipping the input laser light. The optical wave-front shaping device F may comprise an SLM, an LCOS-SLM, a DMD, a TAG lens, or any combination thereof.

In some cases, a DMD may be used to print a 3D biological material. The DMD may be used to project a point-cloud representation or a lines-based representation of a computer model of the 3D biological material. The methods disclosed herein may comprise converting the point-cloud representation or lines-based representation into a holographic image. The DMD may be used to project the holographic image of the computer model of the 3D biological material. The DMD may be used to print the 3D biological material.

In some cases, a combination of at least one SLM and at least one DMD may be used in the methods disclosed herein to print the 3D biological material. The combination of at least one SLM and at least one DMD may be arranged in series. The combination of at least one SLM and at least one DMD may be arranged in parallel. The combination of any number of SLMs and any number of DMDs may be arranged in series when used to print the 3D biological material. The combination of any number of SLMs and any number of DMDs may be arranged in parallel when used to print the 3D biological material.

The combination of at least two SLMs and at least one DMD may be used to print the 3D biological material. The combination of at least three SLMs and at least one DMD may be used to print the 3D biological material. The combination of at least four SLMs and at least one DMD may be used to print the 3D biological material. The combination of at least five SLMs and at least one DMD may be used to print the 3D biological material. The combination of at least ten SLMs and at least one DMD may be used to print the 3D biological material. The combination of at least twenty SLMs and at least one DMD may be used to print the 3D biological material.

The combination of at least one SLM and at least two DMDs may be used to print the 3D biological material. The combination of at least one SLM and at least three DMDs may be used to print the 3D biological material. The combination of at least one SLM and at least four DMDs may be used to print the 3D biological material. The combination of at least one SLM and at least five DMDs may be used to print the 3D biological material. The combination of at least one SLM and at least ten DMDs may be used to print the 3D biological material. The combination of at least one SLM and at least twenty DMDs may be used to print the 3D biological material.

The combination of at least two SLMs and at least two DMDs may be used to print the 3D biological material. The combination of at least three SLMs and at least three DMDs may be used to print the 3D biological material. The combination of at least four SLMs and at least four DMDs may be used to print the 3D biological material. The combination of at least five SLMs and at least five DMDs may be used to print the 3D biological material. The combination of at least ten SLMs and at least ten DMDs may be used to print the 3D biological material. The combination of at least twenty SLMs and at least twenty DMDs may be used to print the 3D biological material.

A liquid crystal SLM may be used to print the 3D biological material. A plurality of SLMs may be used to print the 3D biological material. The plurality of SLMs can be arranged in series. The plurality of SLMs can be arranged in parallel. At least one or more SLMs may be used to print the 3D biological material. At least two or more SLMs may be used to print the 3D biological material. At least three or more SLMs may be used to print the 3D biological material. At least four or more SLMs may be used to print the 3D biological material. At least five or more SLMs may be used to print the 3D biological material. At least ten or more SLMs may be used to print the 3D biological material. At least twenty or more SLMs may be used to print the 3D biological material. At least one to about fifty or more SLMs may be used to print the 3D biological material. At least one to about twenty or more SLMs may be used to print the 3D biological material. At least one to about fifteen or more SLMs may be used to print the 3D biological material. At least one to about ten or more SLMs may be used to print the 3D biological material. At least one to about five or more SLMs may be used to print the 3D biological material.

A plurality of DMDs may be used to print the 3D biological material. The plurality of DMDs can be arranged in series. The plurality of DMDs can be arranged in parallel. At least one or more DMDs may be used to print the 3D biological material. At least two or more DMDs may be used to print the 3D biological material. At least three or more DMDs may be used to print the 3D biological material. At least four or more DMDs may be used to print the 3D biological material. At least five or more DMDs may be used to print the 3D biological material. At least ten or more DMDs may be used to print the 3D biological material. At least twenty or more DMDs may be used to print the 3D biological material. At least one to about fifty or more DMDs may be used to print the 3D biological material. At least one to about twenty or more DMDs may be used to print the 3D biological material. At least one to about fifteen or more DMDs may be used to print the 3D biological material. At least one to about ten or more DMDs may be used to print the 3D biological material. At least one to about five or more DMDs may be used to print the 3D biological material.

In this design, SLM may refer to liquid crystal SLM and the function of the DMD may be similar to the SLM. These lasers may be controlled by one or more computer inputs to address location and print timing of multiple laser lines. An example overall design for the light path, including optional in-series excitations paths is illustrated in FIG. 3A along with further description of the elements provided in Table 1. Because of the extensive pulse-width between packets of two photon excitation light, any combination of these laser lines, which may be non-interfering, may be used simultaneously for printing and printing with simultaneous imaging. This may permit the interference between the beams to be substantially low such that the beams to not intersect. Therefore, the use of multiple laser lines with minimal to no interference is possible as illustrated in FIGS. 3B-3C along with further description of the elements also provided in Table 1. The group delay dispersion optical element in this configuration may be used to disperse two-photon packets such that the peak power output does not damage a fiber optic cable if one is to be used in certain configurations. In addition, group delay dispersion can concentrate photons into shorter pulse-widths such that more energy is imparted at the focal point or in the projected image allowing for more rapid printing.

Two photon excitation pulses may be temporally controlled such that excitation at a single spot occurs with pulses that are femto- to nanosecond range in length (dependent on laser tuning) while the timing between these photon packets is three to six orders of magnitude longer than the pulse width. This may allow for minimal cross-path interference of laser excitations making use of multiple lasers for simultaneous printing possible when using multiple laser lines in series. An example of multiple laser projections at three different theoretical wavelengths for the purpose of structure deposition is presented in FIG. 3B. Multi-photon lasers are tunable; thus, they may allow for a range of wavelengths to be selected. This is advantageous in tissue printing wherein different photoinitiators for polymerization that respond to different wavelengths may be used in combination or in series to prevent unwanted polymerization of left-over materials. Therefore, each of these laser lines may be tuned to a different multi-photon output wavelength, may have different peak power output, and may project a different element of the CAD image that comprises the tissue structure.

TABLE 1

Element descriptions for FIGs. 3A-3C

| Element Label | Description |
|---|---|
| 140a-c | Laser source. A first laser source 140a, a second laser source 140b, and a third laser source 140c may be a tunable multi-photon (femto-second pulsed) laser of a given power (e.g. between 1 and 50 watts and 640 to 1500 nm wavelength output). Femto-second laser sources may be tunable by computer software interaction and thus may be set to various wavelengths before or during the printing process to produce different excitation wavelengths. Optionally, the systems disclosed herein may have a pump laser system. |
| A | Mirror. A mirror with or without an infrared (IR) specific coating to improve reflectance. IR specific coating examples may include protected gold or protected silver based coatings. As shown in FIG. 3A, grating and/or mirrors may be added between elements "F" (i.e., between DMDs, SLMs, or TAG lenses). |
| B | Beam expander. An optional beam expander to expand the area of the laser pulse prior to projection by the DMD or SLM systems. |
| C | Axicon or TAG lens. In some tissue printing applications, the use of a Bessel beam may allow for improved or even power output at greater depths in hydrogels, media, or already printed structures. To produce a Bessel beam, an axicon which produces a fixed Bessel beam or tunable acoustic gradient lens (TAG), may produce a Bessel beam that is tunable and can be altered by altering an electric signal input. In the instance that a TAG lens is used, the input signal may be controlled by integrated computer software. |
| D | Dispersion compensation unit. The purpose of the dispersion compensation unit in this design is to concentrate emitted two-photon packets such that the peak power output is higher at the excitation point. This allows for improved polymerization as a result of improved peak power output at a specific wavelength. |
| E | Beam Dump. Beam dump allows for collection of stray laser light. |
| F | DMD, SLM, or TAG lens. In this example design, a DMD or SLM may be used to create an x, y plane of projection with a specific pattern of light that may be used to polymerize the monomers into structures or nets that contain cells. The addition of the second DMD or SLM may allow for projection of the x, y plane in the z or axial direction for three-dimensional holographic projection of the multiphoton excitation into the print vessel. This may allow for polymerization of the structures in three dimensions wherein all x, y, and z dimension features are deposited at the same time. Each DMD or SLM may be controlled by computer input and may be directed to project a specific CAD image or portion of a CAD image. Having the SLM or DMDs in series may allow for images to be projected simultaneously in different wavelengths of light in the case of multiple laser excitation sources (such as illustrated in FIG. 3B) or in the case of multiple repeating pattern projection SLMs or DMDs can be used to project different aspects of the same tissue without needing to switch the computer input, instead mirrors can be used to re-direct or turn 'off' or 'on' a particular light path and produce a given fixed structure associated with laser light paths 1, 2, 3, or 4. In cases where the Bessel beam is removed (element C), this may allow for different axial accuracies in printing a particular given structure. Therefore, certain elements of tissue structure may be better printed by different light paths. Rapid switching between laser light paths can allow for printing and polymerization to continue while an SLM or DMD series is re-programed for projection of the next tissue structure in a given series of printing steps. In some cases, element "F" can represent a TAG lens. The TAG lens as used as element "F" can manipulate light. The TAG lens as used as element "F" can holographically distribute light. |
| G | Movable mirror. A mirror with or without an IR specific coating to improve reflectance. IR specific coating examples may include protected gold or protected silver based coatings. These mirrors can be moveable and can be adjusted to be in an 'on' or 'off' state to redirect the laser light path through the printing system as desired. Control of mirror positioning may be dictated by computer software. |
| H | Beam combiner. Beam combiner allowing for multiple light paths to be recombined for simultaneous printing at different wavelengths. In FIG. 3B these may also be movable mirrors (G) that can allow for the same wavelengths to be printed with timed on/off states of the mirrors G. |
| I | Light path to the optics housing. |
| J | Band pass filter. The purpose of an optional band-pass filter may be to select a specific wavelength to be used in materials polymerization. Multi-photon excitation may have an emission spread that can span several tens of nanometers potentially leading to overlap in absorption and thus polymerization of materials with otherwise distinct absorption peaks. By selecting for specific wavelengths using a band pass filter the wavelength leading to polymerization may be fine-tuned to prevent undesirable cross-over effects when two different monomers with different responsiveness used in the same formulation. |
| K | Scan head. Two mirrors that represent optional laser light scanning or sintering in the x, y plane. These mirrors may vibrate at a given frequency, for example 20 kHz, one in the x-direction reflecting to the next mirror which may scan in the y direction. This scanning may create a plane of light that can be used to image tissues or polymerized units before, after, and during the polymerization process. This is possible as collagen and many other ordered structures can emit light via a non-linear process call second harmonic generation when polymerized but not when in a monomeric state. Therefore, using an additional excitation source tuned to a wavelength that may allow for second harmonic generation and imaging while not polymerizing the biomaterials can be useful for monitoring the printing process. |

TABLE 1-continued

Element descriptions for FIGs. 3A-3C

| Element Label | Description |
| --- | --- |
| L | Long pass Mirror: A long pass mirror may allow multi-photon excitation from light path number 4 to pass through while reflecting any emission from a sample while in imaging mode (requires engagement of laser light path 4) to the series of photomultiplier tubes (PMT) M detectors and long pass or band pass mirrors of various wavelengths that may allow for specific emission wavelengths to be reflected into the PMTs for image collection via personal computer (PC) (i.e., computer processor) and appropriate imaging processing software. |
| M | Photo multiplier tubes. PMTs may be used in collection of images in microscopy. |
| N | Objective. This objective may serve the purpose of concentrating the multiphoton excitation such that polymerization of monomers to match the projected image may take place. |
| O | Movable long pass mirror. In instances where imaging may be performed with light path #4 the mirror O may be moved via software control to allow for laser light path 4 to enter the objective (N). In some incarnations light path 4 may be tuned to a distinct wavelength from laser light paths 1, 2, or 3 allowing for a long or short pass mirror or beam combiner to be used in place of 0. |
| 1 | Laser light path 1 may be used to by-pass the beam expansion or beam expansion plus Bessel beam lens combination in favor of direct transmittance into the SLM/DMD series or individual SLM or DMD. Laser line one may also be redirected into laser line 5 which creates a single two photon pinpoint excitation, which may be used in optics housing alignment or raster scanning of a sample for imaging purposes. |
| 2 & 5 | Laser light path 2 may be transmitted through an optional beam expander and optional Bessel beam creating lens (axicon or TAG lens) then a single SLM or DMD and may also be re-directed to laser light path 5. |
| 3 & 4 | Laser light paths 3 and 4 may be passed through an optional beam expander and optional Bessel beam creating lens (axicon or TAG lens) followed by a combination of SLM or DMDs in series. Two distinct laser lines may allow for construction of dual SLM, dual DMD or a combination of the two which can increase flexibility in printing different sizes and types of structures. Furthermore, the laser line can be flickered between two different structures projected by each series to allow for near-simultaneous printing of complex structures that may not otherwise be achieved with a single DMD or SLM series. At any time these laser lines may be re-directed to the beam dump E which functions as a default off state. |

Figure 4A:
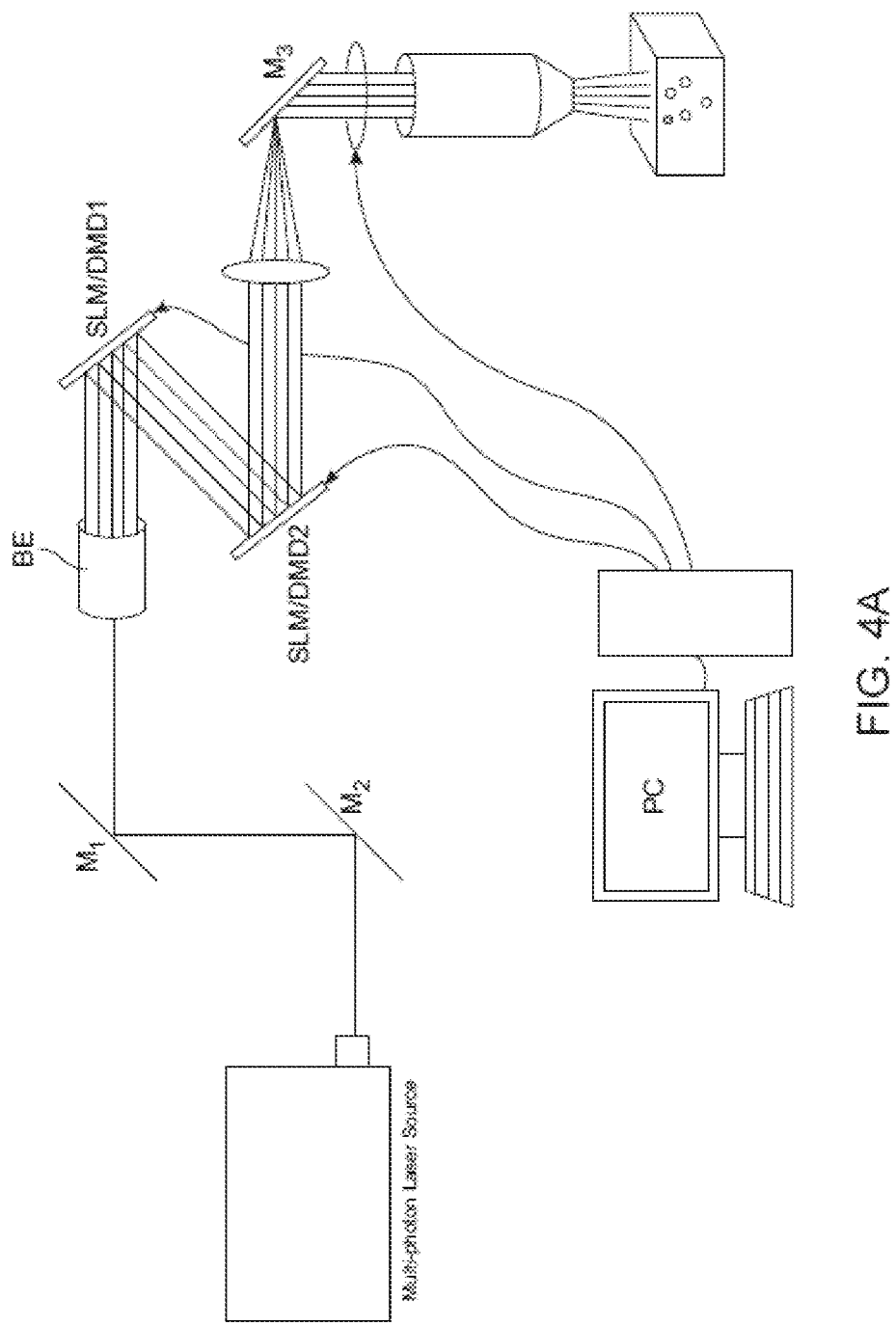
FIGS. 4A-4C illustrate various embodiments of the printing system.
Figure 4B:
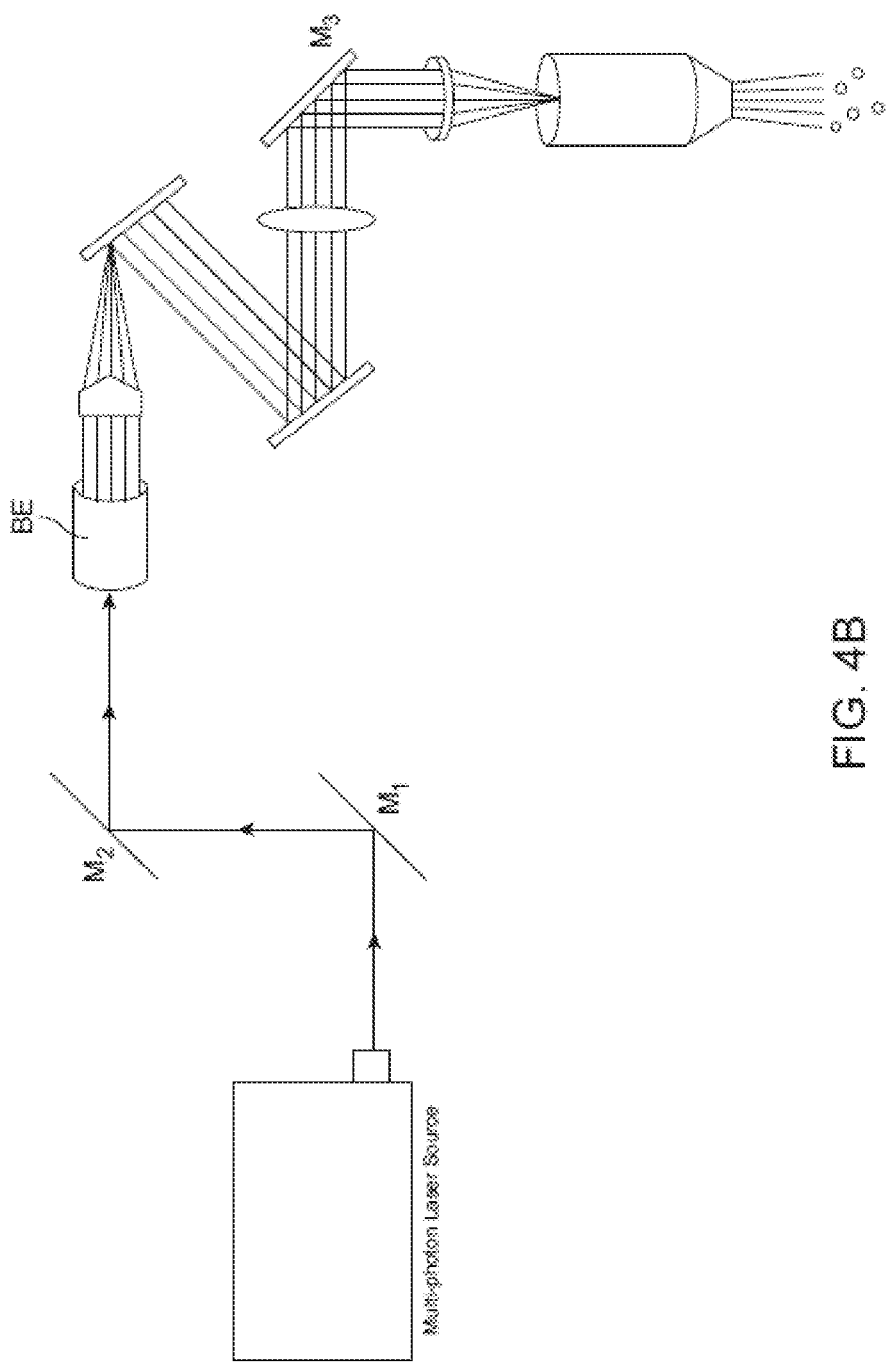

FIGS. 4A-4B demonstrates the placement of an optional beam expander prior to the axicon or tunable acoustic gradient (TAG) lens. This may allow for generation of a Bessel beam for the purpose of increased depth penetration in tissues and turbid media during printing without loss of focus fidelity. This feature may improve depth of printing through turbid media or through already formed tissues without loss of power.

A lens may be used to either widen or pre-focus the laser after the dual SLM or DMD combination. In addition, a laser attenuation device or filtering wheel that is computer controlled may be added prior to focusing optics to control the laser power output at the site of printing.

Figure 4C:
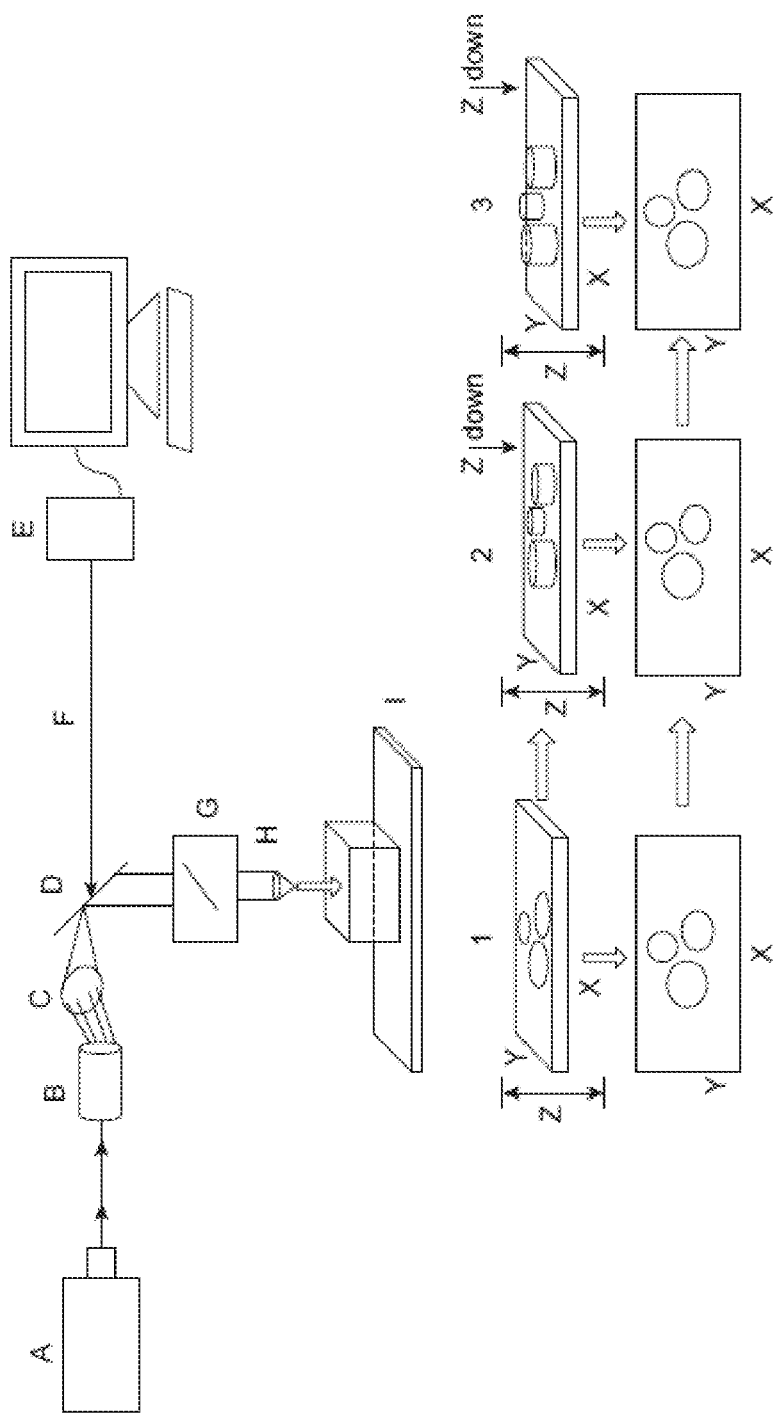

FIG. 4C illustrates a laser source A projecting a laser beam onto a beam collector B. Upon exiting the beam collector B, the laser beam may be directed to an optical TAG or axicon C and further to a movable, single SLM or DMD D for 2D x, y sheet projection for collagen net printing around cells and resultant structures printed with given Z-steps. The laser beam may be directed from the SLM or DMD D into a mirror G and then reflected onto the print head optics H. In this example, a two-dimensional (2D) projection may be created with a single SLM with a z-motor-stepped movement that matches the frame rate of the projection. Two-dimensional video projection of the z-stack slice may be achieved with a single DMD or a single SLM that is timed with z-movement such that each step projects a distinct image printing a 2D image from the top down. In another embodiment, a complex structure may be projected from the side, bottom up, or a different articulation and slice by slice, 2D projected and printed using either multi-photon or alternative laser excitation source. The source of CAD images F may be directed from the computer E into the system. The system may comprise a motorized stage I that may match the step rate (millisecond to second) and the step size of a Z-projection. The step size may be in the order of microns to nanometers. In FIG. 4C, 1, 2, and 3 illustrate examples of planar projection build steps.

Figure 44:
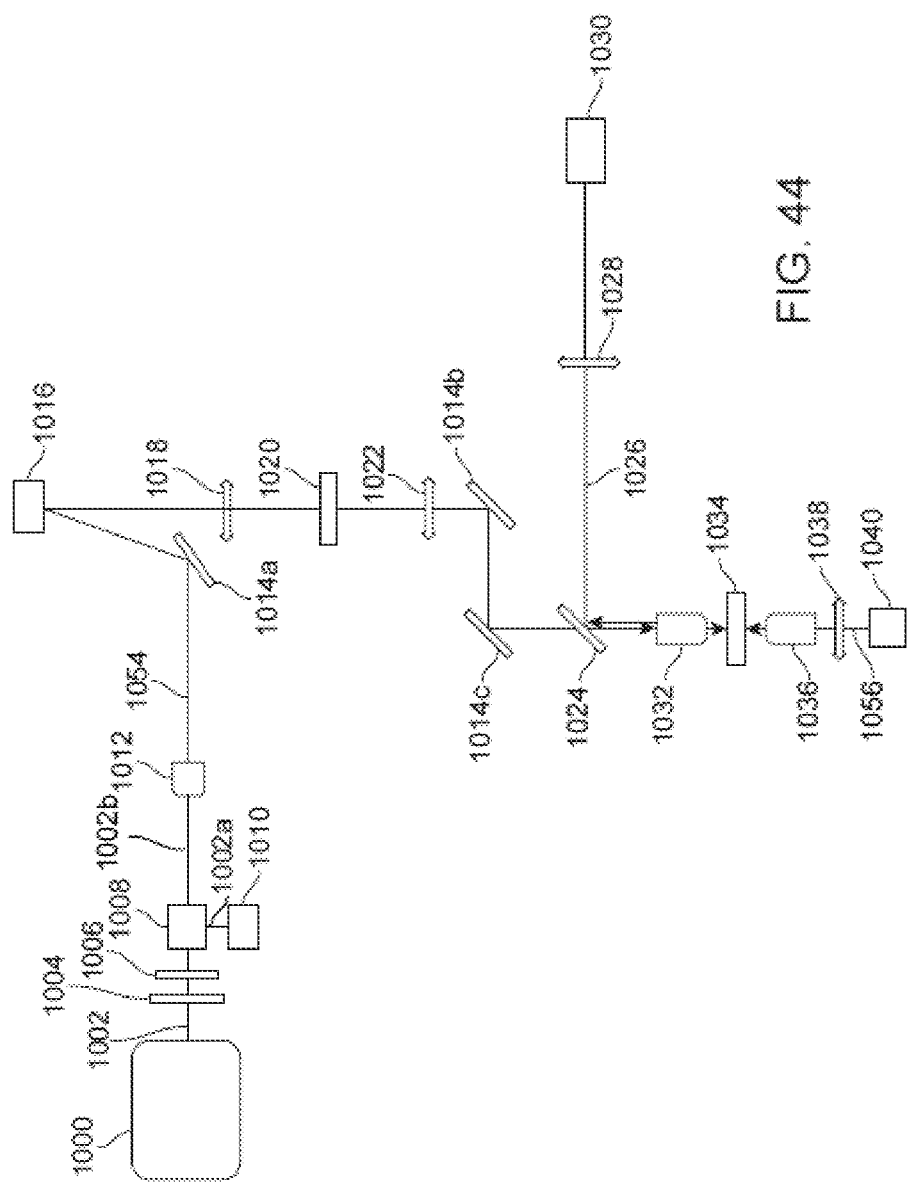
FIG. 44 illustrates the optical components and optical path of an embodiment of the printing system without temporal focusing.

FIG. 44 illustrates the optical components and the optical path of an embodiment of the three-dimensional printing system. The optical components and the optical path shown in FIG. 44 may provide a three-dimensional printing system that may not use temporal focusing. The three-dimensional printing system may comprise an energy source 1000. The energy source 1000 may be a coherent light source. The energy source 1000 may be a laser light. The energy source 1000 may be a femto-second pulsed laser light source. The energy source 1000 may be a first laser source 140a, a second laser source 140b, or a third laser source 140c. The energy source 1000 may be a multi-photon laser beam 120. The energy source 1000 may be a two-photon laser beam. The energy source 1000 may be controlled by a computer system 1101. The energy source 1000 may be tuned by a computer system 1101. The computer system 1101 may control and/or set the energy wavelength of the energy source 1000 prior to or during the printing process. They computer system 1101 may produce different excitation wavelengths by setting the wavelength of the energy source 1000.

The energy source 1000 may be pulsed. The energy source 1000 may be pulsed at a rate of about 500 kilohertz (kHz). The energy source 1000 (e.g., laser) may provide energy (e.g., laser beam) having energy packets with pulsed energies (per packet) from about at least 1 micro joule (µJ)

to 1,000,000 µJ. The energy source 1000 (e.g., laser) may provide energy (e.g., laser beam) having energy packets with pulsed energies (per packet) from about at least 1 micro joule (µJ) to 100,000 µJ or more. The energy source 1000 (e.g., laser) may provide energy (e.g., laser beam) having energy packets with pulsed energies (per packet) from about at least 1 micro joule (µJ) to 1,000 µJ or more. The energy source 1000 (e.g., laser) may provide energy (e.g., laser beam) having energy packets with pulsed energies (per packet) from about at least 1 micro joule (µJ) to 100 µJ or more. The energy source 1000 (e.g., laser) may provide energy (e.g., laser beam) having energy packets with pulsed energies (per packet) from about at least 10 micro joule (µJ) to 100 µJ or more. The energy source 1000 (e.g., laser) may provide energy (e.g., laser beam) having energy packets with pulsed energies (per packet) from about at least 1 micro joule (µJ) to 50 µJ or more. The energy source 1000 (e.g., laser) may provide energy (e.g., laser beam) having energy packets with pulsed energies (per packet) from about at least 1 micro joule (µJ) to 20 µJ or more. The energy source 1000 (e.g., laser) may provide energy (e.g., laser beam) having energy packets with pulsed energies (per packet) from about at least 1 micro joule (µJ) to 50 µJ or more. The energy source 1000 (e.g., laser) may provide energy (e.g., laser beam) having energy packets with pulsed energies (per packet) from about at least 40 micro joule (µJ) to 80 µJ or more. The energy source 1000 (e.g., laser) may provide energy (e.g., laser beam) having energy packets with pulsed energies (per packet) from about at least 120 micro joule (µJ) to 160 µJ or more.

The energy source 1000 (e.g., laser) may provide energy (e.g., laser beam) having energy packets with pulsed energies (per packet) of about 10 µJ. The energy source 1000 (e.g., laser) may provide energy (e.g., laser beam) having energy packets with pulsed energies (per packet) of about 20 µJ. The energy source 1000 (e.g., laser) may provide energy (e.g., laser beam) having energy packets with pulsed energies (per packet) of about 30 µJ. The energy source 1000 (e.g., laser) may provide energy (e.g., laser beam) having energy packets with pulsed energies (per packet) of about 40 µJ. The energy source 1000 (e.g., laser) may provide energy (e.g., laser beam) having energy packets with pulsed energies (per packet) of about 50 µJ. The energy source 1000 (e.g., laser) may provide energy (e.g., laser beam) having energy packets with pulsed energies (per packet) of about 60 µJ. The energy source 1000 (e.g., laser) may provide energy (e.g., laser beam) having energy packets with pulsed energies (per packet) of about 70 µJ. The energy source 1000 (e.g., laser) may provide energy (e.g., laser beam) having energy packets with pulsed energies (per packet) of about 80 µJ. The energy source 1000 (e.g., laser) may provide energy (e.g., laser beam) having energy packets with pulsed energies (per packet) of about 90 µJ. The energy source 1000 (e.g., laser) may provide energy (e.g., laser beam) having energy packets with pulsed energies (per packet) of about 100 µJ. The energy source 1000 (e.g., laser) may provide energy (e.g., laser beam) having energy packets with pulsed energies (per packet) of about 110 µJ. The energy source 1000 (e.g., laser) may provide energy (e.g., laser beam) having energy packets with pulsed energies (per packet) of about 120 µJ. The energy source 1000 (e.g., laser) may provide energy (e.g., laser beam) having energy packets with pulsed energies (per packet) of about 130 µJ. The energy source 1000 (e.g., laser) may provide energy (e.g., laser beam) having energy packets with pulsed energies (per packet) of about 140 µJ. The energy source 1000 (e.g., laser) may provide energy (e.g., laser beam) having energy packets with pulsed energies (per packet) of about 150 µJ. The energy source 1000 (e.g., laser) may provide energy (e.g., laser beam) having energy packets with pulsed energies (per packet) of about 160 µJ. The energy source 1000 (e.g., laser) may provide energy (e.g., laser beam) having energy packets with pulsed energies (per packet) of about 170 µJ. The energy source 1000 (e.g., laser) may provide energy (e.g., laser beam) having energy packets with pulsed energies (per packet) of about 180 µJ. The energy source 1000 (e.g., laser) may provide energy (e.g., laser beam) having energy packets with pulsed energies (per packet) of about 190 µJ. The energy source 1000 (e.g., laser) may provide energy (e.g., laser beam) having energy packets with pulsed energies (per packet) of about 200 µJ. The energy source 1000 (e.g., laser) may provide energy (e.g., laser beam) having energy packets with pulsed energies (per packet) of about 20,000 µJ. The energy source 1000 (e.g., laser) may provide energy (e.g., laser beam) having energy packets with pulsed energies (per packet) of about 100,000 µJ. The energy source 1000 (e.g., laser) may provide energy (e.g., laser beam) having energy packets with pulsed energies (per packet) of about 1,000,000 µJ.

The energy source 1000 (e.g., laser) may provide an energy beam (e.g., light beam) having a wavelength from e.g. about at least 300 nm to about 5 mm or more. The energy source 1000 (e.g., laser) may provide energy (e.g., laser beam) having a wavelength of about at least 600 to about 1500 nm or more. The energy source 1000 (e.g., laser) may provide energy (e.g., laser beam) having a wavelength from about at least 350 nm to about 1800 nm or more. The energy source 1000 (e.g., laser) may provide energy (e.g., laser beam) having a wavelength from about at least 1800 nm to about 5 mm or more. The energy source 1000 (e.g., laser) may provide energy (e.g., laser beam) having a wavelength of about 300 nm. The energy source 1000 (e.g., laser) may provide energy (e.g., laser beam) having a wavelength of about 400 nm. The energy source 1000 (e.g., laser) may provide energy (e.g., laser beam) having a wavelength of about 600 nm. The energy source 1000 (e.g., laser) may provide energy (e.g., laser beam) having a wavelength of about 700 nm. The energy source 1000 (e.g., laser) may provide energy (e.g., laser beam) having a wavelength of about 800 nm. The energy source 1000 (e.g., laser) may provide energy (e.g., laser beam) having a wavelength of about 900 nm. The energy source 1000 (e.g., laser) may provide energy (e.g., laser beam) having a wavelength of about 1000 nm. The energy source 1000 (e.g., laser) may provide energy (e.g., laser beam) having a wavelength of about 1100 nm. The energy source 1000 (e.g., laser) may provide energy (e.g., laser beam) having a wavelength of about 1200 nm. The energy source 1000 (e.g., laser) may provide energy (e.g., laser beam) having a wavelength of about 1300 nm. The energy source 1000 (e.g., laser) may provide energy (e.g., laser beam) having a wavelength of about 1400 nm. The energy source 1000 (e.g., laser) may provide energy (e.g., laser beam) having a wavelength of about 1500 nm. The energy source 1000 (e.g., laser) may provide energy (e.g., laser beam) having a wavelength of about 1600 nm. The energy source 1000 (e.g., laser) may provide energy (e.g., laser beam) having a wavelength of about 1700 nm. The energy source 1000 (e.g., laser) may provide energy (e.g., laser beam) having a wavelength of about 1800 nm. The energy source 1000 (e.g., laser) may provide energy (e.g., laser beam) having a wavelength of about 1900 nm. The energy source 1000 (e.g., laser) may provide energy (e.g., laser beam) having a wavelength of about 2000 nm. The energy source 1000 (e.g., laser) may provide energy (e.g., laser beam) having a wavelength of about 3000 nm. The energy source 1000 (e.g., laser) may provide energy (e.g., laser beam) having a wavelength of about 4000 nm. The energy source 1000 (e.g., laser) may provide energy (e.g., laser beam) having a wavelength of about 5000 nm.

As shown in FIG. 44, the energy source 1000 may project a laser beam 1002 through a shutter 1004. Once the laser beam 1002 exits the shutter 1004, the laser beam 1002 may be directed through a rotating half-wave plate 1006. Rotating half-wave plates may be transparent plates with a specific amount of birefringence that may be used mostly for manipulating the polarization state of light beams. Rotating half-wave plates may have a slow axis and a fast axis (i.e., two polarization directions), which may be both perpendicular to the direction of the laser beam 1002. The rotating half-wave plate 1006 may alter the polarization state of the laser beam 1002 such that the difference in phase delay between the two linear polarization directions is it. The difference in phase delay may correspond to a propagation phase shift over a distance of $\lambda/2$. Other types of wave plates may be utilized with the system disclosed herein; for example, a rotating quarter-wave plate may be used. The rotating half-wave plate 1006 may be a true zero-order wave plate, a low order wave plate, or a multiple-order wave plate. The rotating half-wave plate 1006 may be composed of crystalline quartz ($SiO_2$), calcite ($CaCO_3$), magnesium fluoride ($MgF_2$), sapphire ($Al_2O_3$), mica, or a birefringent polymer.

The laser beam 1002 may exit the rotating half-wave plate 1006 and may be directed through a polarizing beam splitter 1008. The polarizing beam splitter 1008 may split the laser beam 1002 into a first laser beam 1002a and a second laser beam 1002b. The first laser beam 1002a may be directed to a beam dump 1010. The beam dump 1010 is an optical element that may be used to absorb stray portions of a laser beam. The beam dump 1010 may absorb the first laser beam 1002a. The first laser beam 1002a may be a stray laser beam. The beam dump 1010 may absorb the second laser beam 1002b. The second laser beam 1002b may be a stray laser beam. The laser beam 1002 may be directed into the beam dump 1010 in its entirety and thus, may serve as a default "off" state of the printing system. The second laser beam 1002b may be directed to a beam expander 1012. The beam expander 1012 may expand the size of the laser beam 1002b. The beam expander 1012 may increase the diameter of the input second laser beam 1002b to a larger diameter of an output, expanded laser beam 1054. The beam expander 1012 may be a prismatic beam expander. The beam expander 1012 may be a telescopic beam expander. The beam expander 1012 may be a multi-prism beam expander. The beam expander 1012 may be a Galilean beam expander. The beam expander 1012 may provide a beam expander power of about 2×, 3×, 5×, 10×, 20×, or 40×. The beam expander 1012 may provide a beam expander power ranging from about 2× to about 5×. The beam expander 1012 may provide continuous beam expansion between about 2× and about 5×. The beam expander 1012 may provide a beam expander power ranging from about 5× to about 10×. The beam expander 1012 may provide continuous beam expansion between about 5× and about 10×. The expanded laser beam 1054 may be collimated upon exiting the beam expander 1012.

After exiting the beam expander 1012, the expanded laser beam 1054 may be directed to a first mirror 1014a, which may re-direct the expanded laser beam 1054 to a spatial light modulator (SLM) 1016. The SLM 1016 may be controlled by a computer system 1101. The SLM 1016 may be directed to project a specific image or a specific portion of an image of a material to be printed using the methods and systems disclosed herein. The material to be printed may be a biological material. The biological material may be a three-dimensional biological material. The specific image or the specific portion of the image may be one-dimensional, two-dimensional, and/or three-dimensional. The SLM 1016 may be directed to project at least one image simultaneously in different wavelengths of light. The SLM 1016 may be directed to project different aspects of the material to be printed with the use of mirrors instead of with the use of a computer system 1101. In some cases, at least one mirror may be used to re-direct or turn "off" or "on" a particular light path or laser beam in order to print different aspects or portions of the material to be printed.

After exiting the SLM 1016, the expanded laser beam 1054 may be directed to an f1 lens 1018. The f1 lens 1018 may be a focusing lens. After exiting the f1 lens 1018, the expanded laser beam 1054 may be directed to blocking element 1020. The blocking element 1020 may be immovable. The blocking element 1020 may suppress illumination from a zero-order spot. A zero-order may be a part of the energy from the expanded laser beam 1054 that is not diffracted and behaves according to the laws or reflection and refraction. After exiting the blocking element 1020, the expanded energy beam 1054 may be directed through an f2 lens 1022. The f2 lens may be a focusing lens.

After exiting the f2 lens 1022, the expanded laser beam 1054 may be directed onto a second mirror 1014b and may be subsequently directed onto a third mirror 1014c. The third mirror 1014c may re-direct the expanded laser beam 1054 through a long pass dichroic mirror 1024. The first mirror 1014a, the second mirror 1014b, and/or the third mirror 1014c may comprise an infrared (IR) coating to improve reflectance. The first mirror 1014a, the second mirror 1014b, and/or the third mirror 1014c may not comprise an infrared (IR) coating. Non-limiting examples of IR coatings include protected gold-based coatings and protected silver-based coatings. The first mirror 1014a, the second mirror 1014b, and/or the third mirror 1014c may be controlled with a computer system 1101. The computer system 1101 may turn the first mirror 1014a, the second mirror 1014b, and/or the third mirror 1014c "on" or "off" in order to re-direct the expanded laser beam 1054 as desired.

The dichroic mirror may be a short pass dichroic mirror. The long pass dichroic mirror 1024 may reflect the expanded laser beam 1054 into the focusing objective 1032. In some instances, a beam combiner may be used to re-direct the expanded laser beam 1054 into the focusing objective 1032 instead of using the long pass dichroic mirror 1024. The long pass dichroic mirror 1024 may be controlled with a computer system 1101 to re-direct the expanded laser beam 1054 into the focusing objective 1032. The focusing objective 1032 may concentrate the expanded laser beam 1054 as it is projected into the printing chamber 1034. The printing chamber 1034 may be a media chamber 122. The printing chamber 1034 may comprise a cell-containing medium, a plurality of cells, cell constituents (e.g., organelles), and/or at least one polymer precursor.

A light-emitting diode (LED) collimator 1040 may be used as a source of collimated LED light 1056. The LED collimator 1040 may comprise a collimating lens and an LED emitter. The LED may be an inorganic LED, a high brightness LED, a quantum dot LED, or an organic LED. The LED may be a single color LED, a bi-color LED, or a tri-color LED. The LED may be a blue LED, an ultraviolet LED, a white LED, an infrared LED, a red LED, an orange LED, a yellow LED, a green LED, a violet LED, a pink LED, or a purple LED. The LED collimator 1040 may project a beam of collimated LED light 1056 through an f4 lens 1038. The f4 lens 1038 may be a focusing lens. Once the collimated LED light 1056 is transmitted through the f4 lens 1038, the collimated LED light 1056 may be directed into a light focusing objective 1036. The light focusing objective 1036 may focus the collimated LED light 1056 into the printing chamber 1034. The light focusing objective 1036 may focus the collimated LED light 1056 in the sample medium. The light focusing objective 1036 may focus the collimated LED light 1056 in the cell-containing medium. The collimated LED light 1056 may be transmitted through the printing chamber 1034 and into the focusing objective 1032. Once the collimated LED light 1056 exits the focusing objective 1032, the collimated LED light 1056 may be directed onto the long pass dichroic mirror 1024. The collimated LED light 1056 that is reflected off of the long pass dichroic mirror 1024 may be the sample emission 1026. The long pass dichroic mirror 1024 may re-direct the sample emission 1026 into an f3 lens 1028. The f3 lens 1028 may be a focusing lens. Once sample emission 1026 is transmitted through the f3 lens 1028, a detection system 1030 detects and/or collects the sample emission 1026 for imaging. The detection system 1030 may comprise at least one photomultiplier tube (PMT). The detection system 1030 may comprise at least one camera. The camera may be a complementary metal-oxide semiconductor (CMOS) camera, a scientific CMOS camera, a charge-coupled device (CCD) camera, or an electron-multiplying charge-coupled device (EM-CCD). The detection system 1030 may comprise at least one array-based detector.

Figure 45:
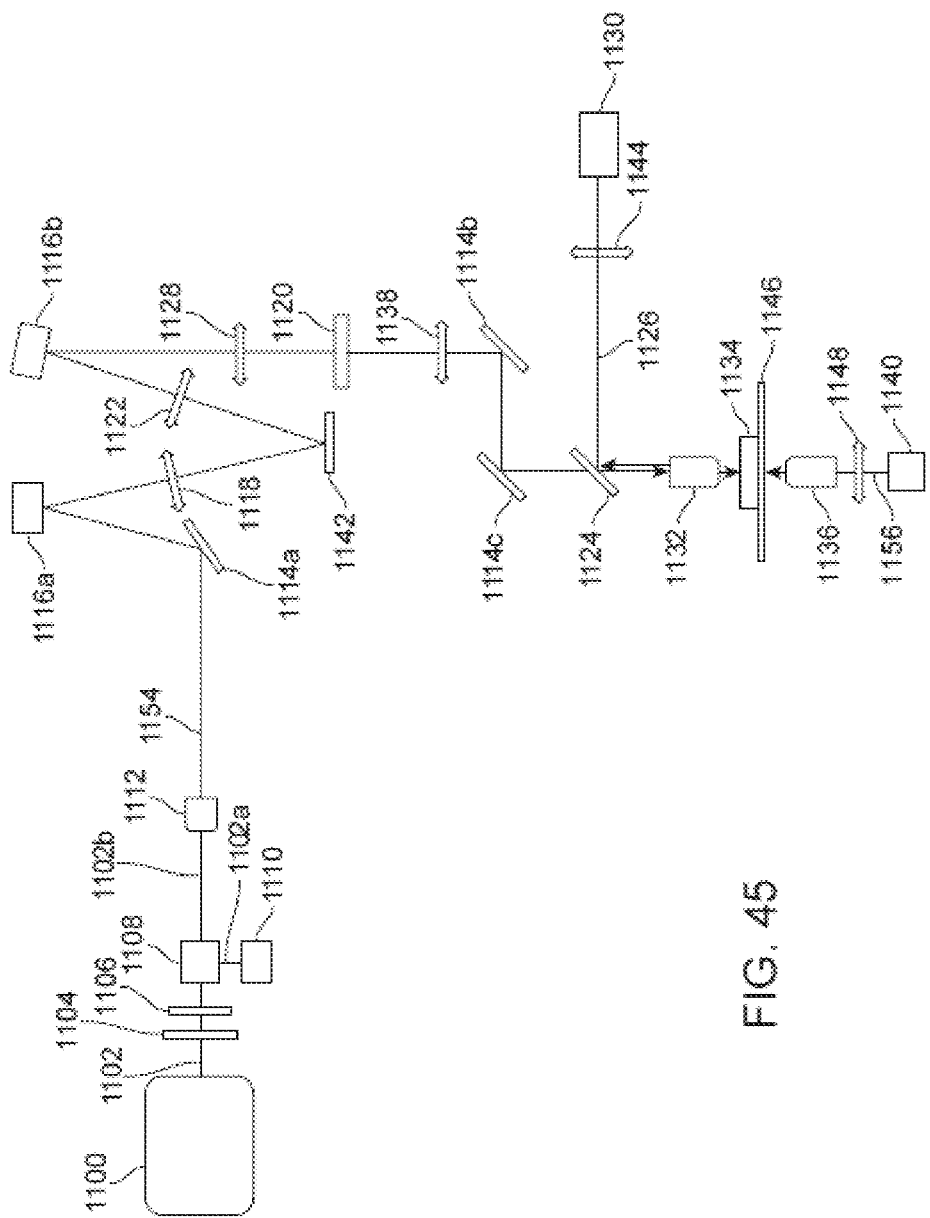
FIG. 45 illustrates the optical components and optical path of an additional embodiment of the printing system with temporal focusing.

FIG. 45 illustrates the optical components and the optical path of yet another embodiment of the three-dimensional printing system. The optical components and the optical path shown in FIG. 45 provide a three-dimensional printing system that may use temporal focusing. The three-dimensional printing system may comprise an energy source 1100. The energy source 1100 may be a coherent light source. The energy source 1100 may be a laser light. The energy source 1100 may be a femto-second pulsed laser light source. The energy source 1100 may be a first laser source 140*a*, a second laser source 140*b*, or a third laser source 140*c*. The energy source 1100 may be a multi-photon laser beam 120. The energy source 1100 may be a two-photon laser beam. The energy source 1100 may be controlled by a computer system 1101. The energy source 1100 may be tuned by a computer system 1101. The computer system 1101 may control and/or set the energy wavelength of the energy source 1100 prior to or during the printing process. They computer system 1101 may produce different excitation wavelengths by setting the wavelength of the energy source 1100.

The energy source 1100 may be pulsed. The energy source 1100 may be pulsed at a rate of about 500 kilohertz (kHz). The energy source 1100 (e.g., laser) may provide energy (e.g., laser beam) having energy packets with pulsed energies (per packet) from about at least 1 micro joule (μJ) to 1,000,000 μJ. The energy source 1100 (e.g., laser) may provide energy (e.g., laser beam) having energy packets with pulsed energies (per packet) from about at least 1 micro joule (μJ) to 100,000 μJ or more. The energy source 1100 (e.g., laser) may provide energy (e.g., laser beam) having energy packets with pulsed energies (per packet) from about at least 1 micro joule (μJ) to 1,000 μJ or more. The energy source 1100 (e.g., laser) may provide energy (e.g., laser beam) having energy packets with pulsed energies (per packet) from about at least 1 micro joule (μJ) to 100 μJ or more. The energy source 1100 (e.g., laser) may provide energy (e.g., laser beam) having energy packets with pulsed energies (per packet) from about at least 10 micro joule (μJ) to 100 μJ or more. The energy source 1100 (e.g., laser) may provide energy (e.g., laser beam) having energy packets with pulsed energies (per packet) from about at least 1 micro joule (μJ) to 50 μJ or more. The energy source 1100 (e.g., laser) may provide energy (e.g., laser beam) having energy packets with pulsed energies (per packet) from about at least 1 micro joule (μJ) to 20 μJ or more. The energy source 1100 (e.g., laser) may provide energy (e.g., laser beam) having energy packets with pulsed energies (per packet) from about at least 1 micro joule (μJ) to 50 μJ or more. The energy source 1100 (e.g., laser) may provide energy (e.g., laser beam) having energy packets with pulsed energies (per packet) from about at least 40 micro joule (μJ) to 80 μJ or more. The energy source 1100 (e.g., laser) may provide energy (e.g., laser beam) having energy packets with pulsed energies (per packet) from about at least 120 micro joule (μJ) to 160 μJ or more.

The energy source 1100 (e.g., laser) may provide energy (e.g., laser beam) having energy packets with pulsed energies (per packet) of about 10 μJ. The energy source 1100 (e.g., laser) may provide energy (e.g., laser beam) having energy packets with pulsed energies (per packet) of about 20 μJ. The energy source 1100 (e.g., laser) may provide energy (e.g., laser beam) having energy packets with pulsed energies (per packet) of about 30 μJ. The energy source 1100 (e.g., laser) may provide energy (e.g., laser beam) having energy packets with pulsed energies (per packet) of about 40 μJ. The energy source 1100 (e.g., laser) may provide energy (e.g., laser beam) having energy packets with pulsed energies (per packet) of about 50 μJ. The energy source 1100 (e.g., laser) may provide energy (e.g., laser beam) having energy packets with pulsed energies (per packet) of about 60 μJ. The energy source 1100 (e.g., laser) may provide energy (e.g., laser beam) having energy packets with pulsed energies (per packet) of about 70 μJ. The energy source 1100 (e.g., laser) may provide energy (e.g., laser beam) having energy packets with pulsed energies (per packet) of about 80 μJ. The energy source 1100 (e.g., laser) may provide energy (e.g., laser beam) having energy packets with pulsed energies (per packet) of about 90 μJ. The energy source 1100 (e.g., laser) may provide energy (e.g., laser beam) having energy packets with pulsed energies (per packet) of about 100 μJ. The energy source 1100 (e.g., laser) may provide energy (e.g., laser beam) having energy packets with pulsed energies (per packet) of about 110 μJ. The energy source 1100 (e.g., laser) may provide energy (e.g., laser beam) having energy packets with pulsed energies (per packet) of about 120 μJ. The energy source 1100 (e.g., laser) may provide energy (e.g., laser beam) having energy packets with pulsed energies (per packet) of about 130 μJ. The energy source 1100 (e.g., laser) may provide energy (e.g., laser beam) having energy packets with pulsed energies (per packet) of about 140 μJ. The energy source 1100 (e.g., laser) may provide energy (e.g., laser beam) having energy packets with pulsed energies (per packet) of about 150 μJ. The energy source 1100 (e.g., laser) may provide energy (e.g., laser beam) having energy packets with pulsed energies (per packet) of about 160 μJ. The energy source 1100 (e.g., laser) may provide energy (e.g., laser beam) having energy packets with pulsed energies (per packet) of about 170 μJ. The energy source 1100 (e.g., laser) may provide energy (e.g., laser beam) having energy packets with pulsed energies (per packet) of about 180 µJ. The energy source 1100 (e.g., laser) may provide energy (e.g., laser beam) having energy packets with pulsed energies (per packet) of about 190 µJ. The energy source 1100 (e.g., laser) may provide energy (e.g., laser beam) having energy packets with pulsed energies (per packet) of about 200 µJ. The energy source 1100 (e.g., laser) may provide energy (e.g., laser beam) having energy packets with pulsed energies (per packet) of about 20,000 µJ. The energy source 1100 (e.g., laser) may provide energy (e.g., laser beam) having energy packets with pulsed energies (per packet) of about 100,000 µJ. The energy source 1100 (e.g., laser) may provide energy (e.g., laser beam) having energy packets with pulsed energies (per packet).

The energy source 1100 (e.g., laser) may provide energy (e.g., laser beam) having a wavelength from about 300 nm to 5 mm, 600 nm to 1500 nm, 350 nm to 1800 nm, or 1800 nm to 5 mm. The energy source 1100 (e.g., laser) may provide energy (e.g., laser beam) having a wavelength of at least about 300 nm, 400 nm, 500 nm, 600 nm, 700 nm, 800 nm, 900 nm, 1 mm, 1.1 mm, 1.2, mm, 1.3 mm, 1.4 mm, 1.5 mm, 1.6 mm, 1.7 mm, 1.8 mm, 1.9 mm, 2 mm, 3 mm, 4 mm, 5 mm, or greater.

As shown in FIG. 45, the energy source 1100 may project a laser beam 1102 through a shutter 1104. Once the laser beam 1102 exits the shutter 1104, the laser beam 1102 may be directed through a rotating half-wave plate 1106. The rotating half-wave plate 1106 may alter the polarization state of the laser beam 1102 such that the difference in phase delay between the two linear polarization directions is $\pi$. The difference in phase delay may correspond to a propagation phase shift over a distance of $\lambda/2$. Other types of wave plates may be utilized with the system disclosed herein; for example, a rotating quarter-wave plate may be used. The rotating half-wave plate 1106 may be a true zero-order wave plate, a low order wave plate, or a multiple-order wave plate. The rotating half-wave plate 1106 may be composed of crystalline quartz ($SiO_2$), calcite ($CaCO_3$), magnesium fluoride ($MgF_2$), sapphire ($Al_2O_3$), mica, or a birefringent polymer.

The laser beam 1102 may exit the rotating half-wave plate 1106 and may be directed through a polarizing beam splitter 1108. The polarizing beam splitter 1108 may split the laser beam 1102 into a first laser beam 1102a and a second laser beam 1102b. The first laser beam 1102a may be directed to a beam dump 1110. The beam dump 1110 is an optical element that may be used to absorb stray portions of a laser beam. The beam dump 1110 may absorb the first laser beam 1102a. The first laser beam 1102a may be a stray laser beam. The beam dump 1110 may absorb the second laser beam 1102b. The second laser beam 1102b may be a stray laser beam. The laser beam 1102 may be directed into the beam dump 1110 in its entirety and thus, may serve as a default "off" state of the printing system. The second laser beam 1102b may be directed to a beam expander 1112. The beam expander 1112 may expand the size of the second laser beam 1102b. The beam expander 1112 may increase the diameter of the input, second laser beam 1102b to a larger diameter of an output, expanded laser beam 1154. The beam expander 1112 may be a prismatic beam expander. The beam expander 1112 may be a telescopic beam expander. The beam expander 1112 may be a multi-prism beam expander. The beam expander 1112 may be a Galilean beam expander. The beam expander 1112 may provide a beam expander power of about 2×, 3×, 5×, 10×, 20×, or 40X. The beam expander 1112 may provide a beam expander power ranging from about 2× to about 5×. The beam expander 1112 may provide continuous beam expansion between about 2× and about 5×. The beam expander 1112 may provide a beam expander power ranging from about 5× to about 10×. The beam expander 1112 may provide continuous beam expansion between about 5× and about 10×. The expanded laser beam 1154 may be collimated upon exiting the beam expander 1112.

After exiting the beam expander 1112, the expanded laser beam 1154 may be directed to a first mirror 1114a, which may re-direct the expanded laser beam 1154 to a first spatial light modulator (SLM) 1116a. After exiting the first SLM 1116, the expanded laser beam 1154 may be directed to an f1 lens 1118. The f1 lens 1118 may be a focusing lens. After exiting the f1 lens, the expanded laser beam 1154 may be directed to a grating 1142. The grating 1142 may be a diffractive laser beam splitter. The grating 1142 may be a holographic grating. The grating 1142 may be a ruled grating. The grating 1142 may be a subwavelength grating. The grating 1142 may split and/or diffract the expanded laser beam 1154 into a plurality of expanded laser beams (not shown in FIG. 45). The grating 1142 may act as a dispersive element. Once the expanded laser beam 1154 is split, diffracted, and/or dispersed by the grating 1142, the expanded laser beam 1154 may be transmitted through an f2 lens 1122. The f2 lens 1122 may be a focusing lens. After exiting the f2 lens 1122, the expanded laser beam 1154 may be directed to a second SLM 1116b. The SLMs (i.e., the first SLM 1116a and the second SLM 1116b) may be controlled by a computer system 1101. The SLMs may perform all of the functions, as described supra, of the SLM 1016 presented in FIG. 44.

After exiting the second SLM 1116b, the expanded laser beam 1154 may be directed to an f3 lens 1128. The f3 lens 1128 may be a focusing lens. After exiting the f3 lens, the expanded laser beam 1154 may be directed to blocking element 1120. The blocking element 1120 may be immovable. The blocking element 1120 may be used to suppress illumination from a zero-order spot. After exiting the blocking element 1120, the expanded energy beam 1154 may be directed through an f4 lens 1138. The f4 lens 1138 may be a focusing lens. After exiting the f4 lens 1138, the expanded laser beam 1154 may be directed onto a second mirror 1114b and may be subsequently directed onto a third mirror 1114c. The third mirror 1114c may re-direct the expanded laser beam 1154 through a long pass dichroic mirror 1124. The first mirror 1114a, the second mirror 1114b, and/or the third mirror 1114c may be controlled with a computer system 1101. The computer system 1101 may turn the first mirror 1114a, the second mirror 1114b, and/or the third mirror 1114c "on" or "off" in order to re-direct the expanded laser beam 1154 as desired. The dichroic mirror may be a short pass dichroic mirror. The long pass dichroic mirror 1124 may reflect the expanded laser beam 1154 into the focusing objective 1132. In some instances, a beam combiner may be used to re-direct the expanded laser beam 1154 into the focusing objective 1132 instead of using the long pass dichroic mirror 1124. The long pass dichroic mirror 1124 may be controlled with a computer system 1101 to re-direct the expanded laser beam 1154 into the focusing objective 1132. The focusing objective 1132 may concentrate the expanded laser beam 1154 as it is projected into the printing chamber 1134. The printing chamber 1134 may be a media chamber 122. The printing chamber 1134 may comprise a cell-containing medium, a plurality of cells, cell constituents (e.g., organelles), and/or at least one polymer precursor.

The printing chamber 1134 may be mounted on a movable stage 1146. The movable stage 1146 may be an xy stage, a z stage, and/or an xyz stage. The movable stage 1146 may be manually positioned. The movable stage 1146 may be automatically positioned. The movable stage 1146 may be a motorized stage. The movable stage 1146 may be controlled by the computer system 1101. The computer system 1101 may control the movement of the movable stage 1146 in the x, y, and/or z directions. The computer system 1101 may automatically position the movable stage 1146 in a desired x, y, and/or z position. The computer system 1101 may position the movable stage 1146 in a desired x, y, and/or z position with a positional accuracy of at most about 3 µm. The computer system 1101 may position the movable stage 1146 in a desired x, y, and/or z position with a positional accuracy of at most about 2 µm. The computer system 1101 may position the movable stage 1146 in a desired x, y, and/or z position with a positional accuracy of at most about 1 µm. The computer system 1101 may automatically adjust the position of the movable stage 1146 prior or during three-dimensional printing. The computer system 1101 may comprise a piezoelectric (piezo) controller to provide computer-controlled z-axis (i.e., vertical direction) positioning and active location feedback. The computer system 1101 may comprise a joystick console to enable a user to control a position of the movable stage 1146. The joystick console may be a z-axis console and/or an x-axis and y-axis console. The movable stage 1146 may comprise a printing chamber holder. The printing chamber holder may be a bracket, a clip, and/or a recessed sample holder. The movable stage 1146 may comprise a multi-slide holder, a slide holder, and/or a petri dish holder. The movable stage 1146 may comprise a sensor to provide location feedback. The sensor may be a capacitive sensor. The sensor may be a piezoresistive sensor. The movable stage 1146 may comprise at least one actuator (e.g., piezoelectric actuator) that moves (or positions) the movable stage 1146.

A light-emitting diode (LED) collimator 1140 may be used as a source of collimated LED light 1156. The LED collimator 1140 may comprise a collimating lens and an LED emitter. The LED may be an inorganic LED, a high brightness LED, a quantum dot LED, or an organic LED. The LED may be a single color LED, a bi-color LED, or a tri-color LED. The LED may be a blue LED, an ultraviolet LED, a white LED, an infrared LED, a red LED, an orange LED, a yellow LED, a green LED, a violet LED, a pink LED, or a purple LED. The LED collimator 1140 may project a beam of collimated LED light 1156 through an f6 lens 1148. The f6 lens 1148 may be a focusing lens. Once the collimated LED light 1156 is transmitted through the f6 lens 1148, the collimated LED light 1156 may be directed into a light focusing objective 1136. The light focusing objective 1136 may focus the collimated LED light 1156 into the printing chamber 1134. The light focusing objective 1136 may focus the collimated LED light 1156 in the sample medium. The light focusing objective 1136 may focus the collimated LED light 1156 in the cell-containing medium. The collimated LED light 1156 may be transmitted through the printing chamber 1134 and into the focusing objective 1132. Once the collimated LED light 1156 exits the focusing objective 1132, the collimated LED light 1156 may be directed onto the long pass dichroic mirror 1124. The collimated LED light 1156 that is reflected off of the long pass dichroic mirror 1124 may be the sample emission 1126. The long pass dichroic mirror 1124 may re-direct the sample emission 1126 into an f5 lens 1144. The f5 lens 1144 may be a focusing lens. Once sample emission 1126 is transmitted through the f5 lens 1144, a detection system 1130 detects and/or collects the sample emission 1126 for imaging. The detection system 1130 may comprise at least one photomultiplier tube (PMT). The detection system 1130 may comprise at least one camera. The camera may be a complementary metal-oxide semiconductor (CMOS) camera, a scientific CMOS camera, a charge-coupled device (CCD) camera, or an electron-multiplying charge-coupled device (EM-CCD). The detection system 1130 may comprise at least one array-based detector.

Figure 46:
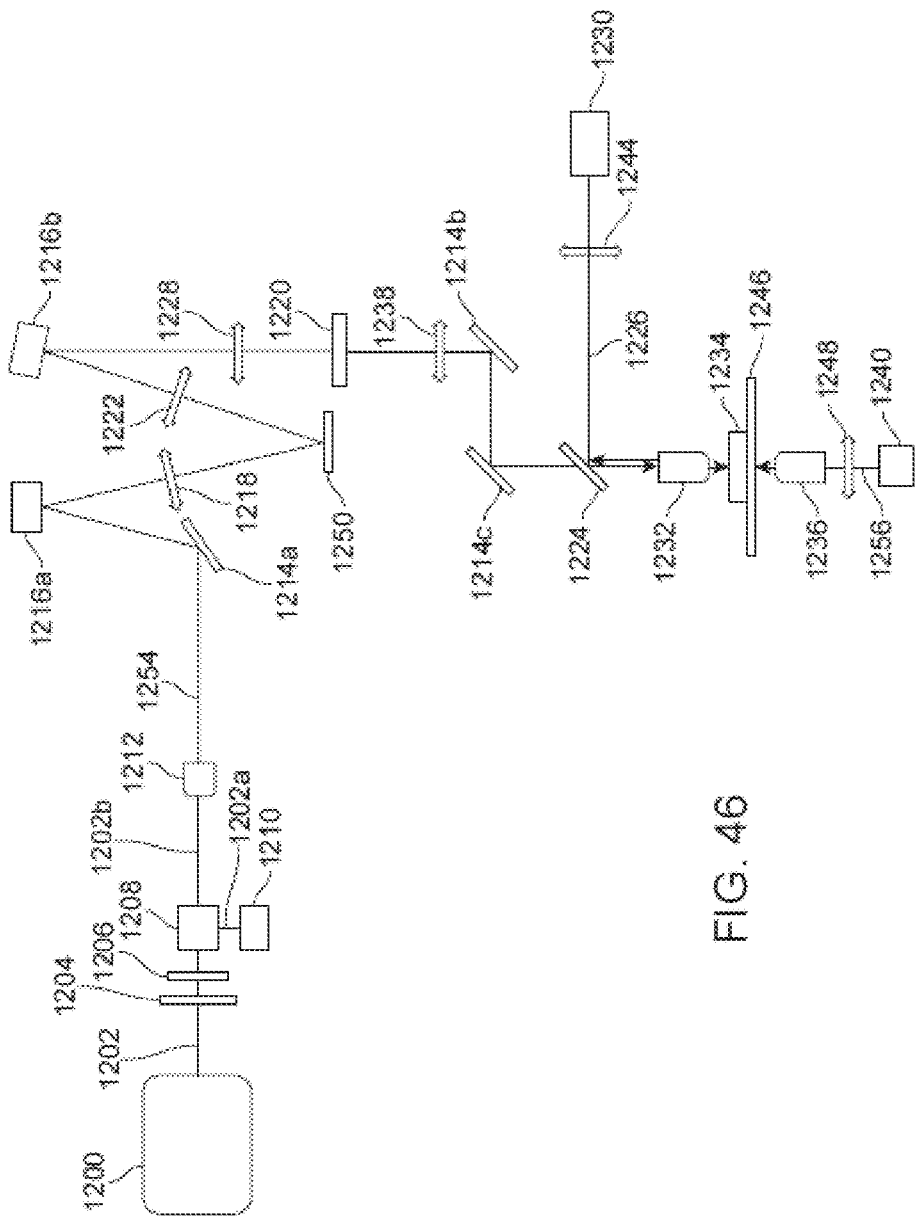
FIG. 46 illustrates the optical components and optical path of yet another embodiment of the printing system without temporal focusing.

FIG. 46 illustrates the optical components and the optical path of an additional embodiment of the three-dimensional printing system. The optical components and the optical path shown in FIG. 46 provide a three-dimensional printing system that may not use temporal focusing. The three-dimensional printing system may comprise an energy source 1200. The energy source 1200 may be a coherent light source. The energy source 1200 may be a laser light. The energy source 1200 may be a femto-second pulsed laser light source. The energy source 1200 may be a first laser source 140a, a second laser source 140b, or a third laser source 140c. The energy source 1200 may be a multi-photon laser beam 120. The energy source 1200 may be controlled by a computer system 1101. The energy source 1200 may be tuned by a computer system 1101. The computer system 1101 may control and/or set the energy wavelength of the energy source 1200 prior to or during the printing process. They computer system 1101 may produce different excitation wavelengths by setting the wavelength of the energy source 1200.

The energy source 1200 may be pulsed. The energy source 1200 may be pulsed at a rate of about 500 kilohertz (kHz). The energy source 1200 (e.g., laser) may provide energy (e.g., laser beam) having energy packets with pulsed energies (per packet) from about at least 1 micro joule (µJ) to 1,000,000 µJ. The energy source 1200 (e.g., laser) may provide energy (e.g., laser beam) having energy packets with pulsed energies (per packet) from about at least 1 micro joule (µJ) to 100,000 µJ or more. The energy source 1200 (e.g., laser) may provide energy (e.g., laser beam) having energy packets with pulsed energies (per packet) from about at least 1 micro joule (µJ) to 1,000 µJ or more. The energy source 1200 (e.g., laser) may provide energy (e.g., laser beam) having energy packets with pulsed energies (per packet) from about at least 1 micro joule (µJ) to 100 µJ or more. The energy source 1200 (e.g., laser) may provide energy (e.g., laser beam) having energy packets with pulsed energies (per packet) from about at least 10 micro joule (µJ) to 100 µJ or more. The energy source 1200 (e.g., laser) may provide energy (e.g., laser beam) having energy packets with pulsed energies (per packet) from about at least 1 micro joule (µJ) to 50 µJ or more. The energy source 1200 (e.g., laser) may provide energy (e.g., laser beam) having energy packets with pulsed energies (per packet) from about at least 1 micro joule (µJ) to 20 µJ or more. The energy source 1200 (e.g., laser) may provide energy (e.g., laser beam) having energy packets with pulsed energies (per packet) from about at least 1 micro joule (µJ) to 50 µJ or more. The energy source 1200 (e.g., laser) may provide energy (e.g., laser beam) having energy packets with pulsed energies (per packet) from about at least 40 micro joule (µJ) to 80 µJ or more. The energy source 1200 (e.g., laser) may provide energy (e.g., laser beam) having energy packets with pulsed energies (per packet) from about at least 120 micro joule (µJ) to 160 µJ or more.

The energy source 1200 (e.g., laser) may provide energy (e.g., laser beam) having energy packets with pulsed energies (per packet) of about 10 µJ. The energy source 1200 (e.g., laser) may provide energy (e.g., laser beam) having energy packets with pulsed energies (per packet) of about 20 µJ. The energy source 1200 (e.g., laser) may provide energy (e.g., laser beam) having energy packets with pulsed energies (per packet) of about 30 µJ. The energy source 1200 (e.g., laser) may provide energy (e.g., laser beam) having energy packets with pulsed energies (per packet) of about 40 µJ. The energy source 1200 (e.g., laser) may provide energy (e.g., laser beam) having energy packets with pulsed energies (per packet) of about 50 µJ. The energy source 1200 (e.g., laser) may provide energy (e.g., laser beam) having energy packets with pulsed energies (per packet) of about 60 µJ. The energy source 1200 (e.g., laser) may provide energy (e.g., laser beam) having energy packets with pulsed energies (per packet) of about 70 µJ. The energy source 1200 (e.g., laser) may provide energy (e.g., laser beam) having energy packets with pulsed energies (per packet) of about 80 µJ. The energy source 1200 (e.g., laser) may provide energy (e.g., laser beam) having energy packets with pulsed energies (per packet) of about 90 µJ. The energy source 1200 (e.g., laser) may provide energy (e.g., laser beam) having energy packets with pulsed energies (per packet) of about 100 µJ. The energy source 1200 (e.g., laser) may provide energy (e.g., laser beam) having energy packets with pulsed energies (per packet) of about 110 µJ. The energy source 1200 (e.g., laser) may provide energy (e.g., laser beam) having energy packets with pulsed energies (per packet) of about 120 µJ. The energy source 1200 (e.g., laser) may provide energy (e.g., laser beam) having energy packets with pulsed energies (per packet) of about 130 µJ. The energy source 1200 (e.g., laser) may provide energy (e.g., laser beam) having energy packets with pulsed energies (per packet) of about 140 µJ. The energy source 1200 (e.g., laser) may provide energy (e.g., laser beam) having energy packets with pulsed energies (per packet) of about 150 µJ. The energy source 1200 (e.g., laser) may provide energy (e.g., laser beam) having energy packets with pulsed energies (per packet) of about 160 µJ. The energy source 1200 (e.g., laser) may provide energy (e.g., laser beam) having energy packets with pulsed energies (per packet) of about 170 µJ. The energy source 1200 (e.g., laser) may provide energy (e.g., laser beam) having energy packets with pulsed energies (per packet) of about 180 µJ. The energy source 1200 (e.g., laser) may provide energy (e.g., laser beam) having energy packets with pulsed energies (per packet) of about 190 µJ. The energy source 1200 (e.g., laser) may provide energy (e.g., laser beam) having energy packets with pulsed energies (per packet) of about 200 µJ. The energy source 1200 (e.g., laser) may provide energy (e.g., laser beam) having energy packets with pulsed energies (per packet) of about 20,000 µJ. The energy source 1200 (e.g., laser) may provide energy (e.g., laser beam) having energy packets with pulsed energies (per packet) of about 100,000 µJ. The energy source 1200 (e.g., laser) may provide energy (e.g., laser beam) having energy packets with pulsed energies (per packet).

The energy source 1200 (e.g., laser) may provide energy (e.g., laser beam) having a wavelength from e.g. about at least 300 nm to about 5 mm or more. The energy source 1200 (e.g., laser) may provide energy (e.g., laser beam) having a wavelength of about at least 600 to about 1500 nm or more. The energy source 1200 (e.g., laser) may provide energy (e.g., laser beam) having a wavelength from about at least 350 nm to about 1800 nm or more. The energy source 1200 (e.g., laser) may provide energy (e.g., laser beam) having a wavelength from about at least 1800 nm to about 5 mm or more. The energy source 1200 (e.g., laser) may provide energy (e.g., laser beam) having a wavelength of about 300 nm. The energy source 1200 (e.g., laser) may provide energy (e.g., laser beam) having a wavelength of about 400 nm. The energy source 1200 (e.g., laser) may provide energy (e.g., laser beam) having a wavelength of about 600 nm. The energy source 1200 (e.g., laser) may provide energy (e.g., laser beam) having a wavelength of about 700 nm. The energy source 1200 (e.g., laser) may provide energy (e.g., laser beam) having a wavelength of about 800 nm. The energy source 1200 (e.g., laser) may provide energy (e.g., laser beam) having a wavelength of about 900 nm. The energy source 1200 (e.g., laser) may provide energy (e.g., laser beam) having a wavelength of about 1200 nm. The energy source 1200 (e.g., laser) may provide energy (e.g., laser beam) having a wavelength of about 1200 nm. The energy source 1200 (e.g., laser) may provide energy (e.g., laser beam) having a wavelength of about 1200 nm. The energy source 1200 (e.g., laser) may provide energy (e.g., laser beam) having a wavelength of about 1300 nm. The energy source 1200 (e.g., laser) may provide energy (e.g., laser beam) having a wavelength of about 1400 nm. The energy source 1200 (e.g., laser) may provide energy (e.g., laser beam) having a wavelength of about 1500 nm. The energy source 1200 (e.g., laser) may provide energy (e.g., laser beam) having a wavelength of about 1600 nm. The energy source 1200 (e.g., laser) may provide energy (e.g., laser beam) having a wavelength of about 1700 nm. The energy source 1200 (e.g., laser) may provide energy (e.g., laser beam) having a wavelength of about 1800 nm. The energy source 1200 (e.g., laser) may provide energy (e.g., laser beam) having a wavelength of about 1900 nm. The energy source 1200 (e.g., laser) may provide energy (e.g., laser beam) having a wavelength of about 2000 nm. The energy source 1200 (e.g., laser) may provide energy (e.g., laser beam) having a wavelength of about 3000 nm. The energy source 1200 (e.g., laser) may provide energy (e.g., laser beam) having a wavelength of about 4000 nm. The energy source 1200 (e.g., laser) may provide energy (e.g., laser beam) having a wavelength of about 5000 nm.

As shown in FIG. 46, the energy source 1200 may project a laser beam 1202 through a shutter 1104. Once the laser beam 1202 exits the shutter 1204, the laser beam 1202 may be directed through a rotating half-wave plate 1206. The rotating half-wave plate 1206 may alter the polarization state of the laser beam 1202 such that the difference in phase delay between the two linear polarization directions is π. The difference in phase delay may correspond to a propagation phase shift over a distance of λ/2. Other types of wave plates may be utilized with the system disclosed herein; for example, a rotating quarter-wave plate may be used. The rotating half-wave plate 1206 may be a true zero-order wave plate, a low order wave plate, or a multiple-order wave plate. The rotating half-wave plate 1206 may be composed of crystalline quartz ($SiO_2$), calcite ($CaCO_3$), magnesium fluoride ($MgF_2$), sapphire ($Al_2O_3$), mica, or a birefringent polymer.

The laser beam 1202 may exit the rotating half-wave plate 1206 and may be directed through a polarizing beam splitter 1208. The polarizing beam splitter 1208 may split the laser beam 1202 into a first laser beam 1202*a* and a second laser beam 1202*b*. The first laser beam 1202*a* may be directed to a beam dump 1210. The beam dump 1210 is an optical element that may be used to absorb stray portions of a laser beam. The beam dump 1210 may absorb the first laser beam 1202*a*. The first laser beam 1202*a* may be a stray laser beam. The beam dump 1210 may absorb the second laser beam 1202*b*. The second laser beam 1202*b* may be a stray laser beam. The laser beam 1202 may be directed into the beam dump 1210 in its entirety and thus, may serve as a default "off" state of the printing system. The second laser beam 1202*b* may be directed to a beam expander 1212. The beam expander 1212 may expand the size of the second laser beam 1202*b*. The beam expander 1212 may increase the diameter of the input, second laser beam 1202*b* to a larger diameter of an output, expanded laser beam 1254. The beam expander 1212 may be a prismatic beam expander. The beam expander 1212 may be a telescopic beam expander. The beam expander 1212 may be a multi-prism beam expander. The beam expander 1212 may be a Galilean beam expander. The beam expander 1212 may provide a beam expander power of about 2×, 3×, 5×, 10×, 20×, or 40×. The beam expander 1212 may provide a beam expander power ranging from about 2× to about 5×. The beam expander 1212 may provide continuous beam expansion between about 2× and about 5×. The beam expander 1212 may provide a beam expander power ranging from about 5× to about 10×. The beam expander 1212 may provide continuous beam expansion between about 5× and about 10×. The expanded laser beam 1254 may be collimated upon exiting the beam expander 1212.

After exiting the beam expander 1212, the expanded laser beam 1254 may be directed to a first mirror 1214*a*, which may re-direct the expanded laser beam 1254 to a first spatial light modulator (SLM) 1216*a*. After exiting the first SLM 1216, the expanded laser beam 1254 may be directed to an f1 lens 1218. The f1 lens 1218 may be a focusing lens. After exiting the f1 lens, the expanded laser beam 1254 may be directed to a mirror with blocking element 1250. The mirror with blocking element 1250 may be used to suppress illumination from a zero-order spot.

Once the expanded laser beam 1254 is reflected by the mirror with blocking element 1250, the expanded laser beam 1254 may be transmitted through an f2 lens 1222. The f2 lens 1222 may be a focusing lens. After exiting the f2 lens 1222, the expanded laser beam 1254 may be directed to a second SLM 1216*b*. The SLMs (i.e., the first SLM 1216*a* and the second SLM 1216*b*) may be controlled by a computer system 1101. The SLMs may perform all of the functions, as described supra, of the SLM 1016 and the SLM 1116, as presented in FIGS. 44 and 45, respectively.

After exiting the second SLM 1216*b*, the expanded laser beam 1254 may be directed to an f3 lens 1228. After exiting the f3 lens, the expanded laser beam 1254 may be directed to blocking element 1220. The blocking element 1220 may be immovable. The blocking element 1220 may be used to suppress illumination from a zero-order spot. After exiting the blocking element 1220, the expanded energy beam 1254 may be directed through an f4 lens 1238. The f4 lens 1238 may be a focusing lens. After exiting the f4 lens 1238, the expanded laser beam 1254 may be directed onto a second mirror 1214*b* and may be subsequently directed onto a third mirror 1214*c*. The third mirror 1214*c* may re-direct the expanded laser beam 1254 through a long pass dichroic mirror 1224. The first mirror 1214*a*, the second mirror 1214*b*, and/or the third mirror 1214*c* may be controlled with a computer system 1101. The computer system 1101 may turn the first mirror 1214*a*, the second mirror 1214*b*, and/or the third mirror 1214*c* "on" or "off" in order to re-direct the expanded laser beam 1254 as desired. The dichroic mirror may be a short pass dichroic mirror. The long pass dichroic mirror 1224 may reflect the expanded laser beam 1254 into the focusing objective 1232. In some instances, a beam combiner may be used to re-direct the expanded laser beam 1254 into the focusing objective 1232 instead of using the long pass dichroic mirror 1224. The long pass dichroic mirror 1224 may be controlled with a computer system 1101 to re-direct the expanded laser beam 1254 into the focusing objective 1232. The focusing objective 1232 may concentrate the expanded laser beam 1254 as it is projected into the printing chamber 1234. The printing chamber 1234 may be a media chamber 122. The printing chamber 1234 may comprise a cell-containing medium, a plurality of cells, cell constituents (e.g., organelles), and/or at least one polymer precursor.

The printing chamber 1234 may be mounted on a movable stage 1246. The movable stage 1246 may be an xy stage, a z stage, and/or an xyz stage. The movable stage 1246 may be manually positioned. The movable stage 1246 may be automatically positioned. The movable stage 1246 may be a motorized stage. The movable stage 1246 may be controlled by the computer system 1101. The computer system 1101 may control the movement of the movable stage 1246 in the x, y, and/or z directions. The computer system 1101 may automatically position the movable stage 1246 in a desired x, y, and/or z position. The computer system 1101 may position the movable stage 1246 in a desired x, y, and/or z position with a positional accuracy of at most about 3 μm. The computer system 1101 may position the movable stage 1246 in a desired x, y, and/or z position with a positional accuracy of at most about 2 μm. The computer system 1101 may position the movable stage 1246 in a desired x, y, and/or z position with a positional accuracy of at most about 1 μm. The computer system 1101 may automatically adjust the position of the movable stage 1246 prior or during three-dimensional printing. The computer system 1101 may comprise a piezo controller to provide computer-controlled z-axis (i.e., vertical direction) positioning and active location feedback. The computer system 1101 may comprise a joystick console to enable a user to control a position of the movable stage 1246. The joystick console may be a z-axis console and/or an x-axis and y-axis console. The movable stage 1246 may comprise a printing chamber holder. The printing chamber holder may be a bracket, a clip, and/or a recessed sample holder. The movable stage 1246 may comprise a multi-slide holder, a slide holder, and/or a petri dish holder. The movable stage 1246 may comprise a sensor to provide location feedback. The sensor may be a capacitive sensor. The sensor may be a piezoresistive sensor. The movable stage 1246 may comprise at least one actuator (e.g., piezoelectric actuator) that moves (or positions) the movable stage 1246.

A light-emitting diode (LED) collimator 1240 may be used as a source of collimated LED light 1256. The LED collimator 1240 may comprise a collimating lens and an LED emitter. The LED may be an inorganic LED, a high brightness LED, a quantum dot LED, or an organic LED. The LED may be a single color LED, a bi-color LED, or a tri-color LED. The LED may be a blue LED, an ultraviolet LED, a white LED, an infrared LED, a red LED, an orange LED, a yellow LED, a green LED, a violet LED, a pink LED, or a purple LED. The LED collimator 1240 may project a beam of collimated LED light 1256 through an f6 lens 1248. The f6 lens 1248 may be a focusing lens. Once the collimated LED light 1256 is transmitted through the f6 lens 1248, the collimated LED light 1156 may be directed into a light focusing objective 1236. The light focusing objective 1236 may focus the collimated LED light 1256 into the printing chamber 1234. The light focusing objective 1236 may focus the collimated LED light 1256 in the sample medium. The light focusing objective 1236 may focus the collimated LED light 1256 in the cell-containing medium. The collimated LED light 1256 may be transmitted through the printing chamber 1234 and into the focusing objective 1232. Once the collimated LED light 1256 exits the focusing objective 1232, the collimated LED light 1256 may be directed onto the long pass dichroic mirror 1224. The collimated LED light 1256 that is reflected off of the long pass dichroic mirror 1224 may be the sample emission 1226. The long pass dichroic mirror 1224 may re-direct the sample emission 1226 into an f5 lens 1244. The f5 lens may be a focusing lens. Once sample emission 1226 is transmitted through the f5 lens 1244, a detection system 1230 detects and/or collects the sample emission 1226 for imaging. The detection system 1230 may comprise at least one photomultiplier tube (PMT). The detection system 1230 may comprise at least one camera. The camera may be a complementary metal-oxide semiconductor (CMOS) camera, a scientific CMOS camera, a charge-coupled device (CCD) camera, or an electron-multiplying charge-coupled device (EM-CCD). The detection system 1230 may comprise at least one array-based detector.

Figure 47:
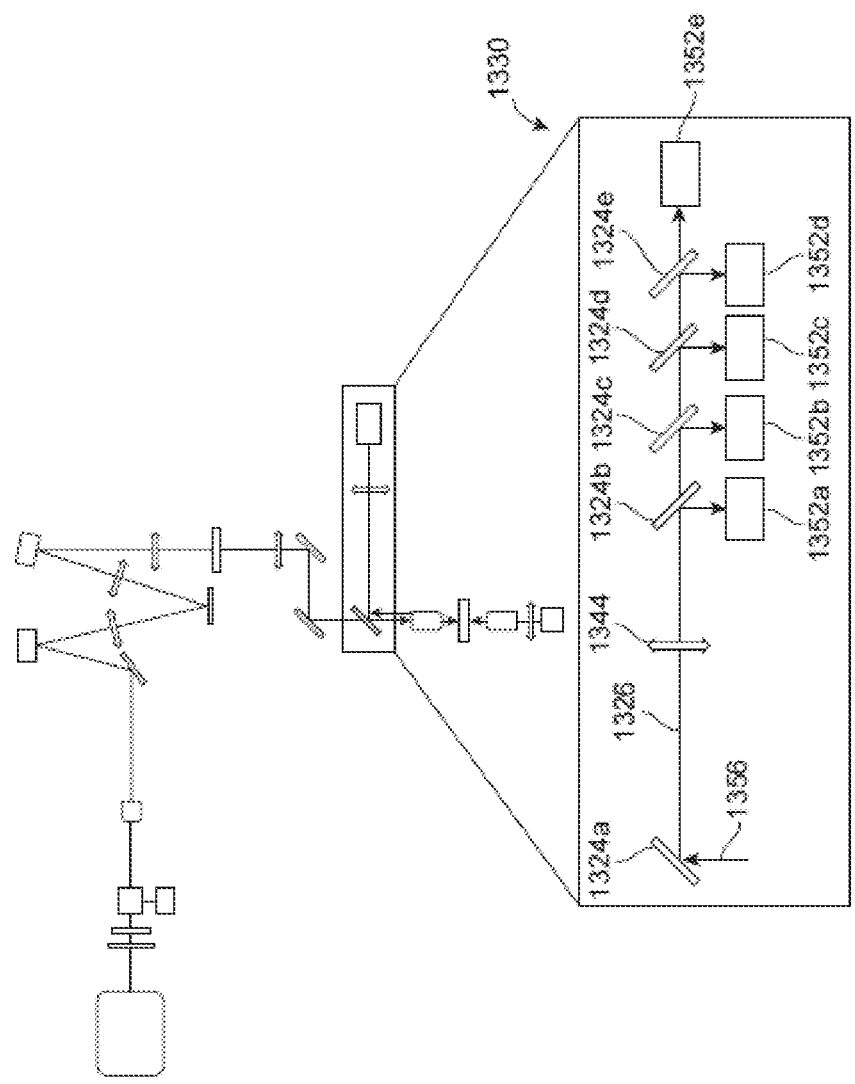
FIG. 47 illustrates a light detection system.

FIG. 47 illustrates a light detection system 1330. The light detection system 1330 may comprise a plurality of long pass dichroic mirrors arranged in series. The light detection system 1330 may comprise a plurality of long pass dichroic mirrors arranged in parallel. The light detection system 1330 may comprise a plurality of long pass dichroic mirrors arranged in series and parallel. As shown in FIGS. 44-46, the optical paths may comprise an LED collimator that projects a beam of collimated LED light 1356 onto the focusing objectives. Once the collimated LED light 1356 is reflected from the first long pass dichroic mirror 1324*a*, the collimated LED light 1356 may be converted to a sample emission 1326. The sample emission 1326 may be directed through an f5 lens 1344. The f5 lens 1344 may be a focusing lens. After the sample emission 1326 exits the f5 lens 1344, the sample emission 1326 may be directed to a series of long pass dichroic mirrors comprising a second long pass dichroic mirror 1324*b*, a third long pass dichroic mirror 1324*c*, a fourth long pass dichroic mirror 1324*d*, and a fifth long pass dichroic mirror 1324*e*, as shown in FIG. 47. The sample emission 1326 may be reflected off of the second long pass dichroic mirror 1324*b* and onto a first light detector 1352*a*. The sample emission 1326 may be reflected off of the third long pass dichroic mirror 1324*c* and onto a second light detector 1352*b*. The sample emission 1326 may be reflected off of the fourth long pass dichroic mirror 1324*d* and onto a third light detector 1352*c*. The sample emission 1326 may be reflected off of the fifth long pass dichroic mirror 1324*e* and onto a fourth light detector 1352*d*. The sample emission 1326 may be reflected off of the fifth long pass dichroic mirror 1324*e* and onto a fifth light detector 1352*e*. The light detector may be a photomultiplier tube (PMT). The light detector may be a camera. The light detector may be a complementary metal-oxide semiconductor (CMOS) camera, a scientific CMOS camera, a charge-coupled device (CCD) camera, or an electron-multiplying charge-coupled device (EM-CCD). The light detector may be an array-based detector. The light detection system 1330 may comprise a plurality of long pass dichroic mirrors that have progressively red-shifted cutoff wavelengths. In some instances, the second long pass dichroic mirror 1324*b* may have a cutoff wavelength of about 460 nm, the third long pass dichroic mirror 1324*c* may have a cutoff wavelength of about 500 nm, the fourth long pass dichroic mirror 1324*d* may have a cutoff wavelength of about 540 nm, the fifth long pass dichroic mirror 1324*e* may have a cutoff wavelength of about 570 nm.

The light detection system 1330 may be controlled by the computer system 1101. The computer system 1101 may collect and/or process the signals obtained by the first light detector 1352*a*, the second light detector 1352*b*, the third light detector 1352*c*, and the fourth light detector 1352*d*. The computer system 1101 may provide control feedback to the three-dimensional printing system based on the light detector signals, of the light detection system 1330, which may be collected and/or processed by the computer system 1101. The computer system 1101 may have control feedback over any optical component and/or hardware of the optical paths described in FIGS. 44-46. The computer system 1101 may have control feedback over any optical component and/or hardware of the light detection system 1330 shown in FIG. 47. The computer system 1101 may control, for example, an SLM, a shutter, a movable stage, a mirror, a lens, a focusing objective, a beam expander, an LED collimator, a grating, and/or a blocking element in response to a signal from the light detection system 1330.

Figure 5A:
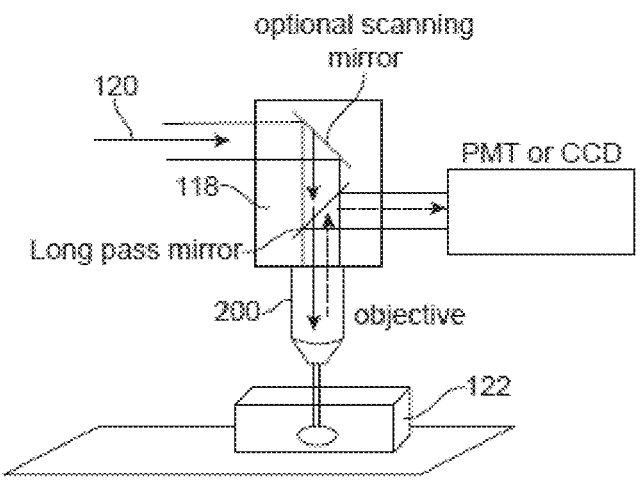
FIGS. 5A-5B illustrate various embodiments of the multi-photon tissue print head.

FIG. 5A illustrates an embodiment of the multi-photon tissue print head 118. The multi-photon print-head 118 may receive the multi-photon laser beam 120 (comprising one or more wavelengths) from the laser system 116 and may focus the beam 120 through the final optical path with is comprised of finishing optics that are comprised of an optional scan head, long pass mirror for use collection and recording of back-scatter light and a focusing objective 200, projecting the beam 120 into the media chamber 122. The light may be collected by the same objective as used to print, and then shunted via a long-pass mirror to the single or bank of PMTs, or a CCD camera.

In some designs, the optics may send the laser through a fiber optic cable for easier control of where the light is deposited in the tissue printing vessel.

The systems disclosed herein can utilize a range of focusing objectives, for example, with an increasingly lower magnification; the field of view may be increasingly larger. In some cases, the field of view may be the print area that the microscope is capable of, in a single projection area. In some cases, 5×, 10×, or 20× objectives may be employed. In some cases, objectives with high numerical apertures ranging between at least about 0.6 and about 1.2 or more may be employed. The systems disclosed herein may use an objective lens with a magnification ranging from e.g., about 1× to about 100×. The systems disclosed herein may use an objective lens with a magnification of about 1×. The systems disclosed herein may use an objective lens with a magnification of about 2×. The systems disclosed herein may use an objective lens with a magnification of about 3×. The systems disclosed herein may use an objective lens with a magnification of about 4×. The systems disclosed herein may use an objective lens with a magnification of about 10×. The systems disclosed herein may use an objective lens with a magnification of about 20×. The systems disclosed herein may use an objective lens with a magnification of about 40×. The systems disclosed herein may use an objective lens with a magnification of about 60×. The systems disclosed herein may use an objective lens with a magnification of about 100×.

To maintain structural fidelity of the printed tissues, a water-immersion objective lens may be ideal so as to substantially match the angle of incidence within the cell-containing liquid biogel media 126. A water-immersion objective lens corrected for refractive index changes may be used as printing takes place in liquid media which has a significantly different refractive index from air.

Figure 5B:
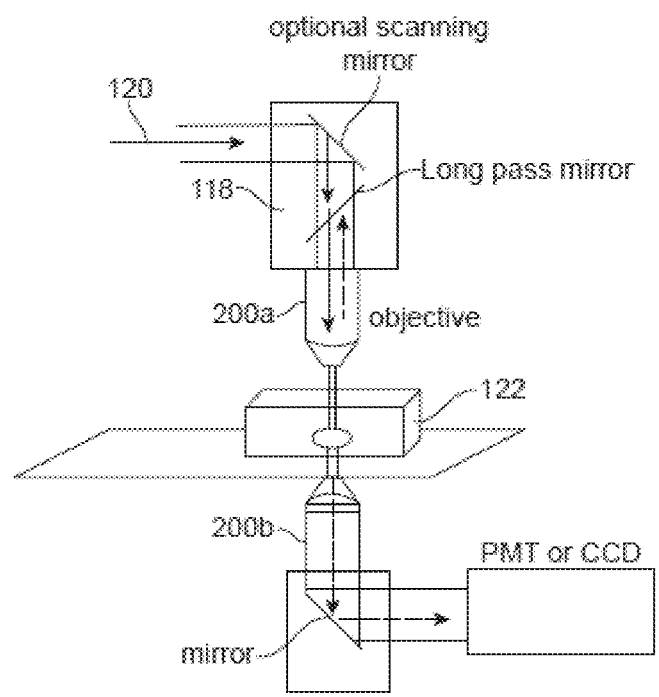

FIG. 5B illustrates a print head 118 comprising a first objective lens 200*a* and a second objective lens 200*b*. FIG. 5B illustrates inverted optics for imaging structures. In this embodiment, light may be collected by inverted optics and channeled to a CCD camera, a single PMT, as shown in FIG. 5B, or a bank of PMTs to create a multi-color image. In some embodiments, a second objective head may be inverted and images may be collected from the underside of the tissue and incident light read by PMTs with a series of long pass or band-pass mirrors.

In order for a multi-photon based printer to switch from a printing mode to an imaging mode, x, y raster scanning may be engaged and the DMD or SLM paths may be bypassed or the devices rendered in an off or inactive position, or removing them from the light path such that there is only a single laser line hitting the x, y scanning optics. DMD or SLM paths may also in some instances be used for imaging.

Switching to imaging mode may have several uses during the printing process: 1) imaging can be used to monitor collagen generation rates as collagen naturally produces an emission via second harmonic generation, which is a process when two-photon excitation is scanned across the structures, 2) the edges of printed tissues can be found using imaging mode facilitating the proper linking of blood vessels and other tissue structures along edges of projection spaces, 3) printed tissue structures can be validated for structural integrity and fidelity to the projected images in real-time, and 4) if cells that are temporarily labeled are used, they can be located within the printed tissues for process validation or monitoring.

It may be appreciated that the laser system 116 of the above embodiments may have a variety of points of software control including, but not limited to: The CAD images may be projected by programing changes that are hardwired to the SLM and/or DMD devices; If TAG lenses are used to create a Bessel beam, the current generated to induce the tunable acoustic gradient (TAG) in the TAG lens may be under the control of computer software; The mirrors that direct the laser excitation in the single beam incarnation and may act as an off/on switch for the multi-laser design may be controlled by computer software; The laser intensity via an attenuation wheel and tuning to different frequencies may be controlled by software input; Microscope stage movement may be under software control; Movement of microscope objective or associated fiber optics may be under software control; Edge finding, illumination, and control of the inverted objective by movement or on/off status may be under software control; any imaging or light path controls (mirrors, shutters, scanning optics, SLMs, DMD etc.) may be under control of software.

Figure 6A:
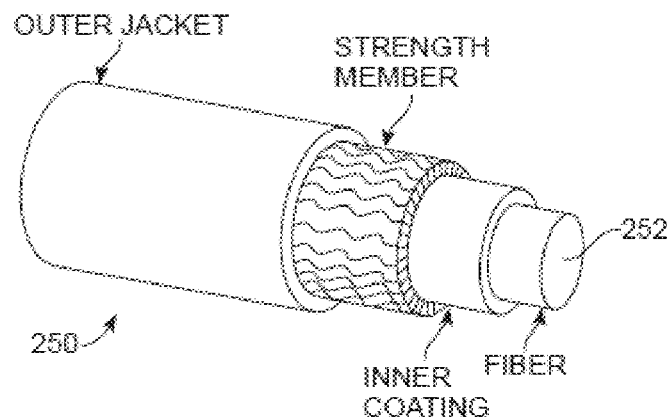
FIGS. 6A-6B illustrate embodiments of a removable and attachable fiber optic cable accessory.
Figure 6B:
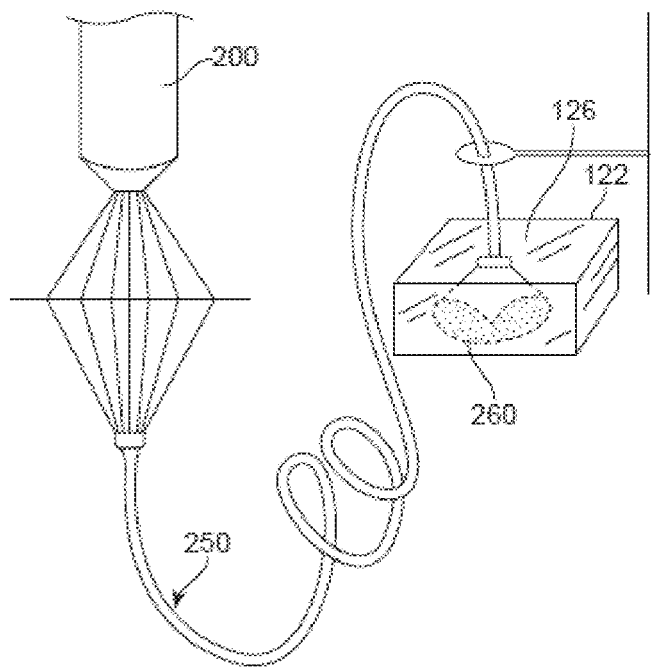

To accommodate rapid printing, the objective 200 may be equipped with a fiber optic cable. FIG. 6A illustrates an embodiment of a removable and attachable fiber optic cable accessory 250. In this embodiment, the accessory 250 may comprise a fiber optic cable 252 and a fitting (not shown in FIGS. 6A-6B) which is attachable to the multi-photon tissue printing print-head (not shown in 6A-6B). The fiber optic cable 252 can then be positioned within the media 126 of the media chamber 122, as illustrated in FIG. 6B. Thus, the multi-photon laser beam 120 may pass through the objective 200 and the fiber optic cable 252 to deliver the laser energy to the media 126, creating the desired complex tissue structure 260. To avoid moving the microscope objective during the printing process or the printing vessel that contains delicate tissue structures, the fiber optic cable itself may be moved if larger regions of tissue need to be printed. In some cases, the accessory 250 can be sterilized or replaced so that direct insertion into the media 126 does not compromise sterility or cross-contaminate printed cells.

Depending upon the power input into the fiber optic cable, multi-photon lasers may be capable of inducing irreversible damage to the core of the fiber optic cable. Thus, in some cases, induced wavelength chirping by group delayed dispersion (GDD) may be provided to minimize this potential damage, by effectively dispersing the photons to elongate the laser pulse. This may be used to either minimize damage to cells in the print media or to extend the life of fiber optic cables. In such instances, a GDD device may be provided in the laser system 116 after the SLM or DMD and before entry to the print-head optics 118.

In some cases, three-dimensional printing of the desired tissue may be carried out with a single objective 200 or an objective 200 with an attached fiber optic accessory 250, wherein the one to three different configurations, each associated with a distinct laser line and representing a distinct shape or portion of the tissue may be pulsed though the same objective 200. In such cases, a timed shutter system may be installed such that there is no or minimal interference between images being projected. Thus, laser multiplexing may be employed to allow generation of portions of the tissue structure simultaneously at multiple points while utilizing the same CAD model of the tissue structure. Likewise, the laser multiplexing may utilize different but contiguous CAD based tissue models, minimizing the movement needed for larger structure printing while decreasing overall print time further. For example, a vascular bed may have internal structures such as valves in the larger blood vessels that prevent venous back flow in normal circulation. These valve structures may be printed simultaneously with the blood vessel walls. In such a case, the scaffolding associated with the valve structure and/or blood vessel walls may be difficult to print separately.

The instantaneously formed three-dimensional structure may be repeated throughout the print space during one round of printing. In biological systems, small units may often be repeated throughout the structure. Therefore, repeated generation of a same structure in one print round may be useful for generating functional tissues. Additional, non-repetitive, fine featured structures and subsequent structures from the same cell-print material may be created that line-up with or link to the first structure printed.

Figure 7:
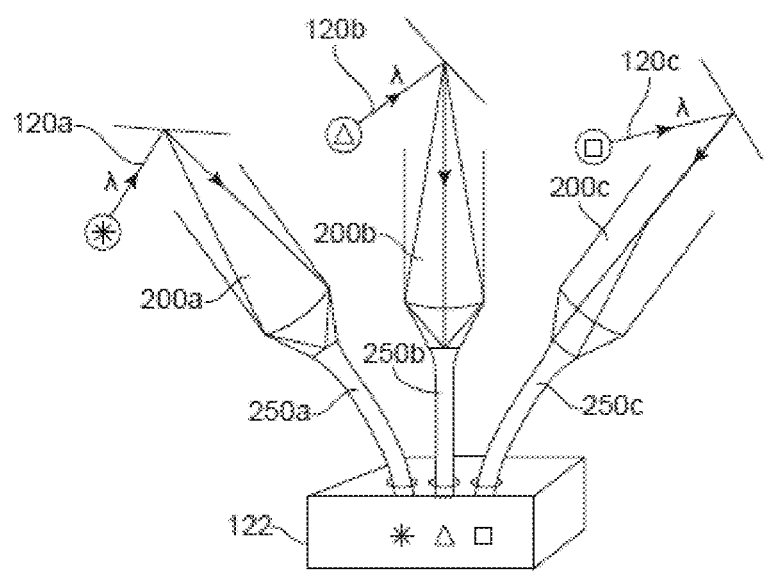
FIG. 7 illustrates an embodiment wherein the print-head optics includes at least three objectives, wherein each objective includes a fiber optic cable accessory directed into a single media chamber.
Figure 8:
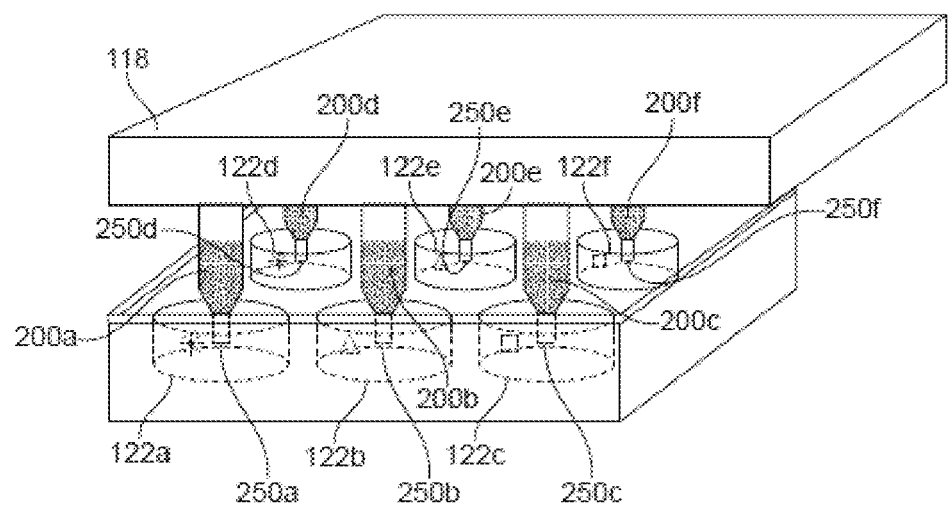
FIG. 8 illustrates an embodiment wherein the print-head optics includes at least six objectives, wherein each objective includes a fiber optic cable accessory directed into a separate media chamber such as a separate well of a multi-well plate.

In some embodiments, the multi-photon tissue printing print-head 118 may include multiple printing "heads" or sources of multi-photon excitation via a first laser objective 200a, a second laser objective 200b, and a third laser objective 200c as illustrated in FIGS. 7-8. FIG. 7 illustrates an embodiment wherein the multi-photon tissue printing print-head 118 may include a first laser objective 200a, a second laser objective 200b, and a third laser objective 200c, wherein the first laser objective 200a may include a first fiber optic cable accessory 250a, the second laser objective 200b may include a second fiber optic cable accessory 250b, and the third laser objective 200c may include a third fiber optic cable accessory 250c. The first fiber optic cable accessory 250a, the second fiber optic cable accessory 250b, and the third fiber optic cable accessory 250c may be directed into a single media chamber 122. The media chamber 122 may have an open top or a sealed top with port access by each accessory fiber optic cable accessory (i.e., via the first fiber optic cable accessory 250a, the second fiber optic cable accessory 250b, and the third fiber optic cable accessory 250c). This arrangement may increase the speed of large, rapid tissue printing, while maintaining control over the final tissue structure. In some cases, the first fiber optic cable accessory 250a, the second fiber optic cable accessory 250b, and the third fiber optic cable accessory 250c may deliver a projection of the same tissue structure. In other cases, each the first fiber optic cable accessory 250a, the second fiber optic cable accessory 250b, and the third fiber optic cable accessory 250c may deliver a first laser beam projection 120a, a second laser beam projection 120b, and a third laser beam projection 120c, respectively, of a different tissue structure. Given the flexible arrangement of the multiple laser objectives and the ability of directing the fiber optic cables into the same area within the media chamber 122, the tissue structures may be simultaneously printed. The resulting tissue structures may be linked or not linked together. The print time of a given tissue structure may have an inverse relationship to the number of laser delivery elements with some consideration for the movement restrictions and considerations to be accounted for with each additional excitation source.

FIG. 8 illustrates an embodiment wherein the multi-photon tissue printing print-head 118 may include a first objective 200a, a second objective 200b, a third objective 200c, a fourth objective 200d, a fifth objective 200e, and a sixth objective 200f, wherein each objective may include a first fiber optic cable accessory 250a, a second fiber optic cable accessory 250b, a third fiber optic cable accessory 250c, a fourth fiber optic cable accessory 250d, a fifth fiber optic cable accessory 250e, and a sixth fiber optic cable accessory 250f, respectively, directed into a separate first media chamber 122a, a second media chamber 122b, a third media chamber 122c, a fourth media chamber 122d, a fifth media chamber 122e, and a sixth media chamber 122f, respectively. The plurality of media chambers may be a multi-well plate, wherein each well of the multi-well plate is a separate, individual media chamber. In some cases, the first fiber optic cable accessory 250a, the second fiber optic cable accessory 250b, the third fiber optic cable accessory 250c, the fourth fiber optic cable accessory 250d, the fifth fiber optic cable accessory 250e, and the sixth fiber optic cable accessory 250f may deliver at least one projection of the same tissue structure. This provides multiple copies of the tissue structure simultaneously. In other cases, the first fiber optic cable accessory 250a, the second fiber optic cable accessory 250b, the third fiber optic cable accessory 250c, the fourth fiber optic cable accessory 250d, the fifth fiber optic cable accessory 250e, and the sixth fiber optic cable accessory 250f may deliver a first multi-photon laser beam projection 120a, a second multi-photon laser beam projection 120b, and a third multi-photon laser beam projection 120c of a different tissue structure. In some cases, the print time may be greatly reduced due to the ability of producing multiple copies simultaneously.

Figure 9:
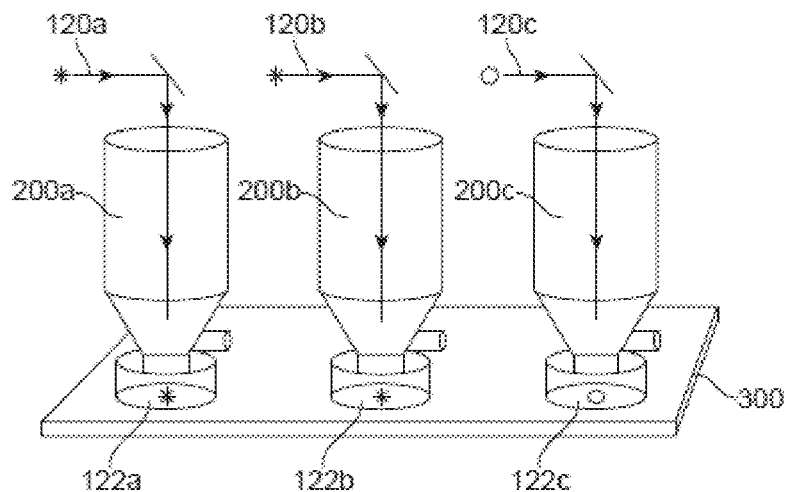
FIG. 9 illustrates embodiments of print-head optics having an array of objectives acting as print heads.
Figure 10:
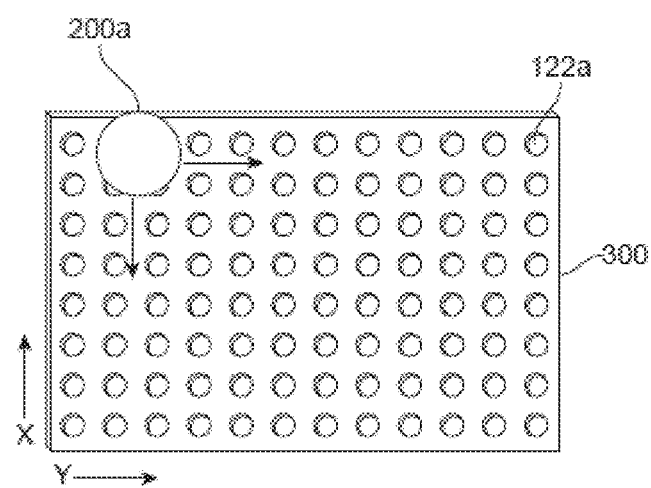
FIG. 10 illustrates objectives programmed to move over the multi-well plate in X and Y directions to deliver the laser beam projections into each well.

In some embodiments, the multi-photon tissue printing print-head 118 may include a serial array of objectives comprising a first objective 200a, a second objective 200b, and a third objective 200c, as illustrated in FIG. 9. In this embodiment, each objective may be aligned with a separate media chamber. For example, the first objective 200a may be aligned with a first media chamber 122a, the second objective 200b may be aligned with a second media chamber 122b, the third objective 200c may be aligned with a third media chamber 122c. In some instances, the multiple media chambers may be wells of a multi-well plate 300. In some embodiments, the first objective 200a, the second objective 200b, and the third objective 200c may deliver projection of the same tissue structure. In other cases, the laser beam projections may differ per well. The first objective 200a, the second objective 200b (not shown in FIG. 10), and the third objective 200c (not shown in FIG. 10) may be programmed to move over the multi-well plate 300 in the x and y directions, as illustrated in FIG. 10, to deliver the laser beam projections into each well. Alternatively, it may be appreciated that the objectives may remain stationary while the multi-well plate 300 moves in the x and y directions. Thus, for example, a serial array having three objectives can print tissue in a six well plate in two steps: three tissue structures simultaneously and then three more tissue structures simultaneously. It may be appreciated that plates having any number of wells may be used including, but not limited to at least about 96 wells to about 394 wells, or more. The multi-well plate 300 may comprise at least a first media chamber 122a. The multi-well plate 300 may comprise at least 1 well. The multi-well plate 300 may comprise at least 4 wells. The multi-well plate 300 may comprise at least 6 wells. The multi-well plate 300 may comprise at least 8 wells. The multi-well plate 300 may comprise at least 12 well. The multi-well plate 300 may comprise at least 16 wells. The multi-well plate 300 may comprise at least 24 wells. The multi-well plate 300 may comprise at least 48 wells. The multi-well plate 300 may comprise at least 96 wells. The multi-well plate 300 may comprise at least 384 wells. The multi-well plate 300 may comprise at least 1536 wells.

It may be appreciated that in the embodiments described herein, the microscope stage may be able to move, the microscope head may be able to move, and/or an associated fiber optic cable attached to the printing objective may be able to move in order to print larger spaces.

3D Printing Methods

In an aspect, the present disclosure provides a method of printing an organ and/or an organoid. The method may comprise polymerization of a photopolymerizable material by a laser light source. The organ and/or the organoid may be two-dimensional or three-dimensional. The organ and/or the organoid may be a lymph node. The organoid may be an islet of Langerhans. The organoid may be a hair follicle. The organ and/or the organoid may be a tumor and/or a tumor spheroid. The organoid may be a neural bundle and support cells such as, but not limited to Schwann cells and glial cells including satellite cells, olfactory ensheathing cells, enteric glia, oligodendroglia, astroglia, and/or microglia. The organoid may be a nephron. The organoid may be a liver organoid. The organoid may be an intestinal crypt. The organ and/or the organoid may be a primary lymphoid organ, a secondary lymphoid organ such as a spleen, a liver, a pancreas, a gallbladder, an appendix, a brain, a small intestine, a large intestine, a heart, a lung, a bladder, a kidney, a bone, a cochlea, an ovary, a thymus, a trachea, a cornea, a heart valve, skin, a ligament, a tendon, a muscle, a thyroid gland, a nerve, and/or a blood vessel.

Organization of an organ or organoid through the printing process, disclosed herein, may require or be implemented by the sequential deposition of at least about 1, 10, 50, 100, 200, 300, 500, 600, 700, 800, 900, 1000, 10000, 100000, 1000000 or more layers of cells. Organization of a lymphoid organ through the printing process may require or be implemented by the sequential deposition of between 1 and 100 layers of cells. The size of a layer of cells may be tissue dependent. The size of a layer of cells may comprise a larger three-dimensional structure that may be one layer of cells or may comprise multiple layers of cells. The layer of cells may comprise about at least 10, $10^2$, $10^3$, $10^4$, $10^5$, $10^6$, $10^7$, $10^8$, $10^9$, $10^{10}$, or more cells. Where precise placement of each cell type relative to the other is desired, cells should be printed in sequential steps with a wash step in between to remove the previously used media. Alternately, two or more cell types of different sizes may be printed simultaneously using two photopolymerizable materials of different polymerization wavelength and pore size, such that the larger cell type may become encapsulated in the pore of larger size and the smaller cell type may become encapsulated in the pore of smaller size. Cells are encapsulated in pores in accordance with the size of their nucleus, as the cytoskeleton is able to remodel based on the available space.

In another aspect, the present disclosure provides a method for using a three-dimensional (3D) cell-containing matrix, comprising: (a) providing a media chamber comprising a medium comprising (i) a plurality of cells and (ii) one or more polymer precursors; (b) directing at least one energy beam to the medium in the media chamber along at least one energy beam path that is patterned into a three-dimensional (3D) projection in accordance with computer instructions for printing the 3D cell-containing medical device in computer memory, to form at least a portion of the 3D cell-containing matrix comprising (i) at least a subset of the plurality of cells, and (ii) a polymer formed from the one or more polymer precursors; and (c) positioning the 3D cell-containing matrix in a subject.

Native architecture may be obtained from imaging data and rendered into two- or three-dimensional images with defined edges and/or grey areas, which are edges that are not precisely defined, but fall somewhere within a designated range, for projection into a polymerizable hydrogel.

In some embodiments, the agent is selected from the group consisting of growth factors, cytokines, chemokines, antibiotics, anticoagulants, anti-inflammatory agents, opioid pain-relieving agents, non-opioid pain-relieving agents, immune-suppressing agents, immune-inducing agents, monoclonal antibodies and stem cell proliferating agents. The plurality of cells may be from a subject. The plurality of cells may be autologous. The plurality of cells may be allogeneic. The plurality of cells may be selected from the list consisting of stromal endothelial cells, endothelial cells, follicular reticular cells or precursors thereof, naïve B cells or other immature B cells, memory B cells, plasma B cells, helper T cells and subsets of the same, effector T cells and subsets of the same CD+8 T cells, CD4+ T cells, regulatory T cells, natural killer T cells, naïve T cells or other immature T cells, dendritic cells and subsets of the same, follicular dendritic cells, Langerhans dendritic cells, dermally-derived dendritic cells, dendritic cell precursors, monocyte-derived dendritic cells, monocytes and subsets of the same macrophages and subsets of the same, leukocytes and subsets of the same. The B cells may be selected from the list consisting of naïve B cells, mature B cells, plasma B cells, B1 B cells, and B2 B cells. The T cells may be selected from the list consisting of CD8+ and CD4+.

Bioprinting materials may contain agents intended to promote growth of vasculature, including microvasculature, and nerves into the printed structure or into the surrounding native architecture. Additionally, printed biomaterials may contain agents intended promote differentiation of a stem or progenitor cell down a specified lineage. Such agents include but are not limited to: growth factors, cytokines, chemokines, antibiotics, anticoagulants, anti-inflammatory agents, opioid or non-opioid pain-relieving agents, immune-suppressing agents, immune-inducing agents, monoclonal antibodies, and/or stem cell proliferating agents.

Three-dimensional lithography may be used to generate functional partial organs or organoids that may serve an augmenting or independent physiologic function not necessarily dependent upon site of implantation. Such three-dimensional lithography can be achieved by holographic projection of light through use of a two light modulating systems in series, as disclosed in commonly invented U.S. Provisional Patent Appl. No. 62/469,948, entitled MULTI-PHOTON TISSUE PRINTING, which is incorporated herein by reference.

The method may comprise positioning the 3D cell-containing matrix in a subject.

A spatial light modulator (SLM) is an electrically programmable device that can modulate amplitude, phase, polarization, propagation direction, intensity or any combination thereof of light waves in space and time according to a fixed spatial (i.e., pixel) pattern. The SLM may be based on translucent, e.g. liquid crystal display (LCD) microdisplays. The SLM may be based on reflective, e.g. liquid crystal on silicon (LCOS) microdisplays. The SLM may be a microchannel spatial light modulator (MSLM), a parallel-aligned nematic liquid crystal spatial light modulator (PAL-SLM), a programmable phase modulator (PPM), a phase spatial light modulator (LCOS-SLM), or any combination thereof. An LCOS-SLM may comprise a chip that includes a liquid crystal layer arranged on top of a silicon substrate. A circuit may be built on the chip's silicon substrate by using semiconductor technology. A top layer of the LCOS-SLM chip may contain aluminum electrodes that are able to control their voltage potential independently. A glass substrate may be placed on the silicon substrate while keeping a constant gap, which is filled by the liquid crystal material. The liquid crystal molecules may be aligned in parallel by the alignment control technology provided in the silicon and glass substrates. The electric field across this liquid crystal layer may be controlled pixel by pixel. The phase of light can be modulated by controlling the electric field; a change in the electric field may cause the liquid crystal molecules to tilt accordingly. When the liquid crystal molecules tilt, the liquid crystal refractive indexes may change further modifying the optical path length and thus, causing a phase difference.

An SLM may be used to print the 3D biological material. A liquid crystal on silicon (LCOS)-SLM may be used to print the 3D biological material. A liquid crystal SLM may be used to print the 3D biological material. The SLM may be used to project a point-cloud representation or a lines-based representation of a computer model of the 3D biological material. The methods disclosed herein may comprise converting the point-cloud representation or lines-based representation into a holographic image. The SLM may be used to project the holographic image of the computer model of the 3D biological material. The SLM may be used to modulate the phase of light of a point-cloud representation or a lines-based representation of a computer model of the 3D biological material. The SLM may be used to modulate the phase of light of the holographic image of the computer model of the 3D biological material.

Projection of multi-photon excitation in three dimensions may also be achieved with the use of a dual digital micro-mirror device (DMD) system alone or in combination with a spatial light modulator (SLM). A pair of DMDs may be used with a pair of SLMs to print a 3D material using the methods described herein. At least one SLM and at least one DMD may be used to print a 3D material using the methods described herein. A pair of SLMs may be used to print a 3D material using the methods described herein. A pair of DMDs may be used to print a 3D material using the methods described herein. At least one SLM may be used to print a 3D material using the methods described herein. At least one DMD may be used to print a 3D material using the methods described herein. A DMD is an electrical input, optical output micro-electrical-mechanical system (MEMS) that allows for high speed, efficient, and reliable spatial light modulation. A DMD may comprise a plurality of microscopic mirrors (usually in the order of hundreds of thousands or millions) arranged in a rectangular array. Each microscopic mirror in a DMD may correspond to a pixel of the image to be displayed and can be rotated about e.g. 10-12° to an "on" or "off" state. In the "on" state, light from a projector bulb can be reflected into the microscopic mirror making its corresponding pixel appear bright on a screen. In the "off" state, the light can be directed elsewhere (usually onto a heatsink), making the microscopic mirror's corresponding pixel appear dark. The microscopic mirrors in a DMD may be composed of highly reflective aluminum and their length across is approximately 16 micrometers (μm). Each microscopic mirror may be built on top of an associated semiconductor memory cell and mounted onto a yoke which in turn is connected to a pair of support posts via torsion hinges. The degree of motion of each microscopic mirror may be controlled by loading each underlying semiconductor memory cell with a "1" or a "0." Next, a voltage is applied, which may cause each microscopic mirror to be electrostatically deflected about the torsion hinge to the associated+/−degree state via electrostatic attraction.

In another aspect, the present disclosure provides a method for printing a three-dimensional (3D) biological material. The x, y, and z dimensions may be simultaneously accessed while using the methods provided herein. The biological material may be a biologically functional tissue. The biological material may develop into a biologically functional tissue. The biological material may comprise a fully formed, a printed vasculature, a microvasculature, a porous network, a tube network, and/or a pore architecture which may provide delivery and/or diffusion of a sufficient concentration of nutrients and oxygen that may be conducive to prevent necrosis. The biological material may comprise a printed lymphatic network, a lymphatic vasculature, and/or a lymphatic microvasculature which may allow for biological functions including, but not limited to interstitial fluid homeostasis, regulation of the immune system, regulation of the circulatory system, regulation of inflammation, and lipid absorptions. The biological material may comprise cells arranged in a structure and/or architecture similar to the native tissue that is trying to replicate; thus, allowing for biological function similar to the biological function of the native tissue. Printing of ultra-fine tissue structures such as, but not limited to fine blood vessels such as capillaries, single cell layers of tissue, and layers of hard and/or soft tissues with mechanical properties of bone, cartilage, and/or tendons may be created.

The method may comprise receiving a computer model of the 3D biological material in computer memory. The computer model may be a computer-aided design (CAD) model. The CAD model may be a 3D wireframe, a 3D solid model such as a parametric model and a direct or explicit model, and/or a freeform surface model. The CAD model may be generated by a computer after a physical prototype is scanned and/or imaged using a device such as a 3D scanner, a computer tomography (CT) scanning device, a structured-light 3D scanner, a modulated light 3D scanner, a laser scanner, a microscope, or a magnetic resonance imaging (MRI) device. In some cases, the prototype image or scan is converted to a CAD model by using an algorithm that converts the prototype image or scan into a surface model, a mesh model, or a volume model. The method may comprise receiving computer model comprising a partial 3D structure and/or a complete 3D structure of the 3D biological material.

Next, the method may comprise providing a media chamber comprising a medium comprising a plurality of cells and one or more polymer precursors. The medium may comprise cell constituents (e.g., organelles). The medium may further comprise glutathione or a functional variant (or derivative) thereof. The plurality of cells may comprise cells of at least two different types. The method may further comprise subjecting at least a portion of the at least subset of the plurality of cells to differentiation to form the cells of the at least two different types. The at least the subset of the plurality of cells may comprise cells of at least two different types. The plurality of cells may comprise the cells of the at least two different types.

The media chamber may be multi-well plate, a chamber slide, a tissue culture slide, a container, a flask, a bioreactor chamber, a vessel, a bag such as a cell culture bag, a petri dish, a roller bottle, or a custom-fabricated well. The media chamber may be composed of polystyrene, glass, quartz, polypropylene, cyclo-olefin, or polyvinyl chloride (PVC). The media chamber may be surface treated. Non-limiting examples of surface treatments include plasma surface treatment, coating with carboxyl groups, hydroxyl groups, free amino groups, and/or poly-D-lysine to promote cell attachment, and/or coating with a hydrophilic and neutrally charged hydrogel layer to inhibit cell attachment. The media chamber may comprise a volume ranging from e.g. at least about 1 μl to about 30 L. The media chamber may comprise a volume ranging from e.g. at least about 1 μl to about 5 L. The media chamber may comprise a volume ranging from e.g. at least about 1 μl to about 1 L. The media chamber may comprise a volume ranging from e.g. at least about 1 μl to about 0.5 L. The media chamber may comprise a volume ranging from e.g. at least about 1 μl to about 250 ml. The media chamber may comprise a volume ranging from e.g. at least about 1 μl to about 100 ml. The media chamber may comprise a volume ranging from e.g. at least about 1 μl to about 50 ml. The media chamber may comprise a volume ranging from e.g. at least about 1 μl to about 25 ml. The media chamber may comprise a volume ranging from e.g. at least about 1 μl to about 10 ml. The media chamber may comprise a volume ranging from e.g. at least about 1 μl to about 5 ml. The media chamber may comprise a volume ranging from e.g. at least about 1 μl to about 1 ml. The media chamber may comprise a volume ranging from e.g. at least about 1 μl to about 500 μl. The media chamber may comprise a volume ranging from e.g. at least about 1 μl to about 100 μl. The media chamber may comprise a volume ranging from e.g. at least about 1 μl to about 50 μl. The media chamber may comprise a volume ranging from e.g. at least about 1 μl to about 25 μl. The media chamber may comprise a volume ranging from e.g. at least about 1 μl to about 10 μl. The media chamber may comprise a volume ranging from e.g. at least about 1 μl to about 5 μl.

The media chamber may comprise a volume of about 1 μl. The media chamber may comprise a volume of about 10 μl. The media chamber may comprise a volume of about 100 μl. The media chamber may comprise a volume of about 1000 μl. The media chamber may comprise a volume of about 5 ml. The media chamber may comprise a volume of about 10 ml. The media chamber may comprise a volume of about 20 ml. The media chamber may comprise a volume of about 30 ml. The media chamber may comprise a volume of about 40 ml. The media chamber may comprise a volume of about 50 ml. The media chamber may comprise a volume of about 60 ml. The media chamber may comprise a volume of about 70 ml. The media chamber may comprise a volume of about 5 ml. The media chamber may comprise a volume of about 80 ml. The media chamber may comprise a volume of about 90 ml. The media chamber may comprise a volume of about 100 ml. The media chamber may comprise a volume of about 200 ml. The media chamber may comprise a volume of about 300 ml. The media chamber may comprise a volume of about 400 ml. The media chamber may comprise a volume of about 500 ml. The media chamber may comprise a volume of about 600 ml. The media chamber may comprise a volume of about 700 ml. The media chamber may comprise a volume of about 800 ml. The media chamber may comprise a volume of about 900 ml. The media chamber may comprise a volume of about 1000 ml. The media chamber may comprise a volume of about 2 L. The media chamber may comprise a volume of about 3 L. The media chamber may comprise a volume of about 4 L. The media chamber may comprise a volume of about 5 L. The media chamber may comprise a volume of about 6 L. The media chamber may comprise a volume of about 7 L. The media chamber may comprise a volume of about 8 L. The media chamber may comprise a volume of about 9 L. The media chamber may comprise a volume of about 10 L. The media chamber may comprise a volume of about 20 L. The media chamber may comprise a volume of about 30 L. The media chamber may comprise a volume of about 40 L. The media chamber may comprise a volume of about 50 L. The media chamber may comprise a volume of about 60 L. The media chamber may comprise a volume of about 70 L. The media chamber may comprise a volume of about 80 L. The media chamber may comprise a volume of about 90 L. The media chamber may comprise a volume of about 100 L or more.

The medium may comprise a plurality of cells, one or more polymer precursors, cell constituents (e.g., organelles), and/or cell culture medium. The polymer precursors may comprise at least two different polymeric precursors. The polymeric precursors may be a polymerizable material. The polymer precursors may comprise collagen. Non-limiting examples of collagen types in the medium include fibrillar collagen such as type I, II, III, V, and XI collagen, fibril associated collagens with interrupted triple helices (FACIT) collagen such as type IX, XII, and XIV collagen, short chain collagen such as type VIII and X collagen, basement membrane collagen such as type IV collagen, type VI collagen, type VII collagen, type XIII collagen, or any combination thereof. The polymer precursors may comprise extracellular matrix components including, but not limited to proteoglycans such as heparan sulfate, chondroitin sulfate, and keratan sulfate, non-proteoglycan polysaccharide such as hyaluronic acid, and elastin, fibronectin, laminin, nidogen, or any combination thereof. In some instances, the polymer precursors may comprise polyglycolic acid (PGA), polylactic acid (PLA), alginate, polyethylene oxide, polyethylene glycol, polypropyleneoxide, poly(N-isopropylacrylamide), chitosan, fibrin, fibrinogen, polylactic acid-polyglycolic acid (PLGA) copolymer, poly(methyl methacrylate) (PMMA), polyvinyl alcohol (PVA), poly(propylene fumarate)s (PPFs), polycaprolactone (PCL), poly(β-amino ester), gelatin, dextran, chondroitin sulfate, or any combination thereof. Non-limiting examples of cell culture medium include Dulbecco's Modified Eagle Medium (DMEM), serum-free cell culture medium, RPMI 1640 medium, Minimum Essential Media (MEM), Iscove's Modified Dulbecco's Medium (IMDM), and Opti-MEM™ I Reduced Serum Medium.

The medium may be physically polymerized in order to form a biogel. The medium may be polymerized by a heat source in order to form a biogel. The medium may be chemically polymerized in order to form a biogel; for example, by use of a cross-linker. Non-limiting examples of cross-linkers include 1-ethyl-3-(3-dimethylaminopropyl)-carbodiimide (EDC), glutaraldehyde, and 1-ethyl-3-3-dimethyl aminopropyl carbodiimide (EDAC). The medium may comprise a photoinitiator, a cross-linker, collagen, hyaluronic acid and other glycosaminoglycans, poly-dl-lactic-co-glycolic acid (PLGA), poly-1-lactic acid (PLLA), polyglycolic acid (PGA), alginate, gelatin, agar, or any combination thereof. The biogel may comprise a photoinitiator, a cross-linker, collagen, hyaluronic acid and other glycosaminoglycans, poly-dl-lactic-co-glycolic acid (PLGA), poly-1-lactic acid (PLLA), polyglycolic acid (PGA), alginate, gelatin, agar, or any combination thereof. The polymer precursor may be collagen, hyaluronic acid and other glycosaminoglycans, poly-dl-lactic-co-glycolic acid (PLGA), poly-1-lactic acid (PLLA), polyglycolic acid (PGA), alginate, gelatin, agar, or any combination thereof.

The medium may further comprise a plurality of beads. In some cases, the at least portion of the 3D biological material, as formed, may include the plurality of beads. The at least portion of the 3D biological material, as formed, may include the plurality of microspheres and/or particles. The beads, microspheres, and/or particles may range in size from about 1 nanometer to about 200 micrometers. The beads, microspheres, and/or particles may be chemically inert. The beads, microspheres, and/or particles may be hollow. The beads, microspheres, and/or particles may be solid. The beads, microspheres, and/or particles may comprise a core and a shell. The beads, microspheres, and/or particles may be polymeric, magnetic, porous, metallic, fluorescent, dyed, hydrogel, lipid, or any combination thereof. The beads, microspheres, and/or particles may comprise latex, at least one type of extracellular matrix protein, a cell, a drug, a biopolymer, a lipid, a biocompatible polymer, a small molecule, or any combination thereof. Non-limiting examples of biopolymers include fibrin, fibrinogen, chitosan, cellulose, dextran, chitin, gelatin, collagen, glycogen, starch, and lignin. Non-limiting examples of biocompatible polymers include collagen, hyaluronic acid, chondroitin sulfate, polyglycolic acid (PGA), polylactic acid, alginate, polyethylene oxide (PEO), polyethylene glycol (PEG), polypropyleneoxide, poly(N-isopropylacrylamide), chitosan, fibrin, polylactic-co-glycolic acid (PLGA) copolymer, or any combinations thereof.

Multiple organoid units may be printed within a single structure to produce larger organs, up to and including a fully sized organ. Multiple lymphoid units may be printed within a single structure to produce larger immune organs, up to and including a fully sized lymph node or thymus.

The beads may further comprise signaling molecules or proteins. The signaling molecules or proteins may promote formation of the 3D biological material to permit organ function. The beads, microspheres, and/or particles may be functionalized with a protein, nucleic acid, and/or dye. The beads, microspheres, and/or particles may be functionalized with streptavidin. The surface of the beads, microspheres, and/or particles may be coated with at least one signaling molecule, a protein such as an antibody, a nucleic acid such as a DNA and/or RNA molecule, a polymer, a small molecule, and/or a dye. The beads, microspheres, and/or particles may encapsulate a payload such as, for example, a cell, a drug, a signaling molecule, a protein, a nucleic acid, a small molecule, a dye, and/or a polymer such as a biopolymer. The biodegradable beads, microspheres, and/or particles may have controlled release of the payload. The beads, microspheres, and/or particles may be biodegradable. The biodegradable beads, microspheres, and/or particles may have a controlled and/or customizable degradation rate. The beads, microspheres, and/or particles may be non-biodegradable. The signaling molecules, proteins, nucleic acids, and/or any other material that is comprised by the beads, microspheres, and/or particles may promote formation of the 3D biological material to permit organ function. Non-limiting examples of the signaling molecules, small molecules, and proteins, such as antibodies, that may have agonist, antagonist, growth, and/or cell differentiating activities include: transforming growth factor-βα(TGF-β), vascular endothelial growth factor (VEGF), fibroblast growth factors (FGFs) such as FGF-1 and FGF-2, platelet-derived growth factor (PDGF), angiopoietin-1 (Ang1), Ang2, matrix metalloproteinases (MMPs), delta-like ligand 4 (Dll4), class 3 semaphorins, macrophage colony-stimulating factor (M-CSF), granulocyte-macrophage colony-stimulating factor (M-CSF), bone morphogenic protein 4 (BMP4), transforming growth factor (TGF), Activin A, retinoic acid (RA), epidermal growth factor (EGF), thiazovivin.

Next, the method may comprise directing at least one energy beam to the medium in the media chamber along at least one energy beam path that is patterned into a 3D projection in accordance with computer instructions for printing the 3D biological material in computer memory, to form at least a portion of the 3D biological material. The portion of the 3D biological material may comprise at least a subset of the plurality of cells and a polymer formed from the one or more polymer precursors. The at least portion of the 3D biological material may comprise microvasculature for providing one or more nutrients to the plurality of cells. The microvasculature may be a blood microvasculature, a lymphatic microvasculature, or any combination thereof. The microvasculature may have a cross-section from about 1 micrometer (μm) to about 20 μm. The 3D biological material may have a thickness or diameter from about 100 μm to about 5 centimeters (cm).

The method may comprise directing at least one energy beam to the medium in the media chamber along at least one energy beam path in accordance with the point-cloud representation or lines-based representation of the computer model of the 3D biological material, to subject at least a portion of the polymer precursors to form at least a portion of the 3D biological material. The method may comprise directing at least one energy beam to the medium in the media chamber along at least one energy beam path in accordance with a computer model of a partial 3D structure and/or a complete 3D structure of the 3D biological material.

The method may further comprise directing at least one energy beam to the medium the media chamber along one or more additional energy beam paths to form at least another portion of the 3D biological material. The method may further comprise directing at least two energy beams to the medium in the media chamber along at least two energy beam paths in accordance with the computer instructions, to permit multiple portions of the medium in the media chamber to simultaneously form at least a portion of the 3D biological material. The at least two energy beams may be of identical wavelengths. The at least two energy beams may be of different wavelengths. The computer instructions may comprise a set of images corresponding to the 3D biological material. The computer instructions may direct adjustment of at least one or more parameters of the at least one energy beam as a function of time during formation of the 3D biological material, and/or location of a stage upon which the 3D biological material is formed. The computer instructions may correspond to a computer model or representation of the 3D biological material. The computer instructions may be part of the computer model.

The at least another portion of the 3D biological material may be linked to the 3D biological material formed by directing at least one energy beam to the medium the media chamber along at least one energy beam path. The at least another portion of the 3D biological material may be linked to the 3D biological material formed by directing at least one energy beam to the medium the media chamber along one or more additional energy beam paths. The at least another portion of the 3D biological material may not be linked to the 3D biological material formed by directing at least one energy beam to the medium the media chamber along at least one energy beam path. The at least another portion of the 3D biological material may not be linked to the 3D biological material formed in by directing at least one energy beam to the medium the media chamber along one or more additional energy beam paths.

The energy beam may be a multi-photon laser beam 120. The at least one energy beam may comprise coherent light. The at least one energy beam may be generated by a laser. The at least one energy beam may be phase modulated. The energy beam may be polarized and/or re-combined with other beams. As an alternative, the energy beam may be non-coherent light. The at least one energy beam may be a multi-photon energy beam. The multi-photon energy beam may be a two-photon energy beam. The energy beam source (e.g., laser) may provide energy (e.g., laser beam) having a wavelength from e.g. about 300 nm to about 5 mm. The energy beam (e.g., laser) may provide energy (e.g., laser beam) having a wavelength from about e.g. 350 nm to about 1800 nm. The energy beam (e.g., laser) may provide energy (e.g., laser beam) having a wavelength from e.g. about 1800 nm to about 5 mm. The energy beam (e.g., laser) may provide energy (e.g., laser beam) having a wavelength of about 300 nm. The energy beam (e.g., laser) may provide energy (e.g., laser beam) having a wavelength of about 400 nm. The energy beam (e.g., laser) may provide energy (e.g., laser beam) having a wavelength of about 600 nm. The energy beam (e.g., laser) may provide energy (e.g., laser beam) having a wavelength of about 700 nm. The energy beam (e.g., laser) may provide energy (e.g., laser beam) having a wavelength of about 800 nm. The energy beam (e.g., laser) may provide energy (e.g., laser beam) having a wavelength of about 900 nm. The energy beam (e.g., laser) may provide energy (e.g., laser beam) having a wavelength of about 1000 nm. The energy beam (e.g., laser) may provide energy (e.g., laser beam) having a wavelength of about nm. The energy beam (e.g., laser) may provide energy (e.g., laser beam) having a wavelength of about 1200 nm. The energy beam (e.g., laser) may provide energy (e.g., laser beam) having a wavelength of about 1300 nm. The energy beam (e.g., laser) may provide energy (e.g., laser beam) having a wavelength of about 1400 nm. The energy beam (e.g., laser) may provide energy (e.g., laser beam) having a wavelength of about 1500 nm. The energy beam (e.g., laser) may provide energy (e.g., laser beam) having a wavelength of about 1600 nm. The energy beam (e.g., laser) may provide energy (e.g., laser beam) having a wavelength of about 1700 nm. The energy beam (e.g., laser) may provide energy (e.g., laser beam) having a wavelength of about 1800 nm. The energy beam (e.g., laser) may provide energy (e.g., laser beam) having a wavelength of about 1900 nm. The energy beam (e.g., laser) may provide energy (e.g., laser beam) having a wavelength of about 2000 nm. The energy beam (e.g., laser) may provide energy (e.g., laser beam) having a wavelength of about 3000 nm. The energy beam (e.g., laser) may provide energy (e.g., laser beam) having a wavelength of about 4000 nm. The energy beam (e.g., laser) may provide energy (e.g., laser beam) having a wavelength of about 5000 nm.

Next, the method may comprise generating a point-cloud representation or lines-based representation of the computer model of the 3D biological material in computer memory. The method may generate such representations prior to directing at least one energy beam to the medium in the media chamber. The method may use the point-cloud representation or the lines-based representation to generate the computer instructions. The point-cloud representation or the lines-based representation may comprise multi-dimensional structural elements corresponding to the 3D biological material. The point-cloud representation or the lines-based representation may comprise structural elements in two dimensions. The point-cloud representation or the lines-based representation may comprise structural elements in three dimensions. The point-cloud representation or the lines-based representation may comprise elements in both two dimensions and three dimensions. The structural elements may be associated with tissue function and/or cellular segregation. The structural elements may be a vessel, a lymph vessel, a vasculature, a microvasculature, a muscle, a ligament, a tendon, a bone matrix, a cartilage matrix, a connective tissue matrix, an extracellular matrix, a nerve network, a scaffold, or any combination thereof. The structural element may be a collagen fiber, a reticular fiber, an elastic fiber, a nerve fiber, a polymer fiber, a channel, a microchannel, or any combination thereof.

A point-cloud representation is a set of data points defined in the x, y, and z planes by x, y, z coordinates that represent the external surface of an object (i.e., a prototype). A point-cloud representation may be generated by a 3D modeling program to produce CAD files, or any line drawing set. In some examples (e.g., printing a plastic or metal part), a 3D scanner may be used to generate a 3D model of the object. Non-limiting examples of 3D scanning technologies include laser triangulation 3D scanning, structured light 3D scanning, photogrammetry, contact based 3D scanning, and laser pulse or time of flight 3D scanning. Laser triangulation 3D scanning technology involves projecting a laser beam on the surface of an object and measuring the deformation of the laser ray via a sensor. Based on the deformation of the laser ray and trigonometric triangulation, the laser triangulation system calculates a specific deviation angle. The calculated deviation angle is directly linked to the distance from the object to the scanner. When the laser triangulation 3D scanner collects enough distances, it is capable of mapping the object's surface and to create a 3D scan. Structured light 3D scanning technology measures the deformation of a light pattern on the surface of an object to generate a 3D scan of the surface of an object. Structured light 3D scanning also uses trigonometric triangulation, but relies on the projection of a series of linear patterns instead of the projection of a laser beam. The structured light 3D scanning system is then capable to examine the edges of each line in the pattern and to calculate the distance from the scanner to the object's surface. Photogrammetry, also called 3D scan from photography, reconstructs in 3D an object captured in a 2D image using computational geometry algorithms. The principle of photogrammetry is to analyze several photographs of a static object, taken from different viewpoints, and to automatically detect pixels corresponding to a same physical point. The data inputs required from the user are the parameters of the camera such as focal length and lens distortion. The computational geometry algorithms then calculate the distances between coordinates and output a 3D image reconstruction of the object. Contact based 3D scanning or digitizing, may rely on the sampling of several points on the surface of an object, measured by the deformation of a probe. Contact 3D scanners probe the object through physical touch, while the object is firmly held in place. A touching probe is moved on the surface of the object to record 3D information. The probe is sometimes attached to an articulated arm capable of collecting all its respective configurations and angles for more precision. Laser pulse-based 3D scanning, or time of flight 3D scanning, may be based on the time of flight of a laser beam. In laser pulse-based 3D scanning, the laser beam is projected on a surface and collected by a sensor. The time of travel of the laser beam between its emission and reception provides the geometrical information of the object's surface.

Methods and systems of the present disclosure may be implemented by way of at least one or more algorithms. An algorithm may be implemented by way of software upon execution by the central processing unit 1105. The algorithm may, for example, create a hologram or a holographic image based on a computer model. The algorithm may create a partial hologram. Pulse shaping of light may be achieved across the one or more SLMs by applying the Gerchberg-Saxton algorithm or weighted Gerchberg-Saxton algorithm to create binary holographic images of structural elements that may then be projected to recreate the image in one, two, and/or three dimensions. Other algorithms that may be useful in wavefront shaping include, but are not limited to Lohmann, Lohmann type III, and mixed-region amplitude freedom (MRAF) algorithms. Additional pre-processing and post-processing of the images may occur to accommodate different types of desired structural prints, different print media responses to the incoming light pulses, and any limitation in the optical system or cell viability or changes in projection systems. These changes in data processing may include, but are not limited to Fourier Transforms, selective masks resulting in pixel removal, and/or overlaying holograms for printing in different planes simultaneously to produce the 3D hologram. In addition, these processes may require additional slicing or redistribution of the holographic data.

A line-based representation of the computer model of the 3D biological material may be defined as a collection of lines, vertices, edges, surfaces, dots or collections of linked dots of various sizes, and/or faces that define the shape of the 3D biological material. The faces may comprise triangles (triangle meshes), quadrilaterals, convex polygons, concave polygons, and/or polygons with holes. Non-limiting examples of lines-based representations of the computer model of the 3D biological material in computer memory may include 3D line drawings, 2D line drawings, polygon meshes, and freeform surface models. A polygon mesh is a collection of vertices, edges and faces that defines the shape of an object in 3D computer modeling. A freeform surface model describes the surface of a 3D object. A freeform surface model may be created by construction of curves from which the 3D surface is then swept through and by the manipulation of the surface via poles or control points that define the shape of the surface.

After generating a point-cloud representation or lines-based representation of the computer model of the 3D biological material, the method may further comprise converting the point-cloud representation or lines-based representation into an image. The image may be a hologram or a holographic image. The image may be a partial hologram. The image may be projected in a holographic manner. The image may be projected as a partial hologram. The image may be deconstructed and reconstructed prior to projection in a holographic manner.

The method may further comprise providing yet another media chamber, comprising a medium comprising a plurality of cells comprising cells of at least two different types and one or more polymer precursors, along one or more additional energy beam paths to form at least another portion of the 3D biological material. The other portion of the 3D biological material may be linked to the first 3D biological material formed. The other portion of the 3D biological material may be chemically cross-linked to the first 3D biological material formed. The other portion of the 3D biological material may be mechanically linked to the first 3D biological material formed. Non-limiting examples of mechanical coupling includes joints, hinges, locking joints and hinges, Velcro-like elements, springs, coils, points of stretch, interlocking loops, sockets, gears, ratchets, screws, and chain links. The other portion of the 3D biological material may be cohesively coupled to the first 3D biological material formed. The other portion of the 3D biological material may be linked to the first 3D biological material via printing and active deposition of structure using 3D holographic printings, cells, extracellular matrix deposited by the cells, and/or a pre-existing structure formed by other non-biological approaches. The other portion of the 3D biological material may be polymerized to the first 3D biological material formed. The other portion of the 3D biological material may not be linked to the first 3D biological material formed.

The method may comprise direct linking of the 3D biological material with other tissue, which linking may be in accordance with a computer model. The method may comprise directly linking, merging, bonding, or welding 3D printed material with already printed structures, where linking is in accordance with a computer model. In some cases, the method may provide linking of the 3D biological material with other tissue, which may involve chemical cross-linking, mechanical linking, and/or cohesively coupling.

The method may further comprise directing at least two energy beams to the medium in the media chamber along at least two energy beam paths in accordance with the computer model of the 3D biological material, to permit multiple portions of the medium in the media chamber to simultaneously form at least a portion of the 3D biological material. The at least two energy beams may be of identical wavelengths. The two energy beams may be of different wavelengths.

The portion of the 3D biological material may comprise microvasculature for providing one or more nutrients to the plurality of cells. The microvasculature may be a blood microvasculature, a lymphatic microvasculature, or any combination thereof. The microvasculature may have a cross-section e.g. from about 1 μm to about 20 μm. The cross-section may be e.g. from about 1 μm to about 10 μm. The 3D biological material may have a thickness or diameter e.g. from about 100 μm to about 5 centimeter (cm). The 3D biological material may have a thickness or diameter e.g. from about 200 μm to about 3 cm. The 3D biological material may have a thickness or diameter e.g. from about 300 μm to about 1 cm.

The 3D biological material may have a thickness or diameter e.g. from about 0.1 μm to about 10 cm. The 3D biological material may have a thickness or diameter e.g. from about 0.1 μm to about 5 cm. The 3D biological material may have a thickness or diameter e.g. from about 0.1 μm to about 4 cm. The 3D biological material may have a thickness or diameter e.g. from about 0.1 μm to about 3 cm. The 3D biological material may have a thickness or diameter e.g. from about 0.1 μm to about 2 cm. The 3D biological material may have a thickness or diameter e.g. from about 0.1 μm to about 1 cm.

The 3D biological material may have a thickness or diameter e.g. from about 0.1 μm to about 9 mm. The 3D biological material may have a thickness or diameter e.g. from about 0.1 μm to about 8 mm. The 3D biological material may have a thickness or diameter e.g. from about 0.1 μm to about 7 mm. The 3D biological material may have a thickness or diameter e.g. from about 0.1 μm to about 6 mm. The 3D biological material may have a thickness or diameter e.g. from about 0.1 μm to about 5 mm. The 3D biological material may have a thickness or diameter e.g. from about 0.1 μm to about 4 mm. The 3D biological material may have a thickness or diameter e.g. from about 0.1 μm to about 3 mm. The 3D biological material may have a thickness or diameter e.g. from about 0.1 μm to about 2 mm. The 3D biological material may have a thickness or diameter e.g. from about 0.1 μm to about 1 mm. The 3D biological material may have a thickness or diameter e.g. from about 0.1 μm to about 0.5 mm. The 3D biological material may have a thickness or diameter e.g. from about 0.1 μm to about 0.1 mm.

The 3D biological material may have a thickness or diameter e.g. from about 0.1 μm to about 90 μm. The 3D biological material may have a thickness or diameter e.g. from about 0.1 μm to about 80 μm. The 3D biological material may have a thickness or diameter e.g. from about 0.1 nm to about 70 μm. The 3D biological material may have a thickness or diameter e.g. from about 0.1 μm to about 60 μm. The 3D biological material may have a thickness or diameter e.g. from about 0.1 μm to about 50 μm. The 3D biological material may have a thickness or diameter e.g. from about 0.1 μm to about 40 μm. The 3D biological material may have a thickness or diameter e.g. from about 0.1 μm to about 30 μm. The 3D biological material may have a thickness or diameter e.g. from about 0.1 μm to about 20 μm. The 3D biological material may have a thickness or diameter e.g. from about 0.1 μm to about 10 μm. The 3D biological material may have a thickness or diameter e.g. from about 0.1 μm to about 5 μm. The 3D biological material may have a thickness or diameter e.g. from about 0.1 μm to about 4 μm. The 3D biological material may have a thickness or diameter e.g. from about 0.1 μm to about 3 μm. The 3D biological material may have a thickness or diameter e.g. from about 0.1 μm to about 2 μm. The 3D biological material may have a thickness or diameter e.g. from about 0.1 μm to about 1 μm. The 3D biological material may have a thickness or diameter e.g. from about 0.1 μm to about 0.75 μm. The 3D biological material may have a thickness or diameter e.g. from about 0.1 μm to about 0.5 μm. The 3D biological material may have a thickness or diameter e.g. from about 0.1 μm to about 0.25 μm.

The 3D biological material may be printed in a time period of e.g. at least about 0.01 hour to about 700 hours. The 3D biological material may be printed in a time period of e.g. at least about 0.01 hour to about 600 hours. The 3D biological material may be printed in a time period of e.g. at least about 0.01 hour to about 500 hours. The 3D biological material may be printed in a time period of e.g. at least about 0.01 hour to about 400 hours. The 3D biological material may be printed in a time period of e.g. at least about 0.01 hour to about 350 hours. The 3D biological material may be printed in a time period of e.g. at least about 0.01 hour to about 300 hours. The 3D biological material may be printed in a time period of e.g. at least about 0.01 hour to about 250 hours. The 3D biological material may be printed in a time period of e.g. at least about 0.01 hour to about 200 hours. The 3D biological material may be printed in a time period of e.g. at least about 0.01 hour to about 150 hours. The 3D biological material may be printed in a time period of e.g. at least about 0.01 hour to about 100 hours. The 3D biological material may be printed in a time period of e.g. at least about 0.01 hour to about 72 hours. The 3D biological material may be printed in a time period of e.g. at least about 0.01 hour to about 48 hours. The 3D biological material may be printed in a time period of e.g. at least about 0.01 hour to about 36 hours. The 3D biological material may be printed in a time period of e.g. at least about 0.01 hour to about 24 hours. The 3D biological material may be printed in a time period of e.g. at least about 0.01 hour to about 12 hours. The 3D biological material may be printed in a time period of e.g. at least about 0.01 hour to about 6 hours. The 3D biological material may be printed in a time period of e.g. at least about 0.01 hour to about 3 hours. The 3D biological material may be printed in a time period of e.g. at least about 0.01 hour to about 2 hours. The 3D biological material may be printed in a time period of e.g. at least about 0.01 hour to about 1 hour. The 3D biological material may be printed in a time period of e.g. at least about 0.01 hour to about 0.5 hours.

The 3D biological material (or object) may be printed in a time period of at most about 350 hours. The 3D biological material may be printed in a time period of at most about 300 hours. The 3D biological material may be printed in a time period of at most about 250 hours. The 3D biological material may be printed in a time period of at most about 200 hours. The 3D biological material may be printed in a time period of at most about 150 hours. The 3D biological material may be printed in a time period of at most about 100 hours. The 3D biological material may be printed in a time period of at most about 72 hours. The 3D biological material may be printed in a time period of at most about 48 hours. The 3D biological material may be printed in a time period of at most about 36 hours. The 3D biological material may be printed in a time period of at most about 24 hours. The 3D biological material may be printed in a time period of at most about 12 hours. The 3D biological material may be printed in a time period of at most about 6 hours. The 3D biological material may be printed in a time period of at most about 2 hours. The 3D biological material may be printed in a time period of at most about 1 hour.

The at least portion of the 3D biological material may comprise a cell-containing scaffold. The cell-containing scaffold may comprise at least a subset of the plurality of cells. The 3D biological material may comprise a cell-containing scaffold, which cell-containing scaffold may comprise at least a subset of the plurality of cells. The 3D biological material, as formed, may include a plurality of cell-containing scaffolds. The 3D biological material may comprise cell-containing scaffolds. The plurality of cell-containing scaffolds may be coupled together. The cell-containing scaffolds may be cohesively or mechanically coupled together. The cell-containing scaffold may be empty, porous, and/or hollow. The cell-containing scaffold may serve as a complete element or portion of a supporting structure, collecting duct, or vascular element. The plurality of cell-containing scaffolds may be cohesively coupled together. The plurality of the cell-containing scaffolds may be mechanically coupled together. The plurality of cell-containing scaffolds may be mechanically coupled together through one or more members selected from the group consisting of joints, hinges, locking joints and hinges, Velcro-like elements, springs, coils, points of stretch, interlocking loops, sockets, gears, ratchets, screw, and chain links.

The cell-containing scaffolds may comprise a network. The network may comprise a plurality of strands. The plurality of strands may form a mesh structure. The plurality of strands may form a grid structure. The plurality of strands may form a sheet structure. The plurality of strands may form a tube structure. The plurality of strands may form a pore network. The plurality of strands may form a cylindrical structure. The plurality of strands may form a rectangular structure. The plurality of strands may form a square structure. The plurality of strands may form a tiered or layered structure. The plurality of strands may form a lattice structure. The plurality of strands may form a porous structure. The plurality of strands may form a net-like structure. The plurality of strands may form an interconnected structure. The plurality of strands may form a channeled structure. The plurality of strands may form a hexagonal structure. The plurality of strands may form a caged structure. The plurality of strands may form a sphere. The plurality of strands may form a polygon.

The individual strands of the plurality of strands may have a thickness from about 0.1 nanometers (nm) to about 5 cm. The plurality of strands may have a thickness e.g. from about 0.1 nm to about 10 cm. The plurality of strands may have a thickness e.g. from about 0.1 nm to about 5 cm. The plurality of strands may have a thickness e.g. from about 0.1 nm to about 4 cm. The plurality of strands may have a thickness e.g. from about 0.1 nm to about 3 cm. The plurality of strands may have a thickness e.g. from about 0.1 nm to about 2 cm. The plurality of strands may have a thickness e.g. from about 0.1 nm to about 1 cm. The plurality of strands may have a thickness e.g. from about 0.1 nm to about 0.5 cm.

The plurality of strands may have a thickness e.g. from about 0.1 nm to about 1000 µm. The plurality of strands may have a thickness e.g. from about 0.1 nm to about 900 µm. The plurality of strands may have a thickness e.g. from about 0.1 nm to about 800 µm. The plurality of strands may have a thickness e.g. from about 0.1 nm to about 700 µm. The plurality of strands may have a thickness e.g. from about 0.1 nm to about 600 µm. The plurality of strands may have a thickness e.g. from about 0.1 nm to about 500 µm. The plurality of strands may have a thickness e.g. from about 0.1 nm to about 400 µm. The plurality of strands may have a thickness e.g. from about 0.1 nm to about 300 µm. The plurality of strands may have a thickness e.g. from about 0.1 nm to about 200 µm. The plurality of strands may have a thickness e.g. from about 0.1 nm to about 100 µm. The plurality of strands may have a thickness e.g. from about 0.1 nm to about 50 µm. The plurality of strands may have a thickness e.g. from about 0.1 nm to about 25 µm. The plurality of strands may have a thickness e.g. from about 0.1 nm to about 10 µm. The plurality of strands may have a thickness e.g. from about 0.1 nm to about 1 µm.

The plurality of strands may have a thickness e.g. from about 0.1 nm to about 900 nm. The plurality of strands may have a thickness e.g. from about 0.1 nm to about 800 nm. The plurality of strands may have a thickness e.g. from about 0.1 nm to about 700 nm. The plurality of strands may have a thickness e.g. from about 0.1 nm to about 600 nm. The plurality of strands may have a thickness e.g. from about 0.1 nm to about 500 nm. The plurality of strands may have a thickness e.g. from about 0.1 nm to about 400 nm. The plurality of strands may have a thickness e.g. from about 0.1 nm to about 300 nm. The plurality of strands may have a thickness e.g. from about 0.1 nm to about 200 nm. The plurality of strands may have a thickness e.g. from about 0.1 nm to about 100 nm. The plurality of strands may have a thickness e.g. from about 0.1 nm to about 50 nm. The plurality of strands may have a thickness e.g. from about 0.1 nm to about 25 nm. The plurality of strands may have a thickness e.g. from about 0.1 nm to about 10 nm. The plurality of strands may have a thickness e.g. from about 0.1 nm to about 1 nm. The plurality of strands may have a thickness e.g. from about 0.1 nm to about 0.5 nm. The plurality of strands may have a thickness e.g. from about 0.1 nm to about 0.25 nm.

The plurality of strands may have a thickness e.g. from about 0.1 nm to about 800 µm. The plurality of strands may have a thickness e.g. from about 0.1 µm to about 1 µm. The plurality of strands may have e.g. a thickness from about 1 µm to about 100 µm. The plurality of strands may have a thickness e.g. from about 1 millimeter (mm) to about 100 mm. The plurality of strands may have a thickness e.g. from about 1 cm to about 5 cm.

The method may comprise at least another portion of the 3D biological material that may be formed within the at least portion of the 3D biological material.

The method may comprise forming another portion of the 3D biological material within the portion of the 3D biological material that is first formed, after first directing the at least one energy beam to the medium in the media chamber. The method may comprise printing a 3D object inside a previously printed 3D object. The method may comprise printing a 3D biological material inside a previously printed 3D object. The previously printed structure may be a 3D object that may be formed of a polymeric material, a metal, metal alloy, composite material, or any combination thereof. The 3D object may be formed of a polymeric material, in some cases including biological material (e.g., one or more cells or cellular components). Printing a 3D object inside a previously printed 3D object can be possible with precision printing and energy beam excitation that is exact in the x, y, and z planes.

The method may comprise printing a 3D object inside a previously printed 3D structure by using at least one energy beam having a wavelength in the near-infrared light spectrum. Near-infrared wavelengths can penetrate tissue and structures. The method may comprise directing the at least one energy beam having a wavelength in the near-infrared light spectrum into the medium as a 3D projection corresponding to a 3D object may allow the 3D projection to penetrate a previously printed 3D object. The method may comprise directing the at least one energy beam having a wavelength in the near-infrared light spectrum into the medium as a 3D projection corresponding to a 3D biological material may allow the 3D projection to penetrate a previously printed 3D biological material. The 3D projection may be a hologram. The 3D projection may be a partial hologram. The energy beam having a wavelength in the near-infrared light spectrum can have minimal or no scattering. When directed as a 3D projection into the medium, the energy beam having a wavelength in the near-infrared light spectrum can coalesce as a hologram inside a tissue or a previously printed 3D object, structure, and/or biological material.

The near-infrared light spectrum can range from about 650 nanometers (nm) to 1 millimeters (mm). Within the near-infrared light spectrum, the near-infrared (NIR) window (i.e., optical window or therapeutic window) defines the range of wavelengths from e.g. about 650 to 1350 nm where light has its maximum depth of penetration in tissue. Furthermore, the far-red light spectrum can range from about 710 nm to about 850 nm. The energy beam used in the methods disclosed herein can be an NIR energy beam having a wavelength in the NIR light spectrum. The energy beam used in the methods disclosed herein can be an NIR energy beam having a wavelength in the NIR window light spectrum. The energy beam used in the methods disclosed herein can be an NIR energy beam having a wavelength in the far-red light spectrum.

The NIR energy beam (e.g., laser) may provide energy (e.g., laser beam) having a wavelength ranging from about 650 nm to about 1 mm. The NIR energy beam (e.g., laser) may provide energy (e.g., laser beam) having a wavelength ranging from about 710 nm to about 850 nm or more. The NIR energy beam (e.g., laser) may provide energy (e.g., laser beam) having a wavelength ranging from about 650 nm to about 1350 nm or more. The NIR energy beam (e.g., laser) may provide energy (e.g., laser beam) having a wavelength of about 650 nm. The NIR energy beam (e.g., laser) may provide energy (e.g., laser beam) having a wavelength of about 700 nm. The NIR energy beam (e.g., laser) may provide energy (e.g., laser beam) having a wavelength of about 710 nm. The NIR energy beam (e.g., laser) may provide energy (e.g., laser beam) having a wavelength of about 750 nm. The NIR energy beam (e.g., laser) may provide energy (e.g., laser beam) having a wavelength of about 800 nm. The NIR energy beam (e.g., laser) may provide energy (e.g., laser beam) having a wavelength of about 850 nm. The NIR energy beam (e.g., laser) may provide energy (e.g., laser beam) having a wavelength of about 900 nm. The NIR energy beam (e.g., laser) may provide energy (e.g., laser beam) having a wavelength of about 950 nm. The NIR energy beam (e.g., laser) may provide energy (e.g., laser beam) having a wavelength of about 1000 nm. The NIR energy beam (e.g., laser) may provide energy (e.g., laser beam) having a wavelength of about 1200 nm. The NIR energy beam (e.g., laser) may provide energy (e.g., laser beam) having a wavelength of about 1300 nm. The NIR energy beam (e.g., laser) may provide energy (e.g., laser beam) having a wavelength of about 1350 nm. The NIR energy beam (e.g., laser) may provide energy (e.g., laser beam) having a wavelength of about 1500 nm. The NIR energy beam (e.g., laser) may provide energy (e.g., laser beam) having a wavelength of about 2000 nm. The NIR energy beam (e.g., laser) may provide energy (e.g., laser beam) having a wavelength of about 2500 nm. The NIR energy beam (e.g., laser) may provide energy (e.g., laser beam) having a wavelength of about 3000 nm. The NIR energy beam (e.g., laser) may provide energy (e.g., laser beam) having a wavelength of about 3500 nm. The NIR energy beam (e.g., laser) may provide energy (e.g., laser beam) having a wavelength of about 4000 nm. The NIR energy beam (e.g., laser) may provide energy (e.g., laser beam) having a wavelength of about 5000 nm.

The energy beam having a wavelength in the NIR light spectrum may be directed to the medium in the media chamber along at least one energy beam path in accordance with a point-cloud representation, lines-based representation, partial 3D structure, complete 3D structure, or a 3D projection (i.e., hologram or partial hologram) of the 3D biological material. In some examples, a partial or complete 3D structured is projected into the medium at the same time. The energy beam having a wavelength in the NIR light spectrum may penetrate previously formed structures within the media chamber. The energy beam having a wavelength in the NIR light spectrum may penetrate previously formed cell-containing scaffolds within the media chamber. The energy beam having a wavelength in the NIR light spectrum may penetrate previously formed 3D biological material located within the media chamber. The energy beam having a wavelength in the NIR light spectrum that is directed to the medium in the media chamber may subject at least a portion of the polymer precursors to form at least a portion of the 3D biological material within a previously formed portion of the 3D biological material. The energy beam having a wavelength in the NIR light spectrum that is directed to the medium in the media chamber may subject at least a portion of the polymer precursors to form at least a portion of the 3D object within a previously formed portion of the 3D object. The specific NIR wavelengths of the energy beam used in the methods provided herein can enable the printing of 3D biological materials within previously formed structures by penetrating the previously formed structures at least one energy beam path in accordance with the 3D projection (i.e., hologram or partial hologram) of the 3D biological material.

In another aspect, the present disclosure provides an additional method of printing a three-dimensional (3D) biological material. The method may comprise receiving a computer model of the 3D biological material in computer memory.

Next, the method may comprise generating a point-cloud representation or lines-based representation of the computer model of the 3D biological material in computer memory.

Next, the method may provide a media chamber comprising a first medium, wherein the first medium comprises a first plurality of cells and a first polymeric precursor. The first medium may comprise glutathione or a functional variant (or derivative) thereof.

Next, the method may comprise directing at least one energy beam to the first medium in the media chamber along at least one energy beam path in accordance with computer instructions for printing the 3D biological material in computer memory, to subject at least a portion of the first medium in the media chamber to form a first portion of the 3D biological material.

Next, the method may comprise providing a second medium in the media chamber, wherein the second medium comprises a second plurality of cells and a second polymeric precursor, wherein the second plurality of cells is of a different type than the first plurality of cells. The second medium may comprise glutathione or a functional variant (or derivative) thereof.

Next, the method may comprise directing at least one energy beam to the second medium in the media chamber along at least one energy beam path in accordance with the computer instructions, to subject at least a portion of the second medium in the media chamber to form at least a second portion of the 3D biological material.

The method may further comprise removing a remainder of the first medium from the media chamber to leave the first portion of the d 3D biological material in the media chamber. The first portion of the 3D biological material left in the medium chamber may be removably fixed to the media chamber.

The method may further comprise generating a point-cloud representation or lines-based representation of the 3D biological material in computer memory. The method may further use the point-cloud representation or lines-based representation to generate the computer instructions. The method may further comprise converting the point-cloud representation or lines-based representation into an image or image set that may be used to spatially modulate an incoming coherent light source such that biological structures may be projected in one dimension. The method may further comprise converting the point-cloud representation or lines-based representation into an image or image set that may be used to spatially modulate an incoming coherent light source such that biological structures may be projected in two dimensions. The method may further comprise converting the point-cloud representation or lines-based representation into an image or image set that may be used to spatially modulate an incoming coherent light source such that biological structures may be projected in three dimensions. The method may further comprise converting the point-cloud representation or lines-based representation into an image or image set that may be used to spatially modulate at least one incoming coherent light source such that biological structures may be projected in a mixture of one-dimensional, two-dimensional and/or three-dimensional structures. The method image or image set may be projected in a holographic manner. The image or image set may be deconstructed and reconstructed into partial elements or representative structures prior to projection in a holographic manner. The point-cloud representation or the lines-based representation may comprise multi-dimensional structural elements corresponding to the 3D biological material. The point-cloud representation or the lines-based representation may comprise structural elements in two dimensions. The structural elements may be associated with tissue function and/or cellular segregation. The point-cloud representation or the lines-based representation may comprise structural elements in three dimensions, wherein the structural elements may be associated with tissue function and/or cellular segregation.

The at least one energy beam may comprise coherent light. The at least one energy beam may be generated by a laser. The at least one energy beam may be phase modulated. The at least one energy beam may be phase modulated and raster-scanned throughout the sample medium. The at least a portion of the 3D biological material may comprise microvasculature for providing one or more nutrients to the plurality of cells. The medium may further comprise a plurality of beads. The at least portion of the 3D biological material, as formed, may include the plurality of beads. The 3D biological material may be printed in a time period of at most about 350 hours. The 3D biological material may be printed in a time period of at most about 72 hours. 3D biological material may be printed in a time period of at most about 12 hours. The method may comprise at least another portion of the 3D biological material that may be formed within the first portion of the 3D biological material and/or the second portion of the 3D biological material.

A variety of tissue structures can be generated with the rapid multi-photon printing system 100 such as thick, complex tissue layers which include blood vessels, lymphatic vasculature, interstitial cell networks, cell niches or a-cellular elastic structures, to name a few. In many instances, the three-dimensional projection from computer generated three dimensional models may be created from scans or maps of native tissue structures which allows for precise replication of native tissues. Such tissues may be comprised of a variety of different cell types, each organizing in a specific manner so as to generate a specific structure or provide a particular function. For example, blood vessels, such as arteries and veins, may be comprised of endothelial cells, basal lamina (a layer of extracellular matrix), connective tissue and layers of smooth muscle cells. A tissue containing blood vessels may also include cells forming the tissue surrounding the blood vessels. For example, liver tissue may also include hepatocytes. Hepatocytes may be grouped in the liver into similar functional units and are similar in appearance, but they may express different genes depending on their location. This compartmentalization may allow the liver to carry out the multiple functions of the liver in different locations. Every cell may not participate in the oxidation of proteins, detoxification of reactive oxygen species, and bile productions. These tasks may be given to different groups of hepatocytes depending on their location in the liver. The rest of the cells in the liver (collectively called non-parenchymal cells) may be found in compartments between the massive numbers of hepatocytes. Thus, when printing liver tissue, the cell types related to the formation of blood vessels may be appropriately arranged so as to promote and support the organization of these cells into blood vessels; and the hepatocytes and non-parenchymal cells may be likewise appropriately arranged to form the desired end result tissue. Such arrangement may be achieved by printing layers of nets and other structures within the tissue for temporary cell organization in three dimensions. The structure of most organs may require multiple cell types to be layered and grouped as functional units wherein some cells support the function of these units as described above and some are actual functional elements. Organs may be vascularized to maintain cellular health within these functional units that comprise the entire organ. In the case of immune system function, the highly organized structure of the lymph node may facilitate the ability of the cells to properly respond to infectious agents. To properly respond to an infection, multiple cell-types may come into contact with each other to exchange information through cell-surface contact about the pathogen or agent that is eliciting the immune response. These contacts may be orchestrated by release of cell-signaling molecules and have patterns and contact timing. Disruption of cell-cell interactions or disorganization of a lymphatic tissue, wherein cells are scattered or not in their normal area within the tissue, may be causal or associated with inability for an immune system to respond properly or develop highly selected for antibodies. Therefore, reconstruction of tissues such as this for the purpose of transplant or drug development may benefit not only from the placement of microvasculature which nourishes and supports cells, but the placement of the cells themselves such that they can be organized to interact and produce the necessary signals to execute tissue function, as is necessary within the lymph node during response to an infectious agent.

In an aspect, the present disclosure provides a method for printing a three-dimensional (3D) object. The method may comprise directing at least one energy beam into a medium comprising one or more precursors to generate the 3D object. The 3D object may comprise a material formed from the one or more precursors. The one or more precursors may be polymeric precursors. The one or more precursors may include one or more metals. The one or more precursors may include glass or sand precursors. The one or more precursors may be a powder. The material may be a polymeric material. The material may include at least one metal. The material may include glass or sand (e.g. green sand). The material may include a mixture of a polymeric precursor, a metallic precursor, and/or a glass precursor. For example, the material may be alumide (i.e., a mixture of polyamide and aluminum), a mixture of polyamide and glass, and/or a mixture of nylon and glass. The polymeric material may be a powder. The polymeric material may be contained in a fabrication powder bed. Non-limiting examples of polymeric materials may include nylon, polystyrene, polyamide, polyethylene, polystyrene, polyether ether ketone (PEEK), polypropylene, polybutylene terephthalate, thermoplastic polyurethane, thermoplastic elastomer, and polyoxomethylene. The nylon material may be glass-filled nylon, fiber-filled nylon, or durable nylon. The polyamide may be flame-retardant polyamide. Non-limiting examples of metals may include steel, titanium, metal alloy mixtures, and aluminum. The metal alloy mixtures may include nickel chromium and cobalt chrome alloys.

Next, the at least one energy beam may be directed into the medium as a 3D projection. The 3D projection may correspond to the 3D object. The 3D projection may be a hologram. The 3D projection may be a partial hologram. The 3D projection may be a holographic image. The hologram or holographic image may be a one-dimensional, two-dimensional, and/or three-dimensional image. The method may comprise receiving a computer model of the 3D object in computer memory. The computer model may be a computer-aided design (CAD) model. The CAD model may be a 3D wireframe, a 3D solid model such as a parametric model and a direct or explicit model, and/or a freeform surface model. The CAD model may be generated by a computer after a physical prototype is scanned and/or imaged using a device such as a 3D scanner, a computer tomography (CT) scanning device, a structured-light 3D scanner, a modulated light 3D scanner, a laser scanner, a microscope, or a magnetic resonance imaging (MRI) device. In some cases, the prototype image or scan is converted to a CAD model by using an algorithm that converts the prototype image or scan into a surface model, a mesh model, or a volume model. The method may comprise receiving a computer model comprising a partial 3D structure and/or a complete 3D structure of the 3D object. The systems disclosed herein used for printing 3D biological materials may be the same as the systems used for printing 3D objects.

The medium may comprise cells or cellular constituents. The cellular constituents may include, but are not limited to organelles such as mitochondria, nuclei, ribosomes, vesicles, Golgi apparatuses, cytoskeleton components, smooth endoplasmic reticulum, vacuoles, and chloroplasts; phospholipids; and cellular membranes.

In an aspect, the present disclosure provides a method for printing a three-dimensional (3D) biological material. The method may comprise directing at least a first energy beam into a media chamber comprising a first medium. The first medium may comprise a first plurality of cells and a first polymeric precursor to generate a first portion of the 3D biological material. The method may comprise directing at least a second energy beam into the media chamber comprising a second medium. The second medium may comprise a second plurality of cells and a second polymeric precursor, to generate a second portion of the 3D biological material. The second portion of the 3D biological material may be adjacent to the first portion of the 3D biological material.

The at least first energy beam and the at least second energy beam may be from the same energy source. The at least first energy beam and the at least second energy beam may be laser beams. The cells of the first plurality of cells and the cells of the second plurality of cells may be of different types. The cells of the first plurality of cells and the cells of the second plurality of cells may be of the same type. The first polymeric precursor and the second polymeric precursor may be different. The first polymeric precursor and the second polymeric precursor may be the same.

Net Creation

Nets may be created within the media 126 by polymerizing the polymerizable material in a pattern and manner so as to create a desired net structure 500 amongst the cells. FIG. 11 illustrates an example of a net structure 500 formed from polymerizable material. In this example, the net structure 500 may have a grid shape formed from net strands 502.

The net strands 502 may have a thickness between e.g. at least about 0.0001 micrometers to about 100 micrometers. FIG. 12A illustrates a net structure 500 comprised of strands 502 having a thickness of approximately 0.1 micrometers and FIG. 12B illustrates a net structure 500 comprised of strands 502 having a thickness of at least about 5 micrometers. Different sized strands may be used for creating mesh networks of different sizes and densities to promote cell-cell communication, allowing cell movement to be promoted or prevented, or supporting tissue properties such that there may be differences in elasticity, strength, or compression forces associated with different mesh net structures. As shown in FIG. 11, in some cases, the net structure 500 may have apertures 504 that are sized to allow specific cells 506 to pass through and restrict the passage of other cells. In some cases, apertures 504 may range in size e.g. from at least about 3 micrometers to about 100 micrometers. FIG. 11 illustrates a net structure 500 having apertures 504 sized and configured so as to prevent passage of any cell 506 which is at least about 4 micrometers in size (such as e.g. about 4 micrometers to about 100 micrometers) therethrough. This may temporarily trap cells 506 within the net structure 500 as the net structure 500 is generated. It may be appreciated that the net structures may have various apertures 504 of any geometric shape, such as round, hexagonal, octagonal or square.

Figure 13:
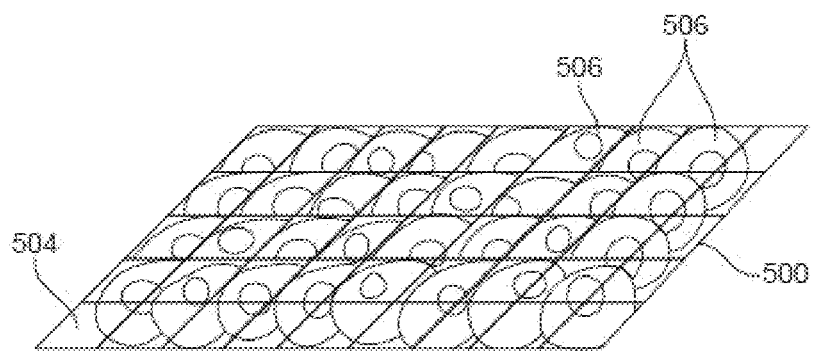
FIG. 13 illustrates rounded cells temporarily trapped within a net.
Figure 14:
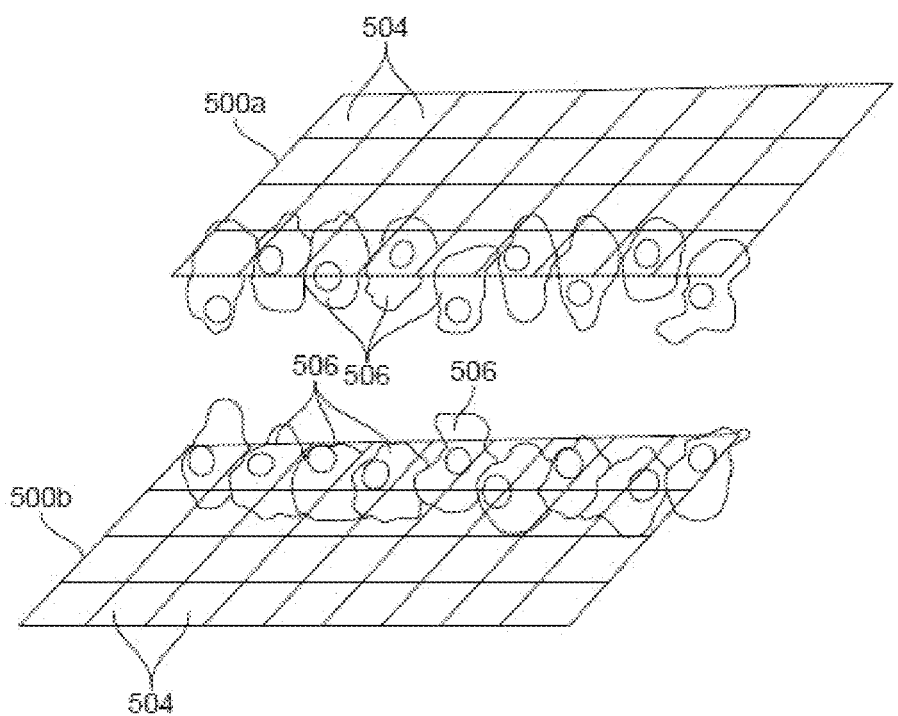
FIG. 14 illustrates a first net and a second net disposed near each other so that cells are able to move through the apertures and engage under physiological conditions.

In some cases, these cell-size specific nets may be designed to isolate rounded cells of specific types. Rounding of cells may be induced by chemical changes to the environment or temperature changes, and a combination of these may be used during the printing process. Rounded cells in certain physiologic conditions may not move or crawl, but may be suspended in place. FIG. 13 illustrates rounded cells 506 temporarily trapped within a net structure 500. In this example, the apertures 504 may be smaller than the rounded diameter of the cell type when suspended in media 126, but larger than the estimated diameter of the cell nucleus. In some instances, the apertures 504 may be the same size as or about 1 micrometer smaller than the cell nucleus. These sizes may be selected to create temporary confinement of the particular cells 506. Cells may pass through an aperture that is larger than the cell nucleus but may be confined by one that is smaller. In this embodiment, the net 500 may be printed under conditions which cause the cells 506 to be rounded so as to be trapped by the net 500. Once the printed materials are returned to physiologic conditions, the cells 506 may no longer round and may be able to crawl and move through the apertures 504, as illustrated in FIG. 14. FIG. 14 shows a first net structure 500a and a second net structure 500b disposed near each other so that cells 506 may be able to move through the apertures 504 and engage under physiological conditions allowing cell-cell contact, reordering and natural proliferation while maintaining gross structural arrangement and support. Together, the cell layers and niches created by the first net structure 500a and the second net structure 500b may form a supra-structure of cell-containing elements designed to facilitate cell-cell contact and movement during three-dimensional tissue development in culture.

The first net structure 500a and the second net structure 500b may then be disposed of, reabsorbed, degraded or otherwise lost by the final stages of tissue development. In some instances, the first net structure 500a and the second net structure 500b may be lost by enzymatic digestion by cells expressing matrix metalloproteinases, or other methods.

Net Features

The nets may include a variety of features to assist in the creation of various types of tissues and tissue structures. Such features may include, but are not limited to variations in thickness, density, and structural design to influence the movement of cells within the net structure 500 and/or to affect the overall shape of the net 500. Additional features may include, but are not limited to various mechanical elements to assist in shaping the overall net 500, such as linking portions of the net to itself or other nets, and to further influence the form of the final tissue structure. These and other net features are described herein.

Figure 15A:
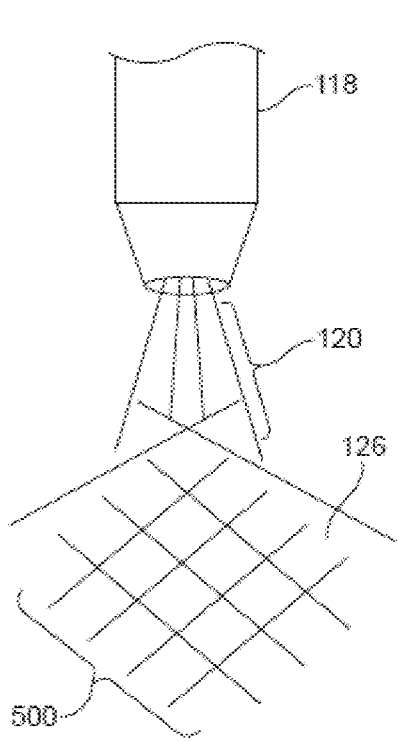
FIGS. 15A-15C illustrate a method of creating areas of such structural features within a net structure 500.
Figure 15B:
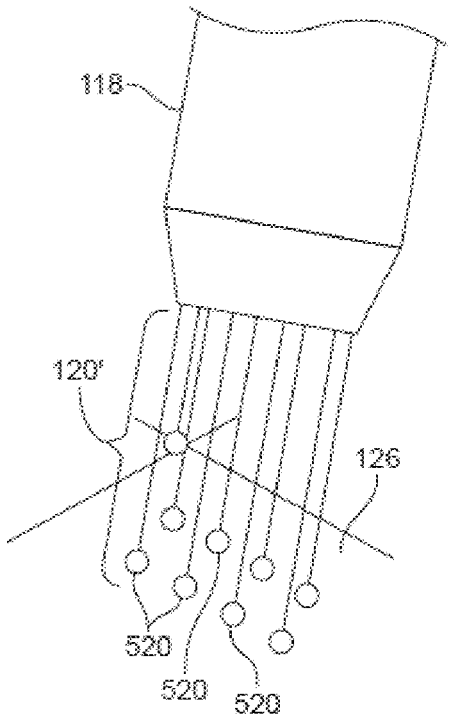
Figure 15C:
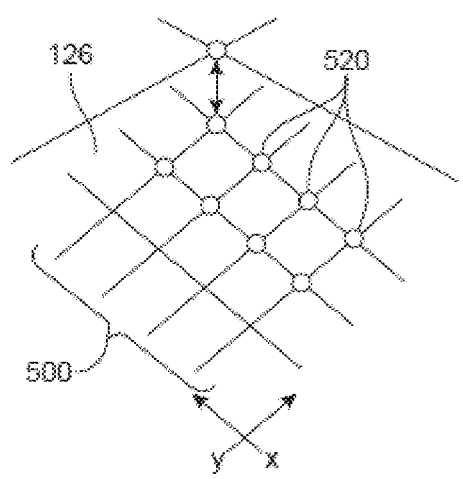

In some cases, the nets may be created with various structural features by changing the intensity, prolonging the exposure or repeating exposure of the multi-photon laser beam 120 projected at various sites within the media 126. In some instances, intensity changes or prolonged exposure at certain critical points in the media 126 may create features in the net structure that may influence the density of cells deposited. This can lead to mechanical differences at these points which can be used in tissue construction. FIGS. 15A-15C illustrate a method of creating areas of such structural features within a net structure 500. FIG. 15A shows the generation of a net structure 500 by projecting the multi-photon laser beam 120 from the optics of the multi-photon tissue printing print-head 118 into the media 126. FIG. 15B illustrates a second projection of a multi-photon laser beam 120' from the laser beam targeting specific coordinates 520 within the net structure 500. In this embodiment, the specific coordinates 520 may coincide with pre-determined intersections of the net strands 502 of the net structure 500. The second projection 120' may be at the same or differing wavelength from the first projection 150. This second projection of a multi-photon laser beam 120' may increase the density of net material at the specific coordinates 520. FIG. 15C illustrates the final net structure 500 having the various points of reinforcement at the pre-determined intersections of the net strands 502.

Figure 16A:
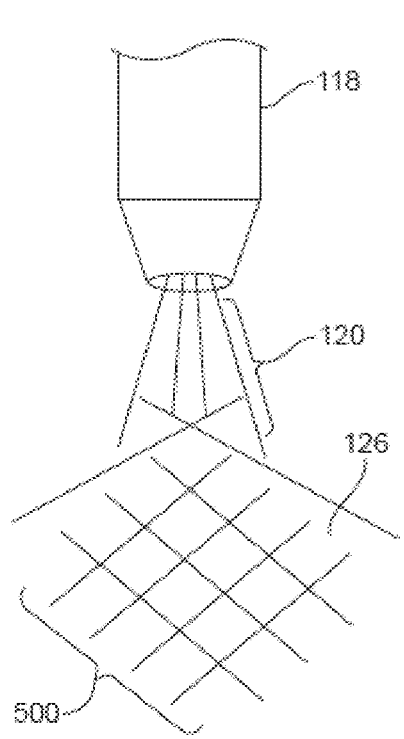
FIGS. 16A-16D illustrate another method of creating areas of such structural features within a net.
Figure 16B:
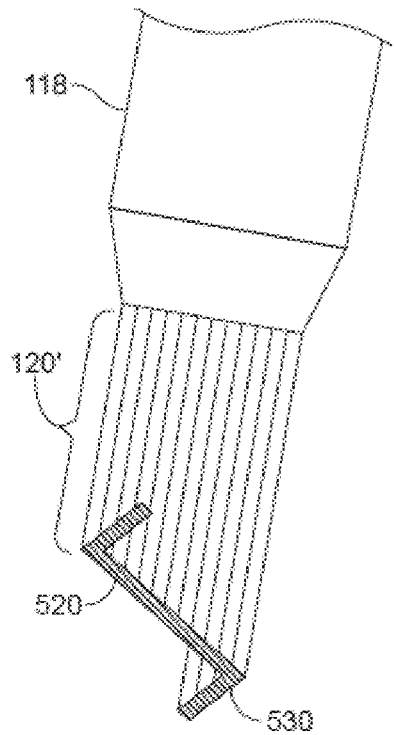
Figure 16C:
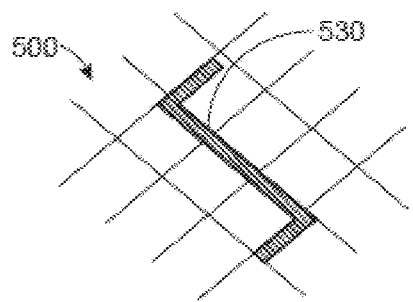

FIGS. 16A-16C illustrate another method of creating areas of such structural features within a net structure 500. FIG. 16A shows the generation of a net structure 500 by projecting the multi-photon laser beam 120 from the optics of the multi-photon tissue printing print-head 118 into the media 126. FIG. 16B illustrates a second projection 120' of a multi-photon laser beam targeting specific coordinates 520 within the net structure 500. In this embodiment, the specific coordinates may coincide with various net strands which together form a structural feature 530 having a zig-zag shape. The second projection of a multi-photon laser beam 120' may be at the same or differing wavelength from the first projection of a multi-photon laser beam 120. This second projection of a multi-photon laser beam 120' may increase the density of net material at the specific coordinates 520. FIG. 16C illustrates the final net structure 500 having the reinforced zig-zag shaped structural feature 530. Similar to parallel tube support and re-enforcements of linear capillaries, many tubes have branches that may be supported. The zigzag shape of reinforcement for tissues and cell nets can be used, in one example, in parallel printed reinforcements to support branched capillary structures in printed tissues. In another embodiment, layers of a zig-zag shape may provide structural support in response to perpendicular compression forces and parallel shear forces.

Figure 16D:
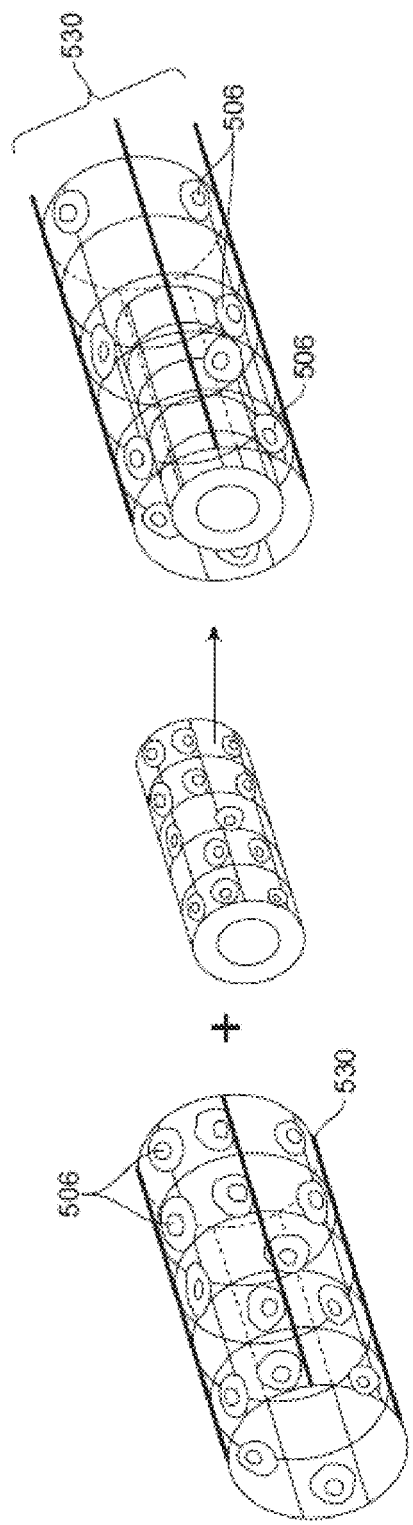

Having lines or regions of high density within cell nets, allows for cells to deform tissues along certain guidelines. One such demonstration of a structural use may be the organization of fibroblasts to form tissues around vascular epithelial cells meant to form blood vessels. A simple sheet of fibroblasts may result in deformation that does not support the tube structure of a capillary and thus compromising the function of and structure of printed capillary structures. Instead, thicker net regions such as parallel line reinforcement can direct structural deformation in a manner that is supportive of the desired tissue structure such as a tube of vascular endothelial cells, as illustrated in FIG. 16D.

Figure 17A:
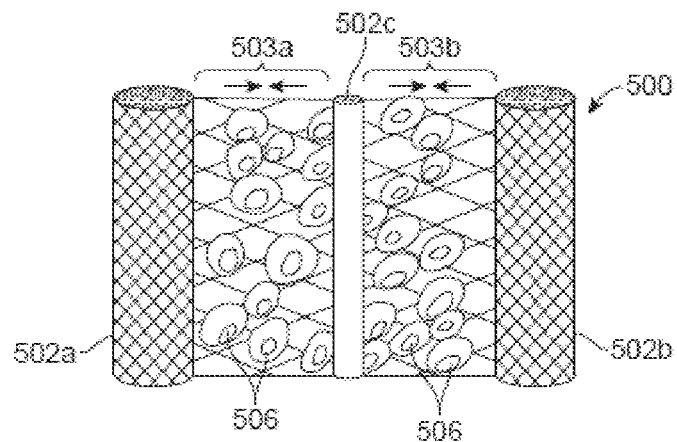
FIGS. 17A-17B illustrate the use of structural features within a net to cause the tissue structure to fold or wrinkle.
Figure 17B:
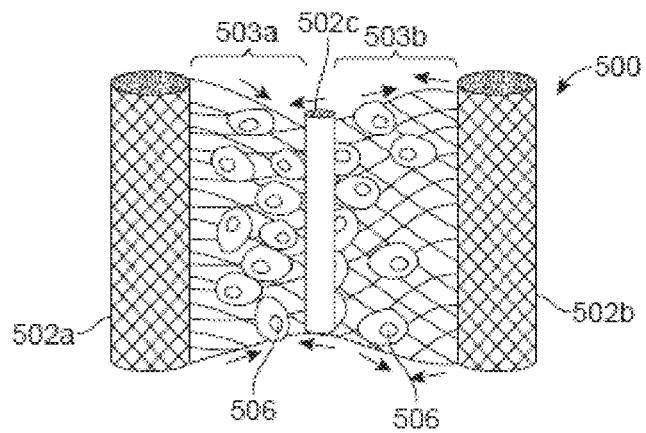
Figure 18A:
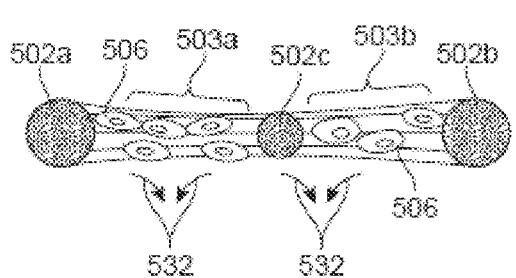
FIGS. 18A-18B illustrate the use of structural features within a net to cause the tissue structure to fold or wrinkle.
Figure 18B:
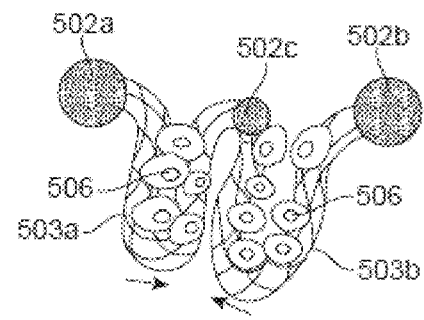

In some embodiments, increased areas of thickness along a net structure 500 are used to influence cells to engage in high-tension interactions. Such interactions may cause the overall net structure 500 to form folds or wrinkles which may be desirable for the ultimate tissue structure. FIGS. 17A-17B and 18A-18B illustrate the use of structural features within a net to cause the tissue structure to fold or wrinkle in a particular manner as a result of cell-cell contact and movement during three-dimensional tissue development in culture. FIG. 17A illustrates a net structure 500 formed within the media 126 wherein the net structure 500 includes structural reinforcements 540 along particular net strands and a first unreinforced portion 503a and a second unreinforced portion 503b of the net therebetween. In some embodiments, such structural reinforcements 540 are made by constructing the net structure 500 with net strands of different diameters. In the embodiment of FIG. 17A, a first net strand 502a and a second net strand 502b have a larger diameter than other strands within the net structure 500 and are arranged in parallel to each other separated by a distance. The larger diameter serves as reinforcement. A third net strand 502c has a smaller diameter than the first net strand 502a and the second net strand 502b and is arranged in parallel to the first net strand 502a and the second net strand 502b located therebetween. The third net strand 502c is also reinforced to a lesser degree. The remaining net portions are unreinforced and reside between the first net strand 502a, the second net strand 502b, and the third net strand 502c that are reinforced, as shown. Cells 506, such as fibroblasts, are trapped within the net structure 500, amongst the first unreinforced portion 503a and a second unreinforced portion 503b of the net structure 500, between the first net strand 502a, the second net strand 502b, and the third net strand 502c that are reinforced. The cells 506 then begin the process of cell interaction and cell movement. Since the cells 506 can freely communicate within the first unreinforced portion 503a and a second unreinforced portion 503b of the net structure 500, tension forces result from cell-cell interactions. This draws the first net strand 502a and the second net strand 502b toward each other, as illustrated in FIG. 17B. The third net strand 502c keeps the first unreinforced portion 503a and a second unreinforced portion 503b separated which begin to fold or wrinkle. Since the third net strand 502c is reinforced to a lesser degree, the cells 506 along the wrinkles are able to interact over and around the third net strand 502c, further stabilizing the folded shape. FIGS. 18A-18B illustrate the net structure 500 embodiment of FIGS. 17A-17B from a side view. FIG. 18A illustrates the downward motion of the cells 506 (indicated by arrows 532) as the cells move and communicate, to form the folds. FIG. 18B illustrates the cells 506 having formed the folds between the first net strand 502a, the second net strand 502b, and the third net strand 502c drawing the first net strand 502a and the second net strand 502b toward each other.

Figure 19A:
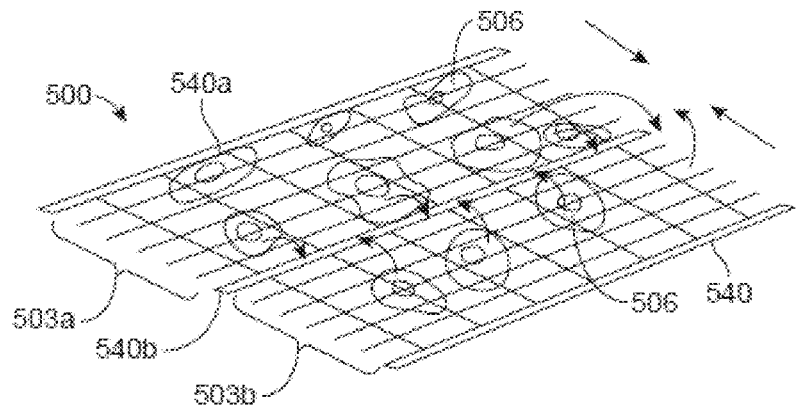
FIGS. 19A-19C illustrate another embodiment of a net having increased areas of thickness.
Figure 19B:
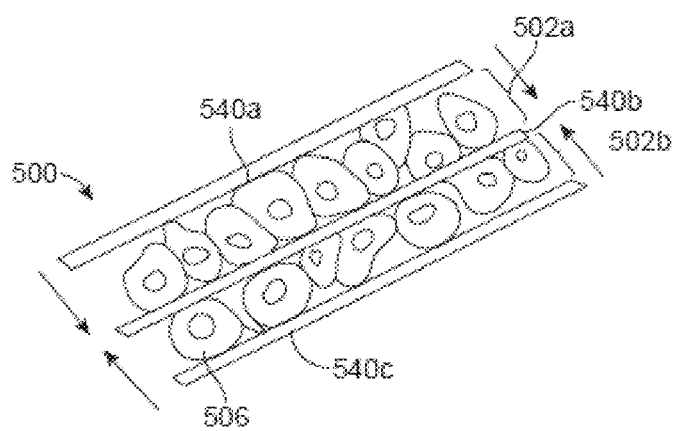
Figure 19C:
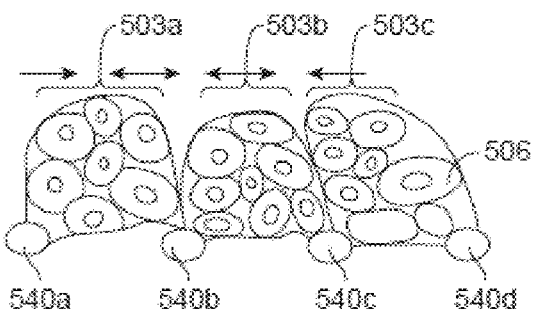

FIGS. 19A-19C illustrate another embodiment of a net structure 500 having increased areas of thickness to influence or force cells to engage in high-tension interactions, leading to folds or wrinkles. FIG. 19A illustrates a net structure 500 formed within media 126 wherein the net structure 500 includes a first structural reinforcement 540a, a second structural reinforcement 540b, and a third structural reinforcement 540c along particular net strands and unreinforced portions of the net therebetween. More specifically, the first structural reinforcement 540a, the second structural reinforcement 540b, and the third structural reinforcement 540c have the shape of lines or elongate areas positioned in a parallel manner so that portions of the first unreinforced portion 503a and the second unreinforced portion 503b of the net structure 500 reside therebetween. Cells 506, such as fibroblasts, are trapped within the net structure 500, amongst the first unreinforced portion 503a and the second unreinforced portion 503b and between the first structural reinforcement 540a, the second structural reinforcement 540b, and the third structural reinforcement 540c. The cells 506 then begin the process of cell interaction and cell movement. Since the cells 506 can freely communicate within the first unreinforced portion 503a and the second unreinforced portion 503b of the net structure 500, tension forces result from cell-cell interactions. This draws the first net strand 502a and the second net strand 502b toward each other, as illustrated in FIG. 19B. The reinforcements keep the first unreinforced portion 503a and the second unreinforced portion 503b separated which begin to fold or wrinkle. FIG. 19C provides a side view of the tissue showing the first unreinforced portion 503a, the second unreinforced portion 503b, and the third unreinforced portion 503cb drawing together, forming folds or wrinkles.

Figure 20:
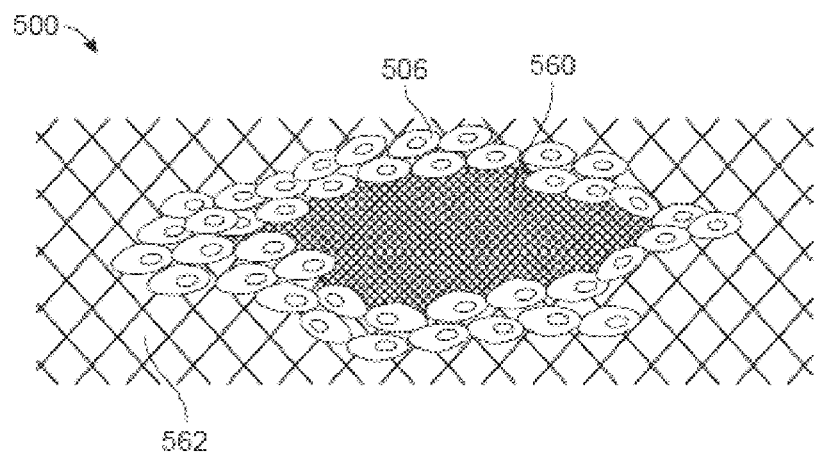
FIG. 20 illustrates a net structure having a high density net region surrounded by a low density net region.

In some embodiments, variations in density of the net structure 500 guide movement and interactions of cells 506. FIG. 20 illustrates an example net structure 500 having a high density net region 560 surrounded by a low density net region 562. The high density net region 560 is comprised of apertures that are smaller than the apertures of the low density net region 562. Therefore, the high density region 560 has a higher number of apertures compared to the low density net region 562. The small aperture size of the high density net region 560 resists movement of cells 506 there through. Thus, when the cells 506 move and interact, the cells 506 avoid the high density net region 560, creating a tissue structure around or surrounding the high density net region 560. Thus, once the net structure 500 dissolves, degrades, or is otherwise removed, a hole or passageway remains in the place of the high density net region 560. When multiple nets are layered so that the high density net regions are aligned, a lumen may be formed through the body of surrounding cells 506. This is one way in which a low density region of cells while concentrating cells in other areas may be done in a single printed structure.

In some cases, the high density net region 560 may comprise a signaling molecule, a cytokine, a protein, a surface coating, a polymer such as a hydrophilic polymer, and/or a surface treatment such as plasma treatment, that inhibits cell migration, adhesion, and/or traction. In some cases, the low density net region 562 may comprise a signaling molecule, a cytokine, a protein, a surface coating, a polymer such as a hydrophobic polymer, and/or a surface treatment, that promotes cell migration, adhesion, and/or traction.

Figure 21:
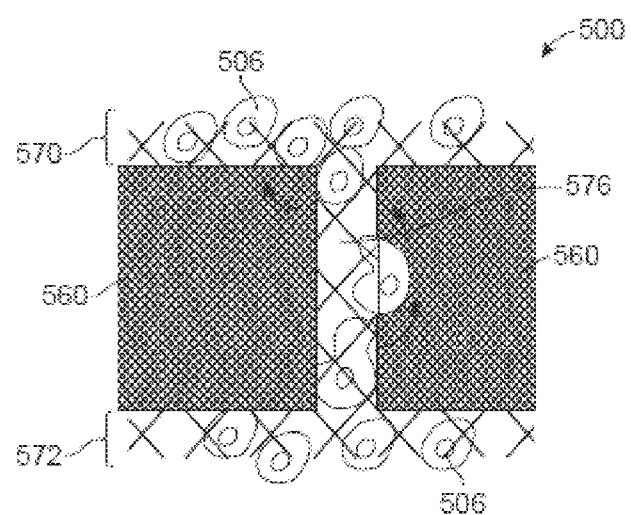
FIG. 21 illustrates another embodiment wherein variations in density of the net structure guide movement and interactions of cells.

FIG. 21 illustrates another embodiment wherein variations in density of the net structure 500 guide movement and interactions of cells 506. In this embodiment, the net structure 500 comprises a first net portion 570 and a second net portion 572, wherein a high density net region 574 resides therebetween. In addition, a ladder 576 is formed of a lower density net region which extends through the high density net region 560, bridging the first net portion 570 and the second net portion 572. Thus, cells 506 trapped in the first net portion 570 and/or the second net portion 572 are able to move along the ladder 576 while avoiding the high density net regions 560. This guides cells 506 in a predetermined direction and allows the cells 506 to form tissue structures according to predetermined shapes. It may be appreciated that in other embodiments the high density net region 560 is absent, wherein no netting material is present. This also guides cells 506 along the ladder 576, particularly when the ladder 576 comprises features which promote cell adhesion or attraction.

Figure 22:
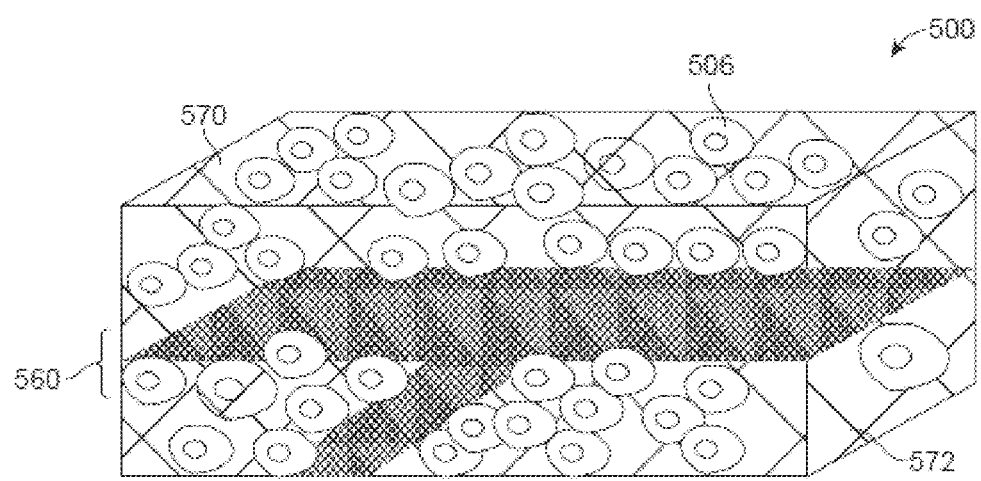
FIG. 22 illustrates another embodiment wherein variations in density of the net structure guide movement and interactions of cells to make a three-dimensional tissue structure.
Figure 23A:
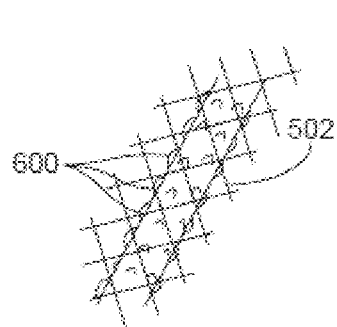
FIGS. 23A-23E illustrate textured elements along net strands which may promote cell adhesion or attraction.
Figure 23B:
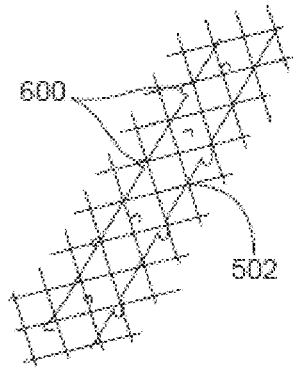
Figure 23C:
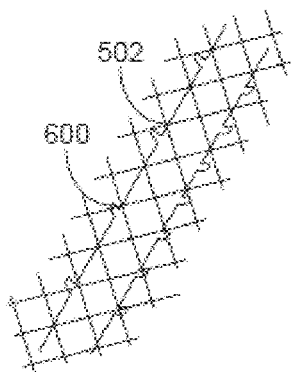
Figures 23D, 23E:
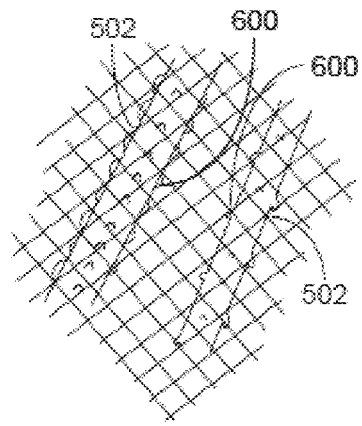
Figure 24A:
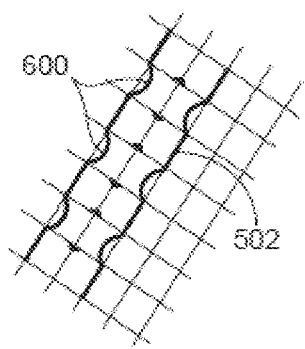
FIGS. 24A-24B illustrate textured elements along net strands which may promote cell adhesion or attraction.
Figure 24B:
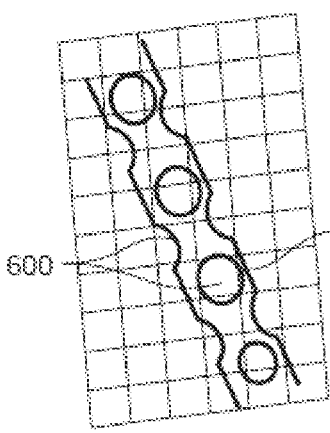
Figure 25:
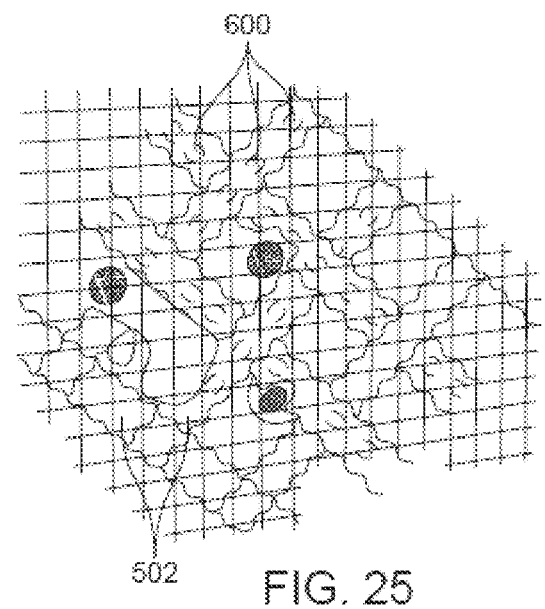
FIG. 25 illustrates yet another example of textured elements along net strands which may promote cell adhesion or attraction.

FIG. 22 illustrates another embodiment wherein variations in density of the net structure 500 guide movement and interactions of cells 506 to make a three-dimensional tissue structure. In this embodiment, the net structure 500 comprises a first net portion 570 and a second net portion 572, wherein a high density net region 560 resides therebetween. Thus, cells 506 trapped in the first net portion 570 and/or the second net portion 572 are unable to move due to the high density net regions 560. This guides cells 506 in a predetermined direction and allows the cells 506 to form tissue structures according to predetermined shapes.

FIGS. 23A-23E, 24A-24B, 25 illustrate textured elements 600 along net strands 502 which promote cell adhesion, attraction, and/or interaction. Textured elements may be constructed with divots, raised notches, rough edges, or any element that purposely creates a surface that is not perfectly smooth for the purpose of cell adhesion and/or cell interaction with the surface.

The cell nets may be formed with specific enzyme cleavage sites as part of the natural structural material such that the native activity of matrix metalloproteinases may be encouraged to remodel printed structures to allow for cell movement, flow, and/or cell-cell interactions. A non-limiting example list of such enzyme cleavage sites within a protein based structure are given in Table 2.

TABLE 2

Examples of enzyme cleavage sites within a protein-based structure.

| Cell express example | Enzyme | Substrate example |
|---|---|---|
| Fibroblast | MMP1 | Collagen |
| Epithelial cell | MMP9 | Gelatin, Collagen |
| Macrophage | MMP12 | Elastin |

Figure 26:
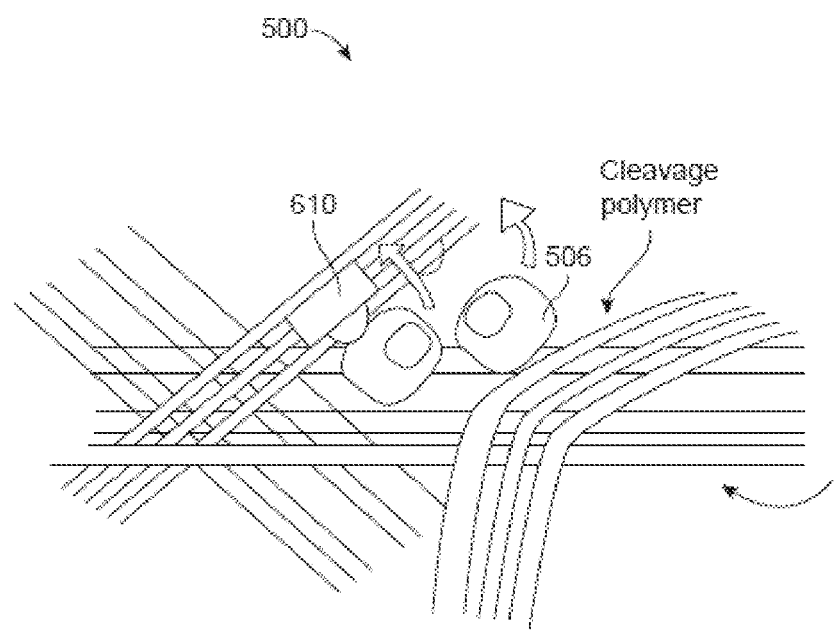
FIG. 26 illustrates an embodiment of a net having a cleavage site.

FIG. 26 illustrates an embodiment of a net structure 500 having a cleavage site 610. Thus, the net structure 500 includes uncleavable polymer strands and cleavable polymer strands. In this embodiment, the net structure 500 includes a fibroblast activation protein (FAP) which allows cells 506 to pass therethrough. Monomers that are polymerized in the printing process to create cell containing biogels may also incorporate proteins that have matrix metalloproteinase (MMP) cleavage sites to allow cells to engage in functional remolding of deposited structures. MMP responsive proteins that may be incorporated in the print media or used to polymerize into specific structures include but are not limited to proteins; collagens I, II, III, VII, VIII, X, gelatin, fibronectin, and elastin.

In some embodiments, the nets include printed mechanical elements which are designed to provide specific functions within a tissue structure or to assist in joining various tissue structures together. Such mechanical elements include joints, hinges, locking joints and hinges, Velcro-like elements, springs, coils, points of stretch, interlocking loops, sockets, gears, ratchets, screws, and chain links, to name a few. The mechanical elements may be printed so as to be embedded within a net, disposed along a surface of a net (such as along a flat surface or along an edge), or in a location so as to assist in joining or linking two portions of the net together or two separate nets together. Thus, in some embodiments, a layered tissue structure is formed by linking together individual nets with the use of mechanical elements. In other embodiments, an unlinked structural niche is embedded within printed vascular networks. When the niche is printed as an unlinked proximal structure, or a new structure with links attached to structures printed previously, these cell containing nets form semi-autonomous, active structures composed of moving cells, and additional elements designed to facilitate cell-cell contact and movement during tissue development in culture.

It may be appreciated that many of the mechanical elements are comprised of individual portions that are mateable together, such as two joinable portions of a hinge or two interlocking loops. In such embodiments, the portions of the mechanical element may be printed in a mated configuration. In other embodiments, the portions may be mated after printing as sheets or edges with mateable units may be brought into close proximity during movement of tissues in response to cell development and exerted forces therein or in response to external forces such as pressures along airways or vasculature. In some embodiments, the mechanical element is printed so that a first portion is attached to a first net and a second portion is attached to a second net. Upon mating, the first and second nets are able to move in relation to each other at the location of the mechanical element. This may assist in joining various net structures together to create a complex three-dimensional tissue structure, particularly in a manner which benefits from relational movement in the development process. It may be appreciated that the mechanical may alternatively or additionally be printed so that the first portion is attached to a first portion of a net and the second portion is attached to a second portion of the same net, wherein the portions of the net move in relation to each other at the location of the mechanical element. This may assist in wrapping, looping, twisting or other desired movement within a net during the development process.

Figure 27A:
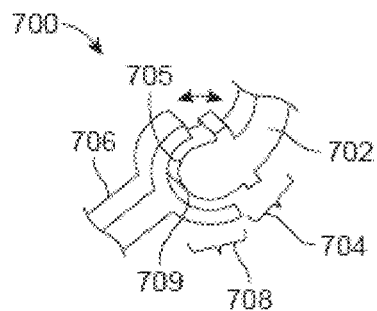
FIGS. 27A-27B illustrate an embodiment of a mechanical element comprising a pivot joint.
Figure 27B:
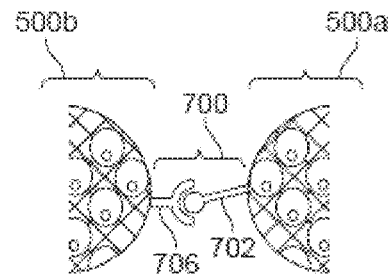

FIGS. 27A-27B illustrate an embodiment of a mechanical element comprising a pivot joint 700. In this embodiment, as shown in FIG. 27A, the pivot joint 700 comprises a first protrusion 702 having a first head 704 with a rounded surface 705 and a second protrusion 706 having a second head 708 with a concave surface 709. The concave surface 709 is mateable with the rounded surface 705 so that the first head 704 is able to pivot against the concave surface 709 in a single direction, such as in a rocking motion. In some embodiments, the joint 700 is printed so that the first protrusion 702 is attached to a first net structure 500a and the second protrusion 706 is attached to a second net structure 500b, as illustrated in FIG. 27B. Upon mating, the first net structure 500a and the second net structure 500b are able to pivot in relation to each other at the location of the pivot joint 700.

Figure 28A:
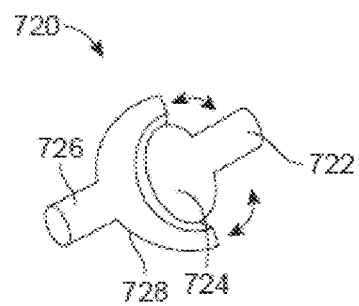
FIGS. 28A-28B illustrate an embodiment of a mechanical element comprising a ball-and-socket joint.
Figure 28B:
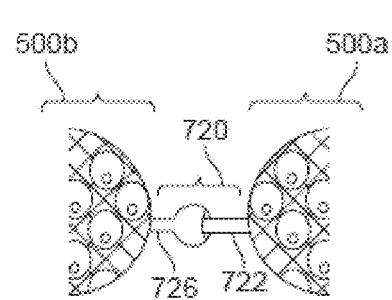

FIGS. 28A-28B illustrate an embodiment of a mechanical element comprising a ball-and-socket joint 720. In this embodiment, as shown as a cross-sectional view in FIG. 28A, the ball-and-socket joint 720 comprises a first protrusion 702 having a rounded ball head 724 and a second protrusion 706 having a concave socket head 728. The concave socket head 728 is mateable with the rounded ball head 724 so that the rounded ball head 724 is able to rotate within the concave socket head 728 in a manner similar to an anatomical ball-and-socket joint. In some embodiments, the ball-and-socket joint 720 is printed so that the first protrusion 702 is attached to a first net structure 500a and the second protrusion 706 is attached to a second net structure 500b, as illustrated in FIG. 28B. Upon mating, the first net structure 500a and the second net structure 500b are able to rotate in relation to each other, in numerous directions, at the location of the ball-and-socket joint 720.

Figure 29A:
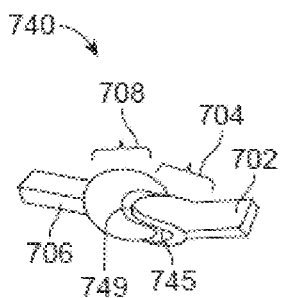
FIGS. 29A-29B illustrate an embodiment of a mechanical element comprising a saddle joint.
Figure 29B:
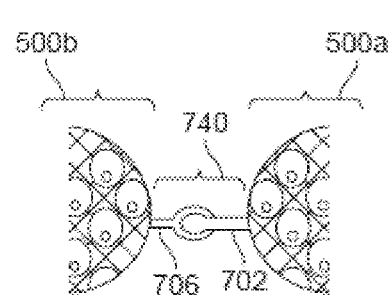

FIGS. 29A-29B illustrate an embodiment of a mechanical element comprising a saddle joint 740. In this embodiment, as shown in FIG. 29A, the saddle joint 740 comprises a first protrusion 702 having a first head 704 with a saddle-shaped indentation 745 and a second protrusion 706 having a second head 708 with a corresponding second saddle-shaped indentation 749. The first head 704 and the second head 706 may be oriented in a 90 degree offset so that the first indentation 745 and the second indentation 749 are mateable as illustrated. Thus, the first head 704 and the second head 706 are able to rotate around each other in a single direction. In some embodiments, the saddle joint 740 is printed so that the first protrusion 702 is attached to a first net structure 500a and the second protrusion 706 is attached to a second net structure 500b, as illustrated in FIG. 29B. Upon mating, the first net structure 500a and the second net structure 500b are able to pivot in relation to each other, in a single direction, at the location of the saddle joint 740.

Figure 30:
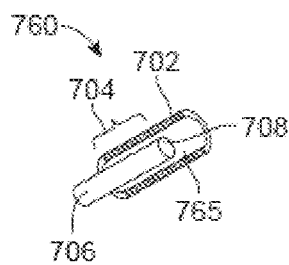
FIG. 30 illustrates an embodiment of a socket joint comprising a first protrusion and a second protrusion having socket-shaped cavities.
Figure 31:
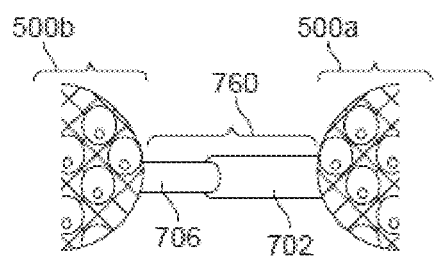
FIG. 31 illustrates an embodiment of a socket joint that is printed so that the first protrusion and the second protrusion are attached to net structures.

FIGS. 30-31 illustrate an embodiment of a mechanical element comprising a socket joint 760. In this embodiment, as shown in FIG. 30, the socket joint 760 comprises a first protrusion 702 having a first head 704 with a socket-shaped cavity 765 and a second protrusion 706 having a second head 708 shaped to fit within the socket-shaped cavity 765. In this embodiment, the socket-shaped cavity 765 is tubular in shape and the second head 708 is cylindrical in shape so as to be insertable into the socket-shaped cavity 765. The second head 708 is able to slide longitudinally and rotate within the socket-shaped cavity 765. In some embodiments, the socket joint 760 is printed so that the first protrusion 702 is attached to a first net structure 500a and the second protrusion 706 is attached to a second net structure 500b, as illustrated in FIG. 31. Upon mating, the first net structure 500a and the second net structure 500b are able to slide and rotate in relation to each other, at the location of the socket joint 760.

Figure 32:
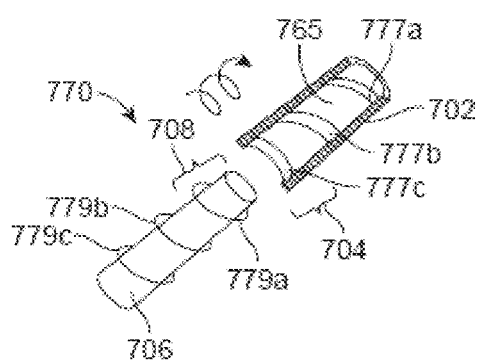
FIG. 32 illustrates an embodiment of threaded joint comprising a first protrusion having a first head and a second head with socket-shaped cavities having grooves and threads.
Figure 33:
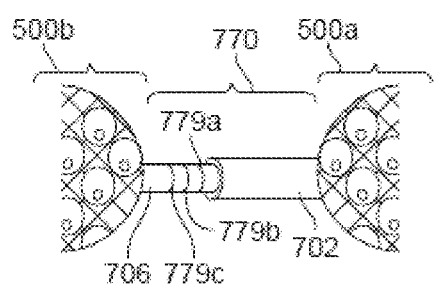
FIG. 33 illustrates an embodiment of threaded joint that is printed so that the first protrusion and second protrusion are attached to net structures.

FIGS. 32-33 illustrate an embodiment of a mechanical element comprising a threaded joint 770. In this embodiment, as shown in FIG. 32, the threaded joint 770 comprises a first protrusion 702 having a first head 704 with a socket-shaped cavity 765 having a first groove 777a, a second groove 777b, and a third groove 777c and a second protrusion 706 having a second head 708 with a first thread 779a, a second thread 779b, and a third thread 779c. Wherein the second head 708 is shaped to fit within the socket-shaped cavity 765 so that the first thread 779a, the second thread 779b, and the third thread 779c mate with the first groove 777a, the second groove 777b, and the third groove 777c in a screw type manner. In some embodiments, the threaded joint 770 is printed so that the first protrusion 702 is attached to a first net structure 500a and the second protrusion 706 is attached to a second net structure 500b, as illustrated in FIG. 33. Upon mating, the first net structure 500a and the second net structure 500b are able to rotate in relation to each other, at the location of the threaded joint 770, with a resistance to longitudinal sliding due to the threads.

Figure 34A:
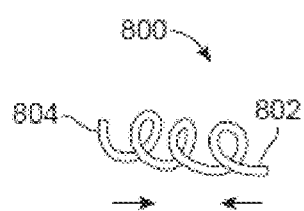
FIGS. 34A-34B illustrate an embodiment of a mechanical element comprising a coil or spring.
Figure 34B:
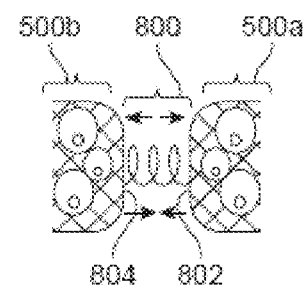

FIGS. 34A-34B illustrate an embodiment of a mechanical element comprising a coil or spring 800. In this embodiment, as shown in FIG. 34A, the spring 800 has a first end 802, a second end 804 and a coiled or spiral configuration therebetween so as to provide spring tension between the first end 802 and the second end 804. In some embodiments, the spring 800 is printed so that the first end 802 is attached to a first net structure 500a and the second end 804 is attached to a second net structure 500b, as illustrated in FIG. 34B. Thus, the first net structure 500a and the second net structure 500b are able to move in relation to each other while the spring 800 maintains connection.

Figure 35A:
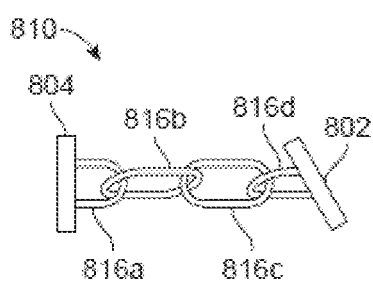
FIGS. 35A-35B illustrate a mechanical element comprising a chain.
Figure 35B:
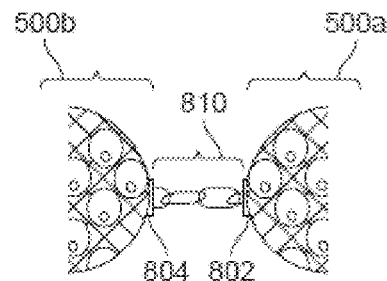

FIGS. 35A-35B illustrate an embodiment of a mechanical element comprising a chain 810. In this embodiment, as shown in FIG. 35A, the chain 810 has a first end 802, a second end 804 and a first link 816a, a second link 816b, a third link 816c, and a fourth link 816d therebetween in a chain configuration so as to connect the first end 802 and the second end 804 together. In some embodiments, the chain 810 is printed so that the first end 802 is attached to a first net structure 500a and the second end 804 is attached to a second net structure 500b, as illustrated in FIG. 35B. Thus, the first net structure 500a and the second net structure 500b are able to move in relation to each other while the chain 810 maintains connection.

Figure 36A:
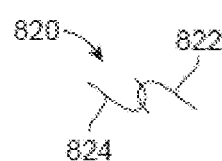
FIGS. 36A-36B illustrate an embodiment of a mechanical element comprising a hooking joint.
Figure 36B:
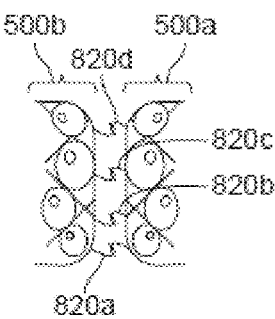

FIGS. 36A-36B illustrate an embodiment of a mechanical element comprising a hooking joint 820. In this embodiment, as shown in FIG. 36A, the hooking joint 820 comprises a first hook 822 having a curved shape and a second hook 824 also having a curved shape. The first hook 822 and the second hook 824 are mateable so that the curved shapes hook together, such as illustrated. In some embodiments, the hooking joint 820 is printed so that the first hook 822 is attached to a first net structure 500a and the second hook 824 is attached to a second net structure 500b, as illustrated in FIG. 36B wherein a plurality of hooking joints (i.e., a first hooking joint 820a, a second hooking joint 820b, a third hooking joint 820c, and a fourth hooking joint 820d) are shown. Thus, the first net structure 500a and the second net structure 500b are able to move in relation to each other while the first hooking joint 820a, the second hooking joint 820b, the third hooking joint 820c, and the fourth hooking joint 820d maintain connection.

Figures 37A, 37B:
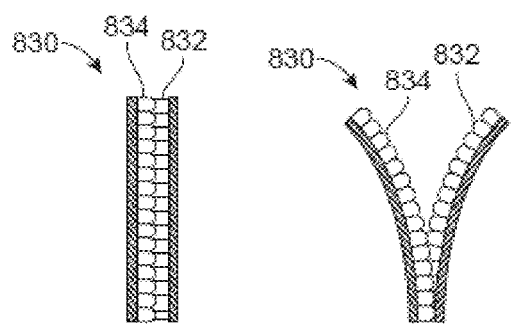
FIGS. 37A-37C illustrate an embodiment of a mechanical element comprising a hook-and-loop joint which functions in a manner similar to Velcro®.
Figure 37C:
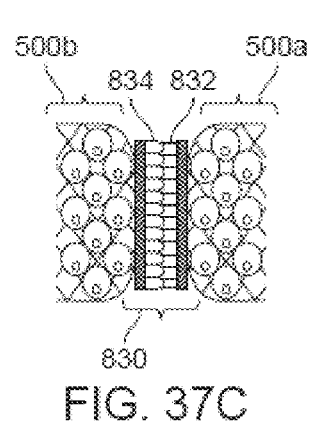

FIGS. 37A-37C illustrate an embodiment of a mechanical element comprising a hook-and-loop joint 830 which functions in a manner similar to Velcro®. In this embodiment, the hook-and-loop joint 830 comprises a hook surface 832 having a plurality of small hooks and a loop surface 834 having a plurality of small loops. The hook surface 832 is mateable with the loop surface 834 wherein the small hooks engage the small loops, as illustrated in FIG. 37A, holding the hook surface 832 and the loop surface 834 together. However, the hook surface 832 and the loop surface 834 may be disengaged by pulling the hook surface 832 and the loop surface 834 away from each other, as illustrated in FIG. 37B. In some embodiments, the hook-and-loop joint 830 is printed so that the hook surface 832 is attached to a first net structure 500a and the loop surface 834 is attached to a second net structure 500b, as illustrated in FIG. 37C. Thus, the first net structure 500a and the second net structure 500b are joined and held in relation to each other by interaction of the hook surface 832 and the loop surface 834 yet can be disengaged with sufficient pulling force.

Figure 38A:
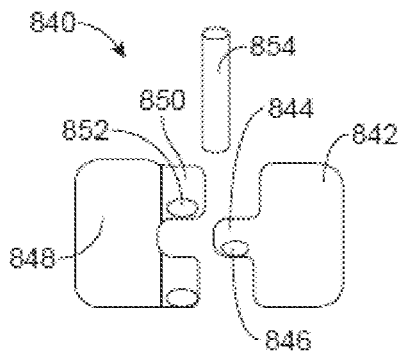
FIGS. 38A-38C illustrate an embodiment of a mechanical element comprising a hinge.
Figure 38B:
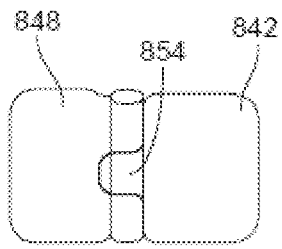
Figure 38C:
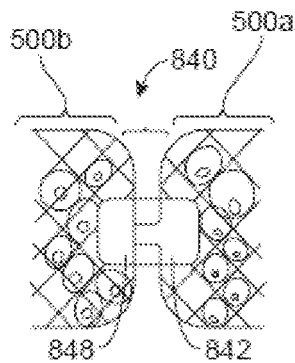

FIGS. 38A-38C illustrate an embodiment of a mechanical element comprising a hinge 840. In some embodiments, such as illustrated in FIG. 38A, the hinge 840 comprises a first bracket 842 having a first bracket protrusion 844 with a first bracket opening 846 therethrough, and a second bracket 848 having a second bracket protrusion 850 with a second bracket opening 852 therethrough. The hinge 840 further comprises a rod 854, which is sized and configured to extend through the first bracket opening 846 and the second bracket opening 852. FIG. 38B illustrates the first bracket 842 and the second bracket 848 so that the rod 854 extends through the first bracket opening 846 and the second bracket opening 852 so as to join the first bracket 842 and the second bracket 848 together while allowing the first bracket 842 and the second bracket 848 to swivel and rotate, moving toward or away from each other. In some embodiments, the hinge 840 is printed so that the first bracket 842 is attached to a first net structure 500a and the second bracket 848 is attached to a second net structure 500b, as illustrated in FIG. 38C. Thus, the first net structure 500a and the second net structure 500b are joined and held in relation to each other by the hinge 840, yet can be swivel and tilt in relation to each other.

Figure 39:
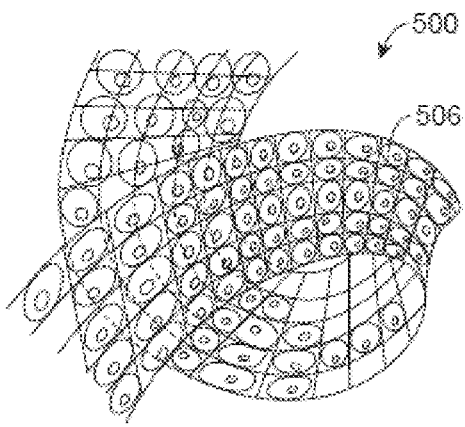
FIG. 39 illustrates an embodiment of a tissue structure comprised of cells captured in a net wherein the net is looping due to the presence of mechanical elements.
Figure 40:
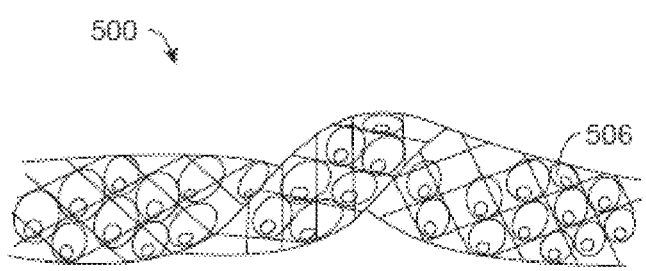
FIG. 40 illustrates an embodiment of a tissue structure comprised of cells captured in a net wherein the net is twisting due to the presence of mechanical elements.

As mentioned previously, the mechanical elements provide a variety of functions, such as joining portions of a net and/or various net structures together to create a complex three-dimensional tissue structure, particularly in a manner which benefits from relational movement in the development process. This may assist in wrapping, looping, twisting or other desired movement within a net during the development process. FIG. 39 illustrates an embodiment of a tissue structure comprised of cells 506 captured in a net structure 500 wherein the net structure 500 is looping due to the presence of mechanical elements. Similarly, FIG. 40 illustrates an embodiment of a tissue structure comprised of cells 506 captured in net structure 500 wherein the net structure 500 is twisting due to the presence of mechanical elements.

In other embodiments, nets are linked or joined together by cells 506 held in close proximity.

Figure 41A:
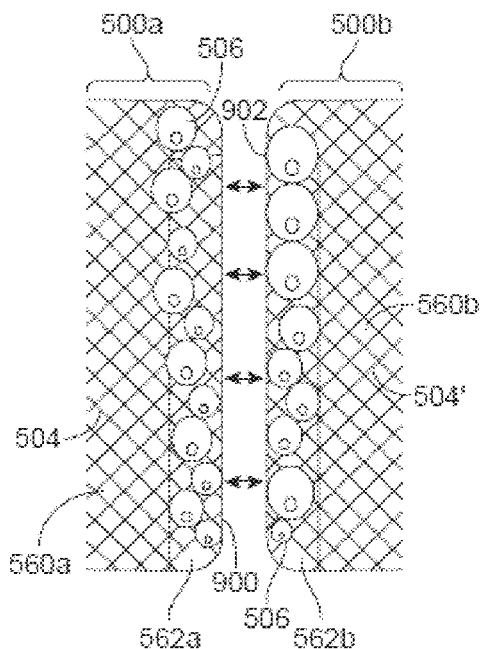
FIGS. 41A-41B illustrate an embodiment designed to induce cell-cell interactions between two separate cell groups located in two separate net structures.
Figure 41B:
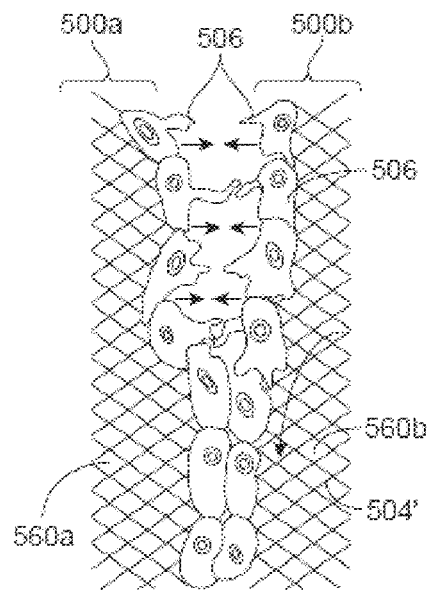

FIGS. 41A-41B illustrate an embodiment designed to induce cell-cell interactions between two separate cell groups located in two separate net structures. FIG. 41A illustrates a first net structure 500a having a first edge 900 and a second net structure 500b having a second edge 902 wherein the first edge 900 and the second edge 902 are in close proximity. The first net structure 500a and the second net structure 500b are printed having a first low density region 562a bordering the first edge 900 and a second low density region 562b bordering the second edge 902. Furthermore, the first net structure 500a and the second net structure 500b are printed having a first high density region 560a bordering the first low density region 562a and a second low density region 562b bordering the second low density region 562b. The first low density region 562a and the second low density region 562b are sized to trap particular cells 506. The first high density region 560a and the second low density region 562b, which are adjacent to first low density region 562a and the second low density region 562b, are sized to exclude cells 506. Thus, the cells 506 are held along the first edge 900 and the second edge 902 and favor cell-cell interactions with each other, as illustrated in FIG. 41B. This binds the first edge 900 and the second edge 902 together, linking or joining the first net structure 500a and the second net structure 500b.

Figure 42A:
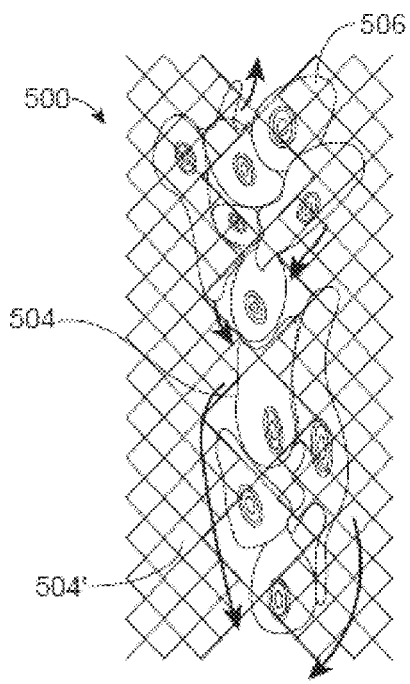
FIGS. 42A-42B illustrate embodiments of variable density nets can be used to generate cell strands.
Figure 42B:
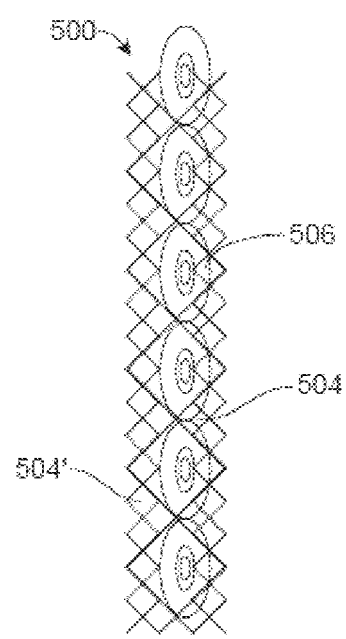

In other embodiments, variable density nets can be used to generate cell strands, such as illustrated in FIG. 42A-42B. For example, as shown in FIG. 42A, in some embodiments, a net structure 500 is printed having a longitudinal region wherein the first apertures 504 are sized to trap particular cells 506 and the surrounding second apertures 504' are sized to exclude cells 506. In such embodiments, the cells 506 are held in close proximity within the longitudinal region and favor cell-cell interactions with each other, creating a longitudinal strand of cells, as shown in FIG. 42B.

It may be appreciated that in some embodiments, nets structures include elements that promote self-assembly, or structural elements that allow for compression without primary structure deformation or other force absorbing, stretching elements to either restrict, facilitate, or allow movement of cell sheets, strands, networks, groups, or individual cells through structures that allow for cell "squeezing" and cytosolic flow. Likewise, some nets allow the formation or differentiation of cells in response to pressure, tension, progressive or pulsatile local shifts in mechanical forces of pressure, stretch, or tissue tension. In some instances, movement, environmental responsiveness, and cell-cell contact within developing tissues is critical for functional organ, tissue, and cell development. Non-limiting examples of these include: individual cell-cell interactions that may or may not be part of a larger network. Movement of cells within coordinated networks that may include two or three dimensional cell-sheet flow, folding, wrapping, deformation, or twisting, or formation of strands, multi-layered spheroid formation or linking necessary for functional tissue development and morphogenesis.

Beads containing bound or secreted signaling molecules, receptors, and/or stimulatory or blocking antibodies may be printed for promoting directional or localized self-assembly. Non-limiting examples of such signaling molecules include VEGF, to promote vascular outgrowth and branching; VEGF-C, to promote lymphatic vasculature outgrowth and development; GDNF, to promote nerve development or, in kidney, ureteric bud branching; or SHH, to promote tissue-dependent developmental patterning. Such signaling molecule beads may also be used for directing axon pathfinding. In normal nerve development, the growth cone of a developing axon responds to attractive cues, which promote axon extension via assembly of cytoskeletal actin comprising the axon, and repulsive cues, which prevent axon extension by inhibiting actin assembly and/or promoting actin disassembly. Both attractive and repulsive cues are essential to proper pathfinding. Attractive cues include EphrinB and netrins; repulsive cues include EphrinA, semaphorins, and Slit. Printing attractive and repulsive cues within signaling beads at desired locations provides a mechanism to promote and control axonal growth from printed neural progenitor cells.

Print Media and Printing Conditions

As mentioned previously, the media chamber 122 contains media comprised of cells, polymerizable material and culture medium. The polymerizable material comprises polymerizable monomeric units that are biologically compatible, dissolvable, and biologically inert. The monomeric units polymerize, cross-link or react in response to the multi-photon laser excitation 120 to create cell containing structures, such as cell matrices and basement membrane structures, specific to the tissue to be generated. The media chamber may contain media comprising glutathione or a functional variant (or derivative) thereof.

In some embodiments, the media comprises a solution e.g. from at least about 0.2 mPa·s to about 10 Pa·s in viscosity, containing either photo-activator or photo-activator-free polymerizable units. The solution may be doped with additional chemical and/or biological components, with or without expressed chemical or biological activity, to alter the solution behavior such that it is non-Newtonian. Such behavior may be particularly useful in the instances of shear thinning properties, wherein media becomes less viscous upon experiencing shear force, or thixotropic media, wherein media becomes less viscous with vibration or shaking; such media may exhibit improved, better controlled draining during media replacement. Non-limiting examples of such components that may be added to the cell-containing printing media include extracellular matrix protein mixtures containing various amounts of hyaluronic acid, heparin sulfate, collagen types I through X, elastin, and fibrinogen. Additional organic or non-organic elements may be introduced to the cell-containing print media to induce an increased rate of avalanche ionization. Non-limiting examples of these particles include non-toxic nanoparticles, moderate increases in elemental substances with a high number of freely available electrons such as selenium or lithium.

In some cases, specific conditions may be used during the printing process to facilitate the building of multiple cell layers using multi-photon printing of net structure 500 and components therein. Such conditions provide for reduced cellular respiration, cell rounding, minimization of migration, and minimization of cellular damage, to name a few. In some cases, rounding of cells and reduction in adhesion may be desired for trapping of cells in nets and efficient removal of cells not trapped in the nets. This can be achieved by maintaining the temperature of the printing media that contains polymerizable units or media that does not contain additional cells or polymerizable monomers in a range e.g. from about at least 1° C. to about 36° C. This temperature range may suppress cellular respiration, may encourage cell "rounding", may reduce laser induced temperature effects, and may minimize cellular migration. The temperature may be controlled by either active or passive cooling mechanisms. Specifically, media or printing media used to create biogels may be cooled by having a heat exchange platform for cell printing or by printing in cooled ambient temperatures such as a cold-room.

In general, infrared photons used for multiphoton printing may be diffuse and/or may be comprised of short, condensed, temporally distinct photon packets. However, near the focal point, these photon packets may become increasingly condensed, resulting in a local increase in the concentration of infrared (IR) radiation. Thus, the printing process can impart heat to the surrounding media outside of the focal plane, an issue that increases in direct correlation to laser power increases. Therefore, heat as a function of infrared radiation, related either directly to the multi-photon wavelength itself or as part of the non-radiative decay (energy loss of an excited electron prior to photon emission) can impart significant heat that can damage to cells. Cold print-media may reduce this potential heat toxicity.

In some instances, highly localized increases in heat due to the energy associated with high-intensity photon absorption near the focal point may lead to undesired polymerization or oxidation of some materials. Cooled media may assist in diffusing general infrared, focal point, and near-focal point heat generation, thereby reducing potential heat toxicity to the living cells. In addition to reducing heat toxicity from infrared radiation, cooled media may improve the structural rigidity of many polymerized materials and may increase the viscosity of print media, such that cells remain uniformly distributed. This increase in structural stiffness at cool temperatures and reduction of flexibility may allow improved rates of cell-containing media exchange for additional rounds of printing without damage to the deposited structure.

In some instances, highly localized increases in heat due to the energy associated with high-intensity photon absorption near the focal point may lead to polymerization or oxidation of some materials. In some formulations of monomer and cell containing print materials, highly localized increases in heat may be desirable, as many biocompatible monomers can be polymerized into strands to create cell nets. This process can be tuned by using radiative heat emission at different wavelengths and polymerization of monomers may be specific only to thermal radiation. In some formulations this may be achieved by using heat polymerized compounds that are otherwise non-responsive to photon absorption, light-induced printing, and/or photopolymerization.

Removal of cations, such as calcium and/or magnesium, by addition of chelating agents can reduce protein-protein interactions between cells and between cells and the extracellular matrix, reducing migration, promoting cell rounding, and temporarily slowing or speeding up the progression of cell differentiation. Therefore, in some cases, the print biogel and media may be kept within a range e.g. from at least about 0 to about 1.8 nanomolar (nM) calcium concentrations. Either naturally low calcium concentration media may be used or the addition of calcium chelating agents may be incorporated in the cell containing print media. In some cases, cation chelating agents may be added to reduce molar concentrations of cations including but not limited to calcium, magnesium, and, or sodium. Non-limiting examples of chelating agents include ethylenediaminetetraacetic acid (EDTA), ethylene glycol-bis(β-aminoethyl ether)-N,N,N',N'-tetraacetic acid (EGTA), and 1,2-bis(o-aminophenoxy)ethane-N,N,N',N'-tetraacetic acid (BAPTA). In some cases, naturally occurring small molecules and chemicals released by cells are added to specific formulations of print media to facilitate reduced cellular respiration, facilitate cell respiration recovery, or quench radicals generated by the printing process. Non-limiting examples include hydrogen sulfide ($H_2S$), sodium hydrosulfide (NaHS), nitrous oxide, glutathione, phosphate, β-glycerophosphate, sodium pyruvate, L-glutamine, carbon-based sugars, micronutrients, mixed human serum proteins and growth factors, metabolic effectors (insulin), cytokines, chemokines, and compounds that interact with internal cell pathways such as the Rho/Rac pathway, PI3-kinase pathways, or ubiquitinase inhibitors. Once the printing process is complete or partially complete, the media surrounding the newly printed structure may be returned to physiologic conditions, to allow for cells to return to normal homeostatic function and active motility.

In some cases, glutathione or a functional variant (or derivative) thereof may be added to a formulation of print media (i.e., to the medium). Glutathione (GSH) is an important antioxidant in living organisms; it is a cellular-health promoting free-radical scavenger. Glutathione may prevent cellular damage caused by reactive oxygen species, such as but not limited to free radicals, peroxides, lipid peroxides, and/or heavy metals. Glutathione or a functional variant (or derivative) thereof may be used in a manufacturing process and/or in a printing process. Glutathione is a free-radical inhibitor that may be used in a manufacturing process and/or a printing process which includes cells. Glutathione or a functional variant (or derivative) may be used in a manufacturing process and/or a printing process that uses cells. In some cases, glutathione or a functional variant (or derivative) thereof may quench radicals generated by the 3D holographic printing process.

Glutathione or a functional variant (or derivative) thereof may suppress any additional polymerization outside of a desired print area by quenching a radical reaction. The methods and systems provided herein may use glutathione or a functional variant (or derivative) thereof for controlling a polymerization reaction during the 3D holographic printing process in order to achieve the printing of ultra-fine architecture necessary for tissue engineering. Functional variants and/or derivatives of glutathione may include, but are not limited to sodium pyruvate and L-glutamine.

The medium may further comprise glutathione or a functional variant (or derivative) thereof. The medium may comprise at least about 0.1 millimolar (mM) to about 50 mM or more of glutathione or a functional variant (or derivative) thereof. The medium may comprise at least about 0.01 millimolar (mM) to about 50 mM or more of glutathione or a functional variant (or derivative) thereof. The medium may comprise at least about 0.05 millimolar (mM) to about 50 mM or more of glutathione or a functional variant (or derivative) thereof. The medium may comprise at least about 0.5 millimolar (mM) to about 50 mM or more of glutathione or a functional variant (or derivative) thereof. The medium may comprise at least about 1 millimolar (mM) to about 50 mM or more of glutathione or a functional variant (or derivative) thereof. The medium may comprise at least about 5 millimolar (mM) to about 50 mM or more of glutathione or a functional variant (or derivative) thereof. The medium may comprise at least about 10 millimolar (mM) to about 50 mM or more of glutathione or a functional variant (or derivative) thereof. The medium may comprise at least about 20 millimolar (mM) to about 50 mM or more of glutathione or a functional variant (or derivative) thereof. The medium may comprise at least about 30 millimolar (mM) to about 50 mM or more of glutathione or a functional variant (or derivative) thereof. The medium may comprise at least about 40 millimolar (mM) to about 50 mM or more of glutathione or a functional variant (or derivative) thereof.

The medium may comprise at least about 0.01 mM of glutathione or a functional variant (or derivative) thereof. The medium may comprise at least about 0.02 mM of glutathione or a functional variant (or derivative) thereof. The medium may comprise at least about 0.03 mM glutathione or a functional variant (or derivative) thereof. The medium may comprise at least about 0.04 mM glutathione or a functional variant (or derivative) thereof. The medium may comprise at least about 0.05 mM glutathione or a functional variant (or derivative) thereof. The medium may comprise at least about 0.06 mM glutathione or a functional variant (or derivative) thereof. The medium may comprise at least about 0.07 mM glutathione or a functional variant (or derivative) thereof. The medium may comprise at least about 0.08 mM glutathione or a functional variant (or derivative) thereof. The medium may comprise at least about 0.09 mM glutathione or a functional variant (or derivative) thereof. The medium may comprise at least about 0.1 mM glutathione or a functional variant (or derivative) thereof. The medium may comprise at least about 0.2 mM glutathione or a functional variant (or derivative) thereof. The medium may comprise at least about 0.3 mM glutathione or a functional variant (or derivative) thereof. The medium may comprise at least about 0.4 mM glutathione or a functional variant (or derivative) thereof. The medium may comprise at least about 0.5 mM glutathione or a functional variant (or derivative) thereof. The medium may comprise at least about 0.6 mM glutathione or a functional variant (or derivative) thereof. The medium may comprise at least about 0.7 mM glutathione or a functional variant (or derivative) thereof. The medium may comprise at least about 0.8 mM glutathione or a functional variant (or derivative) thereof. The medium may comprise at least about 0.9 mM glutathione or a functional variant (or derivative) thereof. The medium may comprise at least about 1 mM glutathione or a functional variant (or derivative) thereof. The medium may comprise at least about 2 mM glutathione or a functional variant (or derivative) thereof. The medium may comprise at least about 3 mM glutathione or a functional variant (or derivative) thereof. The medium may comprise at least about 4 mM glutathione or a functional variant (or derivative) thereof. The medium may comprise at least about 5 mM glutathione or a functional variant (or derivative) thereof. The medium may comprise at least about 6 mM glutathione or a functional variant (or derivative) thereof. The medium may comprise at least about 7 mM glutathione or a functional variant (or derivative) thereof. The medium may comprise at least about 8 mM glutathione or a functional variant (or derivative) thereof. The medium may comprise at least about 9 mM glutathione or a functional variant (or derivative) thereof. The medium may comprise at least about 10 mM glutathione or a functional variant (or derivative) thereof. The medium may comprise at least about 15 mM glutathione or a functional variant (or derivative) thereof. The medium may comprise at least about 20 mM glutathione or a functional variant (or derivative) thereof. The medium may comprise at least about 25 mM glutathione or a functional variant (or derivative) thereof. The medium may comprise at least about 30 mM glutathione or a functional variant (or derivative) thereof. The medium may comprise at least about 35 mM glutathione or a functional variant (or derivative) thereof. The medium may comprise at least about 40 mM glutathione or a functional variant (or derivative) thereof. The medium may comprise at least about 45 mM glutathione or a functional variant (or derivative) thereof. The medium may comprise about 50 mM glutathione or a functional variant (or derivative) thereof or more. The medium may comprise at least about 75 mM glutathione or a functional variant (or derivative) thereof. The medium may comprise at least about 100 mM glutathione or a functional variant (or derivative) thereof.

Together, low calcium and cold temperatures may have important effects on cell behavior, metabolic processes, and physiologic responses to their environment that may be critical for multi-layered tissue printing. These may include, but are not limited to: i) cells maintained in low calcium ($Ca^{2+}$) concentrations and cold media take on a round shape and withdraw protrusions; ii) cellular low calcium ($Ca^{2+}$) and cold media conditions functionally alter integrins, mucins, (and other proteins) are functionally altered by. Low $Ca^{2+}$ concentrations may alter physical protein conformations, such that cell adhesion is significantly reduced if not completely absent. In addition, cold temperatures may reduce veracity of protein-protein interactions. iii) Low $Ca^{2+}$, cold media may halt signaling associated with external cell-cell interactions and intrinsic cell signaling associated with environmental responses and genetic changes; and iv) reduced propensity for cell-cell interactions may allow for high-density single-cell suspensions with low or no cell aggregate formation. Reduction or minimization of cell aggregate formation may be critical for even cell distribution and placement within confined structures.

Together, these conditions may cause important physiologic changes of rounding and reduced matrix-cell and cell-cell interactions, reduced cellular respiration, and biochemical support of cellular respiration functions through $CO_2$ buffering. $CO_2$ buffering can be achieved by adding various small molecules or agents to the cell-containing print media.

Additionally, changes in pH can significantly alter viscosity, cell survival, or print media properties. Therefore, changes to or stabilization of the pH of the cell-containing media, biogel, or print material may be effected by addition of various pH buffers. In some instances, print media pH may be critical for health and function of cells during the print process and during the recovery period. Therefore, in some cases, buffers that assist in controlling the pH of the cell print media may be included in the media. Such pH buffers may be added to reduce pH changes or fluctuations related to the printing process, cellular respiration, or other components that may be added to print media. Non-limiting examples of cell compatible and print compatible pH buffers may include: 2-(N-morpholino)ethanesulfonic acid (MES), bis(2-hydroxyethyl)amino-tris(hydroxymethyl)methane (BIS-TRIS), 2-[(2-amino-2-oxoethyl)-(carboxymethyl) amino]acetic acid (ADA), 2-(carbamoylmethylamino)ethanesulfonic acid (ACES), 1,3-bis(tris(hydroxymethyl)methylamino)propane (BIS-TRIS PROPANE), piperazine-N,N'-bis(2-ethanesulfonic acid) (PIPES), N-(2-Acetamido)-2-aminoethanesulfonic acid (ACES), 2-hydroxy-3-morpholin-4-ylpropane-1-sulfonic acid (MOPSO), cholamine chloride, 3-(N-morpholino)propanesulfonic acid (MOPS), N,N-Bis(2-hydroxyethyl)-2-aminoethanesulfonic acid (BES), 2-[[1,3-dihydroxy-2-(hydroxymethyl)propan-2-yl]amino]ethanesulfonic acid (TES), 2-[4-(2-hydroxyethyl)piperazin-1-yl] ethanesulfonic acid (HEPES), 3-(N,N-Bis[2-hydroxyethyl] amino)-2-hydroxypropanesulfonic acid (DIPSO), 4-(N-Morpholino)butanesulfonic acid (MOBS), 2-Hydroxy-3-[tris(hydroxymethyl)methylamino]-1-propanesulfonic acid (TAPSO), acetamidoglycine, Tris-acetate-ethylenediaminetetraacetic acid (TAE), piperazine-1,4-bis(2-hydroxypropanesulfonic acid) dihydrate (POPSO), 4-(2-hydroxyethyl) piperazine-1-(2-hydroxypropanesulfonic acid) (HEPPSO), 4-(2-hydroxyethyl)-1-piperazinepropanesulfonic acid (EPS), 4-(2-hydroxyethyl)-1-piperazinepropanesulfonic acid (HEPPS), tricine, 2-amino-2-(hydroxymethyl)-1,3-propanediol (TRIZMA), glycinamide, glycyl-glycine, N-(2-hydroxyethyl)piperazine-N'-(4-butanesulfonic acid) (HEPBS), bicine, 3-{[1,3-dihydroxy-2-(hydroxymethyl) propan-2-yl]amino}propane-1-sulfonic acid (TAPS), 2-amino-2-methyl-1-propanol buffer (AMPB), 2-(cyclohexylamino)ethanesulfonic acid (CHES), N-(1,1-Dimethyl-2-hydroxyethyl)-3-amino-2-hydroxypropanesulfonic acid (AMPSO), 3-(cyclohexylamino)-2-hydroxy-1-propanesulfonic acid (CAPSO), 3-(cyclohexylamino)-1-propanesulfonic acid (CAPS), 4-(cyclohexylamino)-1-butanesulfonic acid (CABS).

Additional methods are provided to enhance the printing of polymers process, through photon-based and thermally-induced polymerization process around cells as related to three-dimensional projection of multi-photon excitation. First, biologically compatible or biologically inert electron donors may enhance electron cascade phenomenon, which may increase the rate of multiphoton based polymerization. In some cases, this phenomenon may be utilized with the use of biogels or printing materials containing cells having specific properties, such as having electron shells with close energy states for ease of transition between ground and excited states. Enhancing the effect or likelihood of electron cascade initiation may be achieved by adding additional elements to the biogel to serve as ready electron donors into the system.

In some cases, the speed of bioprinting tissue may be enhanced by doping of cell-compatible electron donors as activators for the purpose of generating electron cascade events, tuning the dynamic range of photopolymerization, or selecting of multi-photon wavelengths that do so. These electron donors may include dyes, nanoparticles, or biologically active electron donors, including but not limited to ions such as lithium, selenium, iodine, or larger organic molecules such as nicotinic acid and riboflavins. Doping of biogels may also expand the range of sensitivity for photon-based polymerization such that polymerization may occur as a result of energy transfer from the particle, molecule, or compound used as a doping agent to induce polymerization. Photon cascade may also be used in the case of two-photon polymerization, wherein a doping particle may be selected for its ability to release light of different wavelengths based on random and alternative paths towards ground state.

Furthermore, in some cases, tuning of the dynamic range for polymerization may allow for additional structural properties to be added to cell nets, including relatively increased or decreased regions of polymer density just by changing the duration of excitation or intensity of excitation both of which increase the voxel size. This increase of density or thickness within the same print pass may be achieved by projecting or flickering off and on only certain portions or components of three dimensional images such that specifically selected spots or regions in the structure experience extended laser exposure times, allowing for introduction of varied structural elements.

Together, these features may allow for extended print-times while printing larger or more structures, longer-lasting and more uniform cell dispersion and distribution in suspension, with minimal damage to cells. Additionally, these conditions may facilitate more complete removal of cells not immobilized in cell nets during the multi-layered printing processes. Together, these print media conditions may allow for more controlled placement of cells and increased cell survival and facilitate removal during extended time periods required for multiple rounds of cell containing structure deposition.

Computer Control Systems

The present disclosure provides computer control systems that are programmed to implement methods of the disclosure. FIG. 43 shows a computer system 1101 that is programmed or otherwise configured to receive a computer model of the 3D biological material in computer memory; generate a point-cloud representation or lines-based representation of the computer model of the 3D biological material in computer memory; and direct the at least one energy source to direct the energy beam to the medium in the media chamber along at least one energy beam path in accordance with the computer model of the 3D biological material, and to subject at least a portion of the polymer precursors to form at least a portion of the 3D biological material. The computer system 1101 can regulate various aspects of computer model generation and design, image generation, holographic projection, and light modulation of the present disclosure, such as, for example, receiving or generating a computer-aided-design (CAD) model of a desired three-dimensional (3D) biological material structure to be printed. The computer system 1101 can convert the CAD model or any other type of computer model such as a point-cloud model or a lines-based model into an image of the desired three-dimensional (3D) biological material structure to be printed. The computer system 1101 can project the image the desired three-dimensional (3D) biological material structure holographically. The computer system 1101 can modulate a light source, an energy source, or an energy beam such that a light path or an energy beam path is created by the computer system 1101. The computer system 1101 can direct the light source, the energy source, or the energy beam along the light path or the energy beam path. The computer system 1101 can be an electronic device of a user or a computer system that is remotely located with respect to the electronic device. The electronic device can be a mobile electronic device.

The computer system 1101 includes a central processing unit (CPU, also "processor" and "computer processor" herein) 1105, which can be a single core or multi core processor, or a plurality of processors for parallel processing. The computer system 1101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 can be a data storage unit (or data repository) for storing data. The computer system 1101 can be operatively coupled to a computer network ("network") 1130 with the aid of the communication interface 1120. The network 1130 can be the Internet, an internet and/or extranet, or an intranet and/or extranet that is in communication with the Internet. The network 1130 in some cases is a telecommunication and/or data network. The network 1130 can include one or more computer servers, which can enable distributed computing, such as cloud computing. The network 1130, in some cases with the aid of the computer system 1101, can implement a peer-to-peer network, which may enable devices coupled to the computer system 1101 to behave as a client or a server.

The CPU 1105 can execute a sequence of machine-readable instructions, which can be embodied in a program or software. The instructions may be stored in a memory location, such as the memory 1110. The instructions can be directed to the CPU 1105, which can subsequently program or otherwise configure the CPU 1105 to implement methods of the present disclosure. Examples of operations performed by the CPU 1105 can include fetch, decode, execute, and writeback.

The CPU 1105 can be part of a circuit, such as an integrated circuit. One or more other components of the system 1101 can be included in the circuit. In some cases, the circuit is an application specific integrated circuit (ASIC).

The storage unit 1115 can store files, such as drivers, libraries and saved programs. The storage unit 1115 can store user data, e.g., user preferences and user programs. The computer system 1101 in some cases can include one or more additional data storage units that are external to the computer system 1101, such as located on a remote server that is in communication with the computer system 1101 through an intranet or the Internet.

The computer system 1101 can communicate with one or more remote computer systems through the network 1130. For instance, the computer system 1101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), cloud based computing services (e.g. Amazon Web Services), or personal digital assistants. The user can access the computer system 1101 via the network 1130.

Methods as described herein can be implemented by way of machine (e.g., computer processor) executable code stored on an electronic storage location of the computer system 1101, such as, for example, on the memory 1110 or electronic storage unit 1115. The machine executable or machine readable code can be provided in the form of software. During use, the code can be executed by the processor 1105. In some cases, the code can be retrieved from the storage unit 1115 and stored on the memory 1110 for ready access by the processor 1105. In some situations, the electronic storage unit 1115 can be precluded, and machine-executable instructions are stored on memory 1110.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1101 can include or be in communication with an electronic display 1135 that comprises a user interface (UI) 1140 for providing, for example, status of the printing process (e.g. displaying an illustration of the 3D biological material representing the 3D tissue portions printed prior to completion of the process), manual controls of the energy beams (e.g. emergency stop buttons controlling the on/off states of the energy beam), and display indicators designed to e.g. display remote oxygen, carbon dioxide, humidity, and temperature measurements within the media chamber. Examples of UI's include, without limitation, a graphical user interface (GUI) and web-based user interface.

EXAMPLES

Example 1—Holographic Printing of a Biologically Functional Aortic Valve Using a Method and System Described Herein In an example, a patient presents with symptoms such as shortness of breath, chest pain, and a heart murmur. A physician diagnoses the patient with aortic valve stenosis and recommends aortic valve replacement surgery. The patient undergoes a computer tomography (CT) scan of the aortic valve. The CT scan of the aortic valve is then converted into a computer-aided-design (CAD) model, which is received by the computer processor of the system disclosed herein. The computer processor generates a point-cloud representation of the aortic valve CAD model in computer memory. The computer processor further converts the point-cloud representation of the aortic valve into an image such as a three-dimensional image. The system further deconstructs and reconstructs the three-dimensional image and projects it in a holographic manner in a media chamber. The media chamber comprises cells such as fibroblasts, cartilage supporting chondrocytes, and partially differentiated mesenchymal stem cells; cell culture medium such as Cardiomyocyte Maintenance Medium; a polymerizable material (e.g., 2 mg/mL collagen methacrylate and 50% w/v polyethylene glycol diacrylate (PEGDA)); and a photoinitiator (e.g., Eosin Y Next, the system directs at least one energy beam to the media chamber along at least one energy beam path in accordance with the point-cloud representation of the aortic valve of the patient to subject the polymerizable material to form a 3D biologically functional aortic valve. The 3D-printed biologically functional aortic valve is then grown in tissue culture media conditions, assessed for functional and structural properties, and ultimately used to replace the diseased aortic valve of the patient during the aortic valve replacement surgery.

Example 2—Holographic Printing of a Vascularized, Three-Dimensional Skin Transplant In another example, a physician treats a patient for a severe skin disorder or burn and a replacement tissue is needed. The physician takes a skin biopsy between about 3 mm and 10 cm, depending upon initial cell number requirement, from a portion of healthy skin that is either from the patient or a genetic match of the patient. The physician sends the skin biopsy to Prellis Biologics. Prellis Biologics dissociates the skin; i.e. Prellis Biologics grows, and expands several of the distinct cell types from the skin such as, but not limited to keratinocytes, fibroblasts, epithelial cells, and stem cells of various differentiation states until sufficient numbers of cells are obtained to print new vascularized skin. A model of vascularized skin and the order of layer printing are loaded into a computer system that controls the optical elements that guide the laser or energy beam to the media chamber where 3D printing of new skin occurs. The order of cells to be printed is determined, for example, vascular cells are printed first. Small blood vessels are printed using the methods and systems described herein. The cell-containing medium comprises endothelial cells and a mixture of 1 mg/mL collagen methacrylate and 50% w/v polyethylene glycol diacrylate (PEGDA). The cell-containing medium may be a bio-ink. Once vasculature is printed, the printed structure is removed from the cell-containing medium and maintained at physiologic conditions until there is a stable vascular system. Next, the stability of the printed vascular system is verified by fluid flow tests, and the remaining cell types that are present in skin layers such as, but not limited to keratinocytes, epithelial cells, stem cells, and/or fibroblasts are printed around the existing printed vasculature, to form dermal and epidermal layers. The remaining cell types are also printed using the methods and systems described herein. Intradermal structures, such as, but not limited to hair follicles and sebaceous glands, are printed around the previously printed three-dimensional structure using a cell-containing medium comprising epithelial stem cells; thus, a printed three-dimensional skin structure is formed. The printed three-dimensional skin structure is then returned to physiologic conditions provided by the cell culture systems. The three-dimensional printed skin structure is supplied with its own perfusion system via pumping of nutrient rich, oxygenated media and/or blood substitute through the plurality of lumens of the vascular system. Differentiation and growth of the three-dimensional printed skin structure is monitored by an occasional biopsy and when a sufficient developmental state is reached, the three-dimensional printed skin structure is returned to the physician for transplantation. The vascularized, three-dimensional, printed skin transplant described herein has many benefits over other solutions, including, but not limited to the fact that the tissue is living and surgical anastomosis, or connection of blood vessels with the patient's own circulatory system, allows for functional incorporation of the graft.

Example 3—Holographic Printing of a Three-Dimensional, Functional Printed Kidneys In another example, a patient presenting with kidney failure is undergoing dialysis three times a week to remove waste and extra fluid from blood. A physician takes a kidney biopsy from the patient or a matched healthy donor kidney and provides the kidney biopsy to Prellis Biologics. Prellis Biologics cultures cells extracted from the kidney biopsy and expands adult kidney progenitor cell populations, including, but not limited to mesenchymal stem cells and dedifferentiated tubular epithelial cells, in vitro. A renal capillary system is printed from CAD models of an adult kidney vasculature system, using laser-initiated polymerization of a cell-containing medium comprising endothelial cells, and mixture of 1 mg/mL collagen methacrylate and 50% w/v polyethylene glycol diacrylate (PEGDA). Printed vasculature is maintained under physiological conditions, using endothelial cell culture media, until functional vasculature is demonstrated. Once functional vasculature is demonstrated, tubule structures of the nephron are printed within and around the vasculature system, using a cell-comprising medium including mesenchymal stem cells, tubular epithelial cells, and photosensitive extracellular matrix (ECM) components. ECM components are printed into 3D convoluted tubule structures with a plurality of perfusable, open lumens. Mesenchymal stem cells and tubular epithelial cells form a confluent epithelial monolayer around the ECM scaffolding. Controlled perfusion of morphogens and growth factors, combined with the unique 3D geometry of the printed tubules, directs differentiation into mature, polarized kidney epithelial cells forming each of the components of a functional nephron. Functional printed kidneys comprise at least 200,000 nephron units. Functionality and tissue viability is tested prior to transplantation into the patient. The three-dimensional, functional printed kidneys are returned to the physician for transplantation into the patient.

Figure 48A:
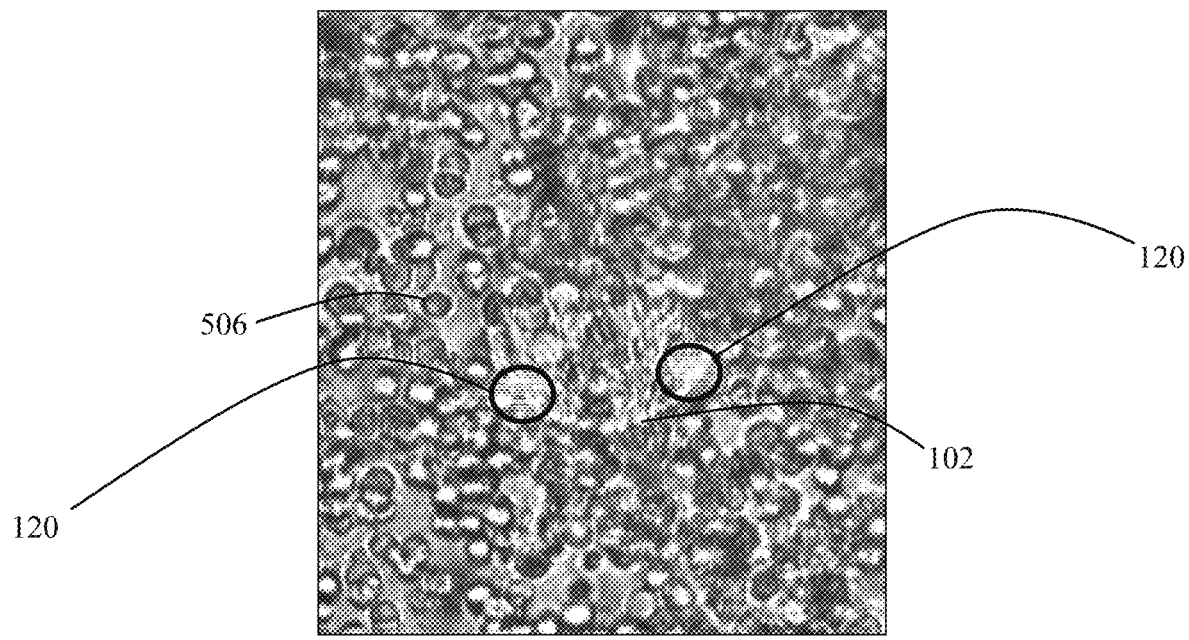
FIGS. 48A-48E show examples of a cellularized, three-dimensional (3D), impermeable microvasculature structure generated by holographic printing.
Figure 48B:
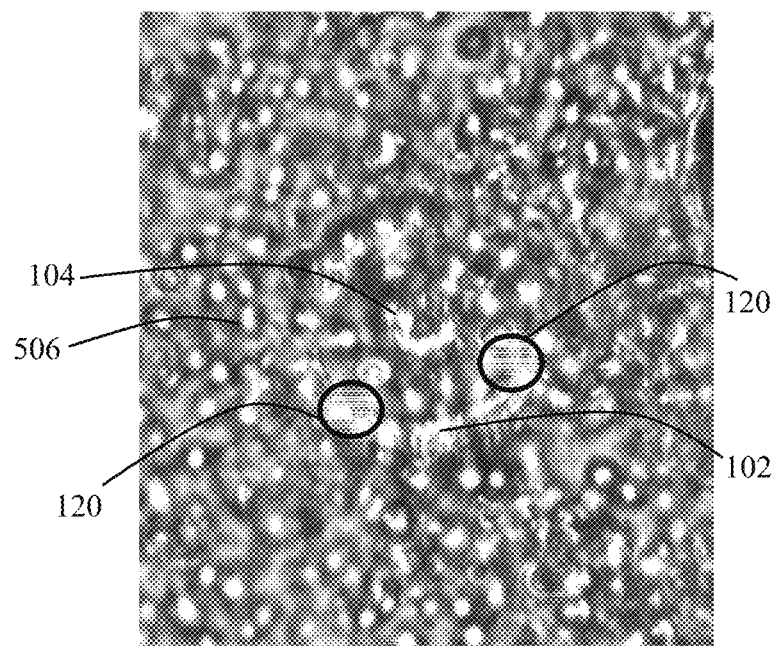
Figure 48C:
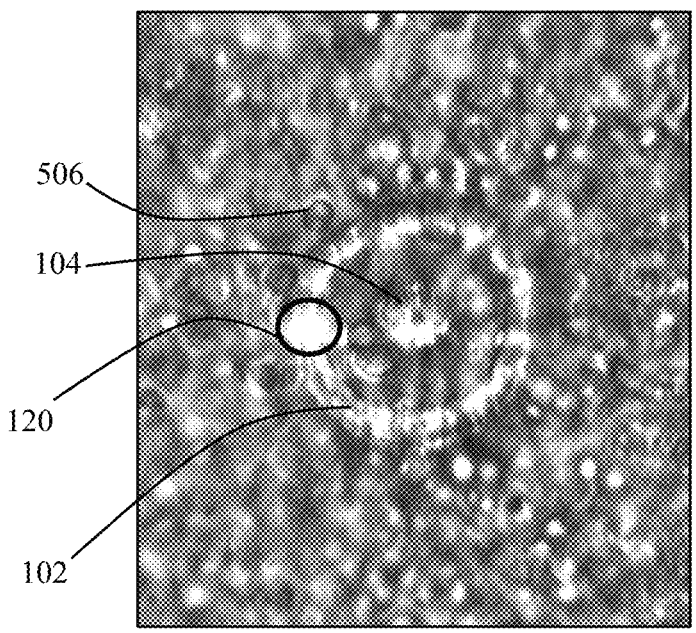
Figure 48D:
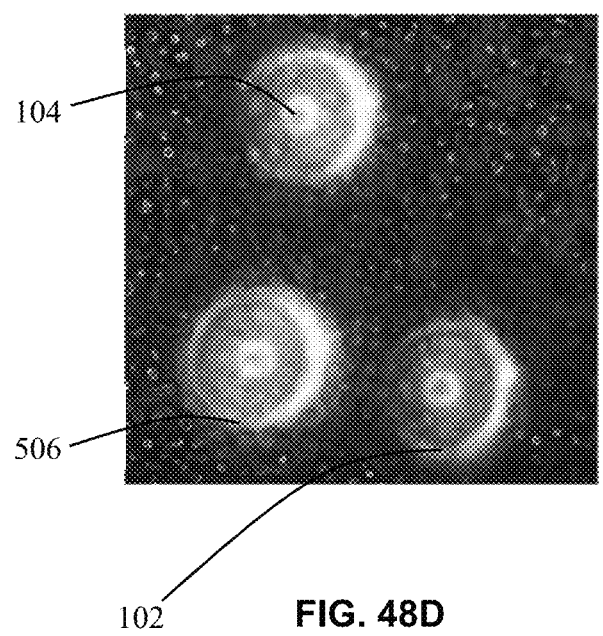
Figure 48E:
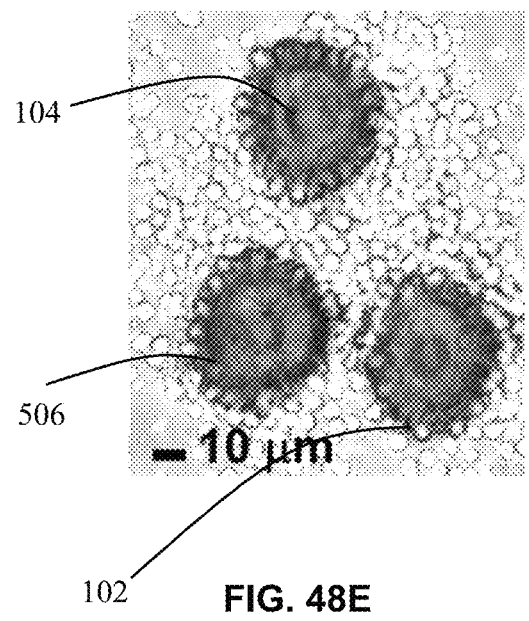

Example 4—Holographic Printing of a Cellularized, Three-Dimensional (3D), Impermeable Microvasculature Structure In another example, the 3D printing methods and systems provided herein were used to print a cellularized, 3D, impermeable microvasculature structure, as shown in FIGS. 48A-48E. FIG. 48A shows a top-down view of the 3D microvasculature structure in one of the initial steps of printing. A multi-photon energy beam 120 was used to project (in a top-down manner) a hologram of the 3D microvasculature structure into a medium. The medium contained cell culture medium, collagen methacrylate, PEGDA, Eosin Y, and cells 506. The cells 506 included endothelial cells. The inner tube 104 of the 3D microvasculature structure had a diameter of about 10 microns (µall) and was completed in the early steps of the 3D printing process, as shown in FIG. 48A. FIG. 48B shows a top-down view of the outer tube 102 of the 3D microvasculature structure as it began to form later in the process. The outer tube 102 had a diameter of about 50 µm. The completed 3D blood vessel structure was polymerized in situ, forming the inner tube 104 inside the outer tube 102 while trapping cells 506 around its structure, as shown in FIG. 48C. The final tube length that was holographically printed ranged from about 250 to 300 µm long. FIG. 48D is a fluorescent image of three microvasculature structures comprising an inner tube 104 and an outer tube 102. The three 3D printed microvasculature structures showed fluorescently-labeled cells 506 trapped within the microvasculature structures. FIG. 48E shows a bright field image of three 3D printed microvasculature structures containing cells 506. The three 3D printed microvasculature structures were placed under physiologic cell-culture conditions and imaged in bright field on day 5 after holographic printing. The 3D microvasculature structures contained dye (darker areas shown in FIG. 48E) after 5 days in culture, indicating the 3D microvasculature structures were impermeable to small molecules and whole cells were retained inside the printed microvasculature structures.

Example 5—Generation of a Cell-Containing Structure Using Holographic Printing

In another example, the 3D printing methods and systems provided herein were used to print a cell-containing structure, as shown in FIGS. 49A-49H. FIG. 49A shows a computer generated three-dimensional (3D) image of a cell-containing structure. A computer processor was then programmed to generate a point-cloud representation of the 3D image of the cell-containing structure shown in FIG. 49B. The computer processor was further programmed by the algorithms provided herein to convert the point-cloud representation into the hologram shown in FIG. 49C. The point-cloud representation and the hologram were used to generate computer instructions for printing the 3D cell-containing structure; these computer instructions were relayed to the computer printing system shown in FIG. 49D. A laser beam was directed into a media chamber (not shown in FIG. 49) containing a cluster of living cells 506 suspended in liquid print media 126, which included at least one polymeric precursor, as shown in FIG. 49E. FIG. 49F shows the same cluster of living cells 506 after three dimensional printing of the point-cloud representation. The printing field in this example was centered on the cell cluster by the user. FIG. 49G shows a cut-away image showing cells 506 inside of the printed, 3D cell-containing structure. FIG. 49H shows a representative image of the complete print of the 3D cell-containing structure. The entire cell-containing structure was printed in about 7 seconds.

Example 6—Holographic Printing of a 3D "Stanford Bunny"

In another example, the 3D printing methods and systems provided herein were used to print a three-dimensional (3D) "Stanford Bunny" structure, as shown in FIGS. 50A-50C. The "Stanford Bunny" is a common computer graphics 3D test model. FIG. 50A shows a computer generated three-dimensional (3D) image of the "Stanford Bunny." FIG. 50B shows a top-down view of the computer generated 3D image of the "Stanford Bunny." A computer processor was programmed to generate a point-cloud representation of the 3D image of the "Stanford Bunny," and the point-cloud representation was converted into a hologram. A laser beam was directed into a media chamber containing liquid print media including at least one polymeric precursor (not shown in FIG. 50). FIG. 50C shows a representative 3D print of the "Stanford Bunny" as imaged using in bright-field microscopy. The entire 3D structure of the "Stanford Bunny" was printed in about 60 seconds.

Figure 51A:
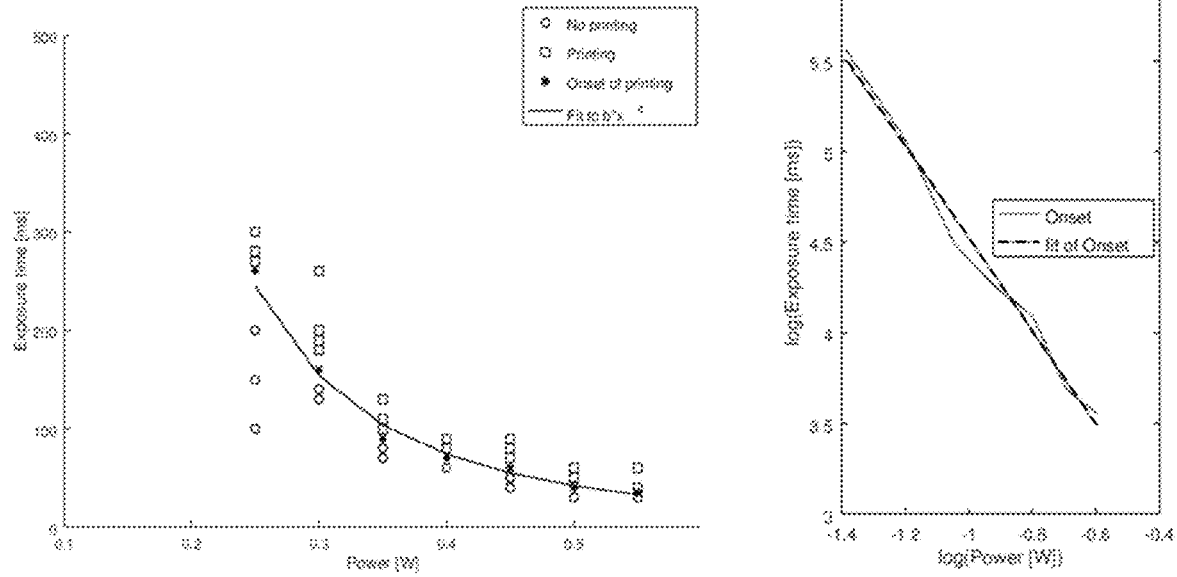
FIGS. 51A-51B show graphs of a two-photon laser beam exposure time (in milliseconds) vs. laser power (Watts) corresponding to holographic printing of two different formulations.
Figure 51B:
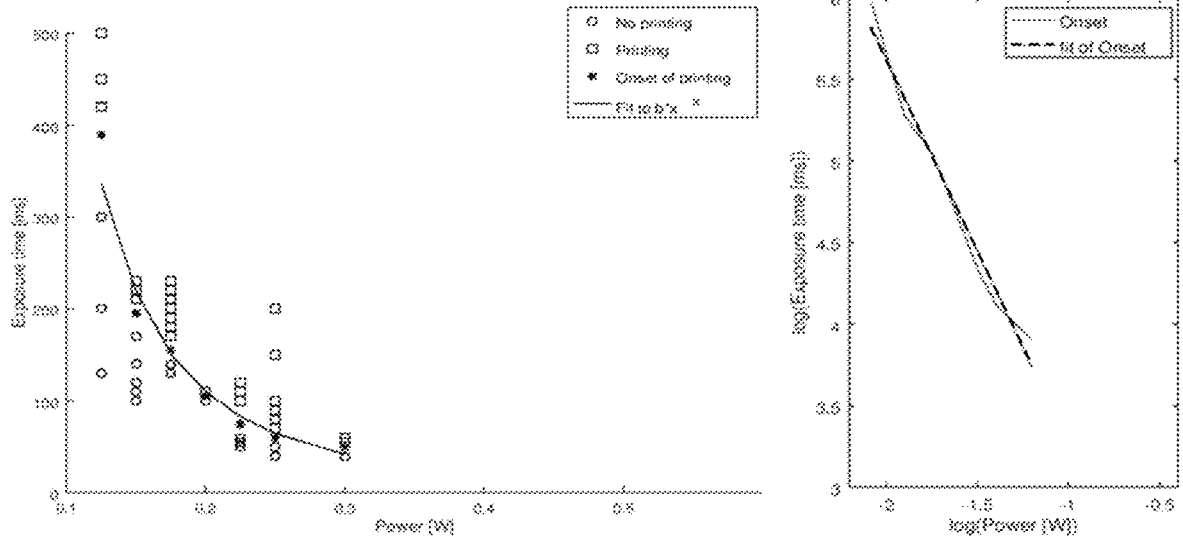

Example 7—Demonstration of Holographic Printing as a Two Photon-Dependent Process In another example, FIGS. 51A-51B show graphs of a two-photon laser beam exposure time (in milliseconds) vs. laser power (Watts) corresponding to holographic printing of two different formulations. Two-photon absorption is a second-order process wherein two photons of identical or different frequencies are absorbed in order to excite a molecule from one state to a higher electronic state. FIGS. 51A-51B demonstrate the process of holographic printing as a two photon dependent process; wherein the two-photon laser exposure time to the print sample was controlled by a computer processor that dictated the rapid opening and closing of the laser shutter to match the described time period and the threshold for printing. Per the standard two-photon absorptive process, the exposure time necessary to print is proportional to the inherent printing material properties divided by the power squared. FIG. 51A shows the threshold for printing in Formulation A which comprised at least about 30% PEG-DA, 0.5% Eosin Y, and 1 mg/mL collagen diacrylate. Extrapolation of the raw data points in a log scale fitted a linear decay, as shown in the graph on the right in FIG. 51A. The linear decay of Formulation A, shown in the log scale graph, matched the linear decay model that is expected for a second order process. FIG. 51B shows the threshold for printing in Formulation B which comprised at least about 45% PEG-DA, 0.5% Eosin Y, and 1 mg/mL collagen diacrylate. Extrapolation of the raw data points of Formulation B in a log scale fitted a linear decay, as shown in the graph on the right in FIG. 51B. The linear decay of Formulation B, shown in the log scale graph, corresponded to the linear decay model that is expected for a second order process.

Example 8—Targeted Single Cell Encapsulation Using Holographic Printing

In another example, the 3D printing methods and systems provided herein were used to perform a targeted single cell encapsulation, as shown in FIGS. 52A-52C. FIG. 52A shows a plurality of encapsulated cells and non-encapsulated cells suspended in print media comprising at least one polymeric precursor. For example, a first encapsulated cell 142a, a second encapsulated cell 142b, a third encapsulated cell 142c, a first non-encapsulated cell 144a, a second non-encapsulated cell 144b, and a third non-encapsulated cell 144c are shown in FIG. 52A. FIG. 52B shows zoomed-in images of a first encapsulated cell 142a, a second encapsulated cell 142b, and a third encapsulated cell 142c. These cells were encapsulated by 3D polymeric spheres with a diameter of about 25 microns (μm) that were printed holographically using the methods and systems provided herein. FIG. 52C shows zoomed-in images of a first non-encapsulated cell 144a, a second non-encapsulated cell 144b, and a third non-encapsulated cell 144c. The non-encapsulated cells were not subjected to holographic printing of a 3D sphere around them. The 3D hologram was projected onto an individual cell (e.g., onto the first encapsulated cell 142a) for at most about 50 milliseconds (ms) per encapsulation event.

Example 9—Expanded Laser Beam Projecting a Holographic Image

Figure 53:
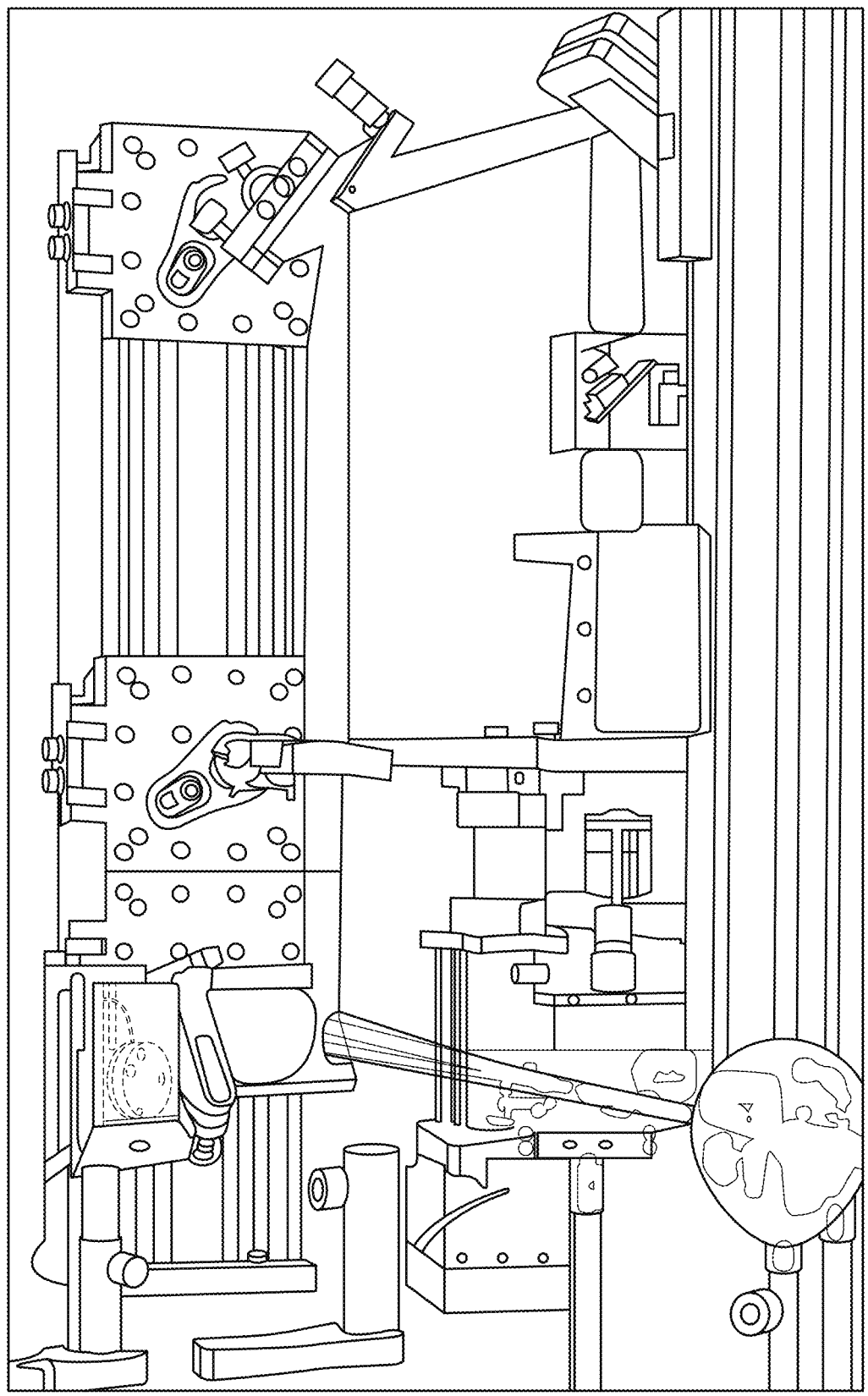
FIG. 53 shows an expanded laser beam projecting a hologram.

In another example, a representative image of the 3D printing system is shown in FIG. 53; in particular, the expanded laser beam projecting a holographic image is shown. FIG. 53 shows a laser beam having a wavelength of 1035 nm (i.e., a wavelength in the far-red light spectrum) as it was projected as an expanded laser beam that was patterned in a holographic form onto the back aperture of the print head. In this embodiment, the print head was a standard physiology grade microscope objective. The image shown in FIG. 53 was taken using long exposure while an infrared-detecting laser card was run through the light path to illuminate the light path in the visible range.

Example 10—Various Laser Printing Modes

Figure 54A:
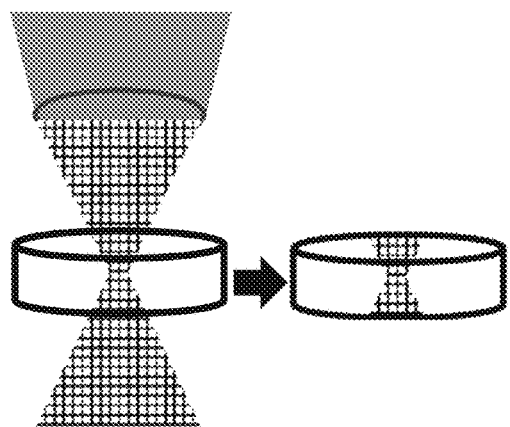
FIGS. 54A-54D illustrate different laser printing modes.
Figure 54B:
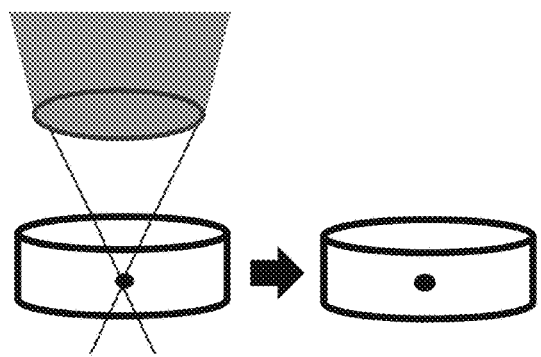
Figure 54C:
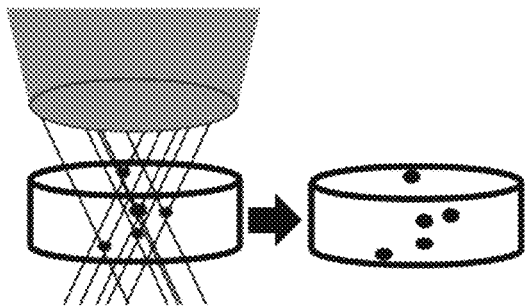
Figure 54D:
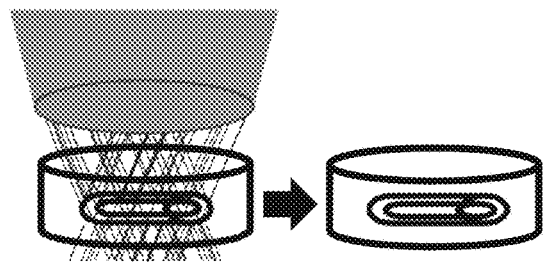

In another example, FIGS. 54A-54D illustrate different laser printing modes based on the optics of single photon and multiphoton printing processes and the expected structural outcomes. FIG. 54A illustrates a single photon laser beam projection into a media chamber containing a photosensitive print medium. The single photon laser beam projection is shown in FIG. 54A without masking or isolation of the intended plane of focus, which may be expected to leave a printed structure behind in the shape of the entire light cone. FIG. 54B illustrates a multi-photon absorption process where the photon density is only high enough at the point of focus, leaving only a pin-point structure behind in a media chamber containing a photosensitive print medium. FIG. 54C illustrates a representative graphic of wavefront shaping to produce a hologram in which the multiphoton absorption process occurs at multiple points of focus in the x, y, and z planes. In this embodiment, rapid switching between 3D projected hologram portions of a complete structure may be used to build the complete structure. FIG. 54D illustrates a complete image projection (i.e., a 3D hologram) in multiple planes allowing for the holographic printing of a complex structure. The complex structure shown in FIG. 54D as an example is a microvasculature structure having an inner tube and an outer tube.

Figure 55A:
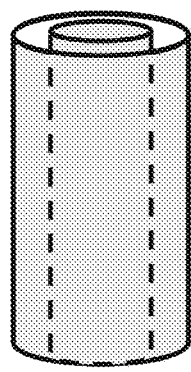
FIGS. 55A-55F show the holographic printing of a sphere within a previously printed 3D microvascular structure.
Figure 55C:
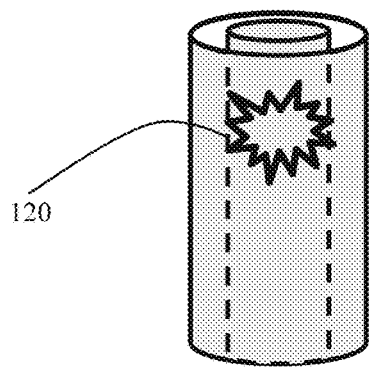
Figure 55E:
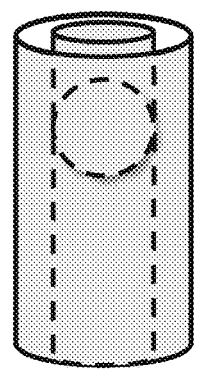
Figure 55B:
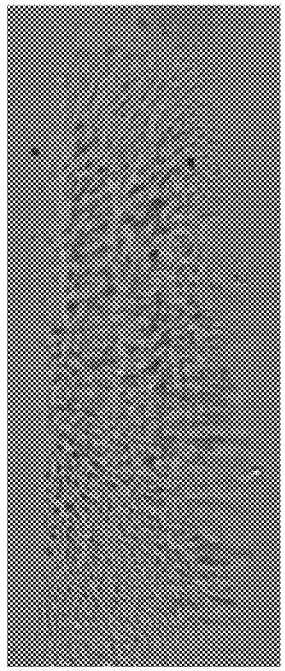
Figure 55D:
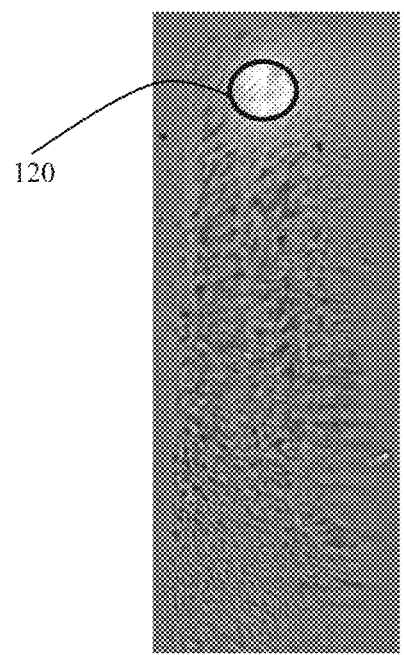
Figure 55F:
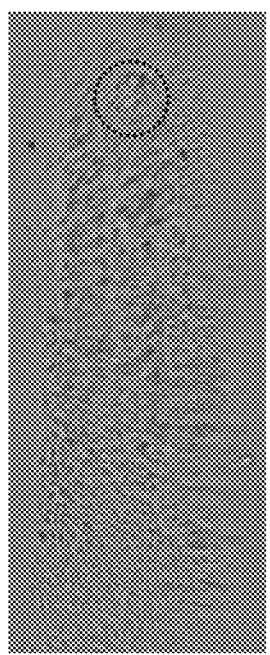

Example 11—Holographic Printing of Spheres within a Previously Printed 3D Microvasculature Structure In another example, the 3D printing methods and systems provided herein were used to print spheres inside a previously printed 3D microvasculature structure, as shown in FIGS. 55A-55F. FIG. 55A illustrates a printed microvasculature structure comprising a hollow tube structure and corresponds to the image shown in FIG. 55B. FIG. 55B shows an image of a printed microvasculature structure prior to the printing of a sphere. As shown in FIGS. 55C-55D, a multi-photon energy beam 120 having a near-infrared wavelength was used to project a hologram of a sphere into the center of the hollow tube of the microvasculature structure. The microvasculature structure was suspended within a medium comprising collagen methacrylate, PEGDA, and Eosin Y. FIG. 55F shows the sphere (outlined by the dashed circle) was deposited within the lumen of the microvasculature structure without disrupting it. FIG. 55E illustrates the image shown in FIG. 55F. The sphere was holographically printed in its entirety in about 5 milliseconds (ms) at most.

Example 12—Holographic Printing of a 3D Microvasculature Bed

Figure 56A:
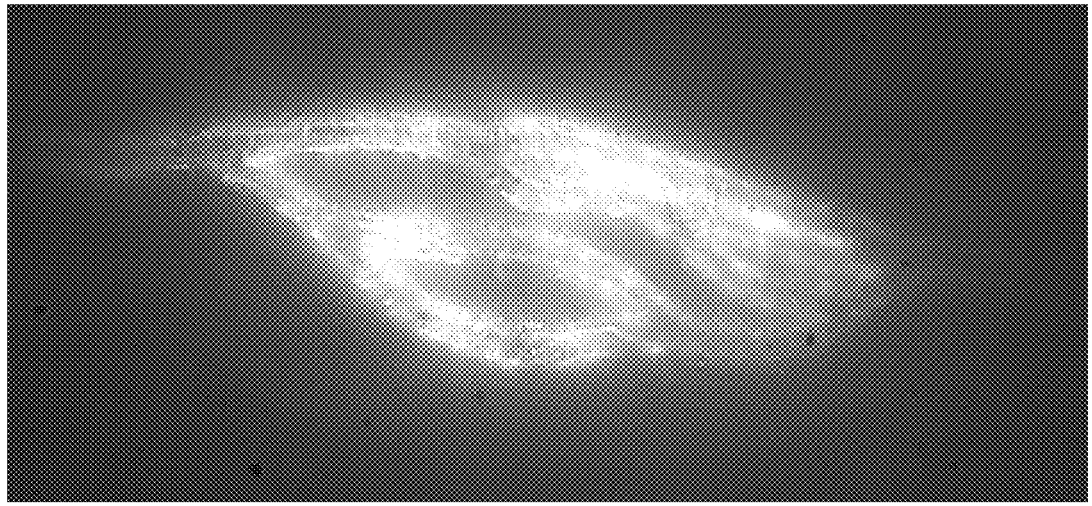
FIGS. 56A-56B show images of a polymeric vasculature bed printed using the methods and systems provided herein.
Figure 56B:
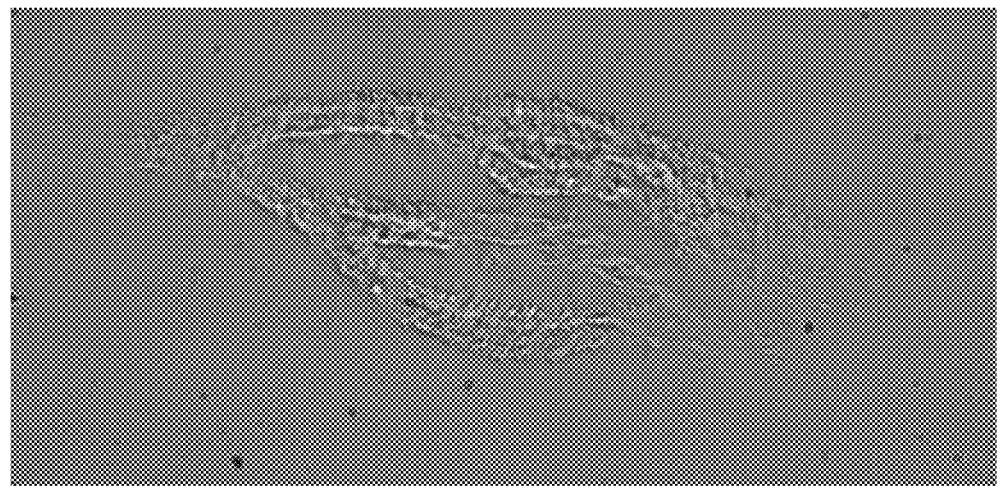

FIGS. 56A-56B show images of a polymeric microvasculature bed printed using the methods and systems provided herein. FIG. 56A shows an image of the vasculature bed during the holographic printing process. The illuminated areas correspond to a multi-photon laser beam projecting a hologram of the 3D microvasculature bed onto a medium. The medium included a polymeric precursor and a photoinitiator. FIG. 56B shows a bright field image of the 3D microvasculature bed after the holographic printing process is completed.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for forming a three-dimensional (3D) object corresponding to an organ or organoid, comprising generating a plurality of discrete non-interfering focal points patterned as a 3D projection corresponding to said organ or organoid in a medium comprising one or more precursors of a polymer, to form at least a portion of said 3D object corresponding to said organ or organoid.

2. The method of claim 1, wherein said medium comprises at least one photoinitiator, at least one cross-linker, collagen, hyaluronic acid, other glycosaminoglycans, poly (dl-lactic-co-glycolic acid), poly(l-lactic acid), poly(glycolic acid), alginate, gelatin, agar, or any combination thereof.

3. The method of claim 1, wherein said organ or organoid is selected from the group consisting of a lymph node, an islet of Langerhans, a hair follicle, a tumor or a tumor spheroid, a neural bundle and support cell(s), a nephron, a liver organoid, an intestinal crypt, a primary lymphoid organ, a secondary lymphoid organ, a spleen, a liver, a pancreas, a gallbladder, an appendix, a small intestine, a large intestine, a heart, a lung, a bladder, a kidney, a bone, a cochlea, an ovary, a thymus, a trachea, a cornea, a heart valve, skin, a ligament, a tendon, a muscle, a thyroid gland, a nerve, and a blood vessel.

4. The method of claim 1, further comprising receiving computer instructions for printing said 3D object, and forming at least said portion of said 3D object based at least in part on said computer instructions.

5. The method of claim 4, wherein said computer instructions comprise a computer model of said 3D object.

6. The method of claim 1, further comprising obtaining a native architecture of said organ or organoid from imaging data of a native organ or organoid.

7. The method of claim 6, wherein said native architecture is rendered into at least one two-dimensional or three-dimensional image.

8. The method of claim 7, wherein said image is a model for said generating said plurality of discrete non-interfering focal points patterned as said 3D projection.

9. The method of claim 1, wherein said 3D object contains at least one cell.

10. The method of claim 9, wherein said at least one cell is of a subject.

11. The method of claim 9, wherein said at least one cell comprises a plurality of cells of different cell types.

12. The method of claim 1, wherein said 3D object is configured to facilitate a growth of at least one cell to yield said organ or organoid.

13. The method of claim 1, wherein said 3D projection comprises a 3D projection corresponding to said organ or organoid, which 3D projection is generated using one or more energy beams from one or more energy sources.

14. The method of claim 13, wherein said 3D projection is a holographic projection.

15. The method of claim 1, further comprising using said 3D object to form said organ or organoid for use in a subject.

16. The method of claim 1, further comprising using said 3D object to form said organ or organoid, and combining said organ or organoid with an additional organ or organoid.

17. The method of claim 1, wherein said 3D object is said organ or organoid.

18. The method of claim 1, wherein said 3D projection is generated in said medium with aid of a spatial light modulator or a digital micromirror device, but not both.

19. The method of claim 1, wherein said 3D projection is generated in said medium with aid of a spatial light modulator.

20. The method of claim 1, wherein said 3D projection is generated in said medium with aid of a digital micromirror device.

21. The method of claim 1, wherein forming said at least said portion of said 3D object occurs via a multi-photon process.

* * * * *